US012545944B2

(12) United States Patent
Larrouy-Maumus et al.

(10) Patent No.: US 12,545,944 B2
(45) Date of Patent: Feb. 10, 2026

(54) METHOD OF DETECTION

(71) Applicant: Imperial College Innovations Limited, London (GB)

(72) Inventors: Gerald Larrouy-Maumus, London (GB); Laurent Dortet, London (GB); Alain Filloux, London (GB)

(73) Assignee: Imperial College Innovations Limited, London (GB)

( * ) Notice: Subject to any disclaimer, the term of this patent is extended or adjusted under 35 U.S.C. 154(b) by 346 days.

(21) Appl. No.: 16/489,627

(22) PCT Filed: Feb. 28, 2018

(86) PCT No.: PCT/GB2018/050522
§ 371 (c)(1),
(2) Date: Aug. 28, 2019

(87) PCT Pub. No.: WO2018/158573
PCT Pub. Date: Sep. 7, 2018

(65) Prior Publication Data
US 2020/0024635 A1 Jan. 23, 2020

(30) Foreign Application Priority Data
Feb. 28, 2017 (GB) ..................................... 1703261

(51) Int. Cl.
*C12Q 1/18* (2006.01)

(52) U.S. Cl.
CPC ..................................... *C12Q 1/18* (2013.01)

(58) Field of Classification Search
None
See application file for complete search history.

(56) References Cited

U.S. PATENT DOCUMENTS

2007/0020292 A1* 1/2007 Caroff ..................... A61P 31/04
424/236.1
2012/0197535 A1 8/2012 Goodlett et al.

FOREIGN PATENT DOCUMENTS

WO 2014/035270 A8 3/2014
WO 2015/052525 A1 4/2015
WO 2015/123664 A1 8/2015

OTHER PUBLICATIONS

Joo, H. S. et al. (2016). Bacterial strategies of resistance to antimicrobial peptides. Philosophical transactions of the Royal Society of London. Series B, Biological sciences, 371(1695), 20150292 (Year: 2016).*

(Continued)

*Primary Examiner* — Erin M. Bowers
(74) *Attorney, Agent, or Firm* — DECODE Legal Inc.

(57) ABSTRACT

The present invention is directed to a method for detecting the presence or absence of a bacterium resistant to a cyclic cationic polypeptide antibiotic, comprising: (a) subjecting a test sample to mass spectrometry analysis and generating a mass spectrum output; wherein said test sample comprises a bacterial membrane or a fragment thereof, wherein the fragment comprises a non-Lipid A component; (b) identifying in said mass spectrum output a first defined peak indicative of the presence of Lipid A modified by phosphoethanolamine, wherein said first defined peak is a peak present in a mass spectrum output for Lipid A modified by phosphoethanolamine and wherein said first defined peak is absent from a corresponding mass spectrum output for native Lipid A; and (c) wherein the presence of said first defined peak indicates the presence of a bacterium resistant to a cyclic cationic polypeptide antibiotic, and wherein the absence of said first defined peak indicates the absence of a bacterium resistant to a cyclic cationic polypeptide antibiotic. This method is also used in a screening method to (Continued)

identify an inhibitor of cyclic cationic polypeptide antibiotic resistance in a bacterium. The matrix solution can contain 2,5-dihydroxybenzoic acid and aids in the selective extraction, co-crystallisation and ionisation of native Lipid A and/or modified Lipid A as an integral part of a bacterial membrane.

28 Claims, 37 Drawing Sheets

Specification includes a Sequence Listing.

(56) References Cited

OTHER PUBLICATIONS

Liu et al. Lancet Infect. Dis. (2016; published online Nov. 18, 2015) 16: 161-68 and the Appendix pp. 1-11 (Year: 2015).*
Larrouy-Mamus et al. J. Microbiol. Methods (2016; available online Dec. 2, 2015) 120: 68-71 (Year: 2015).*
Henderson et al., J. Vis. Exp. E50623, doi:10.3791/50623 (2013).*
Liu et al., Lancet Infect. Dis. 16: 161-68 (2016).*
El Hamidi et al., J. Lipid Res. 46: 1773-1778 (2005).*
Larrouy-Maumus et al., J. Microbiol. Methods 120: 68-71 (2016; available online Dec. 2, 2015).*
Arroyo, L.A., et al., "The pmrCAB Operon Mediates Polymyxin Resistance in Acinetobacter baumannii ATCC 17978 and Clinical Isolates Through Phosphoethanolamine Modification of Lipid A," [published online ahead of print Jun. 6, 2011; doi:10.1128/AAC.00256-11], Antimicrobial Agents and Chemotherapy, 32 pages.
Beceiro, A., et al., "Phosphoethanolamine Modification of Lipid A in Colistin-Resistant Variants of Acinetobacter baumannii Mediated by the pmrAB Two-Component Regulatory System," Antimicrobial Agents and Chemotherapy 55(7):3370-3379, Jul. 2011.
Search Report mailed Nov. 23, 2017, issued in Application No. GB1703261.6, filed Feb. 28, 2017, 5 pages.
International Search Report and Written Opinion mailed Jun. 20, 2018, issued in International Application No. PCT/GB2018/050522, filed Feb. 28, 2018, 24 pages.
Park, Y.K., et al., "Transcriptomic Analysis of Colistin-Susceptible and Colistin-Resistant Isolates Identifies Genes Associated With Colistin Resistance in Acinetobacter baumannii," Clinical Microbiology and Infection 21(8):765.e1-765.e7, Aug. 2015.
Pelletier, M.R., et al., "Unique Structural Modifications Are Present in the Lipopolysaccharide From Colistin-Resistant Strains of Acinetobacter baumannii," Antimicrobial Agents and Chemotherapy 57(10):4831-4840, Oct. 2013.
Pendela, M., et al., "Characterization of Dihydrostreptomycin-Related Substances by Liquid Chromatography Coupled to Ion Trap Mass Spectrometry," Rapid Communications in Mass Spectrometry 23(12):1856-1862, Jun. 2009.
Qureshi, Z.A., et al., "Colistin-Resistant Acinetobacter baumannii: Beyond Carbapenem Resistance," Clinical Infectious Diseases 60(9):1295-1303, May 2015.
Tran, A.X., et al., "Periplasmic Cleavage and Modification of the 1-Phosphate Group of Helicobacter pylori Lipid A," Journal of Biological Chemistry 279(53):55780-55791, Dec. 2004.
European Office Action mailed Sep. 1, 2020, in corresponding Application No. EP18710124.1, filed Feb. 28, 2018, 6 pages.

* cited by examiner

FIGURE 2A
21
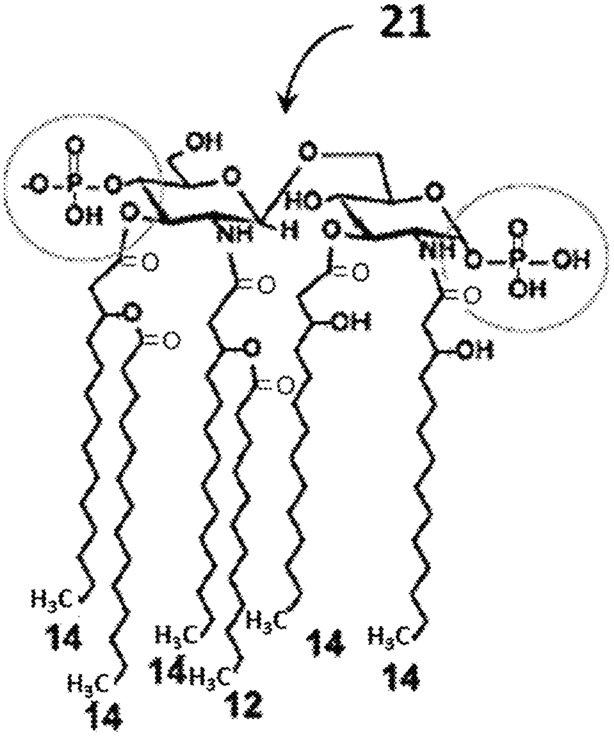
22
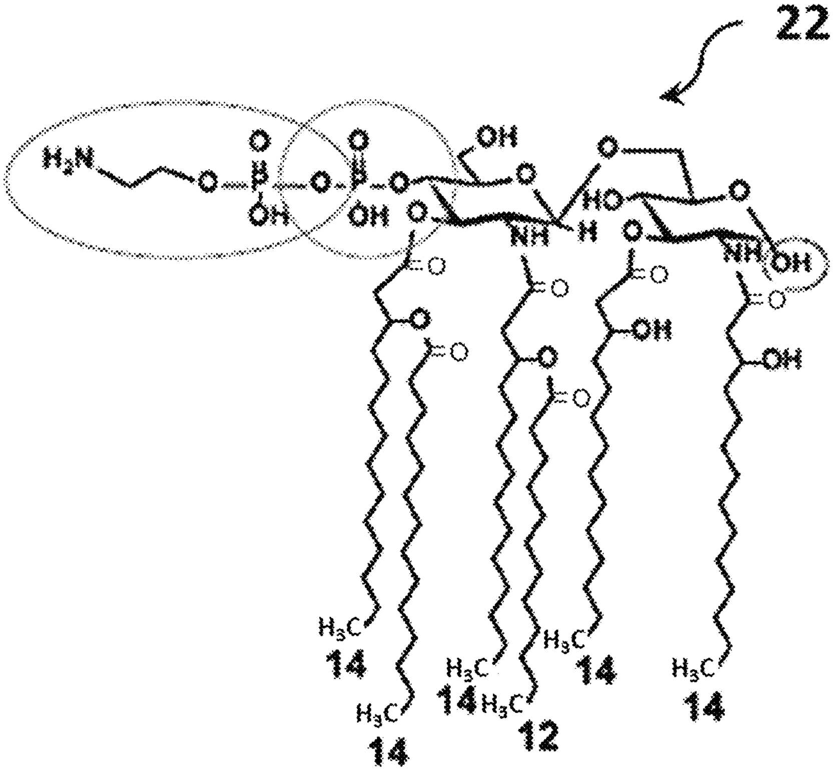

FIGURE 2B
23
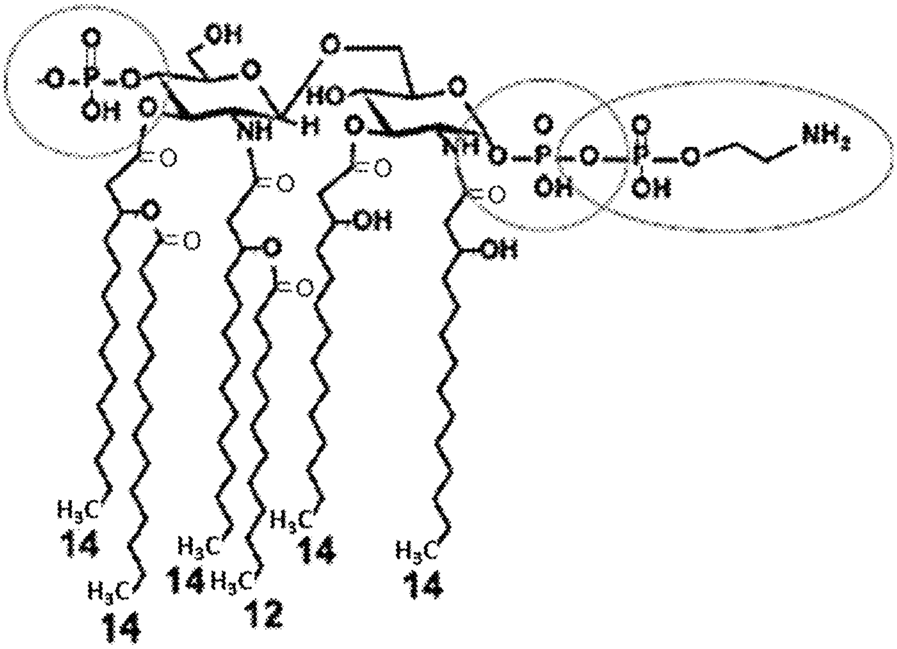
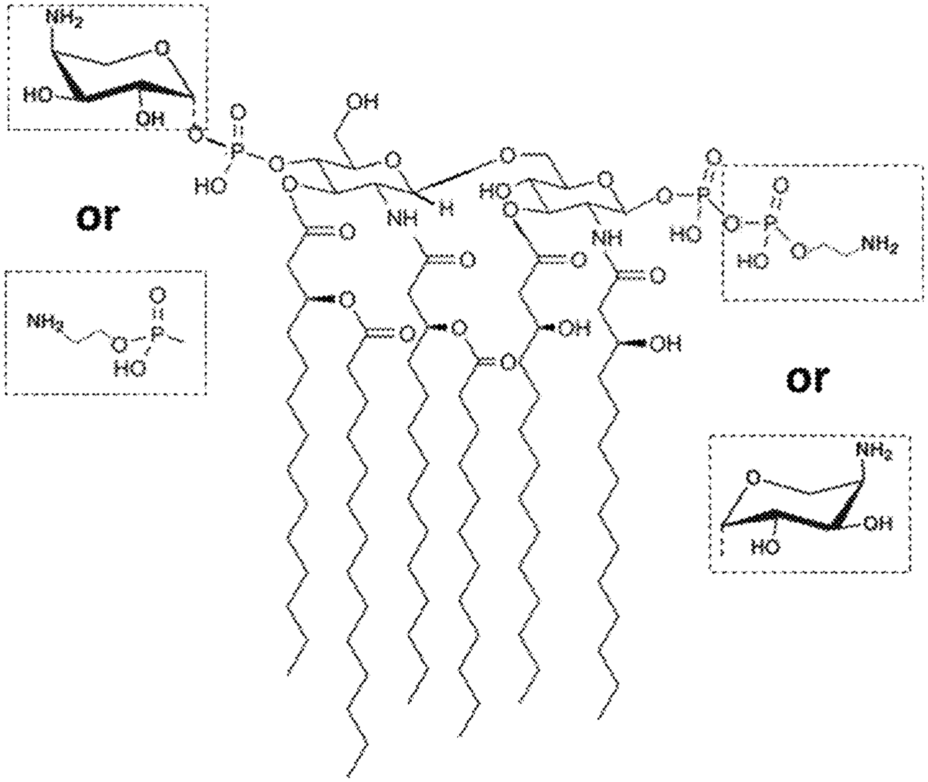
or
or

FIGURE 15

| Species | susceptibility to polymixins | Resistance mechanism | Peaks | | | | | | | | |
|---|---|---|---|---|---|---|---|---|---|---|---|
| | | Chromosome - vs plasmid-encoded | 1796 | 1821 | 1824 | 1840 | 1850 | 1919 | 1910 | 1927 | 1955 |
| *E. coli* | Susceptible | | ++ | - | | - | | - | | | |
| | Resistant | Plasmid | + | ++ | | - | | ++ | | | |
| | Resistant | Chromosome | + | - | | - | | + | | | |
| *K. pneumoniae* | Susceptible | | +/- | - | + | ++ | + | - | | | - |
| | Resistant | Plasmid | + | ++ | + | - | + | ++ | | | - |
| | Resistant | Chromosome | + | - | + | ++ | + | + | | | + |
| *A. baumannii* | Susceptible | | | | | | | | ++ | | |
| | Resistant | Plasmid | | | | | | | | | |
| | Resistant | Chromosome | | | | | | | + | | |
| *Salmonella Spp.* | Susceptible | | ++ | | + | | | - | | - | |
| | Resistant | Plasmid | ++ | | + | | | + | | - | |
| | Resistant | Chromosome | ++ | | + | | | | | + | |

| Species | susceptibility to polymixins | Chromosome - vs plasmid-encoded | 1963 | 1971 | 2033 | 2034 | 2062 | 2078 | 2157 | 2193 | 2201 | 2209 |
|---|---|---|---|---|---|---|---|---|---|---|---|---|
| *E. coli* | Susceptible | | | | | | | | | | | |
| | Resistant | Plasmid | | | | | | | | | | |
| | Resistant | Chromosome | | | | | | | | | | |
| *K. pneumoniae* | Susceptible | | - | - | | | + | ++ | | - | - | - |
| | Resistant | Plasmid | + | - | | | + | ++ | | - | + | - |
| | Resistant | Chromosome | +/- | + | | | + | ++ | | + | +/- | + |
| *A. baumannii* | Susceptible | | | | - | | | | | | | |
| | Resistant | Plasmid | | | | | | | | | | |
| | Resistant | Chromosome | | | ++ | | | | | | | |
| *Salmonella Spp.* | Susceptible | | | | | + | | | - | | | |
| | Resistant | Plasmid | | | | + | | | + | | | |
| | Resistant | Chromosome | | | | + | | | | | | |

FIGURE 16

```
MCR-1.2   ATGATGCTGCATACTTCTGTGTGGTACCGACGCTCGGTCAGTCCGTTTGTTCTTGTGGC-
MCR-1.8   ATGATGCGGCATACTTCTGTGTGGTACCGACGCTCGGTCAGTCCGTTTGTTCTTGTGGC-
MCR-1     ATGATGCAGCATACTTCTGTGTGGTACCGACGCTCGGTCAGTCCGTTTGTTCTTGTGGC-
MCR-1.7   ATGATGCAGCATACTTCTGTGTGGTACCGACGCTCGGTCAGTCCGTTTGTTCTTGTGGC-
MCR-1.5   ATGATGCAGCATACTTCTGTGTGGTACCGACGCTCGGTCAGTCCGTTTGTTCTTGTGGC-
MCR-1.4   ATGATGCAGCATACTTCTGTGTGGTACCGACGCTCGGTCAGTCCGTTTGTTCTTGTGGC-
MCR-1.6   ATGATGCAGCATACTTCTGTGTGGTACCGACGCTCGGTCAGTCCGTTTGTTCTTGTGGC-
MCR-1.3   ATGATGCAGCATACTTCTGTGTGGTACCGACGCTCGGTCAGTCCGTTTGTTCTTGTGGC-
MCR-1.10  ------------------GTGTGGTACCGACGCTCGGTCAGTCCGTTTGTTCTTGTGGC-
MCR-1.9   ------------------GTGTGGTACCGACGCTCGGTCAGTCCGTTTGTTCTTGTGGC-
MCR-2.2   ------------------GTGTGGTACCGACGCTCGGTCAGTCCGTTTGTTCTTGTGGC-
MCR-2     ATGACATCACATCACTCT---TGGTATCGCTATTCTATCAATCCTTTTGTGCTGATGG--
MCR-5     -------ATGCGGTTGTCTGCATT-TATCACTTTCTTGAAAATGCGCCCGCAAGTGCGCAC
MCR-3     ----------------ATGCCTTCCCTTATAAAAATAAAAATTGTTCCGCTTATGTTCT-
MCR-3.2   ----------------ATGCCTTCCCTTATAAAAATAAAAATTGTTCCGCTTATGTTCT-
MCR-4     -------------GTGATTTCTAGATTTAAGACGTTATCGGTTAACCAATTCACTTTCA-
                                  *                    *
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAGGTCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GAGTGTTGCCGTT-TTCTTGACCGCGACCGCCAATCTTA-CCTTTTTTGATAAAATCA
          ---GTTTGGTGGCGTTATTTTTGGCAGCGACAGCGAACCTGA-CATTTTTTGAAAAAGCGA
          TGAATTTTTGACTCTGTTCATCAGCCTTGTGTTCACCCTGC-TGTGCAATGGCGTGTTTT
          ------TTTTGGCACTGTATTTTGCATTTATGCTGAACTGGCGTGGAGTTCTCCATTTT-T
          ------TTTTGGCACTGTATTTTGCATTTATGCTGAACTGGCGTGGAGTTCTCCATTTT-T
          ------TCACTGCGTTGTTTTATGTTGCCATTTTCAATCTAC-CGCTCTTTGGTATAGTGC
               *     *   *  *                   *
MCR-1.2   GCCAAACCTATCCCATCGCGGACAATCTCGGCTTTGTGCTGACGATCGCTG-TCGTGCTC
MCR-1.8   GCCAAACCTATCCCATCGCGGACAATCTCGGCTTTGTGCTGACGATCGCTG-TCGTGCTC
MCR-1     GCCAAACCTATCCCATCGCGGACAATCTCGGCTTTGTGCTGACGATCGCTG-TCGTGCTC
MCR-1.7   GCCAAACCTATCCCATCGCGGACAATCTCGGCTTTGTGCTGACGATCGCTG-TCGTGCTC
MCR-1.5   GCCAAACCTATCCCATCGCGGACAATCTCGGCTTTGTGCTGACGATCGCTG-TCGTGCTC
MCR-1.4   GCCAAACCTATCCCATCGCGGACAATCTCGGCTTTGTGCTGACGATCGCTG-TCGTGCTC
MCR-1.6   GCCAAACCTATCCCATCGCGGACAATCTCGGCTTTGTGCTGACGATCGCTG-TCGTGCTC
MCR-1.3   GCCAAACCTATCCCATCGCGGACAATCTCGGCTTTGTGCTGACGATCGCTG-TCGTGCTC
MCR-1.10  GCCAAACCTATCCCATCGCGGACAATCTCGGCTTTGTGCTGACGATCGCTG-TCGTGCTC
MCR-1.9   GCCAAACCTATCCCATCGCGGACAATCTCGGCTTTGTGCTGACGATCGCTG-TCGTGCTC
MCR-2.2   GCCAAACCTATCCCATCGCGGACAATCTCGGCTTTGTGCTGACGATCGCTG-TCGTGCTC
MCR-2     TGGCGGTCTATCCTGTATCGGATAACTTAGGCTTTATCATCTCAATGGCGG-TGGCGGTG
MCR-5     GGAATGCCCTTCTTGCTGGACGCGACT----CCCTAACTTCTGGAACATGGCTAATGCTC
MCR-3     ACGAAATCCTTTACAAATTAGAAGATTTTAAGTTTGGTTTCGCCATTTCAT-TACCAATA
MCR-3.2   ACGAAATCCTTTACAAATTAGAAGATTTTAAGTTTGGTTTCGCCATTTCAT-TACCAATA
MCR-4     GAAAAGGAATTGAAAAACAACCAGAAGTTGATCCCCTTTTCATCGCATCTA-TGCCGCTA
                  *          *           *         *    *
```

FIGURE 16 (continued)

```
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          TTTGGCGCGATGCTACTGATCACCACGCTGTTATCATCGT-----------ATCGCTATG
          ATGGGTGCTATGCTACTGATTGTCGTGCTGTTATC---CT-----------ATCGCTATG
          CTTTGCACTGGGTTGCTGATCACCGGGCTGCAATGGTTGTTGCTCCTTCTGGTGGCCACG
          TTGCTTGTTGCAGCGCTTAACTTTGTATTTGTTCCATTTT--------CGATACGGTATT
          TTGCTTGTTGCAGCGCTTAACTTTGTATTTGTTCCATTTT--------CGATACGGTATT
          TTTTTAACATTTGCGCTGAGTTTTTTGTTTTCAATTTTTA--------CCGTCAAATACC
           *             ** *          *                             *
MCR-1.2   TGCTA-------AAGCCTGTGTTGATTTTGCTATTAATCATGGGCGCGGTGACCAGTTATT
MCR-1.8   TGCTA-------AAGCCTGTGTTGATTTTGCTATTAATCATGGGCGCGGTGACCAGTTATT
MCR-1     TGCTA-------AAGCCTGTGTTGATTTTGCTATTAATCATGGGCGCGGTGACCAGTTATT
MCR-1.7   TGCTA-------AAGCCTGTGTTGATTTTGCTATTAATCATGGGCGCGGTGACCAGTTATT
MCR-1.5   TGCTA-------AAGCCTGTGTTGATTTTGCTATTAATCATGGGCGCGGTGACCAGTTATT
MCR-1.4   TGCTA-------AAGCCTGTGTTGATTTTGCTATTAATCATGGGCGCGGTGACCAGTTATT
MCR-1.6   TGCTA-------AAGCCTGTGTTGATTTTGCTATTAATCATGGGCGCGGTGACCAGTTATT
MCR-1.3   TGCTA-------AAGCCTGTGTTGATTTTGCTATTAATCATGGGCGCGGTGACCAGTTATT
MCR-1.10  TGCTA-------AAGCCTGTGTTGATTTTGCTATTAATCATGGGCGCGGTGACCAGTTATT
MCR-1.9   TGCTA-------AAGCCTGTGTTGATTTTGCTATTAATCATGGGCGCGGTGACCAGTTATT
MCR-2.2   TGCTA-------AAGCCTGTGTTGATTTTGCTATTAATCATGGGCGCGGTGACCAGTTATT
MCR-2     TGCTA-------AAGCCTGTCCTGATTTTGCTACTGATTATGGGTGCGGTGACGAGCTATT
MCR-5     CGCTGGAGTGTCAAGCCACTACTGATTCTGCTTGCTGTCATGACGCCCGCCGCCGTTTATT
MCR-3     TAATA-------AAGCCTTTTTTTGCACTTCTTATCGCACTTAGTGCAATCGTTAGTTACA
MCR-3.2   TAATA-------AAGCCTTTTTTTGCACTTCTTATCGCACTTAGTGCAATCGTTAGTTACA
MCR-4     TGCTG-------AAGCCCTTTTTTATCGTATTGACGTTACTTTCCTCAAGTGTATTTTTG
             *        *****  *  *     *  *        *     *          *
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACTGACACTTATGGCACGGTCTATGATACGACCATGCTCCAAAATGCCCTACAGACC
          TTACCGATACTTATGGCACGGTCTATGACACCACCATGCTCCAAAATGCCATGCAAACC
          TCATGCGCAACTACGGGGTTTATCTCGACAAGGCCATGCTGCGGAATCTGATGGAGACG
          CAATGATGAAGTATAGAGTCTTGTTTGATCAAAACATGATTCAGAATATTTTTGAAACC
          CAATGATGAAGTATAGAGTCTTGTTTGATCAAAACATGATTCAGAATATTTTTGAAACC
          CAGCCTATCAATACAATGTCGTGTTTGACTACGGCATGATAGAAAACACGTTTCAAACA
                    **              **      **** *     **      *  * **
```

FIGURE 16 (continued)

```
MCR-1.2  GACCAAGCCGAGACCAAGGATCTATTAAACGCAGCGTTTATCATGCGTATCATTGGTTTGG
MCR-1.8  GACCAAGCCGAGACCAAGGATCTATTAAACGCAGCGTTTATCATGCGTATCATTGGTTTGG
MCR-1    GACCAAGCCGAGACCAAGGATCTATTAAACGCAGCGTTTATCATGCGTATCATTGGTTTGG
MCR-1.7  GACCAAGCCGAGACCAAGGATCTATTAAACGCAGCGTTTATCATGCGTATCATTGGTTTGG
MCR-1.5  GACCAAGCCGAGACCAAGGATCTATTAAACGCAGCGTTTATCATGCGTATCATTGGTTTGG
MCR-1.4  GACCAAGCCGAGACCAAGGATCTATTAAACGCAGCGTTTATCATGCGTATCATTGGTTTGG
MCR-1.6  GACCAAGCCGAGACCAAGGATCTATTAAACGCAGCGTTTATCATGCGTATCATTGGTTTGG
MCR-1.3  GACCAAGCCGAGACCAAGGATCTATTAAACGCAGCGTTTATCATGCGTATCATTGGTTTGG
MCR-1.10 GACCAAGCCGAGACCAAGGATCTATTAAACGCAGCGTTTATCATGCGTATCATTGGTTTGG
MCR-1.9  GACCAAGCCGAGACCAAGGATCTATTAAACGCAGCGTTTATCATGCGTATCATTGGTTTGG
MCR-2.2  GACCAAGCCGAGACCAAGGATCTATTAAACGCAGCGTTTATCATGCGTATCATTGGTTTGG
MCR-2    GACCAAGCCGAGTCTAAGGACTTGATGAATTTGGCGTTTTTTGTGCGAATTATCGGGCTTG
MCR-5    GACGTCAGGGAAGCCAGTGAGCTGTTGCA-ATGGAGAATGCTGCCCTACTTGTTGGTTGCA
MCR-3    AATCAAAATGAGGCGTTAGCATATTTAAGCTTACCAATTATAGTATGGGTTACTATTGCTG
MCR-3.2  AATCAAAATGAGGCGTTAGCATATTTAAGCTTACCAATTATAGTATGGGTTACTATTGCTG
MCR-4    CATCCTGCTGAAGCATTGATGTATGTAAATCTTGCATCAATTAC-CAATCTACTGCTGACT
          *        **  *           *

         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GTG-TGCTACCAAGTTTGCTTGTGGCTTTTGTTAAGGTGG---ATTATCCGACTTGGGG
         GCG-TGTTGCCAAGTGTGTTGGTCGCAGTTGCCAAAGTCA---ATTATCCAACATGGGG
         GC--CGTATCCGTGTG-GTGGATTGCGAGAGTCAGGGTTTT--ACGAACGGGCTGGAAA
         GTTTTATCCCTGCCATTTTACTTTTCTTTG-TTGAAATTGAATATGAGGAAAAATGGTT
         GTTTTATCCCTGCCATTTTACTTTTCTTTG-TTGAAATTGAATATGAGGAAAAATGGTT
         GGGCTATTACCGTCATATCTTATTTATAAGGCCGATATTCATTATCAGCC---CTTTTT
         *        *            *              *     *  *
MCR-1.2  CAAGGGTT--TGATGCGCCGATTGGGCTTGATCGTGGCAAGTCTTGCGCTGATTTTACTGC
MCR-1.8  CAAGGGTT--TGATGCGCCGATTGGGCTTGATCGTGGCAAGTCTTGCGCTGATTTTACTGC
MCR-1    CAAGGGTT--TGATGCGCCGATTGGGCTTGATCGTGGCAAGTCTTGCGCTGATTTTACTGC
MCR-1.7  CAAGGGTT--TGATGCGCCGATTGGGCTTGATCGTGGCAAGTCTTGCGCTGATTTTACTGC
MCR-1.5  CAAGGGTT--TGATGCGCCGATTGGGCTTGATCGTGGCAAGTCTTGCGCTGATTTTACTGC
MCR-1.4  CAAGGGTT--TGATGCGCCGATTGGGCTTGATCGTGGCAAGTCTTGCGCTGATTTTACTGC
MCR-1.6  CAAGGGTT--TGATGCGCCGATTGGGCTTGATCGTGGCAAGTCTTGCGCTGATTTTACTGC
MCR-1.3  CAAGGGTT--TGATGCGCCGATTGGGCTTGATCGTGGCAAGTCTTGCGCTGATTTTACTGC
MCR-1.10 CAAGGGTT--TGATGCGCCGATTGGGCTTGATCGTGGCAAGTCTTGCGCTGATTTTACTGC
MCR-1.9  CAAGGGTT--TGATGCGCCGATTGGGCTTGATCGTGGCAAGTCTTGCGCTGATTTTACTGC
MCR-2.2  CAAGGGTT--TGATGCGCCGATTGGGCTTGATCGTGGCAAGTCTTGCGCTGATTTTACTGC
MCR-2    CAAAGGTC--TGATTCAGCGTGCGATGACATGGGGTGTCAGCCTTGTGCTGTTGCTTGTGC
MCR-5    CAAGCGGTAATGATGCGCAGCGCTTGTCTGGCTGGCGC---TCTCGCCATGATTTCCATGG
MCR-3    CAAAGGGA--TTCTAACTCGTGCCCTATCGATGTTTGCATCACTTATAGTGATTGCGGTTA
MCR-3.2  CAAAGGGA--TTCTAACTCGTGCCCTATCGATGTTTGCATCACTTATAGTGATTGCGGTTA
MCR-4    TAAGGAGT--TATTGCATAAATTAGCCTTTATGCTGCTAATGTTCGTTGGCATTGGGATAG
          **       *  *                             *        *     *
```

FIGURE 16 (continued)

```
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CTGTGGTGGCGTTCAGCAGTCATTATGCCAGTTTCTTTCGCGTGCATAAGCCGCTGCGT
          CGATTGGACTATTTAGCAGTCAGTATGCGAGTTTCTTTCGGGTGCATAAGCCAGTGCGT
          GTCTGTGGCCAGTCATGGATGTGCTGATACCCACGCTTCGTGAAAACAAGCCGCTTCGC
          TTGCAGCACTATACTATCAAGATTATGTGTCAGTGGGGCGCAACAATTCAAACCTCCAG
          TTGCAGCACTATACTATCAAGATTATGTGTCAGTGGGGCGCAACAATTCAAACCTCCAG
          TCGCCTTTTTTTACTATCAAGATTATGCTGCATTTGTTCGAAACAACAGTGAGTTAAGG
                                                **      *        *

MCR-1.2   AGCTATGTCAATCCGATCATGCCAATCTACTCGGTGGGTAAGCTTGCCAGTATTGAGTATA
MCR-1.8   AGCTATGTCAATCCGATCATGCCAATCTACTCGGTGGGTAAGCTTGCCAGTATTGAGTATA
MCR-1     AGCTATGTCAATCCGATCATGCCAATCTACTCGGTGGGTAAGCTTGCCAGTATTGAGTATA
MCR-1.7   AGCTATGTCAATCCGATCATGCCAATCTACTCGGTGGGTAAGCTTGCCAGTATTGAGTATA
MCR-1.5   AGCTATGTCAATCCGATCATGCCAATCTACTCGGTGGGTAAGCTTGCCAGTATTGAGTATA
MCR-1.4   AGCTATGTCAATCCGATCATGCCAATCTACTCGGTGGGTAAGCTTGCCAGTATTGAGTATA
MCR-1.6   AGCTATGTCAATCCGATCATGCCAATCTACTCGGTGGGTAAGCTTGCCAGTATTGAGTATA
MCR-1.3   AGCTATGTCAATCCGATCATGCCAATCTACTCGGTGGGTAAGCTTGCCAGTATTGAGTATA
MCR-1.10  AGCTATGTCAATCCGATCATGCCAATCTACTCGGTGGGTAAGCTTGCCAGTATTGAGTATA
MCR-1.9   AGCTATGTCAATCCGATCATGCCAATCTACTCGGTGGGTAAGCTTGCCAGTATTGAGTATA
MCR-2.2   AGCTATGTCAATCCGATCATGCCAATCTACTCGGTGGGTAAGCTTGCCAGTATTGAGTATA
MCR-2     TTTTATATCAACCCGATTACGCCGATTTATTCGGTGGGTAAGCTTGCCAGTATCGAGTACA
MCR-5     TATTTGATCACTCCTGCAAACTACGTCATCTCGGGCATTCGGGTTTTGACTGAACAG-GCG
MCR-3     CGTGAGATTGTTCCAGCCAATTTCGTTAATAGTACCGTTAAATACGTTTACAATCGTTATC
MCR-3.2   CGTGAGATTGTTCCAGCCAATTTCGTTAATAGTACCGTTAAATACGTTTACAATCGTTATC
MCR-4     CGTTACATTGTCCCTACCTATTTTGTCAGTAGTGCATCTAAATATCTCAATGAGCACTAT-
                 *   **           *            *
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTACGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCAGTGCGCCAAAAGATACCATTTATCACGCCAAAGACGCGGTACAAGCAACC
          AAAAAGCCACTGCGCCAACAGACACCATCTATCATGCCAAAGACGCCGTGCAGACCACC
          TCATCGTCAGCAGACGAAGCAAGGGAAGTCGTTGCAGCCGATGCGCATCGAGGGCCTCA
          TTGCTGA-ACCAATCCCATTT--ACAACTTTAGGTG---ATGATGCAAAACGGGATAC-
          TTGCTGA-ACCAATCCCATTT--ACAACTTTAGGTG---ATGATGCAAAACGGGATAC-
          TTGCAGACGCCCATGGAATACCAACAACTTGGCCTA---GATGCGAAGAATGCCAGTCG
               *           *        *                 *            *
```

FIGURE 16 (continued)

```
MCR-1.2  AAGCCTGATATGCGTAAGCCACGCCTAGTGGTGTTCGTCGTCGGTGAGACGGCACGCGCCG
MCR-1.8  AAGCCTGATATGCGTAAGCCACGCCTAGTGGTGTTCGTCGTCGGTGAGACGGCACGCGCCG
MCR-1    AAGCCTGATATGCGTAAGCCACGCCTAGTGGTGTTCGTCGTCGGTGAGACGGCACGCGCCG
MCR-1.7  AAGCCTGATATGCGTAAGCCACGCCTAGTGGTGTTCGTCGTCGGTGAGACGGCACGCGCCG
MCR-1.5  AAGCCTGATATGCGTAAGCCACGCCTAGTGGTGTTCGTCGTCGGTGAGACGGCACGCGCCG
MCR-1.4  AAGCCTGATATGCGTAAGCCACGCCTAGTGGTGTTCGTCGTCGGTGAGACGGCACGCGCCG
MCR-1.6  AAGCCTGATATGCGTAAGCCACGCCTAGTGGTGTTCGTCGTCGGTGAGACGGCACGCGCCG
MCR-1.3  AAGCCTGATATGCGTAAGCCACGCCTAGTGGTGTTCGTCGTCGGTGAGACGGCACGCGCCG
MCR-1.10 AAGCCTGATATGCGTAAGCCACGCCTAGTGGTGTTCGTCGTCGGTGAGACGGCACGCGCCG
MCR-1.9  AAGCCTGATATGCGTAAGCCACGCCTAGTGGTGTTCGTCGTCGGTGAGACGGCACGCGCCG
MCR-2.2  AAGCCTGATATGCGTAAGCCACGCCTAGTGGTGTTCGTCGTCGGTGAGACGGCACGCGCCG
MCR-2    AAGCCGAGCGAGCGTAAGCCACGCCTAGTGGTGTTCGTCGTCGGTGAGACGGCGCGTGCTG
MCR-5    AGAACAAG--GCCGCCGTCCTCGTGCTCTCGTACTGGTTGTCGGGGAAACCGTCAGGGCGG
MCR-3    TAATCAAA--G----TAAGCCCACGTTGATGTTTCTGGTCGTTGGTGAAACCGCTCGTGGTA
MCR-3.2  TAATCAAA--G----TAAGCCCACGTTGATGTTTCTGGTCGTTGGTGAAACCGCTCGTGGTA
MCR-4    TAACCCGA--ACACTAAACCTAACTTATTAGTGGTTGTTGTGGGTGAAACTGCGCGCT-CA
             *              **       *  *  * **  ** ** ** ** *   *
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ATCATGTCAGCTTCA-ATGGCTATGAGCGCGATACTTTCCCACAGCTTGCCAAGATCGA
         ACCATGTGCAGTTCA-ATGGCTATGGCCGTGAGACTTTCCCGCAGCTTGCCAAAGTTGA
         CTAATTGGGGGTTGA-GCGGCTATGAACGACAAACCACCCCTGAGTTGGCCGCACGCGA
         AAAATTTCTCGATGA-ATGGCTATGAGAAAGACACCAATCCATTTACCAGTAAATCTGG
         AAAATTTCTCGATGA-ATGGCTATGAGAAAGACACCAATCCATTTACCAGTAAATCTGG
         ATGAGCTATCAATATTATGGATATAACAAGCCAACCAATGCTCATACC---CAAAATCAG
             *        *     **  ***        **     *
MCR-1.2  TGGCGTGACCAATTTTAGCAATGTCACATCGTGCGGCACATCGACGGCGTATTCTGTGCCG
MCR-1.8  TGGCGTGACCAATTTTAGCAATGTCACATCGTGCGGCACATCGACGGCGTATTCTGTGCCG
MCR-1    TGGCGTGACCAATTTTAGCAATGTCACATCGTGCGGCACATCGACGGCGTATTCTGTGCCG
MCR-1.7  TGGCGTGACCAATTTTAGCAATGTCACATCGTGCGGCACATCGACGGCGTATTCTGTGCCG
MCR-1.5  TGGCGTGACCAATTTTAGCAATGTCACATCGTGCGGCACATCGACGGCGTATTCTGTGCCG
MCR-1.4  TGGCGTGACCAATTTTAGCAATGTCACATCGTGCGGCACATCGACGGCGTATTCTGTGCCG
MCR-1.6  TGGCGTGACCAATTTTAGCAATGTCACATCGTGCGGCACATCGACGGCGTATTCTGTGCCG
MCR-1.3  TGGCGTGACCAATTTTAGCAATGTCACATCGTGCGGCACATCGACGGCGTATTCTGTGCCG
MCR-1.10 TGGCGTGACCAATTTTAGCAATGTCACATCGTGCGGCACATCGACGGCGTATTCTGTGCCG
MCR-1.9  TGGCGTGACCAATTTTAGCAATGTCACATCGTGCGGCACATCGACGGCGTATTCTGTGCCG
MCR-2.2  TGGCGTGACCAATTTTAGCAATGTCACATCGTGCGGCACATCGACGGCGTATTCTGTGCCG
MCR-2    TGGCTTGGCGAATTTTAGCCAAGTGACATCGTGTGGCACATCGACGGCGTATTCTGTGCCG
MCR-5    ---CGTGATCAATTTTTCCGATGTCACCAGTTGCGGGACGGATACGGCTACATCCCTTCCC
MCR-3    TGGCGTGATCTCCTTTAATGATGTTCGTTCGTGTGGGACTGCAACCGCTGTATCCGTCCCC
MCR-3.2  TGGCGTGATCTCCTTTAATGATGTTCGTTCGTGTGGGACTGCAACCGCTGTATCCGTCCCC
MCR-4    GGGC-TGATTGCGTTTAACGATACTAGCTCATGCGGCACGGCCACGGCGGTGTCTCTACCC
            * **      ***    *          ** ** **    ** **    **  * **
```

FIGURE 16 (continued)

```
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGCCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATCTGGGCGCGGATGAGTATGATGTCGATACCGCCAAATACCAAGA
          TGTATGTTCAGCTATTTGGGTCAAGATGACTATGATGTCGATACCGCCAAATACCAAGA
          TGCATGTTTTCCCTCAATGGTCGGCGCGACTACGACGAACGCCAGATTCGTCGGCGCGA
          TGCATGTTCTCCAATATGGGGAGAAAGGAGTTTGATGATAATCGCGCTCGCAATAGCGA
          TGCATGTTCTCCAATATGGGGAGAAAGGAGTTTGATGAAAATCGCGCTCGCAATAGCGA
          TGTATGTTTTCACGAATGGGGCGGGCAGACTATGATCCTCGCCGTGCTAATGCTCAAGA
          ** *****          **       **  *  **                      **
MCR-1.2   AAATGTGCTGGATACGCTGGATCGCTTGGGCGTAAGTATCTTGTGGCGTGATAATAATTCG
MCR-1.8   AAATGTGCTGGATACGCTGGATCGCTTGGGCGTAAGTATCTTGTGGCGTGATAATAATTCG
MCR-1     AAATGTGCTGGATACGCTGGATCGCTTGGGCGTAAGTATCTTGTGGCGTGATAATAATTCG
MCR-1.7   AAATGTGCTGGATACGCTGGATCGCTTGGGCGTAAGTATCTTGTGGCGTGATAATAATTCG
MCR-1.5   AAATGTGCTGGATACGCTGGATCGCTTGGGCGTAAGTATCTTGTGGCGTGATAATAATTCG
MCR-1.4   AAATGTGCTGGATACGCTGGATCGCTTGGGCGTAAGTATCTTGTGGCGTGATAATAATTCG
MCR-1.6   AAATGTGCTGGATACGCTGGATCGCTTGGGCGTAAGTATCTTGTGGCGTGATAATAATTCG
MCR-1.3   AAATGTGCTGGATACGCTGGATCGCTTGGGCGTAAGTATCTTGTGGCGTGATAATAATTCG
MCR-1.10  AAATGTGCTGGATACGCTGGATCGCTTGGGCGTAAGTATCTTGTGGCGTGATAATAATTCG
MCR-1.9   AAATGTGCTGGATACGCTGGATCGCTTGGGCGTAAGTATCTTGTGGCGTGATAATAATTCG
MCR-2.2   AAATGTGCTGGATACGCTGGATCGCTTGGGCGTAAGTATCTTGTGGCGTGATAATAATTCG
MCR-2     AAATGTGCTAGATACGCTTGACCGCTTGGGTGTGGGTATCTTGTGGCGTGATAATAATTCA
MCR-5     GTCCGTGCTGCACGTTTTAAACCGTAGTGACGTCAACATTCTCTGGCGCGATAACCAGTCG
MCR-3     GGGCCTGCTAGATGTGTTGCAAAAAACGGGGATCTCCATTTTTTGGAAGGAGAACGATGGA
MCR-3.2   GGGCCTGCTAGATGTGTTGCAAAAAACGGGGATCTCCATTTTTTGGAAGGAGAACGATGGA
MCR-4     CACAGTGATTGATGTGTTAAGTCATAGTGGTATAAAAGTACAGTGGTTTGATAATGATTCT
               ** *  *     *          *   *     *    ***    ** **  *
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTGCCAAAAGCGCAATTTGCCGATTATAAATCCGC
          GACTCAAAAGGCGTGATGGATAAGCTACCTGCCACGCAGTATTTTGATTATAAATCAGC
          GGCTGTAAAGGCGTCTGTGATGGACTGCC-------------CTTTGA----AAACCTGT
          GGCTGCAAAGGCGTCTGCGACCGAGTACCTAA----------CATCGA----AATC----
          GGCTGCAAAGGCGTCTGCGACCGAGTACCTAA----------CATCGA----AATC----
          GGCTGTAAAGGTGTGTGTGATCAGGTTGAAAA----------TCTCAC----GATA----
          * **  ***** **    **      *                           *
```

FIGURE 16 (continued)

```
MCR-1.2   GACCAACAACGCCATCTGCAACACCAATCCTTATAACGAATGCCGCGATGTCGGTATGCTC
MCR-1.8   GACCAACAACGCCATCTGCAACACCAATCCTTATAACGAATGCCGCGATGTCGGTATGCTC
MCR-1     GACCAACAACGCCATCTGCAACACCAATCCTTATAACGAATGCCGCGATGTCGGTATGCTC
MCR-1.7   GACCAACAACGCCATCTGCAACACCAATCCTTATAACGAATGCCGCGATGTCGGTATGCTC
MCR-1.5   GACCAACAACGCCATCTGCAACACCAATCCTTATAACGAATGCCGCGATGTCGGTATGCTC
MCR-1.4   GACCAACAACGCCATCTGCAACACCAATCCTTATAACGAATGCCGCGATGTCGGTATGCTC
MCR-1.6   GACCAACAACGCCATCTGCAACACCAATCCTTATAACGAATGCCGCGATGTCGGTATGCTC
MCR-1.3   GACCAACAACGCCATCTGCAACACCAATCCTTATAACGAATGCCGCGATGTCGGTATGCTC
MCR-1.10  GACCAACAACGCCATCTGCAACACCAATCCTTATAACGAATGCCGCGATGTCGGTATGCTC
MCR-1.9   GACCAACAACGCCATCTGCAACACCAATCCTTATAACGAATGCCGCGATGTCGGTATGCTC
MCR-2.2   GACCAACAACGCCATCTGCAACACCAATCCTTATAACGAATGCCGCGATGTCGGTATGCTC
MCR-2     AACCAACAATACCATCTGTAACACCAATCCCTATAACGAATGCCGTGATGTCGGTATGCTT
MCR-5     CTTCGGCAG-GCCATC---CCACACTGTGCC---ATGGCGAGCGCTGCCTGGATGAAATTCT-
MCR-3     GAACCAAAGGATCACCCTAAGTTCTGCGATA-AAAACACATGCTATGACGAGGTTGTCCTT
MCR-3.2   GAACCAAAGGATCACCCTAAGTTCTGCGATA-AAAACACATGCTATGACGAGGTTGTCCTT
MCR-4     GATTTGAAGAGTGATCCGAAGCTGTGTTCTG-GCCAATATTGTTTGACCAAGTATTGCTC
                 *     * *                         *          *   * **
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTTGGCTTAGATGACTTTGTCGCTGCCAATAA-CGGCAAAGATATGCTGATCATGCTGC
          GTCGGCTAGATGACTATGTCAGCGCCAATAA-TGGCAAAGATATGCTCATCATGCTAC
          GCTCGAAGGGTTGGCCGAGAAGATAACAACAAGCCGCAGCGATATGCTGATCGTTCTGC
          CAAGACCTCGATAG-TGAAATTGCTCAAATGAAAGG---GGATAAGCTGGTTGGCTTCC
          CAAGACCTCGATAG-TGAAATTGCTCAAATGAAAGG---GGATAAGCTGGTTGGCTTCC
          AACAAATTAGATAA-AATTCTGGCAGTAGCACCAAGTCAAGATACAGTAATTTTTTTGC
                   * *               *        *   ****    *  *     * *
MCR-1.2   ACCAAATGGGCAATCACGGGCCTGCGTATTTTAAGCGATATGATGAAAAGTTTGCCAAATTC
MCR-1.8   ACCAAATGGGCAATCACGGGCCTGCGTATTTTAAGCGATATGATGAAAAGTTTGCCAAATTC
MCR-1     ACCAAATGGGCAATCACGGGCCTGCGTATTTTAAGCGATATGATGAAAAGTTTGCCAAATTC
MCR-1.7   ACCAAATGGGCAATCACGGGCCTGCGTATTTTAAGCGATATGATGAAAAGTTTGCCAAATTC
MCR-1.5   ACCAAATGGGCAATCACGGGCCTGCGTATTTTAAGCGATATGATGAAAAGTTTGCCAAATTC
MCR-1.4   ACCAAATGGGCAATCACGGGCCTGCGTATTTTAAGCGATATGATGAAAAGTTTGCCAAATTC
MCR-1.6   ACCAAATGGGCAATCACGGGCCTGCGTATTTTAAGCGATATGATGAAAAGTTTGCCAAATTC
MCR-1.3   ACCAAATGGGCAATCACGGGCCTGCGTATTTTAAGCGATATGATGAAAAGTTTGCCAAATTC
MCR-1.10  ACCAAATGGGCAATCACGGGCCTGCGTATTTTAAGCGATATGATGAAAAGTTTGCCAAATTC
MCR-1.9   ACCAAATGGGCAATCACGGGCCTGCGTATTTTAAGCGATATGATGAAAAGTTTGCCAAATTC
MCR-2.2   ACCAAATGGGCAATCACGGGCCTGCGTATTTTAAGCGATATGATGAAAAGTTTGCCAAATTC
MCR-2     ACCAAATGGGCAATCATGGGCCGGCGTACTTTAAGCGTTATGATGAGCAATTTGCCAAATTC
MCR-5     ATATGCTGGGCAATCACGGCCCAGCGTATTTCCAGCGCTATCCCGCAAGCTACCGACGCTGG
MCR-3     ACCTGATAGGTAGCCATGGCCCAACCTACTACAAGCGCTACCCTGATGCTCATCGTCAGTTC
MCR-3.2   ACCTGATAGGTAGCCATGGCCCAACCTACTACAAGCGCTACCCTGATGCTCATCGTCAGTTC
MCR-4     ATATCATTGGTAGTCATGGACCAACTTATTATCTTAGATACCCGCCAGAGCATCGTAAATTT
          *     * ** *  ** ** ** * ** *      * **                  *
```

FIGURE 16 (continued)

```
            ACGCCAGTGTGTGAAGGTAATGAGCTTGCCAAGTGCGAACATCAGTCCTTGATCAATG
            ACGCCAGTGTGTGAAGGTAATGAGCTTGCCAAGTGCGAACATCAGTCCTTGATCAATG
            ACGCCAGTGTGTGAAGGTAATGAGCTTGCCAAGTGCGAACATCAGTCCTTGATCAATG
            ACGCCAGTGTGTGAAGGTAATGAGCTTGCCAAGTGCGAACATCAGTCCTTGATCAATG
            ACGCCAGTGTGTGAAGGTAATGAGCTTGCCAAGTGCGAACATCAGTCCTTGATCAATG
            ACGCCAGTGTGTGAAGGTAATGAGCTTGCCAAGTGCGAACATCAGTCCTTGATCAATG
            ACGCCAGTGTGTGAAGGTAATGAGCTTGCCAAATGCGAACATCAGTCCTTGATCAATG
            ACGCCAGTGTGTGAAGGTAATGAGCTTGCCAAGTGCGAACATCAGTCCTTGATCAATG
            ACGCCAGCGTGTGAAGGTAATGAGCTTGCCAAGTGCGAACATCAGTCCTTGATCAATG
            ACGCCAGCGTGTGAAGGTAATGAGCTTGCCAAGTGCGAACATCAGTCCTTGATCAATG
            ACGCCAGCGTGTGAAGGTAATGAGCTTGCCAAGTGCGAACATCAGTCCTTGATCAATG
            ACCCCCGTGTGCGAAGGCAACGAGCTTGCCAAATGCGAACACCAATCACTCATCAATG
            TCGCCAACCTGCGACACCACCGATCTGGCCAGCTGTTCGCATGAAGCCTTGGTGAACA
            ACCCCTGACTGTCCACGCAGTGATATTGAAAACTGCACAGATGAAGAGCTCACCAACA
            ACCCCTGACTGTCCACGCAGTGATATTGAAAACTGCACAGATGAAGAGCTCACCAACA
            ATACCGGATTGTCCGCGCAGTGATATTCAAAATTGCAGTCAAGAAGAACTGATTAACA
               **     **       *  **  *    *  **      *  *     *    **
MCR-1.2     CTTATGACAATGCCTTGCTTGCCACCGATGATTTCATCGCTCAAAGTATCCAGTGGCTGCAG
MCR-1.8     CTTATGACAATGCCTTGCTTGCCACCGATGATTTCATCGCTCAAAGTATCCAGTGGCTGCAG
MCR-1       CTTATGACAATGCCTTGCTTGCCACCGATGATTTCATCGCTCAAAGTATCCAGTGGCTGCAG
MCR-1.7     CTTATGACAATGCCTTGCTTGCCACCGATGATTTCATCGCTCAAAGTATCCAGTGGCTGCAG
MCR-1.5     CTTATGACAATGCCTTGCTTGCCACCGATGATTTCATCGCTCAAAGTATCCAGTGGCTGCAG
MCR-1.4     CTTATGACAATGCCTTGCTTGCCACCGATAATTTCATCGCTCAAAGTATCCAGTGGCTGCAG
MCR-1.6     CTTATGACAATGCCTTGCTTGCCACCGATGATTTCATCGCTCAAAGTATCCAGTGGCTGCAG
MCR-1.3     CTTATGACAATGCCTTGCTTGCCACCGATGATTTCATCGCTCAAAGTATCCAGTGGCTGCAG
MCR-1.10    CTTATGACAATGCCTTGCTTGCCACCGATGATTTCATCGCTCAAAGTATCCAGTGGCTGCAG
MCR-1.9     CTTATGACAATGCCTTGCTTGCCACCGATGATTTCATCGCTCAAAGTATCCAGTGGCTGCAG
MCR-2.2     CTTATGACAATGCCTTGCTTGCCACCGATGATTTCATCGCTCAAAGTATCCAGTGGCTGCAG
MCR-2       CCTATGACAATGCGCTACTTGCGACTGATGATTTTATCGCCAAAAGCATCGATTGGCTAAAA
MCR-5       CCTACGACAACGCCGTGCTTTACACCGATCATGTGCTTGCCCGTACCATTGACCTGCTGT--
MCR-3       CCTATGACAACACCATCCGCTACACCGATTTCGTGATTGGAGAGATGATTGCCAAGTTGAAA
MCR-3.2     CCTATGACAACACCATCCGCTACACCGATTTCGTGATTGGAGAGATGATTGCCAAGTTGAAA
MCR-4       CCTACGACAACACTATTCTATATACGGATTTTATTCTCAGTGAAGTGGTGAATAAATTAAAA
            * ** *****  *  * *     ** ***    *  *            *        *
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGTACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCACAGCAATGCCTATGATGTCTCAATGCTGTATGTCAGCGATCATGGCGAAAGTC
            ACGCATGAAGCGAACTACGATGTCGCCATGCTCTATGTCAGTGACCACGGCGAGAGCT
            -CCGGCATCCGCTCACACGACACGGCGCTGCTGTACGTTTCCGATCATGGGGAATCGC
            ACCTACGAAGATAAGTACAACACCGCGTTGCTCTACGTCTCCGATCATGGTGAATCAC
            ACCTACGAAGATAAGTACAACACCGCGTTGCTCTACGTCTCCGATCATGGTGAATCAC
            GGTAAGCAGGATATGTTCGATACTGCAATGCTGTATCTCTCTGACCATGGTGAGTCTT
                                *     *  **** **  *    ** ** ** **
```

FIGURE 16 (continued)

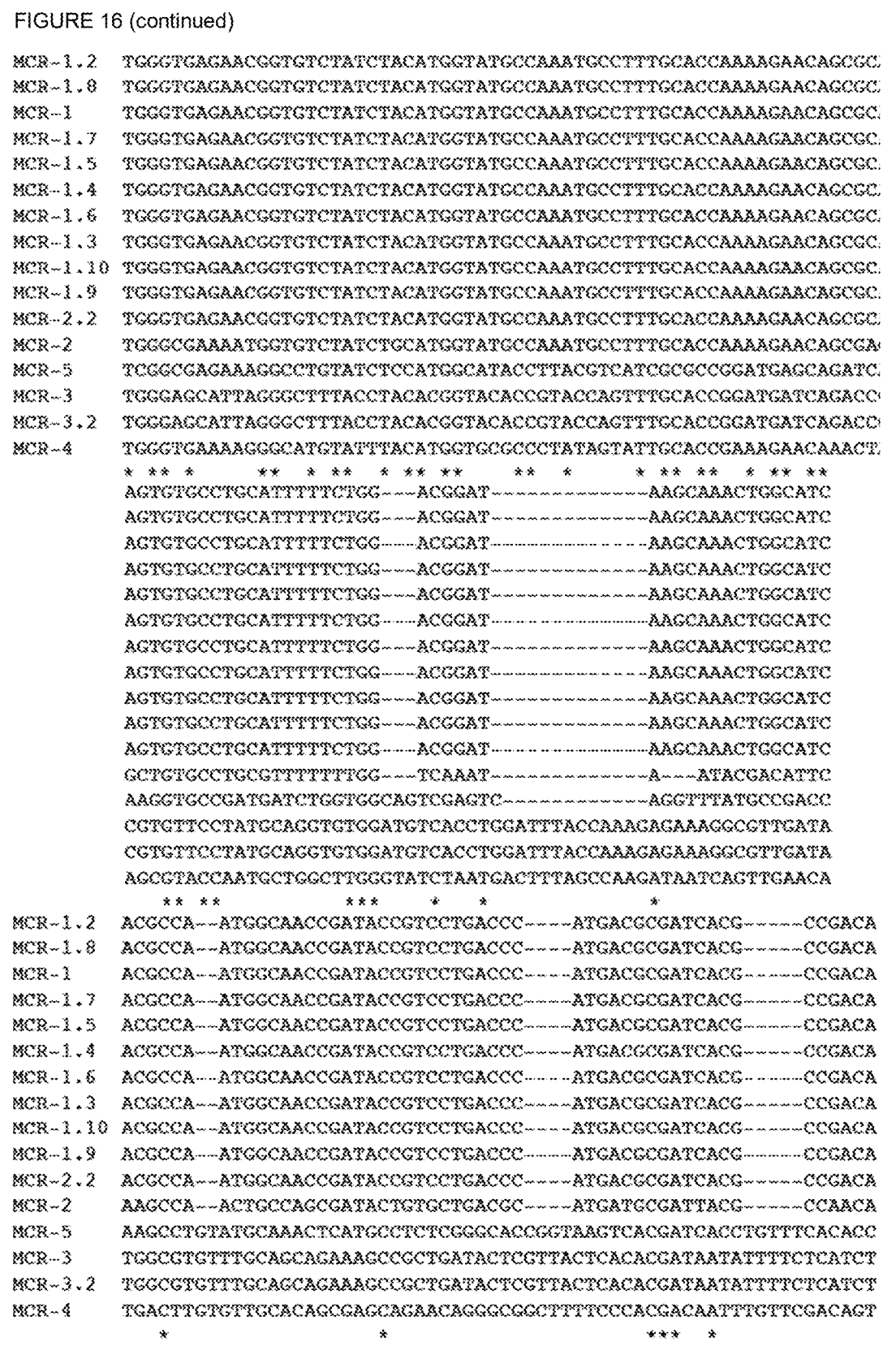

```
MCR-1.2   TGGGTGAGAACGGTGTCTATCTACATGGTATGCCAAATGCCTTTGCACCAAAAGAACAGCGC
MCR-1.8   TGGGTGAGAACGGTGTCTATCTACATGGTATGCCAAATGCCTTTGCACCAAAAGAACAGCGC
MCR-1     TGGGTGAGAACGGTGTCTATCTACATGGTATGCCAAATGCCTTTGCACCAAAAGAACAGCGC
MCR-1.7   TGGGTGAGAACGGTGTCTATCTACATGGTATGCCAAATGCCTTTGCACCAAAAGAACAGCGC
MCR-1.5   TGGGTGAGAACGGTGTCTATCTACATGGTATGCCAAATGCCTTTGCACCAAAAGAACAGCGC
MCR-1.4   TGGGTGAGAACGGTGTCTATCTACATGGTATGCCAAATGCCTTTGCACCAAAAGAACAGCGC
MCR-1.6   TGGGTGAGAACGGTGTCTATCTACATGGTATGCCAAATGCCTTTGCACCAAAAGAACAGCGC
MCR-1.3   TGGGTGAGAACGGTGTCTATCTACATGGTATGCCAAATGCCTTTGCACCAAAAGAACAGCGC
MCR-1.10  TGGGTGAGAACGGTGTCTATCTACATGGTATGCCAAATGCCTTTGCACCAAAAGAACAGCGC
MCR-1.9   TGGGTGAGAACGGTGTCTATCTACATGGTATGCCAAATGCCTTTGCACCAAAAGAACAGCGC
MCR-2.2   TGGGTGAGAACGGTGTCTATCTACATGGTATGCCAAATGCCTTTGCACCAAAAGAACAGCGC
MCR-2     TGGGCGAAAATGGTGTCTATCTGCATGGTATGCCAAATGCCTTTGCACCAAAAGAACAGCGA
MCR-5     TCGGCGAGAAAGGCCTGTATCTCCATGGCATACCTTACGTCATCGCGCCGGATGAGCAGATC
MCR-3     TGGGAGCATTAGGGCTTTACCTACACGGTACACCGTACCAGTTTGCACCGGATGATCAGACC
MCR-3.2   TGGGAGCATTAGGGCTTTACCTACACGGTACACCGTACCAGTTTGCACCGGATGATCAGACC
MCR-4     TGGGTGAAAAGGGCATGTATTTACATGGTGCGCCCTATAGTATTGCACCGAAAGAACAAACT
          * ** *      **  * **  * ** **     **  *     * ** **  * ** **
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          AGTGTGCCTGCATTTTTCTGG---ACGGAT-------------AAGCAAACTGGCATC
          GCTGTGCCTGCGTTTTTTTGG---TCAAAT-------------A---ATACGACATTC
          AAGGTGCCGATGATCTGGTGGCAGTCGAGTC------------AGGTTTATGCCGACC
          CGTGTTCCTATGCAGGTGTGGATGTCACCTGGATTTACCAAAGAGAAAGGCGTTGATA
          CGTGTTCCTATGCAGGTGTGGATGTCACCTGGATTTACCAAAGAGAAAGGCGTTGATA
          AGCGTACCAATGCTGGCTTGGGTATCTAATGACTTTAGCCAAGATAATCAGTTGAACA
             ** **          ***    *    *               *
MCR-1.2   ACGCCA--ATGGCAACCGATACCGTCCTGACCC----ATGACGCGATCACG-----CCGACA
MCR-1.8   ACGCCA--ATGGCAACCGATACCGTCCTGACCC----ATGACGCGATCACG-----CCGACA
MCR-1     ACGCCA--ATGGCAACCGATACCGTCCTGACCC----ATGACGCGATCACG-----CCGACA
MCR-1.7   ACGCCA--ATGGCAACCGATACCGTCCTGACCC----ATGACGCGATCACG-----CCGACA
MCR-1.5   ACGCCA--ATGGCAACCGATACCGTCCTGACCC----ATGACGCGATCACG-----CCGACA
MCR-1.4   ACGCCA--ATGGCAACCGATACCGTCCTGACCC----ATGACGCGATCACG-----CCGACA
MCR-1.6   ACGCCA--ATGGCAACCGATACCGTCCTGACCC----ATGACGCGATCACG-----CCGACA
MCR-1.3   ACGCCA--ATGGCAACCGATACCGTCCTGACCC----ATGACGCGATCACG-----CCGACA
MCR-1.10  ACGCCA--ATGGCAACCGATACCGTCCTGACCC----ATGACGCGATCACG-----CCGACA
MCR-1.9   ACGCCA--ATGGCAACCGATACCGTCCTGACCC----ATGACGCGATCACG-----CCGACA
MCR-2.2   ACGCCA--ATGGCAACCGATACCGTCCTGACCC----ATGACGCGATCACG-----CCGACA
MCR-2     AAGCCA--ACTGCCAGCGATACTGTGCTGACGC----ATGATGCGATTACG-----CCAACA
MCR-5     AAGCCTGTATGCAAACTCATGCCTCTCGGGCACCGGTAAGTCACGATCACCTGTTTCACACC
MCR-3     TGGCGTGTTTGCAGCAGAAAGCCGCTGATACTCGTTACTCACACGATAATATTTTCTCATCT
MCR-3.2   TGGCGTGTTTGCAGCAGAAAGCCGCTGATACTCGTTACTCACACGATAATATTTTCTCATCT
MCR-4     TGACTTGTGTTGCACAGCGAGCAGAACAGGGCGGCTTTTCCCACGACAATTTGTTCGACAGT
             *                   *                     ***   *
```

FIGURE 16 (continued)

```
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCACACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         TTATTAAAGCTGTTTGATGTCA---CCGCGGACAAA--GTCAAAG----ACCGCACCG
         CTGCTTAAGCTGTTTGATGTCA---CAGCGGGCAAG--GTCAAAG----ACCGCGCGG
         TTGCTCGGATGTTCGACGTGAAAACCGCTGCCTACACGCCAGAGTTGGACCTTCTGG
         GTATTGGGTATCTGGGACGTCAAAACATCAGTTTACGAAAAGGGTCTAGATATTTTCA
         GTATTGGGTATCTGGGACGTCAAAACATCAGTTTACGAAAAGGGTCTAGATATTTTCA
         TTGCTAGGACTTATGAATGTAAAAACCACCGTCTATCAGAGCCAACTCGATATTTTTG
          *  *     *     * ** *   *  * *   *              *
MCR-1.2  CATTCATCCGCTGA----------------
MCR-1.8  CATTCATCCGCTGA----------------
MCR-1    CATTCATCCGCTGA----------------
MCR-1.7  CATTCATCCGCTGA----------------
MCR-1.5  CATTCATCCGCTGA----------------
MCR-1.4  CATTCATCCGCTGA----------------
MCR-1.6  CATTCATCCGCTGA----------------
MCR-1.3  CATTCATCCGCTGA----------------
MCR-1.10 CATTCATCCGCTGA----------------
MCR-1.9  CATTCATCCGCTGA----------------
MCR-2.2  CATTCATCCGCTGA----------------
MCR-2    CATTTATCCAGTAA----------------
MCR-5    CAA-CATGCAGAAAAGGACAACCACAATGA
MCR-3    GTC-AATGTCGTAATGTTCAATAA-------
MCR-3.2  GTC-AATGTCGTAATGTTCAATAA-------
MCR-4    CAC-CTTGCAG--GTATTAG----------
              *
```

| Strain[a] | Polymyxin resistance | | | Acquired resistance to β-lactams[c] | [d]PRR$_{E. coli}$ |
|---|---|---|---|---|---|
| | Colistin MIC (mg/L) | Chromosome / Plasmid | Mechanism[b] | | |
| CNR 111J7 | 6 | Chromosome | PmrB mutations (D14N, S71C and V83A) | CTX-M-15 + TEM-1 | 0·25 ± 0·08 |
| CNR20160039 | 4 | Chromosome | Unknown | None | 0·38 ± 0·02 |
| CNR20160235 | 8 | Chromosome | MgrB mutation (V8A) | TEM-1 | 0·19 ± 0·05 |
| CNR 1728 | 8 | Chromosome | PmrB mutation (G160E) | None | 0·30 ± 0·08 |
| 41489 | 4 | Plasmid | MCR-1 | None | 0·92 ± 0·29 |
| J53 + *mcr-1*[*] | 8 | Plasmid | MCR-1 | None | 2·43 ± 1·10 |
| CNR20140385 | 4 | Plasmid | MCR-1 | **OXA-48** | 1·88 ± 0·28 |
| S08-056 | 4 | Plasmid | MCR-1 | **OXA-48** | 3·70 ± 0·40 |
| CNR 117G7 | 4 | Plasmid | MCR-1 | **NDM-1** | 2·28 ± 0·59 |
| CNR 121G9 | 4 | Plasmid | MCR-1 | **OXA-48** | 0·71 ± 0·04 |
| CNR 1745 | 4 | Plasmid | MCR-1 | SHV-12 | 2·08 ± 0·24 |
| CNR 1604 | 4 | Plasmid | MCR-1 | CTX-M-15 | 3·48 ± 0·25 |
| CNR 1667 | 4 | Plasmid | MCR-1 | **OXA-48** + KPC-28 | 1·67 ± 0·80 |
| CNR 1790 | 4 | Plasmid | MCR-1 | TEM-15 | 2·69 ± 0·63 |
| CNR 1859 | 4 | Plasmid | MCR-1 | CTX-M-15 + SHV-12 + TEM-1 | 2·86 ± 0·37 |
| CNR 1886 | 4 | Plasmid | MCR-1 | CTX-M-1 + TEM-1 | 2·61 ± 0·30 |
| 4222 | 4 | Plasmid | MCR-1 | CTX-M-2 | 4·32 ± 0·51 |
| 4070 | 4 | Plasmid | MCR-1 | TEM-1B | 1·65 ± 0·28 |
| 979 | 4 | Plasmid | MCR-1 | CTX-M-2 | 1·21 ± 0·14 |
| 1724 | 4 | Plasmid | MCR-1 | None | 2·07 ± 0·37 |
| DH5α + pDM1-*mcr-1*[**] | 4 | Plasmid | MCR-1 | None | 2·82 ± 0·92 |

FIGURE 18

| | | | | | |
|---|---|---|---|---|---|
| MC1000 + pDM1- *mcr-1*** | 4 | Plasmid | MCR-1 | None | 3·13 ± 0·33 |
| 6383 | 4 | Plasmid | MCR-1.5 | TEM-1B | 2·85 ± 0·76 |
| 1670 | 4 | Plasmid | MCR-1.5 | CTX-M-2 | 0·92 ± 0·18 |
| [e]R12 F5 | 4 | Plasmid | MCR-2 | None | 3·13 ± 1·05 |
| DH5α + pDM1- *mcr-2*** | 4 | Plasmid | MCR-2 | None | 2·24 ± 0·51 |
| MC1000 + pDM1- *mcr-2*** | 4 | Plasmid | MCR-2 | None | 1·80 ± 0·35 |
| DH5α + pDM1- *mcr-3*** | 4 | Plasmid | MCR-3 | None | 2·62 ± 0·47 |
| MC1000 + pDM1- *mcr-3*** | 4 | Plasmid | MCR-3 | None | 2·80 ± 0·15 |
| DH5α + pDM1- *mcr-5*** | 4 | Plasmid | MCR-5 | None | 2·14 ± 0·04 |
| MC1000 + pDM1- *mcr-5** | 4 | Plasmid | MCR-5 | None | 3·12 ± 0·57 |
| TOP 10 + *mcr-5** | 8 | Plasmid | MCR-5 | None | 1·59 ± 0·29 |
| J53 + *mcr-5** | 8 | Plasmid | MCR-5 | None | 1·54 ± 0·36 |
| J53 | 0·5 | - | - | None | 0·00 ± 0·00 |
| TOP 10 | 0·25 | - | - | None | 0·00 ± 0·00 |
| DH5α | 0·5 | - | - | None | 0·00 ± 0·00 |
| DH5α + pDM1-Empty | 0·5 | - | - | None | 0·00 ± 0·00 |
| MC1000 + pDM1-Empty | 0·5 | - | - | None | 0·00 ± 0·00 |
| 1608071881 | 0·25 | - | - | None | 0·00 ± 0·00 |
| 1608072264 | 0·25 | - | - | None | 0·00 ± 0·00 |
| 1608073740 | 0·25 | - | - | None | 0·00 ± 0·00 |

FIGURE 18 (continued)

| | | | | | |
|---|---|---|---|---|---|
| 1608070579 | 0·5 | - | - | None | 0·00 ± 0·00 |
| 1608073561 | 0·25 | - | - | None | 0·00 ± 0·00 |
| 1608073733 | 0·5 | - | - | None | 0·00 ± 0·00 |
| 1608073937 | 0·25 | - | - | None | 0·00 ± 0·00 |
| 1608079010 | 0·25 | - | - | None | 0·00 ± 0·00 |
| 1608079029 | 0·25 | - | - | None | 0·00 ± 0·00 |
| 1608079018 | 0·25 | - | - | None | 0·00 ± 0·00 |
| 1608075385 | 0·12 | - | - | TEM-1 | 0·00 ± 0·00 |
| 1608078198 | 0·25 | - | - | TEM-1 | 0·00 ± 0·00 |
| 1608073301 | 0·25 | - | - | TEM-1 | 0·00 ± 0·00 |
| 1608078105 | 0·25 | - | - | TEM-1 | 0·00 ± 0·00 |
| 1608073228 | 0·25 | - | - | TEM-1 | 0·00 ± 0·00 |
| 1608078635 | 0·25 | - | - | TEM-1 | 0·00 ± 0·00 |
| 1608078858 | 0·25 | - | - | TEM-1 | 0·00 ± 0·00 |
| 1608062671 | 0·25 | - | - | TEM-1 | 0·00 ± 0·00 |
| 1608064819 | 0·25 | - | - | TEM-1 | 0·00 ± 0·00 |
| 1608062559 | 0·12 | - | - | TEM-1 | 0·00 ± 0·00 |
| 2E6 | 0·25 | - | - | CTX-M-1 | 0·00 ± 0·00 |
| 2E7 | 0·25 | - | - | CTX-M-3 | 0·00 ± 0·00 |
| 2E9 | 0·25 | - | - | CTX-M-14 | 0·00 ± 0·00 |
| 2E10 | 0·25 | - | - | CTX-M-14 | 0·00 ± 0·00 |
| 2H6 | 0·25 | - | - | CTX-M-15 | 0·00 ± 0·00 |
| 2F2 | 0·25 | - | - | CTX-M-15 | 0·00 ± 0·00 |
| 2F3 | 0·25 | - | - | CTX-M-15 | 0·00 ± 0·00 |
| LAN 10.48 | 0·25 | - | - | SHV-2a | 0·00 ± 0·00 |
| LEC 11.8 | 0·5 | - | - | SHV-12 | 0·00 ± 0·00 |
| VER 9.39 | 0·25 | - | - | TEM-3 | 0·00 ± 0·00 |
| NEG 11.87 | 0·25 | - | - | TEM-24 | 0·00 ± 0·00 |
| 1F1 | 0·25 | - | - | **KPC-2** | 0·00 ± 0·00 |
| 1A2 | 0·5 | - | - | **NDM-1** + OXA-1 + TEM-1 | 0·00 ± 0·00 |

FIGURE 18 (continued)

| | | | | | |
|---|---|---|---|---|---|
| 1A6 | 0·25 | - | - | **NDM-4** + CTX-M-15 + OXA-1 | 0·00 ± 0·00 |
| 1A8 | 0·25 | - | - | **NDM-5** + CTX-M-15 + TEM-1 | 0·00 ± 0·00 |
| 1C2 | 0·5 | - | - | **VIM-1** | 0·00 ± 0·00 |
| 1D10 | 0·25 | - | - | **IMP-8** + SHV-12 | 0·00 ± 0·00 |
| 2A1 | 0·25 | - | - | **OXA-48** + CTX-M-15 | 0·00 ± 0·00 |
| 2C4 | 0·5 | - | - | **OXA-181** | 0·00 ± 0·00 |
| 2D5 | 0·25 | - | - | **OXA-204** + CMY-4 + CTX-M-15 | 0·00 ± 0·00 |
| 2D9 | 0·25 | - | - | **OXA-244** | 0·00 ± 0·00 |

FIGURE 18 (continued)

| Strain[a] | Polymyxin resistance | | | $PRR_{E. coli}$ for bacterial colonies aged of : | | | |
|---|---|---|---|---|---|---|---|
| | Colistin MIC (mg/L) | Chromosome / Plasmid | Mechanism[b] | 24h | 48h | 1 week | 2 weeks |
| CNR 111J7 | 6 | Chromosome | PmrB mutations (D14N, S71C and V83A) | 0·25 ± 0·08 | 0·20 ± 0·06 | 0·22 ± 0·05 | 0·25 ± 0·10 |
| CNR20160039 | 4 | Chromosome | Unknown | 0·38 ± 0·02 | 0·36 ± 0·05 | 0·32 ± 0·04 | 0·30 ± 0·08 |
| CNR20160235 | 8 | Chromosome | MgrB mutation (V8A) | 0·19 ± 0·05 | 0·22 ± 0·06 | 0·18 ± 0·03 | 0·24 ± 0·09 |
| CNR 1728 | 8 | Chromosome | PmrB mutation (G160E) | 0·30 ± 0·08 | 0·27 ± 0·04 | 0·28 ± 0·06 | 0·32 ± 0·09 |
| 41489 | 4 | Plasmid | MCR-1 | 0·92 ± 0·29 | 0·89 ± 0·12 | 0·81 ± 0·13 | 0·83 ± 0·19 |
| J53 + *mcr-1*[*] | 8 | Plasmid | MCR-1 | 2·43 ± 1·10 | 1·61 ± 0·90 | 1·89 ± 0·83 | 2·06 ± 0·52 |
| CNR20140385 | 4 | Plasmid | MCR-1 | 1·88 ± 0·28 | 1·72 ± 0·15 | 1·68 ± 0·32 | 1·55 ± 0·22 |
| S08-056 | 4 | Plasmid | MCR-1 | 3·70 ± 0·40 | 3·10 ± 0·52 | 3·01 ± 0·38 | 2·92 ± 0·61 |
| CNR 117G7 | 4 | Plasmid | MCR-1 | 2·28 ± 0·59 | 2·32 ± 0·32 | 2·23 ± 0·41 | 2·08 ± 0·14 |
| CNR 121G9 | 4 | Plasmid | MCR-1 | 0·71 ± 0·04 | 0·73 ± 0·12 | 0·81 ± 0·10 | 0·64 ± 0·08 |
| CNR 1745 | 4 | Plasmid | MCR-1 | 2·08 ± 0·24 | 1·92 ± 0·29 | 1·98 ± 0·27 | 1·87 ± 0·33 |
| CNR 1604 | 4 | Plasmid | MCR-1 | 3·48 ± 0·25 | 3·00 ± 0·52 | 3·17 ± 0·37 | 2·88 ± 0·90 |
| CNR 1667 | 4 | Plasmid | MCR-1 | 1·67 ± 0·80 | 1·28 ± 0·42 | 1·46 ± 0·63 | 1·32 ± 0·86 |
| CNR 1790 | 4 | Plasmid | MCR-1 | 2·69 ± 0·63 | 2·04 ± 0·47 | 2·13 ± 0·74 | 1·99 ± 0·58 |
| CNR 1859 | 4 | Plasmid | MCR-1 | 2·86 ± 0·37 | 2·73 ± 0·41 | 2·54 ± 0·23 | 2·06 ± 1·02 |
| CNR 1886 | 4 | Plasmid | MCR-1 | 2·61 ± 0·30 | 2·32 ± 0·48 | 2·31 ± 0·25 | 2·01 ± 0·67 |
| 4222 | 4 | Plasmid | MCR-1 | 4·32 ± 0·51 | 4·17 ± 0·63 | 3·99 ± 0·47 | 3·71 ± 0·39 |
| 4070 | 4 | Plasmid | MCR-1 | 1·65 ± 0·28 | 1·55 ± 0·31 | 1·54 ± 0·24 | 1·42 ± 0·38 |
| 979 | 4 | Plasmid | MCR-1 | 1·21 ± 0·14 | 1·25 ± 0·23 | 1·05 ± 0·18 | 1·09 ± 0·36 |
| 1724 | 4 | Plasmid | MCR-1 | 2·07 ± 0·37 | 2·00 ± 0·41 | 1·92 ± 0·32 | 1·85 ± 0·33 |

FIGURE 19

| | | | | | | | |
|---|---|---|---|---|---|---|---|
| 6383 | 4 | Plasmid | MCR-1.5 | 2·85 ± 0·76 | 2·66 ± 0·63 | 2·65 ± 0·48 | 2·21 ± 0·77 |
| 1670 | 4 | Plasmid | MCR-1.5 | 0·92 ± 0·18 | 1·06 ± 0·38 | 0·91 ± 0·15 | 0·99 ± 0·30 |
| R12 F5 | 4 | Plasmid | MCR-2 | 3·13 ± 1·05 | 2·23 ± 0·55 | 2·79 ± 0·89 | 2·13 ± 1·17 |
| <u>J53</u> | 0·5 | - | - | 0·00 ± 0·00 | 0·00 ± 0·00 | 0·00 ± 0·00 | 0·00 ± 0·00 |
| <u>TOP 10</u> | 0·25 | - | - | 0·00 ± 0·00 | 0·00 ± 0·00 | 0·00 ± 0·00 | 0·00 ± 0·00 |
| <u>DH5α</u> | 0·5 | - | - | 0·00 ± 0·00 | 0·00 ± 0·00 | 0·00 ± 0·00 | 0·00 ± 0·00 |
| 1608071881 | 0·25 | - | - | 0·00 ± 0·00 | 0·00 ± 0·00 | 0·00 ± 0·00 | 0·00 ± 0·00 |
| 1608072264 | 0·25 | - | - | 0·00 ± 0·00 | 0·00 ± 0·00 | 0·00 ± 0·00 | 0·00 ± 0·00 |
| 1608073740 | 0·25 | - | - | 0·00 ± 0·00 | 0·00 ± 0·00 | 0·00 ± 0·00 | 0·00 ± 0·00 |
| 1608070579 | 0·5 | - | - | 0·00 ± 0·00 | 0·00 ± 0·00 | 0·00 ± 0·00 | 0·00 ± 0·00 |
| 1608073561 | 0·25 | - | - | 0·00 ± 0·00 | 0·00 ± 0·00 | 0·00 ± 0·00 | 0·00 ± 0·00 |
| 1608073733 | 0·5 | - | - | 0·00 ± 0·00 | 0·00 ± 0·00 | 0·00 ± 0·00 | 0·00 ± 0·00 |
| 1608073937 | 0·25 | - | - | 0·00 ± 0·00 | 0·00 ± 0·00 | 0·00 ± 0·00 | 0·00 ± 0·00 |
| 1608079010 | 0·25 | - | - | 0·00 ± 0·00 | 0·00 ± 0·00 | 0·00 ± 0·00 | 0·00 ± 0·00 |
| 1608079029 | 0·25 | - | - | 0·00 ± 0·00 | 0·00 ± 0·00 | 0·00 ± 0·00 | 0·00 ± 0·00 |
| 1608079018 | 0·25 | - | - | 0·00 ± 0·00 | 0·00 ± 0·00 | 0·00 ± 0·00 | 0·00 ± 0·00 |
| 1608075385 | 0·12 | - | - | 0·00 ± 0·00 | 0·00 ± 0·00 | 0·00 ± 0·00 | 0·00 ± 0·00 |
| 1608078198 | 0·25 | - | - | 0·00 ± 0·00 | 0·00 ± 0·00 | 0·00 ± 0·00 | 0·00 ± 0·00 |
| 1608073301 | 0·25 | - | - | 0·00 ± 0·00 | 0·00 ± 0·00 | 0·00 ± 0·00 | 0·00 ± 0·00 |
| 1608078105 | 0·25 | - | - | 0·00 ± 0·00 | 0·00 ± 0·00 | 0·00 ± 0·00 | 0·00 ± 0·00 |
| 1608073228 | 0·25 | - | - | 0·00 ± 0·00 | 0·00 ± 0·00 | 0·00 ± 0·00 | 0·00 ± 0·00 |
| 1608078635 | 0·25 | - | - | 0·00 ± 0·00 | 0·00 ± 0·00 | 0·00 ± 0·00 | 0·00 ± 0·00 |
| 1608078858 | 0·25 | - | - | 0·00 ± 0·00 | 0·00 ± 0·00 | 0·00 ± 0·00 | 0·00 ± 0·00 |
| 1608062671 | 0·25 | - | - | 0·00 ± 0·00 | 0·00 ± 0·00 | 0·00 ± 0·00 | 0·00 ± 0·00 |
| 1608064819 | 0·25 | - | - | 0·00 ± 0·00 | 0·00 ± 0·00 | 0·00 ± 0·00 | 0·00 ± 0·00 |

FIGURE 19 (continued)

| | | | | | | | |
|---|---|---|---|---|---|---|---|
| 1608062559 | 0·12 | - | - | 0·00 ± 0·00 | 0·00 ± 0·00 | 0·00 ± 0·00 | 0·00 ± 0·00 |
| 2E6 | 0·25 | - | - | 0·00 ± 0·00 | 0·00 ± 0·00 | 0·00 ± 0·00 | 0·00 ± 0·00 |
| 2E7 | 0·25 | - | - | 0·00 ± 0·00 | 0·00 ± 0·00 | 0·00 ± 0·00 | 0·00 ± 0·00 |
| 2E9 | 0·25 | - | - | 0·00 ± 0·00 | 0·00 ± 0·00 | 0·00 ± 0·00 | 0·00 ± 0·00 |
| 2E10 | 0·25 | - | - | 0·00 ± 0·00 | 0·00 ± 0·00 | 0·00 ± 0·00 | 0·00 ± 0·00 |
| 2H6 | 0·25 | - | - | 0·00 ± 0·00 | 0·00 ± 0·00 | 0·00 ± 0·00 | 0·00 ± 0·00 |
| 2F2 | 0·25 | - | - | 0·00 ± 0·00 | 0·00 ± 0·00 | 0·00 ± 0·00 | 0·00 ± 0·00 |
| 2F3 | 0·25 | - | - | 0·00 ± 0·00 | 0·00 ± 0·00 | 0·00 ± 0·00 | 0·00 ± 0·00 |
| LAN 10.48 | 0·25 | - | - | 0·00 ± 0·00 | 0·00 ± 0·00 | 0·00 ± 0·00 | 0·00 ± 0·00 |
| LEC 11.8 | 0·5 | - | - | 0·00 ± 0·00 | 0·00 ± 0·00 | 0·00 ± 0·00 | 0·00 ± 0·00 |
| VER 9.39 | 0·25 | - | - | 0·00 ± 0·00 | 0·00 ± 0·00 | 0·00 ± 0·00 | 0·00 ± 0·00 |
| NEG 11.87 | 0·25 | - | - | 0·00 ± 0·00 | 0·00 ± 0·00 | 0·00 ± 0·00 | 0·00 ± 0·00 |
| 1F1 | 0·25 | - | - | 0·00 ± 0·00 | 0·00 ± 0·00 | 0·00 ± 0·00 | 0·00 ± 0·00 |
| 1A2 | 0·5 | - | - | 0·00 ± 0·00 | 0·00 ± 0·00 | 0·00 ± 0·00 | 0·00 ± 0·00 |
| 1A6 | 0·25 | - | - | 0·00 ± 0·00 | 0·00 ± 0·00 | 0·00 ± 0·00 | 0·00 ± 0·00 |
| 1A8 | 0·25 | - | - | 0·00 ± 0·00 | 0·00 ± 0·00 | 0·00 ± 0·00 | 0·00 ± 0·00 |
| 1C2 | 0·5 | - | - | 0·00 ± 0·00 | 0·00 ± 0·00 | 0·00 ± 0·00 | 0·00 ± 0·00 |
| 1D10 | 0·25 | - | - | 0·00 ± 0·00 | 0·00 ± 0·00 | 0·00 ± 0·00 | 0·00 ± 0·00 |
| 2A1 | 0·25 | - | - | 0·00 ± 0·00 | 0·00 ± 0·00 | 0·00 ± 0·00 | 0·00 ± 0·00 |
| 2C4 | 0·5 | - | - | 0·00 ± 0·00 | 0·00 ± 0·00 | 0·00 ± 0·00 | 0·00 ± 0·00 |
| 2D5 | 0·25 | - | - | 0·00 ± 0·00 | 0·00 ± 0·00 | 0·00 ± 0·00 | 0·00 ± 0·00 |
| 2D9 | 0·25 | - | - | 0·00 ± 0·00 | 0·00 ± 0·00 | 0·00 ± 0·00 | 0·00 ± 0·00 |

FIGURE 19 (continued)

SEQUENCE LISTING

<160> NUMBER OF SEQ ID NOS: 16

<210> SEQ ID NO 1
<211> LENGTH: 1626
<212> TYPE: DNA
<213> ORGANISM: Escherichia coli

<400> SEQUENCE: 1
atgatgcagc atacttctgt gtggtaccga cgctcggtca gtccgtttgt tcttgtggcg 60
agtgttgccg ttttcttgac cgcgaccgcc aatcttacct tttttgataa aatcagccaa 120
acctatccca tcgcggacaa tctcggcttt gtgctgacga tcgctgtcgt gctctttggc 180
gcgatgctac tgatcaccac gctgttatca tcgtatcgct atgtgctaaa gcctgtgttg 240
attttgctat taatcatggg cgcggtgacc agttatttta ctgacactta tggcacggtc 300
tatgatacga ccatgctcca aaatgcccta cagaccgacc aagccgagac caaggatcta 360
ttaaacgcag cgtttatcat gcgtatcatt ggtttgggtg tgctaccaag tttgcttgtg 420
gcttttgtta aggtggatta tccgacttgg ggcaagggtt tgatgcgccg attgggcttg 480
atcgtggcaa gtcttgcgct gattttactg cctgtggtgg cgttcagcag tcattatgcc 540
agtttctttc gcgtgcataa gccgctgcgt agctatgtca atccgatcat gccaatctac 600
tcggtgggta agcttgccag tattgagtat aaaaaagcca gtgcgccaaa agataccatt 660
tatcacgcca aagacgcggt acaagcaacc aagcctgata tgcgtaagcc acgcctagtg 720
gtgttcgtcg tcggtgagac ggcacgcgcc gatcatgtca gcttcaatgg ctatgagcgc 780
gatactttcc cacagcttgc caagatcgat ggcgtgacca attttagcaa tgtcacatcg 840
tgcggcacat cgacggcgta ttctgtgccg tgtatgttca gctatctggg cgcggatgag 900
tatgatgtcg ataccgccaa ataccaagaa aatgtgctgg atacgctgga tcgcttgggc 960
gtaagtatct tgtggcgtga taataattcg gactcaaaag gcgtgatgga taagctgcca 1020
aaagcgcaat ttgccgatta taaatccgcg accaacaacg ccatctgcaa caccaatcct 1080
tataacgaat gccgcgatgt cggtatgctc gttggcttag atgactttgt cgctgccaat 1140
aacggcaaag atatgctgat catgctgcac caaatgggca atcacgggcc tgcgtatttt 1200
aagcgatatg atgaaaagtt tgccaaattc acgccagtgt gtgaaggtaa tgagcttgcc 1260
aagtgcgaac atcagtcctt gatcaatgct tatgacaatg ccttgcttgc caccgatgat 1320
ttcatcgctc aaagtatcca gtggctgcag acgcacagca atgcctatga tgtctcaatg 1380

-continued

```
ctgtatgtca gcgatcatgg cgaaagtctg ggtgagaacg gtgtctatct acatggtatg   1440

ccaaatgcct ttgcaccaaa agaacagcgc agtgtgcctg catttttctg gacggataag   1500

caaactggca tcacgccaat ggcaaccgat accgtcctga cccatgacgc gatcacgccg   1560

acattattaa agctgtttga tgtcaccgcg gacaaagtca aagaccgcac cgcattcatc   1620

cgctga                                                              1626
```

<210> SEQ ID NO 2
<211> LENGTH: 1626
<212> TYPE: DNA
<213> ORGANISM: Escherichia coli

<400> SEQUENCE: 2

```
atgatgctgc atacttctgt gtggtaccga cgctcggtca gtccgtttgt tcttgtggcg     60

agtgttgccg ttttcttgac cgcgaccgcc aatcttacct tttttgataa aatcagccaa    120

acctatccca tcgcggacaa tctcggcttt gtgctgacga tcgctgtcgt gctctttggc    180

gcgatgctac tgatcaccac gctgttatca tcgtatcgct atgtgctaaa gcctgtgttg    240

attttgctat taatcatggg cgcggtgacc agttatttta ctgacactta tggcacggtc    300

tatgatacga ccatgctcca aaatgcccta cagaccgacc aagccgagac caaggatcta    360

ttaaacgcag cgtttatcat gcgtatcatt ggtttgggtg tgctaccaag tttgcttgtg    420

gcttttgtta aggtggatta tccgacttgg ggcaagggtt tgatgcgccg attgggcttg    480

atcgtggcaa gtcttgcgct gattttactg cctgtggtgg cgttcagcag tcattatgcc    540

agtttctttc gcgtgcataa gccgctgcgt agctatgtca atccgatcat gccaatctac    600

tcggtgggta agcttgccag tattgagtat aaaaaagcca gtgcgccaaa agataccatt    660

tatcacgcca aagacgcggt acaagcaacc aagcctgata tgcgtaagcc acgcctagtg    720

gtgttcgtcg tcggtgagac ggcacgcgcc gatcatgtca gcttcaatgg ctatgagcgc    780

gatactttcc cacagcttgc caagatcgat ggcgtgacca attttagcaa tgtcacatcg    840

tgcggcacat cgacggcgta ttctgtgccg tgtatgttca gctatctggg cgcggatgag    900

tatgatgtcg ataccgccaa ataccaagaa aatgtgctgg atacgctgga tcgcttgggc    960

gtaagtatct tgtggcgtga taataattcg gactcaaaag gcgtgatgga taagctgcca   1020

aaagcgcaat ttgccgatta taaatccgcg accaacaacg ccatctgcaa caccaatcct   1080

tataacgaat gccgcgatgt cggtatgctc gttggcttag atgactttgt cgctgccaat   1140

aacggcaaag atatgctgat catgctgcac caaatgggca atcacgggcc tgcgtatttt   1200

aagcgatatg atgaaaagtt tgccaaattc acgccagtgt gtgaaggtaa tgagcttgcc   1260

aagtgcgaac atcagtcctt gatcaatgct tatgacaatg ccttgcttgc caccgatgat   1320

ttcatcgctc aaagtatcca gtggctgcag acgcacagca atgcctatga tgtctcaatg   1380

ctgtatgtca gcgatcatgg cgaaagtctg ggtgagaacg gtgtctatct acatggtatg   1440

ccaaatgcct ttgcaccaaa agaacagcgc agtgtgcctg catttttctg gacggataag   1500

caaactggca tcacgccaat ggcaaccgat accgtcctga cccatgacgc gatcacgccg   1560

acattattaa agctgtttga tgtcaccgcg gacaaagtca aagaccgcac cgcattcatc   1620

cgctga                                                              1626
```

<210> SEQ ID NO 3
<211> LENGTH: 1626
<212> TYPE: DNA

-continued

<213> ORGANISM: Escherichia coli

<400> SEQUENCE: 3

```
atgatgcagc atacttctgt gtggtaccga cgctcggtca gtccgtttgt tcttgtggcg     60
agtgttgccg ttttcttgac cgcgaccgcc aatcttacct tttttgataa ggtcagccaa    120
acctatccca tcgcggacaa tctcggcttt gtgctgacga tcgctgtcgt gctctttggc    180
gcgatgctac tgatcaccac gctgttatca tcgtatcgct atgtgctaaa gcctgtgttg    240
attttgctat taatcatggg cgcggtgacc agttatttta ctgacactta tggcacggtc    300
tatgatacga ccatgctcca aaatgcccta cagaccgacc aagccgagac caaggatcta    360
ttaaacgcag cgtttatcat gcgtatcatt ggtttgggtg tgctaccaag tttgcttgtg    420
gcttttgtta aggtggatta tccgacttgg ggcaagggtt tgatgcgccg attgggcttg    480
atcgtggcaa gtcttgcgct gattttactg cctgtggtgg cgttcagcag tcattatgcc    540
agtttctttc gcgtgcataa gccgctgcgt agctatgtca atccgatcat gccaatctac    600
tcggtgggta agcttgccag tattgagtat aaaaaagcca gtgcgccaaa agataccatt    660
tatcacgcca aagacgcggt acaagcaacc aagcctgata tgcgtaagcc acgcctagtg    720
gtgttcgtcg tcggtgagac ggcacgcgcc gatcatgtca gcttcaatgg ctatgagcgc    780
gatactttcc cacagcttgc caagatcgat ggcgtgacca attttagcaa tgtcacatcg    840
tgcggcacat cgacggcgta ttctgtgccg tgtatgttca gctatctggg cgcggatgag    900
tatgatgtcg ataccgccaa ataccaagaa aatgtgctgg atacgctgga tcgcttgggc    960
gtaagtatct tgtggcgtga taataattcg gactcaaaag gcgtgatgga taagctgcca   1020
aaagcgcaat ttgccgatta taaatccgcg accaacaacg ccatctgcaa caccaatcct   1080
tataacgaat gccgcgatgt cggtatgctc gttggcttag atgactttgt cgctgccaat   1140
aacggcaaag atatgctgat catgctgcac caaatgggca atcacgggcc tgcgtatttt   1200
aagcgatatg atgaaaagtt tgccaaattc acgccagtgt gtgaaggtaa tgagcttgcc   1260
aagtgcgaac atcagtcctt gatcaatgct tatgacaatg ccttgcttgc caccgatgat   1320
ttcatcgctc aaagtatcca gtggctgcag acgcacagca atgcctatga tgtctcaatg   1380
ctgtatgtca gcgatcatgg cgaaagtctg ggtgagaacg gtgtctatct acatggtatg   1440
ccaaatgcct ttgcaccaaa agaacagcgc agtgtgcctg catttttctg gacggataag   1500
caaactggca tcacgccaat ggcaaccgat accgtcctga cccatgacgc gatcacgccg   1560
acattattaa agctgtttga tgtcaccgcg gacaaagtca aagaccgcac cgcattcatc   1620
cgctga                                                              1626
```

<210> SEQ ID NO 4
<211> LENGTH: 1626
<212> TYPE: DNA
<213> ORGANISM: Escherichia coli

<400> SEQUENCE: 4

```
atgatgcagc atacttctgt gtggtaccga cgctcggtca gtccgtttgt tcttgtggcg     60
agtgttgccg ttttcttgac cgcgaccgcc aatcttacct tttttgataa aatcagccaa    120
acctatccca tcgcggacaa tctcggcttt gtgctgacga tcgctgtcgt gctctttggc    180
gcgatgctac tgatcaccac gctgttatca tcgtatcgct atgtgctaaa gcctgtgttg    240
attttgctat taatcatggg cgcggtgacc agttatttta ctgacactta tggcacggtc    300
tatgatacga ccatgctcca aaatgcccta cagaccgacc aagccgagac caaggatcta    360
```

ttaaacgcag cgtttatcat gcgtatcatt ggtttgggtg tgctaccaag tttgcttgtg 420
gcttttgtta aggtggatta tccgacttgg ggcaagggtt tgatgcgccg attgggcttg 480
atcgtggcaa gtcttgcgct gattttactg cctgtggtgg cgttcagcag tcattatgcc 540
agtttctttc gcgtgcataa gccgctgcgt agctatgtca atccgatcat gccaatctac 600
tcggtgggta agcttgccag tattgagtat aaaaaagcca gtgcgccaaa agataccatt 660
tatcacgcca aagacgcggt acaagcaacc aagcctgata tgcgtaagcc acgcctagtg 720
gtgttcgtcg tcggtgagac ggcacgcgcc gatcatgtca gcttcaatgg ctatgagcgc 780
gatactttcc cacagcttgc caagatcgat ggcgtgacca attttagcaa tgtcacatcg 840
tgcggcacat cgacggcgta ttctgtgccg tgtatgttca gctatctggg cgcggatgag 900
tatgatgtcg ataccgccaa ataccaagaa aatgtgctgg atacgctgga tcgcttgggc 960
gtaagtatct tgtggcgtga taataattcg gactcaaaag gcgtgatgga taagctgcca 1020
aaagcgcaat ttgccgatta taaatccgcg accaacaacg ccatctgcaa caccaatcct 1080
tataacgaat gccgcgatgt cggtatgctc gttggcttag atgactttgt cgctgccaat 1140
aacggcaaag atatgctgat catgctgcac caaatgggca atcacgggcc tgcgtatttt 1200
aagcgatatg atgaaaagtt tgccaaattc acgccagtgt gtgaaggtaa tgagcttgcc 1260
aagtgcgaac atcagtcctt gatcaatgct tatgacaatg ccttgcttgc caccgataat 1320
ttcatcgctc aaagtatcca gtggctgcag acgcacagca atgcctatga tgtctcaatg 1380
ctgtatgtca gcgatcatgg cgaaagtctg ggtgagaacg gtgtctatct acatggtatg 1440
ccaaatgcct ttgcaccaaa agaacagcgc agtgtgcctg cattttctg gacggataag 1500 caaactggca tcacgccaat ggcaaccgat accgtcctga cccatgacgc gatcacgccg 1560
acattattaa agctgtttga tgtcaccgcg gacaaagtca aagaccgcac cgcattcatc 1620
cgctga 1626

<210> SEQ ID NO 5
<211> LENGTH: 1626
<212> TYPE: DNA
<213> ORGANISM: Escherichia coli

<400> SEQUENCE: 5
atgatgcagc atacttctgt gtggtaccga cgctcggtca gtccgtttgt tcttgtggcg 60
agtgttgccg ttttcttgac cgcgaccgcc aatcttacct tttttgataa aatcagccaa 120
acctatccca tcgcggacaa tctcggcttt gtgctgacga tcgctgtcgt gctctttggc 180
gcgatgctac tgatcaccac gctgttatca tcgtatcgct atgtgctaaa gcctgtgttg 240
attttgctat taatcatggg cgcggtgacc agttatttta ctgacactta tggcacggtc 300
tatgatacga ccatgctcca aaatgcccta cagaccgacc aagccgagac caaggatcta 360
ttaaacgcag cgtttatcat gcgtatcatt ggtttgggtg tgctaccaag tttgcttgtg 420
gcttttgtta aggtggatta tccgacttgg ggcaagggtt tgatgcgccg attgggcttg 480
atcgtggcaa gtcttgcgct gattttactg cctgtggtgg cgttcagcag tcattatgcc 540
agtttctttc gcgtgcataa gccgctgcgt agctatgtca atccgatcat gccaatctac 600
tcggtgggta agcttgccag tattgagtat aaaaaagcca gtgcgccaaa agataccatt 660
tatcacgcca aagacgcggt acaagcaacc aagcctgata tgcgtaagcc acgcctagtg 720
gtgttcgtcg tcggtgagac ggcacgcgcc gatcatgtca gcttcaatgg ctatgagcgc 780

-continued

```
gatactttcc cacagcttgc caagatcgat ggcgtgacca attttagcaa tgtcacatcg    840

tgcggcacat cgacggcgta ttctgtgccg tgtatgttca gctatctggg cgcggatgag    900

tatgatgtcg ataccgccaa ataccaagaa aatgtgctgg atacgctgga tcgcttgggc    960

gtaagtatct tgtggcgtga taataattcg gactcaaaag gcgtgatgga taagctgcca   1020

aaagcgcaat ttgccgatta taaatccgcg accaacaacg ccatctgcaa caccaatcct   1080

tataacgaat gccgcgatgt cggtatgctc gttggcttag atgactttgt cgctgccaat   1140

aacggcaaag atatgctgat catgctgcac caaatgggca atcacgggcc tgcgtatttt   1200

aagcgatatg atgaaaagtt tgccaaattc acgccagtgt gtgaaggtaa tgagcttgcc   1260

aagtgcgaac atcagtcctt gatcaatgct tatgacaatg ccttgcttgc caccgatgat   1320

ttcatcgctc aaagtatcca gtggctgcag acgtacagca atgcctatga tgtctcaatg   1380

ctgtatgtca gcgatcatgg cgaaagtctg ggtgagaacg gtgtctatct acatggtatg   1440

ccaaatgcct ttgcaccaaa agaacagcgc agtgtgcctg catttttctg gacggataag   1500

caaactggca tcacgccaat ggcaaccgat accgtcctga cccatgacgc gatcacgccg   1560

acattattaa agctgtttga tgtcaccgcg gacaaagtca aagaccgcac cgcattcatc   1620

cgctga                                                              1626


<210> SEQ ID NO 6
<211> LENGTH: 1626
<212> TYPE: DNA
<213> ORGANISM: Escherichia coli

<400> SEQUENCE: 6

atgatgcagc atacttctgt gtggtaccga cgctcggtca gtccgtttgt tcttgtggcg     60

agtgttgccg ttttcttgac cgcgaccgcc aatcttacct tttttgataa aatcagccaa    120

acctatccca tcgcggacaa tctcggcttt gtgctgacga tcgctgtcgt gctctttggc    180

gcgatgctac tgatcaccac gctgttatca tcgtatcgct atgtgctaaa gcctgtgttg    240

attttgctat taatcatggg cgcggtgacc agttatttta ctgacactta tggcacggtc    300

tatgatacga ccatgctcca aaatgcccta cagaccgacc aagccgagac caaggatcta    360

ttaaacgcag cgtttatcat gcgtatcatt ggtttgggtg tgctaccaag tttgcttgtg    420

gcttttgtta aggtggatta tccgacttgg ggcaagggtt tgatgcgccg attgggcttg    480

atcgtggcaa gtcttgcgct gattttactg cctgtggtgg cgttcagcag tcattatgcc    540

agtttctttc gcgtgcataa gccgctgcgt agctatgtca atccgatcat gccaatctac    600

tcggtgggta agcttgccag tattgagtat aaaaaagcca gtgcgccaaa agataccatt    660

tatcacgcca aagacgcggt acaagcaacc aagcctgata tgcgtaagcc acgcctagtg    720

gtgttcgtcg tcggtgagac ggcacgcgcc gatcatgtca gcttcaatgg ctatgagcgc    780

gatactttcc cacagcttgc caagatcgat ggcgtgacca attttagcaa tgtcacatcg    840

tgcggcacat cgacggcgta ttctgtgccg tgtatgttca gctatctggg cgcggatgag    900

tatgatgtcg ataccgccaa ataccaagaa aatgtgctgg atacgctgga tcgcttgggc    960

gtaagtatct tgtggcgtga taataattcg gactcaaaag gcgtgatgga taagctgcca   1020

aaagcgcaat ttgccgatta taaatccgcg accaacaacg ccatctgcaa caccaatcct   1080

tataacgaat gccgcgatgt cggtatgctc gttggcttag atgactttgt cgctgccaat   1140

aacggcaaag atatgctgat catgctgcac caaatgggca atcacgggcc tgcgtatttt   1200

aagcgatatg atgaaaagtt tgccaaattc acgccagtgt gtgaaggtaa tgagcttgcc   1260
```

-continued

```
aaatgcgaac atcagtcctt gatcaatgct tatgacaatg ccttgcttgc caccgatgat   1320

ttcatcgctc aaagtatcca gtggctgcag acgcacagca atgcctatga tgtctcaatg   1380

ctgtatgtca gcgatcatgg cgaaagtctg ggtgagaacg gtgtctatct acatggtatg   1440

ccaaatgcct ttgcaccaaa agaacagcgc agtgtgcctg catttttctg gacggataag   1500

caaactggca tcacgccaat ggcaaccgat accgtcctga cccatgacgc gatcacgccg   1560

acattattaa agctgtttga tgtcaccgcg gacaaagtca aagaccacac cgcattcatc   1620

cgctga                                                              1626
```

```
<210> SEQ ID NO 7
<211> LENGTH: 1626
<212> TYPE: DNA
<213> ORGANISM: Escherichia coli

<400> SEQUENCE: 7

atgatgcagc atacttctgt gtggtaccga cgctcggtca gtccgtttgt tcttgtggcg     60

agtgttgccg ttttcttgac cgcgaccgcc aatcttacct tttttgataa aatcagccaa    120

acctatccca tcgcggacaa tctcggcttt gtgctgacga tcgctgtcgt gctctttggc    180

gcgatgctac tgatcaccac gctgttatca tcgtatcgct atgtgctaaa gcctgtgttg    240

attttgctat taatcatggg cgcggtgacc agttatttta ctgacactta tggcacggtc    300

tatgatacga ccatgctcca aaatgcccta cagaccgacc aagccgagac caaggatcta    360

ttaaacgcag cgtttatcat gcgtatcatt ggtttgggtg tgctaccaag tttgcttgtg    420

gcttttgtta aggtggatta tccgacttgg ggcaagggtt tgatgcgccg attgggcttg    480

atcgtggcaa gtcttgcgct gattttactg cctgtggtgg cgttcagcag tcattatgcc    540

agtttctttc gcgtgcataa gccgctgcgt agctatgtca atccgatcat gccaatctac    600

tcggtgggta agcttgccag tattgagtat aaaaaagcca gtacgccaaa agataccatt    660

tatcacgcca aagacgcggt acaagcaacc aagcctgata tgcgtaagcc acgcctagtg    720

gtgttcgtcg tcggtgagac ggcacgcgcc gatcatgtca gcttcaatgg ctatgagcgc    780

gatactttcc cacagcttgc caagatcgat ggcgtgacca attttagcaa tgtcacatcg    840

tgcggcacat cgacggcgta ttctgtgccg tgtatgttca gctatctggg cgcggatgag    900

tatgatgtcg ataccgccaa ataccaagaa aatgtgctgg atacgctgga tcgcttgggc    960

gtaagtatct tgtggcgtga taataattcg gactcaaaag gcgtgatgga taagctgcca   1020

aaagcgcaat ttgccgatta taaatccgcg accaacaacg ccatctgcaa caccaatcct   1080

tataacgaat gccgcgatgt cggtatgctc gttggcttag atgactttgt cgctgccaat   1140

aacggcaaag atatgctgat catgctgcac caaatgggca atcacgggcc tgcgtatttt   1200

aagcgatatg atgaaaagtt tgccaaattc acgccagtgt gtgaaggtaa tgagcttgcc   1260

aagtgcgaac atcagtcctt gatcaatgct tatgacaatg ccttgcttgc caccgatgat   1320

ttcatcgctc aaagtatcca gtggctgcag acgcacagca atgcctatga tgtctcaatg   1380

ctgtatgtca gcgatcatgg cgaaagtctg ggtgagaacg gtgtctatct acatggtatg   1440

ccaaatgcct ttgcaccaaa agaacagcgc agtgtgcctg catttttctg gacggataag   1500

caaactggca tcacgccaat ggcaaccgat accgtcctga cccatgacgc gatcacgccg   1560

acattattaa agctgtttga tgtcaccgcg gacaaagtca aagaccgcac cgcattcatc   1620

cgctga                                                              1626
```

-continued

<210> SEQ ID NO 8
<211> LENGTH: 1626
<212> TYPE: DNA
<213> ORGANISM: Escherichia coli

<400> SEQUENCE: 8
atgatgcggc atacttctgt gtggtaccga cgctcggtca gtccgtttgt tcttgtggcg 60
agtgttgccg ttttcttgac cgcgaccgcc aatcttacct tttttgataa aatcagccaa 120
acctatccca tcgcggacaa tctcggcttt gtgctgacga tcgctgtcgt gctctttggc 180
gcgatgctac tgatcaccac gctgttatca tcgtatcgct atgtgctaaa gcctgtgttg 240
attttgctat taatcatggg cgcggtgacc agttatttta ctgacactta tggcacggtc 300
tatgatacga ccatgctcca aaatgcccta cagaccgacc aagccgagac caaggatcta 360
ttaaacgcag cgtttatcat gcgtatcatt ggtttgggtg tgctaccaag tttgcttgtg 420
gcttttgtta aggtggatta tccgacttgg ggcaagggtt tgatgcgccg attgggcttg 480
atcgtggcaa gtcttgcgct gattttactg cctgtggtgg cgttcagcag tcattatgcc 540
agtttctttc gcgtgcataa gccgctgcgt agctatgtca atccgatcat gccaatctac 600
tcggtgggta agcttgccag tattgagtat aaaaaagcca gtgcgccaaa agataccatt 660
tatcacgcca aagacgcggt acaagcaacc aagcctgata tgcgtaagcc acgcctagtg 720
gtgttcgtcg tcggtgagac ggcacgcgcc gatcatgtca gcttcaatgg ctatgagcgc 780
gatactttcc cacagcttgc caagatcgat ggcgtgacca attttagcaa tgtcacatcg 840
tgcggcacat cgacggcgta ttctgtgccg tgtatgttca gctatctggg cgcggatgag 900
tatgatgtcg ataccgccaa ataccaagaa aatgtgctgg atacgctgga tcgcttgggc 960
gtaagtatct tgtggcgtga taataattcg gactcaaaag gcgtgatgga taagctgcca 1020
aaagcgcaat ttgccgatta taaatccgcg accaacaacg ccatctgcaa caccaatcct 1080
tataacgaat gccgcgatgt cggtatgctc gttggcttag atgactttgt cgctgccaat 1140
aacggcaaag atatgctgat catgctgcac caaatgggca atcacgggcc tgcgtatttt 1200
aagcgatatg atgaaaagtt tgccaaattc acgccagtgt gtgaaggtaa tgagcttgcc 1260
aagtgcgaac atcagtcctt gatcaatgct tatgacaatg ccttgcttgc caccgatgat 1320
ttcatcgctc aaagtatcca gtggctgcag acgcacagca atgcctatga tgtctcaatg 1380
ctgtatgtca gcgatcatgg cgaaagtctg ggtgagaacg gtgtctatct acatggtatg 1440
ccaaatgcct ttgcaccaaa agaacagcgc agtgtgcctg cattttctg gacggataag 1500 caaactggca tcacgccaat ggcaaccgat accgtcctga cccatgacgc gatcacgccg 1560
acattattaa agctgtttga tgtcaccgcg gacaaagtca aagaccgcac cgcattcatc 1620
cgctga 1626

<210> SEQ ID NO 9
<211> LENGTH: 1608
<212> TYPE: DNA
<213> ORGANISM: Escherichia coli

<400> SEQUENCE: 9
gtgtggtacc gacgctcggt cagtccgttt gttcttgtgg cgagtgttgc cgttttcttg 60
accgcgaccg ccaatcttac cttttttgat aaaatcagcc aaacctatcc catcgcggac 120
aatctcggct ttgtgctgac gatcgctgtc gtgctctttg gcgcgatgct actgatcacc 180
acgctgttat catcgtatcg ctatgtgcta aagcctgtgt tgattttgct attaatcatg 240
ggcgcggtga ccagttattt tactgacact tatggcacgg tctatgatac gaccatgctc 300
caaaatgccc tacagaccga ccaagccgag accaaggatc tattaaacgc agcgtttatc 360
atgcgtatca ttggtttggg tgtgctacca agtttgcttg tggcttttgt taaggtggat 420
tatccgactt ggggcaaggg tttgatgcgc cgattgggct tgatcgtggc aagtcttgcg 480
ctgattttac tgcctgtggt ggcgttcagc agtcattatg ccagtttctt tcgcgtgcat 540
aagccgctgc gtagctatgt caatccgatc atgccaatct actcggtggg taagcttgcc 600
agtattgagt ataaaaaagc cagtgcgcca aaagatacca tttatcacgc caaagacgcg 660
gtacaagcaa ccaagcctga tatgcgtaag ccacgcctag tggtgttcgt cgtcggtgag 720
acggcacgcg ccgatcatgt cagcttcaat ggctatgagc gcgatacttt cccacagctt 780
gccaagatcg atggcgtgac caattttagc aatgtcacat cgtgcggcac atcgacggcg 840
tattctgtgc cgtgtatgtt cagctatctg ggcgcggatg agtatgatgt cgataccgcc 900
aaataccaag aaaatgtgct ggatacgctg gatcgcttgg gcgtaagtat cttgtggcgt 960
gataataatt cggactcaaa aggcgtgatg gataagctgc caaaagcgca atttgccgat 1020
tataaatccg cgaccaacaa cgccatctgc aacaccaatc cttataacga atgccgcgat 1080
gtcggtatgc tcgttggctt agatgacttt gtcgctgcca ataacggcaa agatatgctg 1140
atcatgctgc accaaatggg caatcacggg cctgcgtatt ttaagcgata tgatgaaaag 1200
tttgccaaat tcacgccagc gtgtgaaggt aatgagcttg ccaagtgcga acatcagtcc 1260
ttgatcaatg cttatgacaa tgccttgctt gccaccgatg atttcatcgc tcaaagtatc 1320
cagtggctgc agacgcacag caatgcctat gatgtctcaa tgctgtatgt cagcgatcat 1380
ggcgaaagtc tgggtgagaa cggtgtctat ctacatggta tgccaaatgc ctttgcacca 1440
aaagaacagc gcagtgtgcc tgcatttttc tggacggata agcaaactgg catcacgcca 1500
atggcaaccg ataccgtcct gacccatgac gcgatcacgc cgacattatt aaagctgttt 1560
gatgtcaccg cggacaaagt caaagaccgc accgcattca tccgctga 1608

<210> SEQ ID NO 10
<211> LENGTH: 1608
<212> TYPE: DNA
<213> ORGANISM: Escherichia coli

<400> SEQUENCE: 10
gtgtggtacc gacgctcggt cagtccgttt gttcttgtgg cgagtgttgc cgttttcttg 60
accgcgaccg ccaatcttac cttttttgat aaaatcagcc aaacctatcc catcgcggac 120
aatctcggct ttgtgctgac gatcgctgtc gtgctctttg gcgcgatgct actgatcacc 180
acgctgttat catcgtatcg ctatgtgcta aagcctgtgt tgattttgct attaatcatg 240
ggcgcggtga ccagttattt tactgacact tatggcacgg tctatgatac gaccatgctc 300
caaaatgccc tacagaccga ccaagccgag accaaggatc tattaaacgc agcgtttatc 360
atgcgtatca ttggtttggg tgtgctacca agtttgcttg tggcttttgt taaggtggat 420
tatccgactt ggggcaaggg tttgatgcgc cgattgggct tgatcgtggc aagtcttgcg 480
ctgattttac tgcctgtggt ggcgttcagc agtcattatg ccagtttctt tcgcgtgcat 540
aagccgctgc gtagctatgt caatccgatc atgccaatct actcggtggg taagcttgcc 600
agtattgagt ataaaaaagc cagtgcgcca aaagatacca tttatcacgc caaagacgcg 660
gtacaagcaa ccaagcctga tatgcgtaag ccacgcctag tggtgttcgt cgtcggtgag 720

-continued

```
acggcacgcg ccgatcatgt cagcttcaat ggctatgagc gcgatacttt cccacagctt    780
gccaagatcg atggcgtgac caattttagc aatgtcacat cgtgcggcac atcgacggcg    840
tattctgtgc cgtgtatgtt cagctatctg ggcgcggatg agtatgatgt cgataccgcc    900
aaataccaag aaaatgtgct ggatacgctg gatcgcttgg gcgtaagtat cttgtggcgt    960
gataataatt cggactcaaa aggcgtgatg gataagctgc caaaagcgca atttgccgat   1020
tataaatccg cgaccaacaa cgccatctgc aacaccaatc cttataacga atgccgcgat   1080
gtcggtatgc tcgttggctt agatgacttt gtcgctgcca ataacggcaa agatatgctg   1140
atcatgctgc accaaatggg caatcacggg cctgcgtatt ttaagcgata tgatgaaaag   1200
tttgccaaat tcacgccagc gtgtgaaggt aatgagcttg ccaagtgcga acatcagtcc   1260
ttgatcaatg cttatgacaa tgccttgctt gccaccgatg atttcatcgc tcaaagtatc   1320
cagtggctgc agacgcacag caatgcctat gatgtctcaa tgctgtatgt cagcgatcat   1380
ggcgaaagtc tgggtgagaa cggtgtctat ctacatggta tgccaaatgc ctttgcacca   1440
aaagaacagc gcagtgtgcc tgcatttttc tggacggata agcaaactgg catcacgcca   1500
atggcaaccg ataccgtcct gacccatgac gcgatcacgc cgacattatt aaagctgttt   1560
gatgtcaccg cggacaaagt caaagaccgc accgcattca tccgctga                1608
```

<210> SEQ ID NO 11
<211> LENGTH: 1617
<212> TYPE: DNA
<213> ORGANISM: Escherichia coli

<400> SEQUENCE: 11

```
atgacatcac atcactcttg gtatcgctat tctatcaatc cttttgtgct gatgggtttg     60
gtggcgttat ttttggcagc gacagcgaac ctgacatttt ttgaaaaagc gatggcggtc    120
tatcctgtat cggataactt aggctttatc atctcaatgg cggtggcggt gatgggtgct    180
atgctactga ttgtcgtgct gttatcctat cgctatgtgc taaagcctgt cctgattttg    240
ctactgatta tgggtgcggt gacgagctat tttaccgata cttatggcac ggtctatgac    300
accaccatgc tccaaaatgc catgcaaacc gaccaagccg agtctaagga cttgatgaat    360
ttggcgtttt ttgtgcgaat tatcgggctt ggcgtgttgc caagtgtgtt ggtcgcagtt    420
gccaaagtca attatccaac atggggcaaa ggtctgattc agcgtgcgat gacatggggt    480
gtcagccttg tgctgttgct tgtgccgatt ggactattta gcagtcagta tgcgagtttc    540
tttcgggtgc ataagccagt gcgtttttat atcaacccga ttacgccgat ttattcggtg    600
ggtaagcttg ccagtatcga gtacaaaaaa gccactgcgc caacagacac catctatcat    660
gccaaagacg ccgtgcagac caccaagccg agcgagcgta agccacgcct agtggtgttc    720
gtcgtcggtg agacggcgcg tgctgaccat gtgcagttca atggctatgg ccgtgagact    780
ttcccgcagc ttgccaaagt tgatggcttg gcgaatttta gccaagtgac atcgtgtggc    840
acatcgacgg cgtattctgt gccgtgtatg ttcagctatt tgggtcaaga tgactatgat    900
gtcgataccg ccaaatacca agaaaatgtg ctagatacgc ttgaccgctt gggtgtgggt    960
atcttgtggc gtgataataa ttcagactca aaaggcgtga tggataagct acctgccacg   1020
cagtattttg attataaatc agcaaccaac aataccatct gtaacaccaa tccctataac   1080
gaatgccgtg atgtcggtat gcttgtcggg ctagatgact atgtcagcgc caataatggc   1140
aaagatatgc tcatcatgct acaccaaatg ggcaatcatg ggccggcgta ctttaagcgt   1200
tatgatgagc aatttgccaa attcaccccc gtgtgcgaag gcaacgagct tgccaaatgc   1260
```

gaacaccaat cactcatcaa tgcctatgac aatgcgctac ttgcgactga tgattttatc 1320
gccaaaagca tcgattggct aaaaacgcat gaagcgaact acgatgtcgc catgctctat 1380
gtcagtgacc acggcgagag cttgggcgaa aatggtgtct atctgcatgg tatgccaaat 1440
gcctttgcac caaaagaaca gcgagctgtg cctgcgtttt tttggtcaaa taatacgaca 1500
ttcaagccaa ctgccagcga tactgtgctg acgcatgatg cgattacgcc aacactgctt 1560
aagctgtttg atgtcacagc gggcaaggtc aaagaccgcg cggcatttat ccagtaa 1617

<210> SEQ ID NO 12
<211> LENGTH: 1608
<212> TYPE: DNA
<213> ORGANISM: Escherichia coli

<400> SEQUENCE: 12
gtgtggtacc gacgctcggt cagtccgttt gttcttgtgg cgagtgttgc cgttttcttg 60
accgcgaccg ccaatcttac ctttttttgat aaaatcagcc aaacctatcc catcgcggac 120
aatctcggct ttgtgctgac gatcgctgtc gtgctctttg gcgcgatgct actgatcacc 180
acgctgttat catcgtatcg ctatgtgcta aagcctgtgt tgattttgct attaatcatg 240
ggcgcggtga ccagttattt tactgacact tatggcacgg tctatgatac gaccatgctc 300
caaaatgccc tacagaccga ccaagccgag accaaggatc tattaaacgc agcgtttatc 360
atgcgtatca ttggtttggg tgtgctacca agtttgcttg tggcttttgt taaggtggat 420
tatccgactt ggggcaaggg tttgatgcgc cgattgggct tgatcgtggc aagtcttgcg 480
ctgattttac tgcctgtggt ggcgttcagc agtcattatg ccagtttctt tcgcgtgcat 540
aagccgctgc gtagctatgt caatccgatc atgccaatct actcggtggg taagcttgcc 600
agtattgagt ataaaaaagc cagtgcgcca aaagatacca tttatcacgc caaagacgcg 660
gtacaagcaa ccaagcctga tatgcgtaag ccacgcctag tggtgttcgt cgtcggtgag 720
acggcacgcg ccgatcatgt cagcttcaat ggctatgagc gcgatacttt cccacagctt 780
gccaagatcg atggcgtgac caattttagc aatgtcacat cgtgcggcac atcgacggcg 840
tattctgtgc cgtgtatgtt cagctatctg ggcgcggatg agtatgatgt cgataccgcc 900
aaataccaag aaaatgtgct ggatacgctg gatcgcttgg gcgtaagtat cttgtggcgt 960
gataataatt cggactcaaa aggcgtgatg gataagctgc caaaagcgca atttgccgat 1020
tataaatccg cgaccaacaa cgccatctgc aacaccaatc cttataacga atgccgcgat 1080
gtcggtatgc tcgttggctt agatgacttt gtcgctgcca ataacggcaa agatatgctg 1140
atcatgctgc accaaatggg caatcacggg cctgcgtatt ttaagcgata tgatgaaaag 1200
tttgccaaat tcacgccagc gtgtgaaggt aatgagcttg ccaagtgcga acatcagtcc 1260
ttgatcaatg cttatgacaa tgccttgctt gccaccgatg atttcatcgc tcaaagtatc 1320
cagtggctgc agacgcacag caatgcctat gatgtctcaa tgctgtatgt cagcgatcat 1380
ggcgaaagtc tgggtgagaa cggtgtctat ctacatggta tgccaaatgc ctttgcacca 1440
aaagaacagc gcagtgtgcc tgcatttttc tggacggata agcaaactgg catcacgcca 1500
atggcaaccg ataccgtcct gacccatgac gcgatcacgc cgacattatt aaagctgttt 1560
gatgtcaccg cggacaaagt caaagaccgc accgcattca tccgctga 1608

<210> SEQ ID NO 13
<211> LENGTH: 1626
<212> TYPE: DNA

<213> ORGANISM: Escherichia coli

<400> SEQUENCE: 13
atgccttccc ttataaaaat aaaaattgtt ccgcttatgt tctttttggc actgtatttt 60
gcatttatgc tgaactggcg tggagttctc catttttacg aaatccttta caaattagaa 120
gattttaagt ttggtttcgc catttcatta ccaatattgc ttgttgcagc gcttaacttt 180
gtatttgttc cattttcgat acggtattta ataaagcctt tttttgcact tcttatcgca 240
cttagtgcaa tcgttagtta cacaatgatg aagtatagag tcttgtttga tcaaaacatg 300
attcagaata tttttgaaac caatcaaaat gaggcgttag catatttaag cttaccaatt 360
atagtatggg ttactattgc tggttttatc cctgccattt tacttttctt tgttgaaatt 420
gaatatgagg aaaaatggtt caaagggatt ctaactcgtg ccctatcgat gtttgcatca 480
cttatagtga ttgcggttat tgcagcacta tactatcaag attatgtgtc agtggggcgc 540
aacaattcaa acctccagcg tgagattgtt ccagccaatt tcgttaatag taccgttaaa 600
tacgtttaca atcgttatct tgctgaacca atcccattta caactttagg tgatgatgca 660
aaacgggata ctaatcaaag taagcccacg ttgatgtttc tggtcgttgg tgaaaccgct 720
cgtggtaaaa atttctcgat gaatggctat gagaaagaca ccaatccatt taccagtaaa 780
tctggtggcg tgatctcctt taatgatgtt cgttcgtgtg ggactgcaac cgctgtatcc 840
gtcccctgca tgttctccaa tatggggaga aaggagtttg atgataatcg cgctcgcaat 900
agcgagggcc tgctagatgt gttgcaaaaa acggggatct ccattttttg gaaggagaac 960
gatggaggct gcaaaggcgt ctgcgaccga gtacctaaca tcgaaatcga accaaaggat 1020
caccctaagt tctgcgataa aaacacatgc tatgacgagg ttgtccttca agacctcgat 1080
agtgaaattg ctcaaatgaa aggggataag ctggttggct tccacctgat aggtagccat 1140
ggcccaacct actacaagcg ctaccctgat gctcatcgtc agttcacccc tgactgtcca 1200
cgcagtgata ttgaaaactg cacagatgaa gagctcacca acacctatga caacaccatc 1260
cgctacaccg atttcgtgat tggagagatg attgccaagt tgaaaaccta cgaagataag 1320
tacaacaccg cgttgctcta cgtctccgat catggtgaat cactgggagc attagggctt 1380
tacctacacg gtacaccgta ccagtttgca ccggatgatc agacccgtgt tcctatgcag 1440
gtgtggatgt cacctggatt taccaaagag aaaggcgttg atatggcgtg tttgcagcag 1500
aaagccgctg atactcgtta ctcacacgat aatattttct catctgtatt gggtatctgg 1560
gacgtcaaaa catcagttta cgaaaagggt ctagatattt tcagtcaatg tcgtaatgtt 1620
caataa 1626

<210> SEQ ID NO 14
<211> LENGTH: 1626
<212> TYPE: DNA
<213> ORGANISM: Escherichia coli

<400> SEQUENCE: 14
atgccttccc ttataaaaat aaaaattgtt ccgcttatgt tctttttggc actgtatttt 60
gcatttatgc tgaactggcg tggagttctc catttttacg aaatccttta caaattagaa 120
gattttaagt ttggtttcgc catttcatta ccaatattgc ttgttgcagc gcttaacttt 180
gtatttgttc cattttcgat acggtattta ataaagcctt tttttgcact tcttatcgca 240
cttagtgcaa tcgttagtta cacaatgatg aagtatagag tcttgtttga tcaaaacatg 300
attcagaata tttttgaaac caatcaaaat gaggcgttag catatttaag cttaccaatt 360

-continued atagtatggg ttactattgc tggttttatc cctgccattt tacttttctt tgttgaaatt 420
gaatatgagg aaaaatggtt caaagggatt ctaactcgtg ccctatcgat gtttgcatca 480
cttatagtga ttgcggttat tgcagcacta tactatcaag attatgtgtc agtggggcgc 540
aacaattcaa acctccagcg tgagattgtt ccagccaatt tcgttaatag taccgttaaa 600
tacgtttaca atcgttatct tgctgaacca atcccattta caactttagg tgatgatgca 660
aaacgggata ctaatcaaag taagcccacg ttgatgtttc tggtcgttgg tgaaaccgct 720
cgtggtaaaa atttctcgat gaatggctat gagaaagaca ccaatccatt taccagtaaa 780
tctggtggcg tgatctcctt taatgatgtt cgttcgtgtg ggactgcaac cgctgtatcc 840
gtcccctgca tgttctccaa tatgggggaga aaggagtttg atgaaaatcg cgctcgcaat 900
agcgagggcc tgctagatgt gttgcaaaaa acggggatct ccattttttg gaaggagaac 960
gatggaggct gcaaaggcgt ctgcgaccga gtacctaaca tcgaaatcga accaaaggat 1020
caccctaagt tctgcgataa aaacacatgc tatgacgagg ttgtccttca agacctcgat 1080
agtgaaattg ctcaaatgaa aggggataag ctggttggct tccacctgat aggtagccat 1140
ggcccaacct actacaagcg ctaccctgat gctcatcgtc agttcacccc tgactgtcca 1200
cgcagtgata ttgaaaactg cacagatgaa gagctcacca acacctatga caacaccatc 1260
cgctacaccg atttcgtgat tggagagatg attgccaagt tgaaaaccta cgaagataag 1320
tacaacaccg cgttgctcta cgtctccgat catggtgaat cactgggagc attagggctt 1380
tacctacacg gtacaccgta ccagtttgca ccggatgatc agacccgtgt tcctatgcag 1440
gtgtggatgt cacctggatt taccaaagag aaaggcgttg atatggcgtg tttgcagcag 1500
aaagccgctg atactcgtta ctcacacgat aatattttct catctgtatt gggtatctgg 1560
gacgtcaaaa catcagttta cgaaaagggt ctagatattt tcagtcaatg tcgtaatgtt 1620
caataa 1626

<210> SEQ ID NO 15
<211> LENGTH: 1626
<212> TYPE: DNA
<213> ORGANISM: Escherichia coli

<400> SEQUENCE: 15
gtgatttcta gatttaagac gttatcggtt aaccaattca ctttcatcac tgcgttgttt 60
tatgttgcca ttttcaatct accgctcttt ggtatagtgc gaaaaggaat tgaaaaacaa 120
ccagaagttg atcccctttt catcgcatct atgccgctat tttaacatt tgcgctgagt 180 tttttgtttt caatttttac cgtcaaatac ctgctgaagc cctttttat cgtattgacg 240 ttactttcct caagtgtatt ttttgcagcc tatcaataca atgtcgtgtt tgactacggc 300
atgatagaaa acacgtttca aacacatcct gctgaagcat tgatgtatgt aaatcttgca 360
tcaattacca atctactgct gactgggcta ttaccgtcat atcttattta taaggccgat 420
attcattatc agcccttttt taaggagtta ttgcataaat tagcctttat gctgctaatg 480
ttcgttggca ttgggatagt cgcctttttt tactatcaag attatgctgc atttgttcga 540
aacaacagtg agttaaggcg ttacattgtc cctacctatt ttgtcagtag tgcatctaaa 600
tatctcaatg agcactattt gcagacgccc atggaatacc aacaacttgg cctagatgcg 660
aagaatgcca gtcgtaaccc gaacactaaa cctaacttat tagtggttgt tgtgggtgaa 720
actgcgcgct caatgagcta tcaatattat ggatataaca agccaaccaa tgctcatacc 780
caaaatcagg ggctgattgc gtttaacgat actagctcat gcggcacggc cacggcggtg 840
tctctaccct gtatgttttc acgaatgggg cgggcagact atgatcctcg ccgtgctaat 900
gctcaagaca cagtgattga tgtgttaagt catagtggta taaaagtaca gtggtttgat 960
aatgattctg gctgtaaagg tgtgtgtgat caggttgaaa atctcacgat agatttgaag 1020
agtgatccga agctgtgttc tggccaatat tgttttgacc aagtattgct caacaaatta 1080
gataaaattc tggcagtagc accaagtcaa gatacagtaa tttttttgca tatcattggt 1140
agtcatggac caacttatta tcttagatac ccgccagagc atcgtaaatt tataccggat 1200
tgtccgcgca gtgatattca aaattgcagt caagaagaac tgattaacac ctacgacaac 1260
actattctat atacggattt tattctcagt gaagtggtga ataaattaaa aggtaagcag 1320
gatatgttcg atactgcaat gctgtatctc tctgaccatg gtgagtcttt gggtgaaaag 1380
ggcatgtatt tacatggtgc gccctatagt attgcaccga aagaacaaac tagcgtacca 1440
atgctggctt gggtatctaa tgactttagc caagataatc agttgaacat gacttgtgtt 1500
gcacagcgag cagaacaggg cggcttttcc cacgacaatt tgttcgacag tttgctagga 1560
cttatgaatg taaaaaccac cgtctatcag agccaactcg atatttttgc accttgcagg 1620
tattag 1626

<210> SEQ ID NO 16
<211> LENGTH: 1644
<212> TYPE: DNA
<213> ORGANISM: Escherichia coli

<400> SEQUENCE: 16
atgcggttgt ctgcatttat cactttcttg aaaatgcgcc cgcaagtgcg cactgaattt 60
ttgactctgt tcatcagcct tgtgttcacc ctgctgtgca atggcgtgtt ttggaatgcc 120
cttcttgctg gacgcgactc cctaacttct ggaacatggc taatgctcct ttgcactggg 180
ttgctgatca ccgggctgca atggttgttg ctccttctgg tggccacgcg ctggagtgtc 240
aagccactac tgattctgct tgctgtcatg acgcccgccg ccgtttattt catgcgcaac 300
tacggggttt atctcgacaa ggccatgctg cggaatctga tggagacgga cgtcagggaa 360
gccagtgagc tgttgcaatg gagaatgctg ccctacttgt tggttgcagc cgtatccgtg 420
tggtggattg cgagagtcag ggttttacga acgggctgga aacaagcggt aatgatgcgc 480
agcgcttgtc tggctggcgc tctcgccatg atttccatgg gtctgtggcc agtcatggat 540
gtgctgatac ccacgcttcg tgaaaacaag ccgcttcgct atttgatcac tcctgcaaac 600
tacgtcatct cgggcattcg ggttttgact gaacaggcgt catcgtcagc agacgaagca 660
agggaagtcg ttgcagccga tgcgcatcga gggcctcaag aacaaggccg ccgtcctcgt 720
gctctcgtac tggttgtcgg ggaaaccgtc agggcggcta attgggggtt gagcggctat 780
gaacgacaaa ccacccctga gttggccgca cgcgacgtga tcaatttttc cgatgtcacc 840
agttgcggga cggatacggc tacatccctt ccctgcatgt tttccctcaa tggtcggcgc 900
gactacgacg aacgccagat tcgtcggcgc gagtccgtgc tgcacgtttt aaaccgtagt 960
gacgtcaaca ttctctggcg cgataaccag tcgggctgta aaggcgtctg tgatggactg 1020
ccctttgaaa acctgtcttc ggcaggccat cccacactgt gccatggcga gcgctgcctg 1080
gatgaaattc tgctcgaagg gttggccgag aagataacaa caagccgcag cgatatgctg 1140
atcgttctgc atatgctggg caatcacggc ccagcgtatt tccagcgcta tcccgcaagc 1200
taccgacgct ggtcgccaac ctgcgacacc accgatctgg ccagctgttc gcatgaagcc 1260

-continued

```
ttggtgaaca cctacgacaa cgccgtgctt tacaccgatc atgtgcttgc ccgtaccatt   1320

gacctgctgt ccggcatccg ctcacacgac acggcgctgc tgtacgtttc cgatcatggg   1380

gaatcgctcg gcgagaaagg cctgtatctc catggcatac cttacgtcat cgcgccggat   1440

gagcagatca aggtgccgat gatctggtgg cagtcgagtc aggtttatgc cgaccaagcc   1500

tgtatgcaaa ctcatgcctc tcgggcaccg gtaagtcacg atcacctgtt tcacaccttg   1560

ctcgggatgt tcgacgtgaa aaccgctgcc tacacgccag agttggacct tctggcaaca   1620

tgcagaaaag gacaaccaca atga                                          1644
```

METHOD OF DETECTION

The present invention relates to detection of antibiotic resistant bacteria, in particular bacteria resistant to cyclic cationic polypeptide antibiotics.

The increasing trend in antibiotic resistance continues to threaten global health due to the limited pipeline of new antibiotics. Multidrug resistance in Gram-negative bacteria is of special concern since it may be associated, in single isolates, with resistance to the three main classes of antibiotics that are (i) the β-lactams with plasmid-encoded extended-spectrum β-lactamases (ESBLs) hydrolyzing cephalosporins and with carbapenemases hydrolyzing additionally carbapenems, (ii) the aminoglycosides with 16S rRNA methylases modifying their cellular target and conferring pan-aminoglycoside resistance, (iii) the fluoroquinolones mostly with topoisomerases mutations. Due to the paucity of remaining antibiotics for treating infections, cyclic cationic polypeptide antibiotics (e.g. polymyxins such as colistin and polymyxin B) have become the last resort in particular for treating infections due to carbapenem-resistant Enterobacteriaceae. In addition, these carbapenem-resistant Enterobacteriaceae are more and more prevalent worldwide leading to increased use of polymyxins as first line treatment for highly invasive infections (e.g. bacteriaemia) in "endemic" countries. For example, according to European Antimicrobial Resistance Surveillance Network (EARS-Net), the prevalence of carbapenem-resistant *Klebsiella pneumoniae* isolated from blood culture reached 35% in Italy and 63% in Greece in 2015 compared to 1.3% and 43.5% in 2009, respectively. Unfortunately, this increased resistance to carbapenems in Enterobacteriaceae, that led to an increased use of polymyxins, is strongly correlated with increased resistance to polymyxins.

Acquired resistance to colistin in Enterobacteriaceae results mostly from modification of the polymyxin target, the lipopolysaccharide. Lipopolysaccharide (LPS), composed of the O-antigen, the oligosaccharide core and the Lipid A, is the major surface glycolipid located in the outer membrane of Gram-negative bacteria. Polymyxins (e.g. Colistin, Polymyxin B and Polymyxin M) are antibiotics, with a general structure having a cyclic peptide with a hydrophobic tail. They disrupt the structure of the bacterial cell membrane by interacting with its phospholipids. After binding to lipopolysaccharide (LPS) in the outer membrane of Gram-negative bacteria, polymyxins disrupt both the outer and inner membranes. The hydrophobic tail is important in causing membrane damage, suggesting a detergent-like mode of action.

Addition of phosphoethanolamine, 4-amino-L-arabinose cationic groups, or both to lipopolysaccharide (e.g. to the Lipid A) decreases cyclic cationic peptide antibiotic (e.g. polymyxin) binding to the bacterial outer membrane. Addition of these groups may be due to chromosome-encoded mechanisms (e.g. mutations in the PmrAB or PhoPQ two-component systems or alterations of the mgrB gene). Such alteration leads to a lower negative charge of the outer membrane of the bacterium, leading to reduced interaction of this membrane with cyclic cationic peptide antibiotic (e.g. polymyxin). A recent report revealed that addition of phosphoethanolamine may also be plasmid mediated through the mcr-1 gene, which confers the first known plasmid-encoded resistance to colistin in isolates from humans and animals. More recently, the mcr-1 gene was identified in several plasmid backbones, mostly in *Escherichia coli*. There is therefore an urgent need for a test that enables rapid detection of polymyxin resistance in bacteria (e.g. Enterobacteriaceae) and that may contribute to its containment.

The standard reference technique for determining susceptibility to polymyxins is broth microdilution, which requires fastidious attention and a long time (24 h) to perform. Other techniques for determining susceptibility to polymyxins (disk diffusion and Etest) have been proposed but require 18-24 hours to yield results. Because of poor diffusion of polymyxin molecules in agar, rates of false susceptibility are high (up to 32%).

A biochemical test (the rapid polymyxin NP test) that detects bacterial growth in the presence of a defined concentration of a polymyxin has also been used. In this colorimetric test, bacterial growth detection (or absence) is based on carbohydrate metabolism. Acid formation associated with carbohydrate metabolism in Enterobacteriaceae can be observed through the color change of a pH indicator. The interpretation of results of this test is subjective, leading to issues with reproducibility, and requiring more vigilance from laboratory technicians leading to reading errors. Whilst an improvement on other conventional methods, this biochemical test can take as long as 2 hours to yield a result.

Due to the variety of genes that can be involved in cyclic cationic peptide antibiotic (e.g. polymyxin) resistance (e.g. plasmid-encoded mcr-like genes, such as mcr-1 and mcr-2, share only 79% identity; and the chromosome encoded genes related to polymyxin resistance are numerous), the use of molecular biology tools (e.g. amplification and sequencing of target genes) for the detection of polymyxin resistant bacteria is unreliable. For chromosome-encoded genes associated with polymyxin resistance, the gene modifications (disruptions, deletions mutations) involved are also not systematically described nor characterized. As for plasmid-encoded resistance, five families of mcr genes are known in Enterobacteriaceae. MCR-2, MCR-3, MCR-4 and MCR-5 share only 81%, 34%, 33% and 31% amino acid identity with MCR-1, respectively. This diversity would inevitably lead to failure in systematic detection of polymyxin resistance, when relying on using available molecular biology tools dedicated to mcr-1 and/or mcr-2 detection.

Other conventional approaches have employed the use of mass-spectrometry (MS). In fact, MS has emerged as a standard technique available in most clinical laboratories. The "Bioyper" systems from Bruker and the "VITEK-MS" systems from bioMerieux are examples of standard mass spectrometry systems and have been used for bacteria identification based on the mass spectrum profile obtained using Matrix-Assisted Laser Desorption Ionization Time Of Flight Mass Spectrometry (MALDI-TOF MS). The system allows discrimination of bacteria mainly based on proteins. Indeed, all current diagnostic MS applications rely on the profiling of proteins. This is because proteins can be more easily ionized than hydrophobic and strongly hydrophilic molecules such as lipids and polysaccharides respectively. Therefore, the analysis of LPS and the modification of LPS composition on bacteria, which occurs during cyclic cationic peptide antibiotic (e.g. polymyxin) resistance, through conventional MALDI-TOF MS is challenging.

Recently, this technology has also been developed to detect antimicrobial resistance mechanisms (e.g. to the β-lactam antibiotic) by detecting the presence or absence of some β-lactamases (e.g. ESBL or carbapenemase). Here, the degradation (meaning hydrolysis) of the β-lactam is followed by MS analysis to generate a mass spectrum—absence of the peak corresponding to the native β-lactam indicates antimicrobial resistance to β-lactam antibiotics. However, in the case of polymyxin, resistance is not due to the modifications or destruction of the antibiotic itself—therefore the strategy to detecting polymyxin modification or destruction using MALDI-TOF MS to detect polymyxin resistant bacteria is not applicable.

To-date, the use of mass spectrometry (e.g. MALDI-TOF MS) based methods for the detection of Lipid A and modified Lipid A has required the purification of the actual molecule (Lipid A) from large amounts of culture (e.g. from 500 ml up to several litres). The global procedure takes approximately 2 to 3 weeks which is not compatible with clinic analysis. Thus, the conventional methods are costly and/or time-consuming and/or inefficient for the detection of cyclic cationic polypeptide antibiotic (e.g. polymyxin) resistant bacteria in a sample and require a significant amount of skilled labour and costly equipment. No current MS based method is adequate for detecting cyclic cationic polypeptide antibiotic (e.g. polymyxin) resistant bacteria in a crude sample comprising intact bacteria.

The present invention solves at least one (e.g. more than one) of the above mentioned problems, by allowing cyclic cationic polypeptide antibiotic resistant bacteria detection in a sample comprising an intact bacterium, or bacterial membranes. The present invention is therefore uniquely compatible with the clinic (e.g. clinical analysis) and may allow detection of a cyclic cationic polypeptide antibiotic (e.g. polymyxin) resistant bacterium in less than 15 minutes.

Advantageously, said method does not require the purification of a Lipid A molecule, and indeed allows the identification of any Lipid A and any modified Lipid A directly on intact bacteria or in an unpurified sample containing bacterial membranes or fragments thereof. Furthermore, the present method is can be used with a small bacterial sample (e.g. comprising fewer than $10^7$ bacterial cells). This allows the time and materials required to detect the presence or absence of a bacterium resistant to a cyclic cationic polypeptide antibiotic in a sample to be greatly reduced.

Advantageously, the method allows for the detection of both plasmid encoded and chromosome encoded cyclic cationic polypeptide antibiotic resistant bacteria in a single analysis. For example, wherein the bacteria have been isolated from an infected patient, this allows patients infected with such bacteria to be separated, for example for the quarantine of patients infected with plasmid encoded polymyxin resistant bacteria. Further, the detection of chromosome encoded cyclic cationic polypeptide antibiotic resistant bacteria through a method of the present invention, advantageously providing information on the physiological state of Lipid A, circumvents the need for molecular analysis of samples requiring the amplification and sequencing of many genes whose mutation may give rise to cyclic cationic polypeptide antibiotic resistance.

The present invention provides rapid (15-minute) and accurate methods (e.g. diagnostic methods), providing major advances for the detection of polymyxin resistance by directly assessing Lipid A modifications, the cellular target of the polymyxins, on intact bacteria. The combination of excellent performance, cost-effectiveness and high-throughput scalability are all desirable attributes distinguishing the present methods from the prior art. Finally, the methods of the present invention use technology that is already available in many clinical microbiology laboratories, thus allowing no-cost and hassle free implementation.

In one aspect of the invention, there is provided a method for detecting the presence or absence of a bacterium resistant to a cyclic cationic polypeptide antibiotic, comprising:

a. subjecting a test sample to mass spectrometry analysis and generating a mass spectrum output;
b. identifying in said mass spectrum output a first defined peak indicative of the presence of Lipid A modified by phosphoethanolamine, wherein said first defined peak is a peak present in a mass spectrum output for Lipid A modified by phosphoethanolamine and wherein said first defined peak is absent from a corresponding mass spectrum output for native Lipid A; and
c. wherein the presence of said first defined peak indicates the presence of a bacterium resistant to a cationic polypeptide antibiotic, and wherein the absence of said first defined peak indicates the absence of a bacterium resistant to a cyclic cationic polypeptide antibiotic.

In another aspect of the invention, there is provided a method for detecting the presence or absence of a bacterium resistant to a cyclic cationic polypeptide antibiotic, comprising:

a. subjecting a test sample to mass spectrometry analysis and generating a mass spectrum output;
    wherein said test sample comprises a bacterial membrane or a fragment thereof, wherein the fragment comprises a non-Lipid A component;
b. identifying in said mass spectrum output a first defined peak indicative of the presence of Lipid A modified by phosphoethanolamine, wherein said first defined peak is a peak present in a mass spectrum output for Lipid A modified by phosphoethanolamine and wherein said first defined peak is absent from a corresponding mass spectrum output for native Lipid A; and
c. wherein the presence of said first defined peak indicates the presence of a bacterium resistant to a cationic polypeptide antibiotic, and wherein the absence of said first defined peak indicates the absence of a bacterium resistant to a cyclic cationic polypeptide antibiotic.

The term "bacterium" as used herein refers to a Gram-negative bacterium. A bacterium may be an intact bacterium or a fragmented bacterium. The bacterium may have been subjected to any chemical (e.g. treatment with alkaline agents) or physical treatment (e.g. heating, vortexing or pipetting).

The term "test sample" as used herein is not a purified sample of native Lipid A or modified Lipid A. The "test sample" comprises a bacterial membrane or a fragment thereof. The bacterial membrane comprises a native Lipid A or a modified Lipid A. Suitably the bacterial membrane may comprise a modified Lipid A. Suitably, a native Lipid A or a modified Lipid A is present as an integral part of the bacterial membrane or a fragment thereof in the test sample.

Advantageously, the utilisation of a test sample comprising a bacterial membrane or a fragment thereof (e.g. a crude sample) in a method of the present invention avoids the need to purify Lipid A and/or modified Lipid A (e.g. from large volumes of bacterial culture) prior to the detection of said Lipid A molecules (e.g. by mass spectrometry). Thus, the present invention is distinguished from prior art methods which require purification (e.g. pre-purification) of Lipid A and/or modified Lipid A.

The term "fragment" as used in the context of a bacterial membrane refers to a fragment comprising a non-lipid A component optionally in combination with a native Lipid A or modified Lipid A. In one embodiment a "fragment" is a non-Lipid A component optionally in combination with a modified Lipid A.

In one embodiment, a bacterial membrane is part of an intact bacterium.

The "test sample" may be a biological sample such as a clinical sample. In one embodiment a test sample is whole blood, serum, plasma, oral samples such as saliva, pus, vaginal sample, stool samples, vomitus, cerebrospinal fluid, tear fluid, synovial fluid, sputum, prepared or processed clinical samples (e.g. for the removal of salt), environmental samples (e.g. water, soil, air samples), bulk liquids, culled animal material, pharmaceuticals and biological matrices. A test sample may be prepared, for example where appropriate diluted or concentrated, or dialysed and stored by standard means. A test sample typically comprises or is suspected of comprising a bacterium (between $10^1$ to $10^{10}$ bacterial cells). A test sample also encompasses tissue homogenates, tissue sections and biopsy specimens from a live subject, or taken post-mortem. Alternatively, a test sample may be a bacterial colony or suspension recovered from any bacterial growth medium or clinical sample, prepared or processed clinical sample or environmental sample as outlined above.

The test sample may comprise, or may be suspected of comprising a bacterium resistant to a cyclic cationic polypeptide antibiotic. Suitably, the test sample may comprise a bacterium resistant a cyclic cationic polypeptide antibiotic.

A biological sample may be a clinical sample. The clinical sample may be a clinical sample that has been subjected to one or more processing steps. For example, dialysis (e.g. to to reduce the concentration of a salt in said sample). In one embodiment, the test sample is processed to remove salt. The reduced concentration of salt may allow the prevention of undesirable non-Lipid A species detection on a mass spectrum, thus improving the interpretability of the mass spectrum. Standard techniques for reducing the concentration of a salt (e.g. dialysis) are known in the art. In one embodiment, the test sample is subjected to several rounds of washing (e.g. centrifuging and resuspension in a low salt buffer or in a no salt buffer). A test sample may comprise a salt concentration of less than 200 mM or 100 mM. Suitably, a test sample may comprise a salt concentration of less than 50 mM, 30 mM or 10 mM.

The term "detecting" as used herein means confirming the presence or absence of a cyclic cationic polypeptide antibiotic (e.g. polymyxin) resistant bacteria in a sample. Detecting may be performed on the test sample, or indirectly on an extract therefrom, or on a dilution or concentrate thereof. The term "identifying" as used herein means confirming the presence or absence of a peak assigned to a modified Lipid A in the mass spectrum output. Said identified peak also allows the quantification of the modified Lipid A. In methods of the invention, quantification may be performed by measuring the intensity (e.g. largest y-axis value) of a peak in a mass spectrum output.

The term "mass spectrometry analysis" encompasses any mass spectrometry technique suitable for the determination of the mass-to-charge ratio of a biological molecule, and embraces both negative and positive ion modes of mass spectrometry. Such mass spectrometry techniques include Matrix-assisted laser desorption/ionization time-of-flight mass spectrometry (MALDI-TOF MS), Surface Enhanced Laser Desorption Ionization time-of-flight mass spectrometry (SELDI-TOF MS), Accelerator Mass Spectrometry, Gas chromatography MS, liquid chromatography MS, Inductively coupled plasma MS, Isotope ratio mass spectrometry (IRMS), Rapid Evaporative Ionization Mass Spectrometry (REIMS), and Ion Mobility Spectrometry-MS. Preferably, mass spectrometry analysis comprises (or consists of) MALDI-TOF mass spectrometry.

MALDI is an ionization technique used in mass spectrometry, allowing the analysis of biomolecules (biopolymers such as DNA, proteins, peptides and sugars) and large organic molecules (such as polymers, dendrimers and other macromolecules), which tend to be fragile and fragment when ionized by other ionization methods. In one embodiment, the matrix solution acts as a proton source to encourage ionization of the analyte (e.g. Lipid A).

In one embodiment, mass spectrometry analysis comprises the ionisation of an analyte. In one embodiment, mass spectrometry analysis comprises the ionisation of Lipid A or a modified Lipid A.

The term "mass spectrum output" encompasses any data providing the mass-to-charge ratio (m/z) of a molecule (e.g. analyte) in a test sample together with an estimation of the quantity of said molecule in a test sample, for example across the range of 400 m/z to 30,000 m/z, 1,600 m/z to 2,200 m/z or 1,000 m/z to 3,000 m/z. The experimental procedure of the invention may be optimised to selectively provide the m/z of Lipid A molecules with minimal background (e.g. where "background" is m/z data on non-Lipid A species).

The term "native Lipid A" as used herein refers to a Lipid A that has not been modified, i.e. does not comprise a phosphoethanolamine and/or a 4-amino-L-arabinose modification. The term "native Lipid A" embraces (inter alia): hexa-acyl diphosphoryl Lipid A containing four C14:0 3-OH, one C14:0 and one C12:0; Lipid A with hydroxylation (—OH) of the C'-2 acyl-oxo-acyl chain; Lipid A with palmitoylation (—C-16) of the C-1 acyl-oxo-acyl chain; and Lipid A with hydroxylation (—OH) of the C'-2 acyl-oxo-acyl chain and palmitoylation (—C-16) of the C-1 acyl-oxo-acyl chain.

In one embodiment, native Lipid A comprises one or more of the following structures:

A

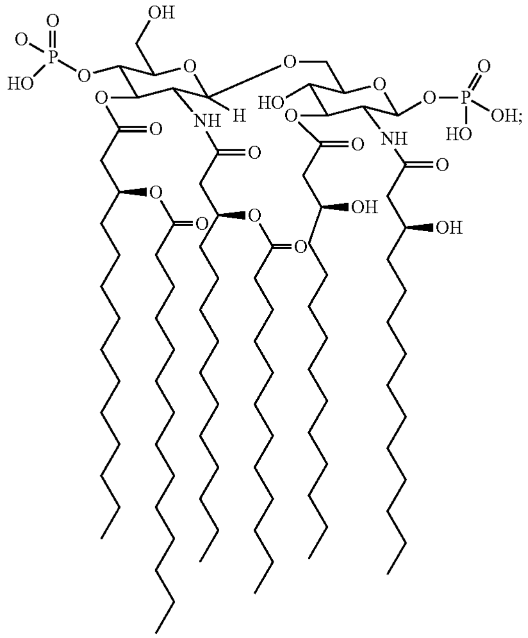

-continued

B

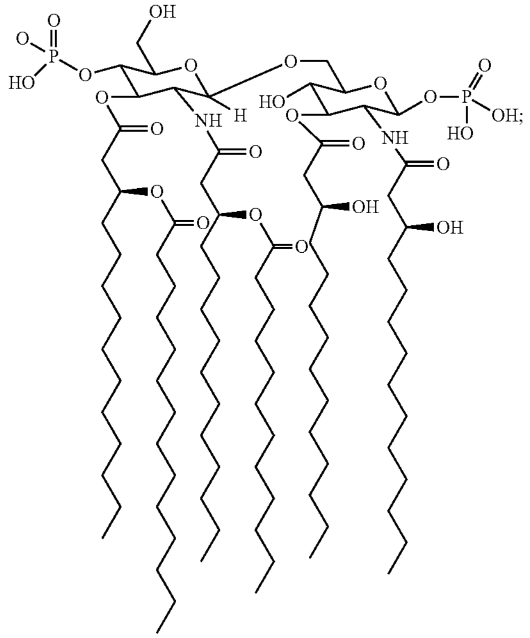

C

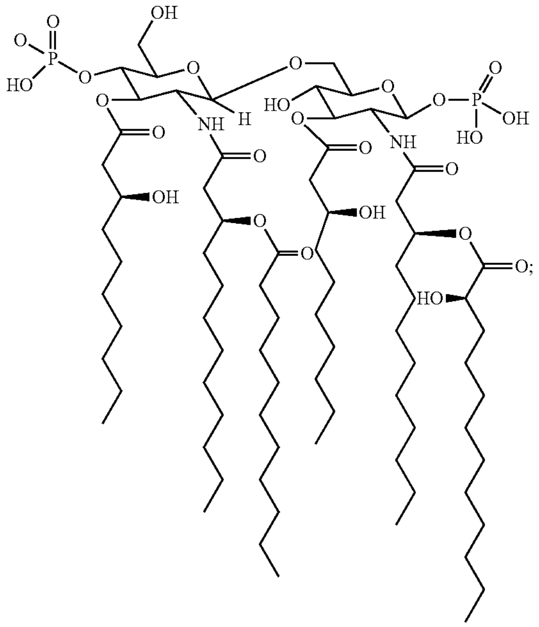

or

-continued

D

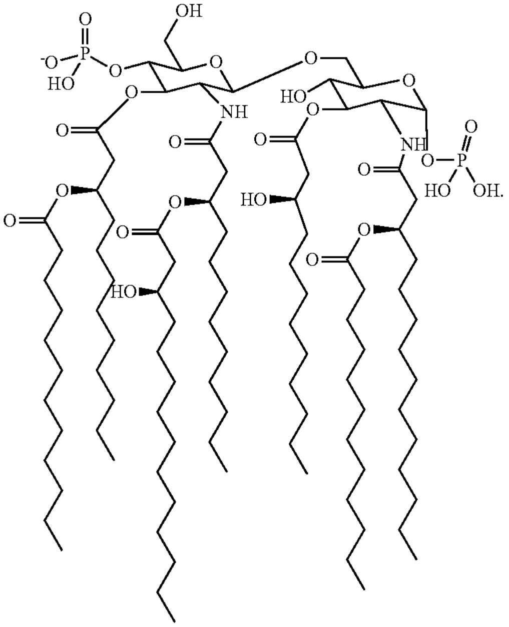

In embodiments where the bacterium is *Escherichia coli, Klebsiella* spp., *Shigella* spp., or *Salmonella* spp., native Lipid A comprises the structure as defined in (a) above.

In embodiments where the bacterium is *Klebsiella* spp, native Lipid A comprises the structure as defined in (b) above. In embodiments where the bacterium is *Pseudomonas aeruginosa*, native Lipid A comprises the structure as defined in (c) above.

In embodiments where the bacterium is *Acinetobacter baumannii*, native Lipid A comprises the structure as defined in (d) above.

In one embodiment, native Lipid A comprises one or more of the following structures:

A

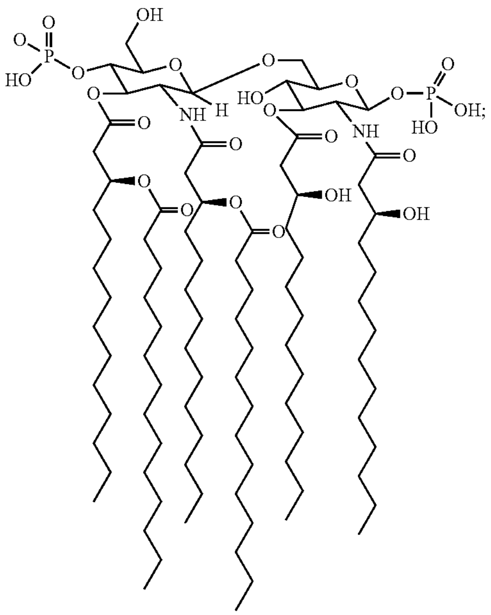

-continued

B

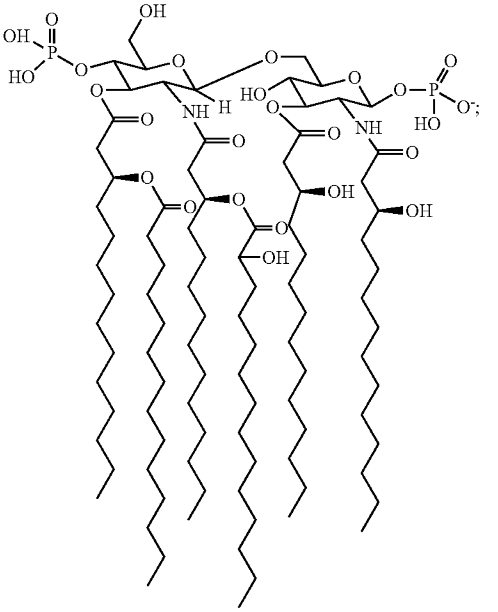

C

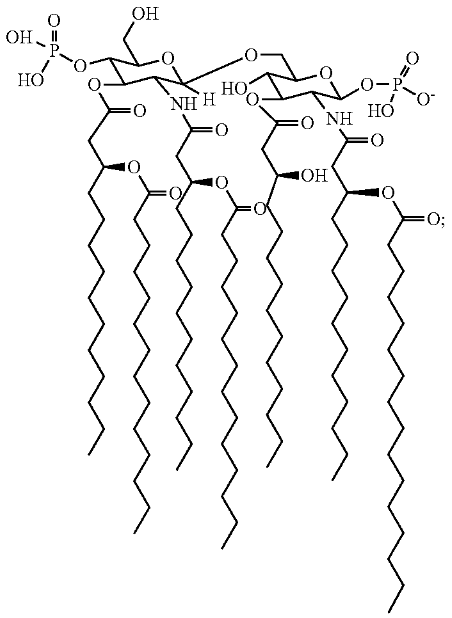

or

-continued

D

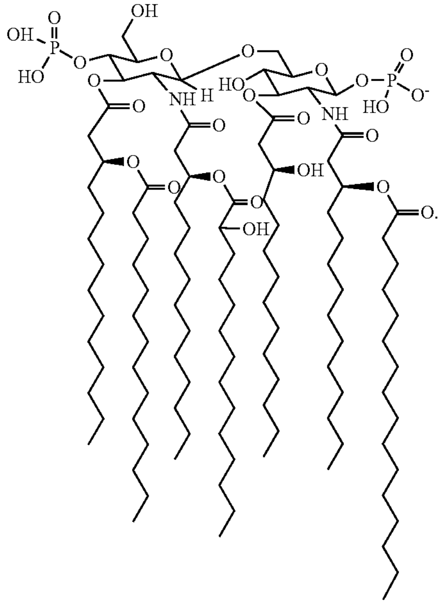

In embodiments where the bacterium is *Escherichia coli*, *Klebsiella* spp., *Shigella* spp., or *Salmonella* spp (preferably *Klebsiella* spp,), native Lipid A comprises the structure as defined in any one of (a)-(d) above.

In one embodiment, Lipid A with hydroxylation (—OH) of the C'-2 acyl-oxo-acyl chain comprises the structure as defined in (b) above. Suitably, said Lipid A comprises a mass-to-charge ratio (m/z) of about 1837 to about 1843 m/z, preferably 1840 m/z. In one embodiment, Lipid A with palmitoylation (—C-16) of the C-1 acyl-oxo-acyl chain comprises the structure as defined in (c) above. Suitably, said Lipid A comprises a mass-to-charge ratio (m/z) of about 2060 to about 2066 m/z, preferably 2063 m/z. In one embodiment, Lipid A with hydroxylation (—OH) of the C'-2 acyl-oxo-acyl chain and palmitoylation (—C-16) of the C-1 acyl-oxo-acyl chain comprises the structure as defined in (d) above. Suitably, said Lipid A comprises a mass-to-charge ratio (m/z) of about 2076 to about 2082 m/z, preferably 2079 m/z.

The term "modified Lipid A" as used herein refers to a Lipid A that has been modified with a phosphoethanolamine and/or a 4-amino-L-arabinose. 4-amino-L-arabinose may alternatively be referred to as 4-amino-4-deoxy-L-arabinose. Lipid A modified with 4-amino-L-arabinoase and/or phosphoethanolamine may be a biomarker of cyclic cationic polypeptide antibiotic (e.g. polymyxin) resistance.

The structure of Lipid A is known in the art and can vary between bacteria (e.g. between genera, species or strains). The present invention encompasses different structures of Lipid A comprising a phosphoethanolamine modification and/or a 4-amino-L-arabinose at the 4' phosphate and/or the 1' phosphate position.

"Modified Lipid A" (e.g. modified with 4-amino-L-arabinoase and/or phosphoethanolamine) is distinct (both structurally and functionally) from a native Lipid A. Without wishing to be bound by theory, it is believed that modification of Lipid A with phosphoethanolamine and/or a 4-amino-L-arabinose leads to a lower negative charge of the outer membrane of a bacterium, leading to reduced interaction of this membrane with a cyclic cationic peptide antibiotic (e.g. polymyxin). Said modification of Lipid A with phosphoethanolamine and/or a 4-amino-L-arabinose is believed to cause remodeling of the bacterial outer membrane and decreases membrane permeability. Advantageously, the present invention provides a method that surprisingly allows detection of both a native Lipid A and a modified Lipid A in a test sample comprising a bacterial membrane or a fragment thereof. The ability to detect both a native Lipid A and a modified Lipid A in the same test sample is particularly advantageous, as the relative amounts (e.g. concentrations) of a native Lipid A and a modified Lipid A in the same test sample may be directly compared and contrasted.

In one embodiment Lipid A modified with phosphoethanolamine comprises a modification with phosphoethanolamine at the 1' phosphate and/or 4' phosphate of Lipid A. Suitably, Lipid A modified with phosphoethanolamine comprises a modification with phosphoethanolamine at the 1' phosphate.

In one embodiment Lipid A modified with phosphoethanolamine comprises a modification with phosphoethanolamine at the 1' phosphate of Lipid A with concomitant loss of the 4' phosphate group. In another embodiment Lipid A modified with phosphoethanolamine comprises a modification with phosphoethanolamine at the 4' phosphate group of Lipid A with concomitant loss of the 1' phosphate group. Suitably, Lipid A modified with phosphoethanolamine comprises a modification with phosphoethanolamine at the 1' phosphate group of Lipid A with concomitant loss of the 4' phosphate group.

In one embodiment, Lipid A modified with 4-amino-L-arabinose comprises a modification with 4-amino-L-arabinose at the 1' phosphate of Lipid A. In one embodiment, Lipid A modified with 4-amino-L-arabinose comprises a modification with 4-amino-L-arabinose at the 4' phosphate of Lipid A. Suitably, Lipid A modified with 4-amino-L-arabinose comprises a modification with 4-amino-L-arabinose at the 4' phosphate of Lipid A.

In one embodiment, Lipid A modified with phosphoethanolamine and 4-amino-L-arabinose comprises a modification with phosphoethanolamine at the 1' phosphate and/or 4' phosphate of Lipid A. Suitably, Lipid A modified with phosphoethanolamine and 4-amino-L-arabinose comprises a modification with phosphoethanolamine at the 1' phosphate and a modification with 4-amino-L-arabinose at the 4' phosphate.

By way of example, an *Escherichia coli, Klebsiella* spp., *Shigella* spp., or *Salmonella* spp Lipid A modified by phosphoethanolamine and 4-amino-L-arabinose may comprise the following structure:

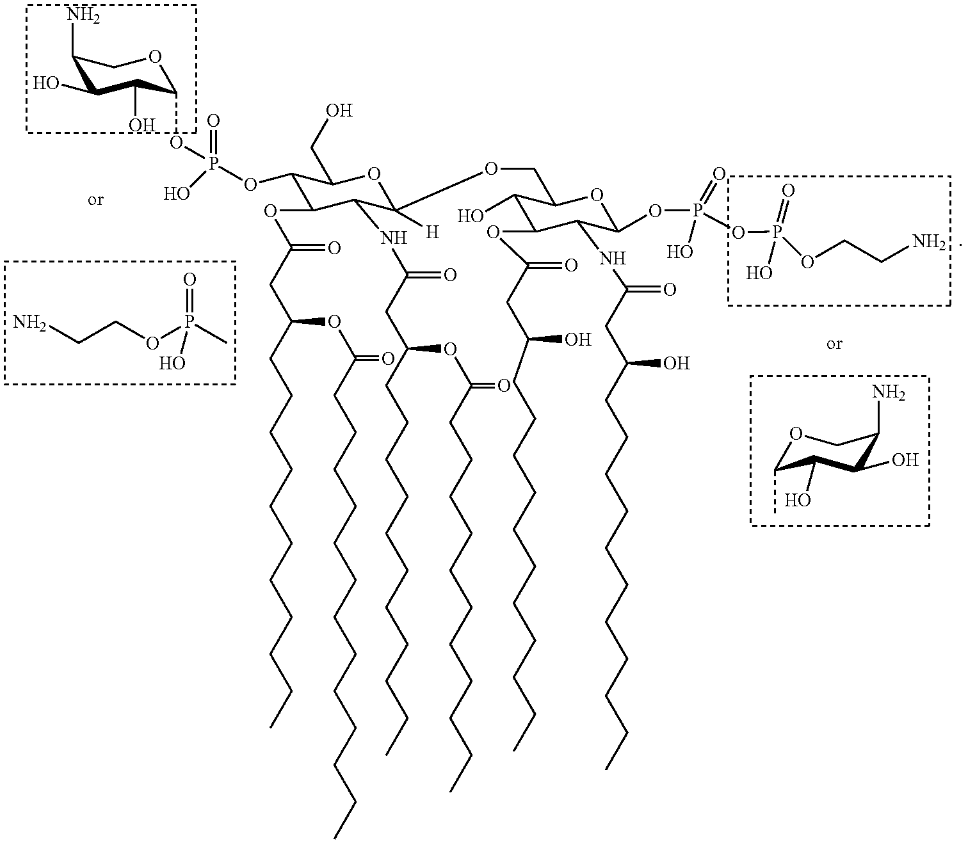

In one embodiment, Lipid A modified with 4-amino-L-arabinose comprises a modification with 4-amino-L-arabinose at the 1' phosphate and/or 4' phosphate of Lipid A, preferably at the 4' phosphate.

Preferably, Lipid A modified by phosphoethanolamine may comprise one or more of the following structures:

A

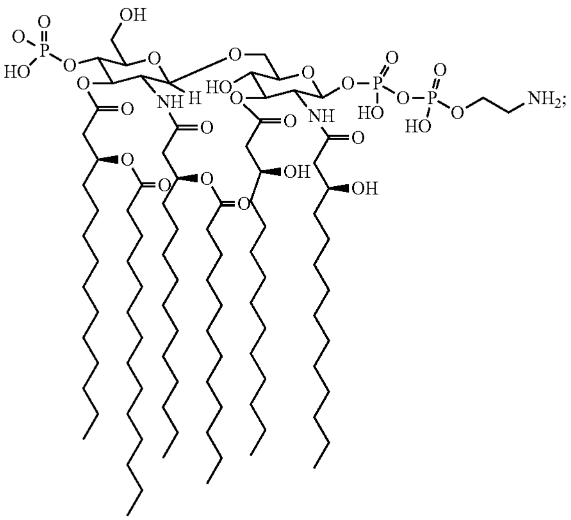

B

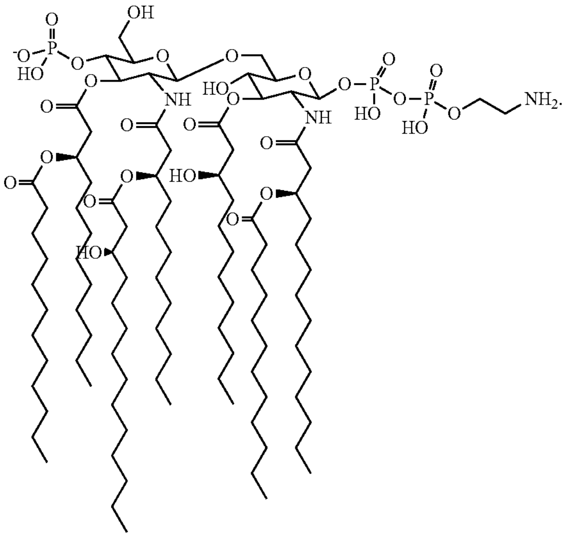

In embodiments where the bacterium is *Escherichia coli*, *Klebsiella* spp., *Shigella* spp., or *Salmonella* spp, Lipid A modified by phosphoethanolamine may comprise the structure as defined in (a) above. In embodiments where the bacterium is *Acinetobacter baumannii*, Lipid A modified by phosphoethanolamine may comprise the structure as defined in (b) above. In one embodiment, Lipid A modified by phosphoethanolamine and 4-amino-L-arabinose comprises the structure as defined above for *E. coli*, *Klebsiella* spp., *Shigella* spp., and *Salmonella* spp.

Preferably, Lipid A modified with 4-amino-L-arabinose may comprise one or more of the following structures:

A

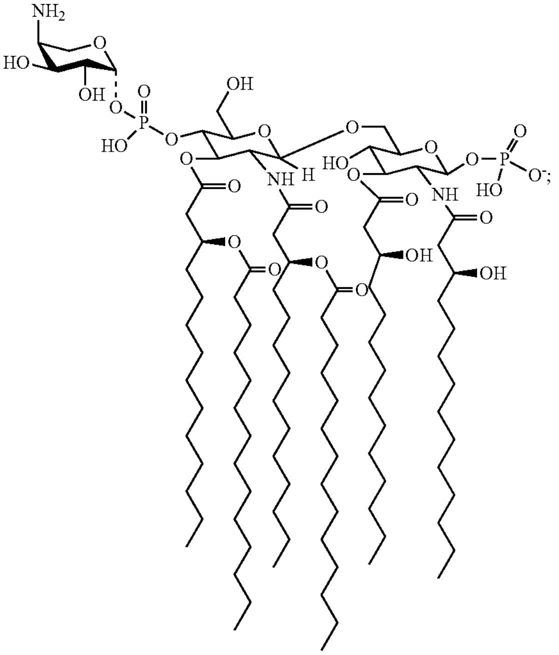

or

B

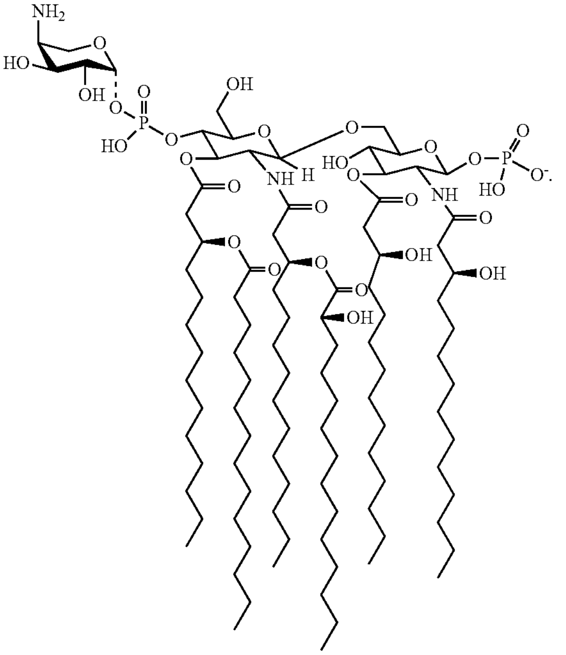

The method of the invention may be used for diagnosing infection of a subject with a bacterium resistant to a cyclic cationic polypeptide antibiotic through plasmid-encoded resistance, or infection of a subject with a bacterium resistant to a cyclic cationic polypeptide antibiotic through chromosome-encoded resistance.

The term "diagnosis" as used herein encompasses identification, confirmation and/or characterisation of cyclic cationic polypeptide resistant bacterial infections. Methods of diagnosis according to the invention are useful to confirm the existence of an infection. Methods of diagnosis are also useful in methods for assessment of clinical screening, prognosis, choice of therapy, evaluation of therapeutic benefit, i.e. for drug screening and drug development. Efficient diagnosis allows rapid identification of the most appropriate treatment (thus lessening unnecessary exposure to harmful drug side effects), and reducing relapse rates.

Also provided is a method for monitoring the efficacy of a therapy for cyclic cationic polypeptide antibiotic resistant bacterial infections, comprising identifying and/or quantifying the modified Lipid A in a test sample taken from a subject through a method of the present invention following therapy. In monitoring methods, test samples may be taken on one more occasion. The method may further comprise comparing the level of the modified Lipid A in a test sample with one or more control(s) and/or with one or more previous test sample(s) taken earlier from the same test subject, e.g. prior to commencement of therapy, and/or from the same test subject at an earlier stage of therapy. The method may comprise detecting a change in the level of a modified Lipid A in test samples taken on different occasions.

In one embodiment, the first defined peak indicative of the presence of Lipid A modified by phosphoethanolamine comprises a mass-to-charge ratio (m/z) of about 120 to about 125 m/z units (preferably about 123 m/z units) greater than a second defined peak indicative of the presence of native Lipid A.

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Klebsiella pneumoniae, Salmonella enterica, Enterobacter* spp. and *Klebsiella oxytoca;* b. a peak comprising a mass-to-charge ratio (m/z) of about 1820 to about 1826 m/z, preferably 1823.9 m/z, for *Klebsiella pneumoniae;* c. a peak comprising a mass-to-charge ratio (m/z) of about 1614 to about 1620 m/z, preferably 1617.2 m/z, for *Pseudomonas aeruginosa*; or d. a peak comprising a mass-to-charge ratio (m/z) of about 1907 to about 1913 m/z, preferably 1910.3 m/z, for *Acinetobacter baumannii.*

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Klebsiella pneumoniae, Salmonella enterica, Enterobacter* spp. and *Klebsiella oxytoca;* b. a peak comprising a mass-to-charge ratio (m/z) of about 1820 to about 1826 m/z, preferably 1823.9 m/z, for *Klebsiella pneumoniae;* c. a peak comprising a mass-to-charge ratio (m/z) of about 1837 to about 1843 m/z, preferably 1840 m/z, for *Klebsiella pneumoniae;* d. a peak comprising a mass-to-charge ratio (m/z) of about 1847 to about 1853 m/z, preferably 1850 m/z, for *Klebsiella pneumoniae;* e. a peak comprising a mass-to-charge ratio (m/z) of about 2059 to about 2065 m/z, preferably 2062 m/z, for *Klebsiella pneumoniae;* f. a peak comprising a mass-to-charge ratio (m/z) of about 2075 to about 2081 m/z, preferably 2078 m/z, for *Klebsiella pneumoniae;* g. a peak comprising a mass-to-charge ratio (m/z) of about 1614 to about 1620 m/z, preferably 1617.2 m/z, for *Pseudomonas aeruginosa;* h. a peak comprising a mass-to-charge ratio (m/z) of about 1907 to about 1913 m/z, preferably 1910.3 m/z, for *Acinetobacter baumannii.* i. a peak comprising a mass-to-charge ratio (m/z) of about 1793 to about 1799 m/z, preferably 1796.2 m/z, for *Salmonella* spp;

j. a peak comprising a mass-to-charge ratio (m/z) of about 1820 to about 1826 m/z, preferably 1824 m/z, for *Salmonella* spp; or k. a peak comprising a mass-to-charge ratio (m/z) of about 2031 to about 2037 m/z, preferably 2034 m/z, for *Salmonella* spp.

In one embodiment, native Lipid A comprises a mass-to-charge ratio (m/z) of about 1793 to about 1799 m/z, preferably about 1796.2 m/z for *Escherichia coli, Shigella, Klebsiella pneumoniae, Salmonella enterica, Enterobacter* spp. and *Klebsiella oxytoca*). In another embodiment, native Lipid A comprises a mass-to-charge ratio (m/z) of about 1820 to about 1826 m/z, preferably 1823.9 m/z for *Klebsiella pneumoniae.* In another embodiment, native Lipid A comprises a mass-to-charge ratio (m/z) of about 1837 to about 1843 m/z, preferably 1840 m/z for *Klebsiella pneumoniae.* In another embodiment, native Lipid A comprises a mass-to-charge ratio (m/z) of about 1847 to about 1853 m/z, preferably 1850 m/z for *Klebsiella pneumoniae.* In another embodiment, native Lipid A comprises a mass-to-charge ratio (m/z) of about 2059 to about 2065 m/z, preferably 2062 m/z for *Klebsiella pneumoniae.* In another embodiment, native Lipid A comprises a mass-to-charge ratio (m/z) of about 2075 to about 2081 m/z, preferably 2078 m/z for *Klebsiella pneumoniae.* In yet another embodiment, native Lipid A comprises a mass-to-charge ratio (m/z) of about 1614 to about 1620 m/z, preferably 1617.2 m/z, for *Pseudomonas aeruginosa.* In another embodiment, native Lipid A comprises a mass-to-charge ratio (m/z) of about 1907 to about 1913 m/z, preferably 1910.3 m/z, for *Acinetobacter baumannii.* In another embodiment, native Lipid A comprises a mass-to-charge ratio (m/z) of about 1793 to about 1799 m/z, preferably 1796.2 m/z, for *Salmonella* spp. In another embodiment, native Lipid A comprises a mass-to-charge ratio (m/z) of about 1820 to about 1826 m/z, preferably 1824 m/z, for *Salmonella* spp. In another embodiment, native Lipid A comprises a mass-to-charge ratio (m/z) of about 2031 to about 2037 m/z, preferably 2034 m/z, for *Salmonella* spp.

In some embodiments, the first defined peak indicative of the presence of Lipid A modified by phosphoethanolamine comprises a mass-to-charge ratio (m/z) of about 1960 to about 1966 m/z, preferably 1963 m/z for *Klebsiella pneumoniae*; between about 1970 to about 1976 m/z, preferably 1973 m/z for *Klebsiella pneumoniae*; between about 2182 to about 2188 m/z, preferably 2185 m/z for *Klebsiella pneumoniae*; between about 2198 to about 2204 m/z, preferably 2201 m/z for *Klebsiella pneumoniae*; between about 1918 and about 1920 m/z, preferably about 1919.2 m/z for *Salmonella* spp.; between about 1944 to about 1950 m/z, preferably 1947 m/z, for *Salmonella* spp. between about 2154 to about 2160 m/z, preferably 2157 m/z, for *Salmonella* spp.; between about 1913 and about 1924 m/z, or between about 1918 and about 1920 m/z, preferably about 1919.2 m/z for *Escherichia coli, Shigella, Klebsiella pneumoniae, Salmonella enterica, Enterobacter* spp., *Klebsiella oxytoca*; between about 1940 and about 1951 m/z, or between about 1946 and about 1947 m/z, preferably about 1946.9 m/z for *Klebsiella pneumoniae*; between about 1734 and about 1745 m/z, or between about 1939 and about 1741 m/z, preferably about 1740.2 m/z for *Pseudomonas aerugi-*

*nosa*; and between about 2027 and about 2038 m/z, or between about 2032 and about 2034 m/z, preferably about 2033.3 m/z for *Acinetobacter baumannii.*

In some embodiments, the first defined peak indicative of the presence of Lipid A modified by phosphoethanolamine comprises a mass-to-charge ratio (m/z) of between about 1913 and about 1924 m/z, or between about 1918 and about 1920 m/z, preferably about 1919.2 m/z for *Escherichia coli, Shigella, Klebsiella pneumoniae, Salmonella enterica, Enterobacter* spp., *Klebsiella oxytoca*; between about 1940 and about 1951 m/z, or between about 1946 and about 1947 m/z, preferably about 1946.9 m/z for *Klebsiella pneumoniae*; between about 1734 and about 1745 m/z, or between about 1939 and about 1741 m/z, preferably about 1740.2 m/z for *Pseudomonas aeruginosa*; and between about 2027 and about 2038 m/z, or between about 2032 and about 2034 m/z, preferably about 2033.3 m/z for *Acinetobacter baumannii.*

In one embodiment, native Lipid A comprises a mass-to-charge ratio (m/z) of between about 1793 to about 1799 m/z, preferably 1796.2 m/z and a first defined peak indicative of the presence of Lipid A modified by phosphoethanolamine comprises a mass-to-charge ratio (m/z) of between about 1913 and about 1924 m/z, or between about 1918 and about 1920 m/z, preferably about 1919.2 m/z for *Escherichia coli, Shigella, Klebsiella pneumoniae, Salmonella enterica, Enterobacter* spp., *Klebsiella oxytoca*. In another embodiment, native Lipid A comprises a mass-to-charge ratio (m/z) of between about 1820 to about 1826 m/z, preferably 1823.9 m/z and a first defined peak indicative of the presence of Lipid A modified by phosphoethanolamine comprises a mass-to-charge ratio (m/z) of between about 1940 and about 1951 m/z, or between about 1946 m/z and about 1947 m/z, preferably about 1946.9 m/z for *Klebsiella pneumoniae*. In yet another embodiment, native Lipid A comprises a mass-to-charge ratio (m/z) of between about 1614 to about 1620 m/z, preferably 1617.2 m/z, and a first defined peak indicative of the presence of Lipid A modified by phosphoethanolamine comprises a mass-to-charge ratio (m/z) of between about 1734 and about 1745 m/z, or between about 1939 and about 1741 m/z, preferably about 1740.2 m/z for *Pseudomonas aeruginosa*. In another embodiment, native Lipid A comprises a mass-to-charge ratio (m/z) of between about 1907 to about 1913 m/z, preferably 1910.3 m/z, and a first defined peak indicative of the presence of Lipid A modified by phosphoethanolamine comprises a mass-to-charge ratio (m/z) between about 2027 and about 2038 m/z, or between about 2032 and about 2034 m/z, preferably about 2033.3 m/z for *Acinetobacter baumannii*. In another embodiment, native Lipid A comprises a mass-to-charge ratio (m/z) of about 1837 to about 1843 m/z, preferably 1840 m/z for *Klebsiella pneumoniae* and a first defined peak indicative of the presence of Lipid A modified by phosphoethanolamine comprises a mass-to-charge ratio (m/z) of about 1960 to about 1966 m/z, preferably 1963 m/z for *Klebsiella pneumoniae*. In another embodiment, native Lipid A comprises a mass-to-charge ratio (m/z) of about 1847 to about 1853 m/z, preferably 1850 m/z for *Klebsiella pneumoniae* and a first defined peak indicative of the presence of Lipid A modified by phosphoethanolamine comprises a mass-to-charge ratio (m/z) of between about 1970 to about 1976 m/z, preferably 1973 m/z for *Klebsiella pneumoniae*. In another embodiment, native Lipid A comprises a mass-to-charge ratio (m/z) of about 2059 to about 2065 m/z, preferably 2062 m/z for *Klebsiella pneumoniae* and a first defined peak indicative of the presence of Lipid A modified by phosphoethanolamine comprises a mass-to-charge ratio (m/z) of between about 2182 to about 2188 m/z, preferably 2185 m/z for *Klebsiella pneumoniae*. In another embodiment, native Lipid A comprises a mass-to-charge ratio (m/z) of about 2075 to about 2081 m/z, preferably 2078 m/z for *Klebsiella pneumoniae* and a first defined peak indicative of the presence of Lipid A modified by phosphoethanolamine comprises a mass-to-charge ratio (m/z) of between about 2198 to about 2204 m/z, preferably 2201 m/z for *Klebsiella pneumoniae*.

In another embodiment, native Lipid A comprises a mass-to-charge ratio (m/z) of about 1793 to about 1799 m/z, preferably 1796.2 m/z, for *Salmonella* spp and a first defined peak indicative of the presence of Lipid A modified by phosphoethanolamine comprises a mass-to-charge ratio (m/z) of between about 1918 and about 1920 m/z, preferably about 1919.2 m/z for *Salmonella* spp. In another embodiment, native Lipid A comprises a mass-to-charge ratio (m/z) of about 1820 to about 1826 m/z, preferably 1824 m/z, for *Salmonella* spp and a first defined peak indicative of the presence of Lipid A modified by phosphoethanolamine comprises a mass-to-charge ratio (m/z) of between about 1944 to about 1950 m/z, preferably 1947 m/z, for *Salmonella* spp. In another embodiment, native Lipid A comprises a mass-to-charge ratio (m/z) of about 2031 to about 2037 m/z, preferably 2034 m/z, for *Salmonella* spp and a first defined peak indicative of the presence of Lipid A modified by phosphoethanolamine comprises a mass-to-charge ratio (m/z) of between about 2154 to about 2160 m/z, preferably 2157 m/z, for *Salmonella* spp.

Intensity may be normalised to native Lipid A. In one embodiment, a ratio between a defined peak and native Lipid A may be calculated.

The term "intensity" refers to the highest value of a peak along the y-axis of a mass spectrum output, representing signal intensity of the ion (e.g. analyte).

The skilled person appreciates that a "peak" on a mass spectrum has a de minimus intensity value above the background. In one embodiment, a peak may be any m/z value(s) having an intensity of at least twice (e.g. 2×) the intensity of the average intensity of background peaks. Suitably, a peak may be any m/z value(s) having an intensity of at least six times (e.g. 6×) or eight times (e.g. 8×) the intensity of the average intensity of background peaks. Suitably, a peak may be any m/z value(s) having an intensity of at least ten times (e.g. 10×) or twelve times (e.g. 12×) the intensity of the average intensity of background peaks.

In one embodiment a ratio of intensity of the first defined peak (indicative of the presence of Lipid A modified by phosphoethanolamine) to the second defined peak (indicative of the presence of native Lipid A) is least 0.10.

Suitably, the ratio of intensity of the first defined peak (indicative of the presence of Lipid A modified by phosphoethanolamine) to the second defined peak may be at least about 0.10:1, 0.15:1, 0.30:1. 0.45:1, 1:1, 1.15:1, 1.30:1, 1.45:1, 2:1, 2.15:1, 2.30:1 or 2.45:1. Preferably, the ratio may be between 0.15:1 and 2.5:1, or the ratio may be between 0.15:1 and 1:1.

Advantageously, a ratio of at least about 0.10 as described above indicates the presence of bacterium resistant to a cyclic cationic polypeptide antibiotic (e.g. polymyxin). Calculation of this ratio may prevent false-positive detection of the presence of a bacterium resistant to a cyclic cationic polypeptide antibiotic (e.g. due to background peaks).

In one embodiment, a method of the invention further comprises identifying in a mass spectrum output a third defined peak comprising a mass-to-charge ratio (m/z) of about 22 to about 28 m/z units (preferably 25 m/z units) greater than a second defined peak. Without wishing to be bound by theory, it is believed that such a third defined peak is only detecting in a test sample comprising a bacterium resistant to a cyclic cationic polypeptide antibiotic through plasmid-encoded resistance. Advantageously, the methods of the invention thus allow for the detection of both plasmid encoded and chromosome encoded cyclic cationic polypeptide antibiotic resistant bacteria in a single analysis. For example, wherein the bacteria have been isolated from an infected patient, this allows patients infected with such bacteria to be separated, for example for the quarantine of patients infected with plasmid encoded polymyxin resistant bacteria.

In one embodiment, said third defined peak as identified in a mass spectrum output in any method of the present invention is indicative of the presence of Lipid A modified by phosphoethanolamine. In a preferable embodiment, said third defined peak as identified in a mass spectrum output in any method of the present invention is indicative of the presence Lipid A modified by phosphoethanolamine at the 1' phosphate group of Lipid A with concomitant loss of the 4' phosphate group.

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Salmonella enterica, Enterobacter* spp. and *Klebsiella oxytoca;*
b. a peak comprising a mass-to-charge ratio (m/z) of about 1820 to about 1826 m/z, preferably 1823.9 m/z, for *Klebsiella pneumoniae.*
c. peak comprising a mass-to-charge ratio (m/z) of about 1837 to about 1843 m/z, preferably 1840 m/z, for *Klebsiella pneumoniae;*
d. peak comprising a mass-to-charge ratio (m/z) of about 1847 to about 1853 m/z, preferably 1850 m/z, for *Klebsiella pneumoniae;*
e. peak comprising a mass-to-charge ratio (m/z) of about 2059 to about 2065 m/z, preferably 2062 m/z, for *Klebsiella pneumoniae;*
f. a peak comprising a mass-to-charge ratio (m/z) of about 2075 to about 2081 m/z, preferably 2078 m/z, for *Klebsiella pneumoniae;*
g. a peak comprising a mass-to-charge ratio (m/z) of about 1793 to about 1799 m/z, preferably 1796.2 m/z, for *Salmonella* spp;
h. a peak comprising a mass-to-charge ratio (m/z) of about 1820 to about 1826 m/z, preferably 1824 m/z, for *Salmonella* spp; or
i. a peak comprising a mass-to-charge ratio (m/z) of about 2031 to about 2037 m/z, preferably 2034 m/z, for *Salmonella* spp.

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Salmonella enterica, Enterobacter* spp. and *Klebsiella oxytoca;*
b. a peak comprising a mass-to-charge ratio (m/z) of about 1820 to about 1826 m/z, preferably 1823.9 m/z, for *Klebsiella pneumoniae.*

In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1793 to about 1799 m/z, or between about 1796 to about 1797 m/z, preferably 1796.2 m/z, for *Escherichia coli, Shigella, Klebsiella pneumoniae, Salmonella enterica, Enterobacter* spp. and *Klebsiella oxytoca*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1820 to about 1826 m/z, preferably 1823.9 m/z, for *Klebsiella pneumoniae*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1837 to about 1843 m/z, preferably 1840 m/z, for *Klebsiella pneumoniae*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1847 to about 1853 m/z, preferably 1850 m/z, for *Klebsiella pneumoniae*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 2059 to about 2065 m/z, preferably 2062 m/z, for *Klebsiella pneumoniae*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 2075 to about 2081 m/z, preferably 2078 m/z, for *Klebsiella pneumoniae*. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1793 to about 1799 m/z, preferably 1796.2 m/z, for *Salmonella* spp. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 1820 to about 1826 m/z, preferably 1824 m/z, for *Salmonella* spp. In one embodiment, a third defined peak comprises a mass-to-charge ratio (m/z) of between about 22 and about 28 m/z units, preferably about 25 m/z units, greater than a second defined peak, wherein a second defined peak comprises a mass-to-charge ratio (m/z) of between about 2031 to about 2037 m/z, preferably 2034 m/z, for *Salmonella* spp.

In one embodiment, a third defined peak is selected from the group consisting of:

a. a peak comprising a mass-to-charge ratio (m/z) of about 1818 to about 1824 m/z, preferably 1821 m/z, for *Escherichia coli, Shigella, Klebsiella pneumoniae, Salmonella enterica, Enterobacter* spp. and *Klebsiella oxytoca;*
b. a peak comprising a mass-to-charge ratio (m/z) of about 1845 to about 1852 m/z, preferably 1848.9 m/z, for *Klebsiella pneumoniae;*
c. peak comprising a mass-to-charge ratio (m/z) of about 1863 to about 1868 m/z, preferably 1865 m/z, for *Klebsiella pneumoniae;*
d. peak comprising a mass-to-charge ratio (m/z) of about 1872 to about 1878 m/z, preferably 1875 m/z, for *Klebsiella pneumoniae;* e. peak comprising a mass-to-charge ratio (m/z) of about 2084 to about 2090 m/z, preferably 2087 m/z, for *Klebsiella pneumoniae;* f. a peak comprising a mass-to-charge ratio (m/z) of about 2100 to about 2105 m/z, preferably 2103 m/z, for *Klebsiella pneumoniae;* g. a peak comprising a mass-to-charge ratio (m/z) of about 1818 to about 1824 m/z, preferably 1821.2 m/z, for *Salmonella* spp;

h. a peak comprising a mass-to-charge ratio (m/z) of about 1846 to about 1852 m/z, preferably 1849 m/z, for *Salmonella* spp; or i. a peak comprising a mass-to-charge ratio (m/z) of about 2056 to about 2062 m/z, preferably 2059 m/z, for *Salmonella* spp.

In one embodiment, native Lipid A (second defined peak) comprises a mass-to-charge ratio (m/z) of between about 1793 to about 1799 m/z, preferably 1796.2 m/z and a third defined peak comprises a mass-to-charge ratio (m/z) of between about 1818 to about 1824 m/z, preferably about 1821 m/z for *Escherichia coli, Shigella, Salmonella enterica, Enterobacter* spp. and *Klebsiella oxytoca*. In one embodiment, native Lipid A (second defined peak) comprises a mass-to-charge ratio (m/z) of between about 1820 to about 1826 m/z, preferably 1823.9 m/z and a third defined peak comprises a mass-to-charge ratio (m/z) of between 1845 to about 1852 m/z, preferably 1848.9 m/z, for *Klebsiella pneumoniae*. In one embodiment, native Lipid A (second defined peak) comprises a mass-to-charge ratio (m/z) of between about 1837 to about 1843 m/z, preferably 1840 m/z and a third defined peak comprises a mass-to-charge ratio (m/z) of between 1863 to about 1868 m/z, preferably 1865 m/z, for *Klebsiella pneumoniae*.

In one embodiment, native Lipid A (second defined peak) comprises a mass-to-charge ratio (m/z) of between about 1847 to about 1853 m/z, preferably 1850 m/z and a third defined peak comprises a mass-to-charge ratio (m/z) of between about 1872 to about 1878 m/z, preferably 1875 m/z, for *Klebsiella pneumoniae*. In one embodiment, native Lipid A (second defined peak) comprises a mass-to-charge ratio (m/z) of between about 2059 to about 2065 m/z, preferably 2062 m/z and a third defined peak comprises a mass-to-charge ratio (m/z) of between about 2084 to about 2090 m/z, preferably 2087 m/z, for *Klebsiella pneumoniae*. In one embodiment, native Lipid A (second defined peak) comprises a mass-to-charge ratio (m/z) of between about 2075 to about 2081 m/z, preferably 2078 m/z and a third defined peak comprises a mass-to-charge ratio (m/z) of between about 2100 to about 2105 m/z, preferably 2103 m/z, for *Klebsiella pneumoniae*. In one embodiment, native Lipid A (second defined peak) comprises a mass-to-charge ratio (m/z) of between about 1793 to about 1799 m/z, preferably 1796.2 m/z and a third defined peak comprises a mass-to-charge ratio (m/z) of between about 1818 to about 1824 m/z, preferably 1821.2 m/z, for *Salmonella* spp. In one embodiment, native Lipid A (second defined peak) comprises a mass-to-charge ratio (m/z) of between about 1820 to about 1826 m/z, preferably 1824 m/z and a third defined peak comprises a mass-to-charge ratio (m/z) of between about 1846 to about 1852 m/z, preferably 1849 m/z, for *Salmonella* spp. In one embodiment, native Lipid A (second defined peak) comprises a mass-to-charge ratio (m/z) of between about 1820 to about 1826 m/z, preferably 1824 m/z and a third defined peak comprises a mass-to-charge ratio (m/z) of between about 1846 to about 1852 m/z, preferably 1849 m/z, for *Salmonella* spp. In one embodiment, native Lipid A (second defined peak) comprises a mass-to-charge ratio (m/z) of between about 2031 to about 2037 m/z, preferably 2034 m/z and a third defined peak comprises a mass-to-charge ratio (m/z) of between 2056 to about 2062 m/z, preferably 2059 m/z, for *Salmonella* spp.

Advantageously, identification of the presence of the third defined as described above indicates the presence of a bacterium resistant to a cyclic cationic polypeptide antibiotic through plasmid-encoded resistance, preferably wherein said bacterium is of the family Enterobacteriaceae. Likewise, absence of the third defined peak may indicate the absence of a bacterium resistant to a cyclic cationic polypeptide through plasmid encoded resistance, preferably wherein said bacterium is of the family Enterobacteriaceae.

In one embodiment, the presence of said third defined peak indicates the presence of a bacterium of the family Enterobacteriaceae (e.g. *Escherichia coli, Klebsiella pneumoniae, Klebsiella oxytoca, Enterobacter aerogenes, Enterobacter cloacae, Enterobacter asburiae, Shigella sonnei, Shigella flexneri, Salmonella enterica, Citrobacter freundii, Citrobacter koseri, Citrobacter amalonaticus* or *Citrobacter youngae*) resistant to a cyclic cationic polypeptide antibiotic through plasmid-encoded resistance.

In another aspect of the invention, there is provided a method for detecting the presence or absence of a bacterium resistant to a cyclic cationic polypeptide antibiotic, comprising:

a. subjecting a test sample to mass spectrometry analysis and generating a mass spectrum output;

wherein said test sample comprises a bacterial membrane or a fragment thereof, wherein the fragment comprises a non-Lipid A component;

b. identifying in said mass spectrum output a first defined peak and/or a third defined peak indicative of the presence of Lipid A modified by phosphoethanolamine, wherein said first defined peak and/or third defined peak is a peak present in a mass spectrum output for Lipid A modified by phosphoethanolamine and wherein said first defined peak and or/said third defined peak is absent from a corresponding mass spectrum output for native Lipid A; and c. wherein the presence of said first defined peak indicates the presence of a bacterium resistant to a cationic polypeptide antibiotic, and wherein the absence of said first defined peak indicates the absence of a bacterium resistant to a cyclic cationic polypeptide antibiotic; and/or wherein the presence of said third defined peak indicates the presence of a bacterium resistant to a cationic polypeptide antibiotic through plasmid-encoded resistance, and wherein the absence of said third defined peak indicates the absence of a bacterium resistant to a cyclic cationic polypeptide through plasmid-encoded resistance.

In one embodiment, a ratio of intensity of:

the third defined peak; to the second defined peak is at least about 0.15:1, or at least about 0.6:1.

Suitably, the ratio of intensity of the third defined peak to the second defined peak may be between at least about 0.15:1 to about 2.5:1. Suitably, the ratio may be between about 0.6:1 to about 1:1. Suitably, the ratio may be at least about 0.15:1, 0.3:1, 0.45:1, 0.6:1, 0.75:1, 0.9:1, 1.15:1, 1.3:1; 1.45:1, 1.6:1, 1.75:1, 1.9:1, 2.15:1, 2.3:1 or 2.45:1.

Thus, in one embodiment a ratio of intensity of the third defined peak to the second defined peak, wherein the ratio is at least about 0.15:1, indicates the presence of a bacterium (e.g. of the family Enterobacteriaceae) resistant to a cyclic cationic polypeptide antibiotic through plasmid-encoded resistance. Likewise, a ratio of less than 0.15:1 indicates the absence of a bacterium resistant to a cyclic cationic polypeptide through plasmid-encoded resistance.

In one embodiment, a ratio of:

the sum of the intensity of the first defined peak and the intensity of the third defined peak; to the intensity of the second defined peak is at least about 0.15:1.

Suitably, the ratio of the sum of the intensity of the first defined peak and the intensity of the third defined peak to the intensity of the second defined peak is at least 0.15:1, 0.3:1, 0.45:1, 0.6:1, 0.75:1, 0.9:1, 1.15:1, 1.3:1; 1.45:1, 1.6:1, 1.75:1, 1.9:1, 2.15:1, 2.3:1 or 2.45:1.

In a preferable embodiment, a ratio of:

the sum of the intensity of the first defined peak and the intensity of the third defined peak; to the intensity of the second defined peak is at least about 0.5:1.

Suitably, the ratio of the sum of the intensity of the first defined peak and the intensity of the third defined peak to the intensity of the second defined peak is at least about 0.5:1, 0.75:1, 0.9:1, 1.15:1, 1.3:1; 1.45:1, 1.6:1, 1.75:1, 1.9:1, 2.15:1, 2.3:1, 2.45:1, 2.6:1. 2.75:1, 2.9:1, 3.15:1, 3.3:1, 3.45:1, 3.6:1, 3.75:1, 3.9:1, 4.15:1, 4.3:1. 4.45:1, 4.6:1, 4.75:1, 4.9:1 or 5:1.

Advantageously, where a bacterium (e.g. of the family Enterobacteriaceae such as *Escherichia coli, Klebsiella pneumoniae, Shigella* spp., *Salmonella* spp) resistant to a cyclic cationic polypeptide antibiotic, comparing the ratio of intensity of the third defined peak to the second defined peak provides further information as to the mechanism underlying the mechanism of resistance. The detection of a bacterium (e.g. of the family Enterobacteriaceae) resistant to a cyclic cationic polypeptide antibiotic through plasmid encoded resistance in a test sample is of particular importance, as said test samples or patients from which said test samples are derived should be safely contained/quarantined to prevent spread (or risk thereof) of the transmissible plasmid to another bacterium, thus spreading the plasmid encoded resistance.

In one embodiment, a ratio of the sum of the intensity of the first defined peak and the intensity of the third defined peak to the intensity of the second defined peak of at least about 0.5:1 is indicative of the presence of a bacterium resistant to a cyclic cationic polypeptide antibiotic through plasmid-encoded resistance.

In one embodiment, a ratio of:

the sum of the intensity of the first defined peak and the intensity of the third defined peak; to the intensity of the second defined peak is between about 0.1:1 and 0.5:1.

Suitably, the ratio of the sum of the intensity of the first defined peak and the intensity of the third defined peak to the intensity of the second defined peak is between about 0.15:1 and 0.45:1, between about 0.2:1 and 0.4:1 or between about 0.25:1 and 0.35:1.

In one embodiment, a ratio of the sum of the intensity of the first defined peak and the intensity of the third defined peak to the intensity of the second defined peak of between about 0.1:1 and 0.5:1 is indicative of the presence of a bacterium resistant to a cyclic cationic polypeptide antibiotic through chromosome-encoded resistance.

In one embodiment, a ratio of:

the sum of the intensity of the first defined peak and the intensity of the third defined peak; to the intensity of the second defined peak is less than about 0.1:1.

Suitably, the ratio of the sum of the intensity of the first defined peak and the intensity of the third defined peak to the intensity of the second defined peak is less than about 0.1:1, 0.08:1, 0.06:1, 0.04:1, 0.02:1 or 0.01:1.

In one embodiment, a ratio of the sum of the intensity of the first defined peak and the intensity of the third defined peak to the intensity of the second defined peak of less than about 0.1:1 is indicative of the absence of a bacterium resistant to a cyclic cationic polypeptide antibiotic.

In one embodiment, a method of the invention further comprises identifying in said mass spectrum output a fourth defined peak indicative of the presence of Lipid A modified by 4-amino-L-arabinose, comprising a mass-to-charge ratio of about 129 to 133 m/z units (preferably about 131 m/z units) greater than the second defined peak indicative of the presence of native Lipid A.

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Klebsiella pneumoniae, Salmonella enterica, Enterobacter* spp. and *Klebsiella oxytoca;* b. a peak comprising a mass-to-charge ratio (m/z) of about 1820 to about 1826 m/z, preferably 1823.9 m/z, for *Klebsiella pneumoniae;* c. a peak comprising a mass-to-charge ratio (m/z) of about 1837 to about 1843 m/z, preferably 1840 m/z, for *Klebsiella pneumoniae;* d. a peak comprising a mass-to-charge ratio (m/z) of about 1847 to about 1853 m/z, preferably 1850 m/z, for *Klebsiella pneumoniae;* e. a peak comprising a mass-to-charge ratio (m/z) of about 2059 to about 2065 m/z, preferably 2062 m/z, for *Klebsiella pneumoniae;* f. a peak comprising a mass-to-charge ratio (m/z) of about 2075 to about 2081 m/z, preferably 2078 m/z, for *Klebsiella pneumoniae;* g. a peak comprising a mass-to-charge ratio (m/z) of about 1614 to about 1620 m/z, preferably 1617.2 m/z, for *Pseudomonas aeruginosa;* h. a peak comprising a mass-to-charge ratio (m/z) of about 1907 to about 1913 m/z, preferably 1910.3 m/z, for *Acinetobacter baumannii;* i. a peak comprising a mass-to-charge ratio (m/z) of about 1793 to about 1799 m/z, preferably 1796.2 m/z, for *Salmonella* spp;

j. a peak comprising a mass-to-charge ratio (m/z) of about 1820 to about 1826 m/z, preferably 1824 m/z, for *Salmonella* spp; or k. a peak comprising a mass-to-charge ratio (m/z) of about 2031 to about 2037 m/z, preferably 2034 m/z, for *Salmonella* spp.

In one embodiment, the fourth defined peak indicative of the presence of Lipid A modified by 4-amino-L-arabinose is selected from the group consisting of:

a. a peak comprising a mass-to-charge ratio (m/z) of about 1924 to about 1930 m/z, preferably 1927.2 m/z, for *Escherichia coli, Shigella, Klebsiella pneumoniae, Salmonella enterica, Enterobacter* spp. and *Klebsiella oxytoca;* b. a peak comprising a mass-to-charge ratio (m/z) of about 1951 to about 1957 m/z, preferably 1954.9 m/z, for *Klebsiella pneumoniae;* c. a peak comprising a mass-to-charge ratio (m/z) of about 1968 to about 1974 m/z, preferably 1971 m/z, for *Klebsiella pneumoniae;*
d. a peak comprising a mass-to-charge ratio (m/z) of about 1978 to about 1984 m/z, preferably 1981 m/z, for *Klebsiella pneumoniae;*
e. a peak comprising a mass-to-charge ratio (m/z) of about 2190 to about 2196 m/z, preferably 2193 m/z, for *Klebsiella pneumoniae;*
f. a peak comprising a mass-to-charge ratio (m/z) of about 2206 to about 2212 m/z, preferably 2209 m/z, for *Klebsiella pneumoniae;*
g. a peak comprising a mass-to-charge ratio (m/z) of about 1745 to about 1751 m/z, preferably 1748.2 m/z, for *Pseudomonas aeruginosa;*
h. a peak comprising a mass-to-charge ratio (m/z) of about 2038 to about 2044 m/z, preferably 2041.3 m/z, for *Acinetobacter baumannii;*
i. a peak comprising a mass-to-charge ratio (m/z) of about 1924 to about 1930 m/z, preferably 1927.2 m/z, for *Salmonella* spp;
j. a peak comprising a mass-to-charge ratio (m/z) of about 1952 to about 1958 m/z, preferably 1955 m/z, for *Salmonella* spp; or
k. a peak comprising a mass-to-charge ratio (m/z) of about 2162 to about 2168 m/z, preferably 2165 m/z, for *Salmonella* spp.

In one embodiment, native Lipid A comprises a mass-to-charge ratio (m/z) of between about 1793 to about 1799 m/z, preferably 1796.2 m/z and a fourth defined peak indicative of the presence of Lipid A modified by 4-amino-L-arabinose comprises a mass-to-charge ratio (m/z) of between about 1924 to about 1930 m/z, preferably 1927.2 m/z, for *Escherichia coli, Shigella, Klebsiella pneumoniae, Salmonella enterica, Enterobacter* spp. and *Klebsiella oxytoca*. In one embodiment, native Lipid A comprises a mass-to-charge ratio (m/z) of between about 1820 to about 1826 m/z, preferably 1823.9 m/z and a fourth defined peak indicative of the presence of Lipid A modified by 4-amino-L-arabinose comprises a mass-to-charge ratio (m/z) of between about 1951 to about 1957 m/z, preferably 1954.9 m/z, for *Klebsiella pneumoniae*. In one embodiment, native Lipid A comprises a mass-to-charge ratio (m/z) of between about 1837 to about 1843 m/z, preferably 1840 m/z and a fourth defined peak indicative of the presence of Lipid A modified by 4-amino-L-arabinose comprises a mass-to-charge ratio (m/z) of between about 1968 to about 1974 m/z, preferably 1971 m/z, for *Klebsiella pneumoniae*. In one embodiment, native Lipid A comprises a mass-to-charge ratio (m/z) of between about 1847 to about 1853 m/z, preferably 1850 m/z and a fourth defined peak indicative of the presence of Lipid A modified by 4-amino-L-arabinose comprises a mass-to-charge ratio (m/z) of between about 1978 to about 1984 m/z, preferably 1981 m/z, for *Klebsiella pneumoniae*. In one embodiment, native Lipid A comprises a mass-to-charge ratio (m/z) of between about 2059 to about 2065 m/z, preferably 2062 m/z and a fourth defined peak indicative of the presence of Lipid A modified by 4-amino-L-arabinose comprises a mass-to-charge ratio (m/z) of between about 2190 to about 2196 m/z, preferably 2193 m/z, for *Klebsiella pneumoniae*. In one embodiment, native Lipid A comprises a mass-to-charge ratio (m/z) of between about 2075 to about 2081 m/z, preferably 2078 m/z and a fourth defined peak indicative of the presence of Lipid A modified by 4-amino-L-arabinose comprises a mass-to-charge ratio (m/z) of between about 2206 to about 2212 m/z, preferably 2209 m/z, for *Klebsiella pneumoniae*. In one embodiment, native Lipid A comprises a mass-to-charge ratio (m/z) of between about 1614 to about 1620 m/z, preferably 1617.2 m/z and a fourth defined peak indicative of the presence of Lipid A modified by 4-amino-L-arabinose comprises a mass-to-charge ratio (m/z) of between about 1745 to about 1751 m/z, preferably 1748.2 m/z, for *Pseudomonas aeruginosa*. In one embodiment, native Lipid A comprises a mass-to-charge ratio (m/z) of between about 1907 to about 1913 m/z, preferably 1910.3 m/z and a fourth defined peak indicative of the presence of Lipid A modified by 4-amino-L-arabinose comprises a mass-to-charge ratio (m/z) of between about 2038 to about 2044 m/z, preferably 2041.3 m/z, for *Acinetobacter baumannii*. In one embodiment, native Lipid A comprises a mass-to-charge ratio (m/z) of between about 1793 to about 1799 m/z, preferably 1796.2 m/z and a fourth defined peak indicative of the presence of Lipid A modified by 4-amino-L-arabinose comprises a mass-to-charge ratio (m/z) of between about 1924 to about 1930 m/z, preferably 1927.2 m/z, for *Salmonella* spp. In one embodiment, native Lipid A comprises a mass-to-charge ratio (m/z) of between about 1820 to about 1826 m/z, preferably 1824 m/z and a fourth defined peak indicative of the presence of Lipid A modified by 4-amino-L-arabinose comprises a mass-to-charge ratio (m/z) of between about 1952 to about 1958 m/z, preferably 1955 m/z, for *Salmonella* spp. In one embodiment, native Lipid A comprises a mass-to-charge ratio (m/z) of between about 2031 to about 2037 m/z, preferably 2034 m/z and a fourth defined peak indicative of the presence of Lipid A modified by 4-amino-L-arabinose comprises a mass-to-charge ratio (m/z) of between about 2162 to about 2168 m/z, preferably 2165 m/z, for *Salmonella* spp.

In one embodiment, the presence of said fourth defined peak indicates the presence of a bacterium resistant to a cyclic cationic polypeptide antibiotic through chromosome-encoded resistance. In one embodiment, the absence of said fourth defined peak indicates the absence of a bacterium resistant to a cyclic cationic polypeptide antibiotic through chromosome-encoded resistance.

In one embodiment, the presence of said first defined peak (e.g. indicative of the presence of Lipid A modified by phosphoethanolamine) and the absence of said fourth defined peak indicates the presence of a bacterium resistant to a cyclic cationic polypeptide antibiotic through plasmid-encoded resistance. In one embodiment, the absence of said first defined peak and the presence of said fourth defined peak indicates the presence of a bacterium resistant to a cyclic cationic polypeptide antibiotic through chromosome encoded resistance. Plasmid-encoded polymyxin resistance is typically associated with Lipid A modified by phosphoethanolamine (e.g. not additionally modified by 4-amino-L-arabinose).

In one embodiment, the presence of said third defined peak (e.g. indicative of the presence of Lipid A modified by phosphoethanolamine at the 1' phosphate group with concomitant loss of the 4' phosphate) and the absence of said fourth defined peak indicates the presence of a bacterium resistant to a cyclic cationic polypeptide antibiotic through plasmid-encoded resistance and the absence of a bacterium resistant to a cyclic cationic polypeptide antibiotic through chromosome-encoded resistance. In one embodiment, the absence of said third defined peak and the presence of said fourth defined peak indicates the presence of a bacterium resistant to a cyclic cationic polypeptide antibiotic through chromosome-encoded resistance and the absence of a bacterium resistant to a cyclic cationic polypeptide antibiotic through plasmid-encoded resistance.

In one aspect, there is proved a method for detecting the presence or absence of a bacterium resistant to a cyclic cationic polypeptide antibiotic, comprising:

a. subjecting a test sample to mass spectrometry analysis and generating a mass spectrum output;
   wherein said test sample comprises a bacterial membrane or a fragment thereof, wherein the fragment comprises a non-Lipid A component;
b. identifying in said mass spectrum output a fourth defined peak (e.g. any fourth defined peak as defined above) indicative of the presence of Lipid A modified by 4-amino-L-arabinose, wherein said fourth defined peak is a peak present in a mass spectrum output for Lipid A modified by 4-amino-L-arabinose and wherein said fourth defined peak is absent from a corresponding mass spectrum output for native Lipid A; and
c. wherein the presence of said fourth defined peak indicates the presence of a bacterium resistant to a cyclic cationic polypeptide antibiotic, and wherein the absence of said fourth defined peak indicates the absence of a bacterium resistant to a cyclic cationic polypeptide antibiotic.

In one embodiment, a method of the invention further comprises identifying in said mass spectrum output a fifth defined peak indicative of the presence of Lipid A modified by phosphoethanolamine and 4-amino-L-arabinose, comprising a mass-to-charge ratio of about 253 to 257 m/z units (preferably about 254 m/z units) greater than the second defined peak indicative of the presence of native Lipid A.

In one embodiment, the second defined peak is selected from the group consisting of:

a. a peak comprising a mass-to-charge ratio (m/z) of about 1793 to about 1799 m/z, preferably 1796.2 m/z, for *Escherichia coli, Shigella, Klebsiella pneumoniae, Salmonella enterica, Enterobacter* spp. and *Klebsiella oxytoca;*
b. a peak comprising a mass-to-charge ratio (m/z) of about 1820 to about 1826 m/z, preferably 1823.9 m/z, for *Klebsiella pneumoniae;*
c. a peak comprising a mass-to-charge ratio (m/z) of about 1837 to about 1843 m/z, preferably 1840 m/z, for *Klebsiella pneumoniae;*
d. a peak comprising a mass-to-charge ratio (m/z) of about 1847 to about 1853 m/z, preferably 1850 m/z, for *Klebsiella pneumoniae;*
e. a peak comprising a mass-to-charge ratio (m/z) of about 2059 to about 2065 m/z, preferably 2062 m/z, for *Klebsiella pneumoniae;*
f. a peak comprising a mass-to-charge ratio (m/z) of about 2075 to about 2081 m/z, preferably 2078 m/z, for *Klebsiella pneumoniae;*
g. a peak comprising a mass-to-charge ratio (m/z) of about 1614 to about 1620 m/z, preferably 1617.2 m/z, for *Pseudomonas aeruginosa;*
h. a peak comprising a mass-to-charge ratio (m/z) of about 1907 to about 1913 m/z, preferably 1910.3 m/z, for *Acinetobacter baumannii;*
i. a peak comprising a mass-to-charge ratio (m/z) of about 1793 to about 1799 m/z, preferably 1796.2 m/z, for *Salmonella* spp;
j. a peak comprising a mass-to-charge ratio (m/z) of about 1820 to about 1826 m/z, preferably 1824 m/z, for *Salmonella* spp; or
k. a peak comprising a mass-to-charge ratio (m/z) of about 2031 to about 2037 m/z, preferably 2034 m/z, for *Salmonella* spp.

In one embodiment, the fifth defined peak indicative of the presence of Lipid A modified by phosphoethanolamine and 4-amino-L-arabinose is selected from the group consisting of:

a. a peak comprising a mass-to-charge ratio (m/z) of about 2047 to about 2053 m/z, preferably 2050 m/z, for *Escherichia coli, Shigella, Klebsiella pneumoniae, Salmonella enterica, Enterobacter* spp. and *Klebsiella oxytoca;*
b. a peak comprising a mass-to-charge ratio (m/z) of about 2074 to about 2080 m/z, preferably 2077 m/z, for *Klebsiella pneumoniae;*
c. a peak comprising a mass-to-charge ratio (m/z) of about 2091 to about 2097 m/z, preferably 2094 m/z, for *Klebsiella pneumoniae;*
d. a peak comprising a mass-to-charge ratio (m/z) of about 2101 to about 2107 m/z, preferably 2104 m/z, for *Klebsiella pneumoniae;*
e. a peak comprising a mass-to-charge ratio (m/z) of about 2313 to about 2319 m/z, preferably 2316 m/z, for *Klebsiella pneumoniae;*
f. a peak comprising a mass-to-charge ratio (m/z) of about 2329 to about 2335 m/z, preferably 2332 m/z, for *Klebsiella pneumoniae;*
g. a peak comprising a mass-to-charge ratio (m/z) of about 1868 to about 1874 m/z, preferably 1871.2 m/z, for *Pseudomonas aeruginosa;*
h. a peak comprising a mass-to-charge ratio (m/z) of about 2161 to about 2167 m/z, preferably 2164.3 m/z, for *Acinetobacter baumannii;*
i. a peak comprising a mass-to-charge ratio (m/z) of about 2047 to about 2053 m/z, preferably 2050.2 m/z, for *Salmonella* spp;
j. a peak comprising a mass-to-charge ratio (m/z) of about 2075 to about 2081 m/z, preferably 2078 m/z, for *Salmonella* spp; or
k. a peak comprising a mass-to-charge ratio (m/z) of about 2285 to about 2291 m/z, preferably 2288 m/z, for *Salmonella* spp.

In one embodiment, native Lipid A comprises a mass-to-charge ratio (m/z) of between about 1793 to about 1799 m/z, preferably 1796.2 m/z and a fifth defined peak indicative of the presence of Lipid A modified by phosphoethanolamine and 4-amino-L-arabinose comprises a mass-to-charge ratio (m/z) of between about 2047 to about 2053 m/z, preferably 2050 m/z, for *Escherichia coli, Shigella, Klebsiella pneumoniae, Salmonella enterica, Enterobacter* spp. and *Klebsiella oxytoca*. In one embodiment, native Lipid A comprises a mass-to-charge ratio (m/z) of between about 1820 to about 1826 m/z, preferably 1823.9 m/z and a fifth defined peak indicative of the presence of Lipid A modified by phosphoethanolamine and 4-amino-L-arabinose comprises a mass-to-charge ratio (m/z) of between about 2074 to about 2080 m/z, preferably 2077 m/z, for *Klebsiella pneumoniae*. In one embodiment, native Lipid A comprises a mass-to-charge ratio (m/z) of between about 1837 to about 1843 m/z, preferably 1840 m/z and a fifth defined peak indicative of the presence of Lipid A modified by phosphoethanolamine and 4-amino-L-arabinose comprises a mass-to-charge ratio (m/z) of between about 2091 to about 2097 m/z, preferably 2094 m/z, for *Klebsiella pneumoniae*. In one embodiment, native Lipid A comprises a mass-to-charge ratio (m/z) of between about 1847 to about 1853 m/z, preferably 1850 m/z and a fifth defined peak indicative of the presence of Lipid A modified by phosphoethanolamine and 4-amino-L-arabinose comprises a mass-to-charge ratio (m/z) of between about 2101 to about 2107 m/z, preferably 2104 m/z, for

*Klebsiella pneumoniae*. In one embodiment, native Lipid A comprises a mass-to-charge ratio (m/z) of between about 2059 to about 2065 m/z, preferably 2062 m/z and a fifth defined peak indicative of the presence of Lipid A modified by phosphoethanolamine and 4-amino-L-arabinose comprises a mass-to-charge ratio (m/z) of between about 2313 to about 2319 m/z, preferably 2316 m/z, for *Klebsiella pneumoniae*. In one embodiment, native Lipid A comprises a mass-to-charge ratio (m/z) of between about 2075 to about 2081 m/z, preferably 2078 m/z and a fifth defined peak indicative of the presence of Lipid A modified by phosphoethanolamine and 4-amino-L-arabinose comprises a mass-to-charge ratio (m/z) of between about 2329 to about 2335 m/z, preferably 2332 m/z, for *Klebsiella pneumoniae*. In one embodiment, native Lipid A comprises a mass-to-charge ratio (m/z) of between about 1614 to about 1620 m/z, preferably 1617.2 m/z and a fifth defined peak indicative of the presence of Lipid A modified by phosphoethanolamine and 4-amino-L-arabinose comprises a mass-to-charge ratio (m/z) of between about 1868 to about 1874 m/z, preferably 1871.2 m/z, for *Pseudomonas aeruginosa*. In one embodiment, native Lipid A comprises a mass-to-charge ratio (m/z) of between about 1907 to about 1913 m/z, preferably 1910.3 m/z and a fifth defined peak indicative of the presence of Lipid A modified by phosphoethanolamine and 4-amino-L-arabinose comprises a mass-to-charge ratio (m/z) of between about 2161 to about 2167 m/z, preferably 2164.3 m/z, for *Acinetobacter baumannii*. In one embodiment, native Lipid A comprises a mass-to-charge ratio (m/z) of between about 1793 to about 1799 m/z, preferably 1796.2 m/z and a fifth defined peak indicative of the presence of Lipid A modified by phosphoethanolamine and 4-amino-L-arabinose comprises a mass-to-charge ratio (m/z) of between about 2047 to about 2053 m/z, preferably 2050.2 m/z, for *Salmonella* spp. In one embodiment, native Lipid A comprises a mass-to-charge ratio (m/z) of between about 2075 to about 2081 m/z, preferably 2078 m/z and a fifth defined peak indicative of the presence of Lipid A modified by phosphoethanolamine and 4-amino-L-arabinose comprises a mass-to-charge ratio (m/z) of between about 2075 to about 2081 m/z, preferably 2078 m/z, for *Salmonella* spp. In one embodiment, native Lipid A comprises a mass-to-charge ratio (m/z) of between about 2031 to about 2037 m/z, preferably 2034 m/z and a fifth defined peak indicative of the presence of Lipid A modified by phosphoethanolamine and 4-amino-L-arabinose comprises a mass-to-charge ratio (m/z) of between about 2285 to about 2291 m/z, preferably 2288 m/z, for *Salmonella* spp.

In one embodiment, the presence of said fifth defined peak indicates the presence of a bacterium resistant to a cyclic cationic polypeptide antibiotic through chromosome-encoded resistance. In one embodiment, the absence of said fifth defined peak indicates the absence of a bacterium resistant to a cyclic cationic polypeptide antibiotic through chromosome-encoded resistance. Chromosome-encoded polymyxin resistance may typically be associated with Lipid A modified by phosphoethanolamine, and/or Lipid A modified with both phosphoethanolamine and 4-amino-L-arabinose (e.g. the presence of both the first defined peak and the fifth defined peak).

In one embodiment, the presence of said first defined peak (e.g. indicative of the presence of Lipid A modified by phosphoethanolamine) and the absence of said fifth defined peak indicates the presence of a bacterium resistant to a cyclic cationic polypeptide antibiotic through plasmid encoded resistance. In one embodiment, the absence of said first defined peak and the presence of said fifth defined peak indicates the presence of a bacterium resistant to a cyclic cationic polypeptide antibiotic through chromosome encoded resistance.

In one embodiment, the presence of said third defined peak (e.g. indicative of the presence of Lipid A modified by phosphoethanolamine at the 1' phosphate group with concomitant loss of the 4' phosphate) and the absence of said fifth defined peak indicates the presence of a bacterium resistant to a cyclic cationic polypeptide antibiotic through plasmid encoded resistance and the absence of a bacterium resistant to a cyclic cationic polypeptide antibiotic through chromosome encoded resistance. In one embodiment, the absence of said third defined peak and the presence of said fifth defined peak indicates the presence of a bacterium resistant to a cyclic cationic polypeptide antibiotic through chromosome-encoded resistance and the absence of a bacterium resistant to a cyclic cationic polypeptide antibiotic through plasmid-encoded resistance.

Without wishing to be bound by theory it is believed that a bacterium resistant to a cyclic cationic polypeptide antibiotic through plasmid-encoded resistance comprises a plasmid having an mcr-1, mcr-2, an mcr-like gene or a combination thereof. A bacterium resistant to a cyclic cationic polypeptide antibiotic through plasmid-encoded resistance may comprise a plasmid having an mcr-1 gene (e.g. mcr-1, mcr-1.1, mcr-1.2, mcr-1.3, mcr-1.4, mcr-1.5, mcr-1.6, mcr-1.7, mcr-1.8, mcr-1.9 and/or mcr-1.10), an mcr-2 gene (e.g. mcr-2 and/or mcr-2.2), an gene mcr-3 (e.g. mcr-3 and/or mcr-3.2), an mcr-4 gene (e.g. mcr-4), an mcr-5 gene (e.g. mcr-5), an mcr-like gene or a combination thereof. Suitably, Lipid A modified with phosphoethanolamine at the 1' phosphate group of Lipid A with concomitant loss of the 4' phosphate group (e.g. as per the third defined peak as described herein) is only detectable in a bacterium comprising a plasmid comprising one or more of said mcr genes, and is not detectable in a bacterium lacking such a plasmid.

In one embodiment, a bacterium resistant to a cyclic cationic polypeptide antibiotic through plasmid-encoded resistance or a bacterium of the family Enterobacteriaceae resistant to a cyclic cationic polypeptide antibiotic through plasmid-encoded resistance comprises a plasmid having a mobilised colistin resistance gene. In one embodiment, a mobilised colistin resistance gene comprises one of more of mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4, mcr-5 gene or an mcr-like gene. In one embodiment, a mobilised colistin resistance gene comprises one of more of mcr-1, mcr-2 or an mcr-like gene.

An "mcr-like gene" as used herein is a gene comprising a sequence having a nucleotide sequence encoding a functionally and/or structurally equivalent polypeptide to the polypeptide encoded by a mcr-1 or mcr-2 gene. An "mcr-like gene" as used herein is a gene comprising a sequence having a nucleotide sequence encoding a functionally and/or structurally equivalent polypeptide to the polypeptide encoded by mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4 or mcr-5.

In one embodiment an mcr-like gene is a gene comprising a sequence having at least 50% sequence identity to mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4 or mcr-5. In one embodiment, said mcr-like gene comprises at least 60% or 70% sequence identity to mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4 or mcr-5. Suitably, mcr-like gene comprises at least 80% or 90% (e.g. at least 95%) sequence identity to mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4 or mcr-5.

In one embodiment an mcr-like gene is a gene comprising a sequence having at least 50% sequence identity to mcr-1 or mcr-2. In one embodiment, said mcr-like gene comprises at least 60% or 70% sequence identity to mcr-1 or mcr-2. Suitably, mcr-like gene comprises at least 80% or 90% (e.g. at least 95%) sequence identity to mcr-1 or mcr-2.

In one embodiment, an mcr-1 gene has a sequence selected from the group consisting of: SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9 and SEQ ID NO: 10 or a sequence having at least 50% sequence identity thereto, suitably at least 60%, 70%, 80% or 90% sequence identity thereto. In one embodiment, an mcr-1 gene has the sequence SEQ ID NO: 1, or a sequence having at least 50% sequence identity thereto, suitably at least 60%, 70%, 80% or 90% sequence identity thereto.

In one embodiment, an mcr-2 gene has the sequence SEQ ID NO: 11, SEQ ID NO: 12, or a sequence having at least 50% sequence identity thereto, suitably at least 60%, 70%, 80% or 90% sequence identity thereto. In one embodiment, an mcr-2 gene has the sequence SEQ ID NO: 11, or a sequence having at least 50% sequence identity thereto, suitably at least 60%, 70%, 80% or 90% sequence identity thereto.

In one embodiment, an mcr-3 gene has the sequence SEQ ID NO: 13, SEQ ID NO: 14 or a sequence having at least 50% sequence identity thereto, suitably at least 60%, 70%, 80% or 90% sequence identity thereto.

In one embodiment, an mcr-4 gene has the sequence SEQ ID NO: 15, or a sequence having at least 50% sequence identity thereto, suitably at least 60%, 70%, 80% or 90% sequence identity thereto.

In one embodiment, an mcr-5 gene has the sequence SEQ ID NO: 16, or a sequence having at least 50% sequence identity thereto, suitably at least 60%, 70%, 80% or 90% sequence identity thereto.

A bacterium may be resistant to a cyclic cationic polypeptide antibiotic through chromosome-encoded resistance. Without wishing to be bound by theory, it is believed that a bacterium resistant to a cyclic cationic polypeptide antibiotic through chromosome-encoded resistance comprises a mutation in one or more gene selected from pmrA, pmrB, pmrC, pmrD, pmrE, pmrR, phoP, phoQ, mgrB, arnA, amB, arnC, arnD, arnE, arnF, arnF, arnT, cptA, eptB and combinations thereof. Said mutations may result, either directly or indirectly, in the modification of Lipid A with 4-amino-L-arabinose and/or phosphoethanolamine. A "mutation" encompasses any alteration of the nucleotide sequence of a gene, a point mutation, a missense mutation, a nonsense mutation, an insertion, a deletion, a duplication, a frameshift mutation or a repeat expansion.

In one embodiment, a test sample is admixed with a matrix solution prior to subjecting said test sample to mass spectrometry analysis. A matrix solution facilitates mass spectrometry of a test sample, suitably wherein the mass spectrometry is MALDI-TOF mass spectrometry.

In one embodiment, a matrix solution of the invention allows for the selective extraction, co-crystallization and ionisation of native Lipid A and/or modified Lipid A as an integral part of a bacterial membrane. In one embodiment, a matrix solution of the invention allows for the identification of a peak assigned to native Lipid A and/or modified Lipid A (e.g. by allowing the selective extraction, co-crystallization and ionisation of native Lipid A and/or modified Lipid A) as an integral part of a bacterial membrane.

Thus in one aspect the present invention provides a prepared composition for use in mass spectrometry, said composition comprising a bacterial membrane or fragment thereof and a matrix solution.

In one embodiment, a matrix solution comprises 2,5-dihydroxybenzoic acid suspended in an organic solvent. In one embodiment, a matrix solution comprises 2,5-dihydroxybenzoic acid suspended in an organic solvent at a concentration of about 1 to 100 mg/ml. In one embodiment, a matrix solution comprises 2,5-dihydroxybenzoic acid suspended in an organic solvent at a concentration of about 7 to 13 mg/ml. Preferably 2,5-dihydroxybenzoic acid is suspended in an organic solvent at a concentration of about 10 mg/ml.

In one embodiment, a matrix solution comprises one or more selected from norharmane (NRM), 3-Hydroxymethyl-β-carboline, 3-Methyl-a-carboline, Ethyl 2,3,4,9-tetrahydro-1H-β-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido[3,4-b]indole, harmane, harmine, harmaline or a combination thereof suspended in an organic solvent. In one embodiment, a matrix solution comprises one or more selected from norharmane (NRM), 3-Hydroxymethyl-β-carboline, 3-Methyl-a-carboline, Ethyl 2,3,4,9-tetrahydro-1H-β-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido[3,4-b]indole, harmane, harmine, harmaline or a combination thereof suspended in an organic solvent at a concentration of 1 to 100 mg/ml. In one embodiment, a matrix solution comprises one or more selected from norharmane (NRM), 3-Hydroxymethyl-β-carboline, 3-Methyl-a-carboline, Ethyl 2,3,4,9-tetrahydro-1H-β-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido[3,4-b]indole, harmane, harmine, harmaline or a combination thereof suspended in an organic solvent at a concentration of 7 to 13 mg/ml. In a preferable embodiment, a matrix solution comprises one or more selected from norharmane (NRM), 3-Hydroxymethyl-β-carboline, 3-Methyl-a-carboline, Ethyl 2,3,4,9-tetrahydro-1H-β-carboline-3-carboxylate, Ethyl β-carboline-3-carboxylate, 1-Methylindole-2-carboxylic acid, norharman methiodide, β-Carboline-3-carboxylic acid N-methylamide, harmaline hydrochloride dehydrate, 1,2,3,4-tetrahydro-beta-carboline-1-carboxylic acid, 1,2,3,4-Tetrahydro-9H-pyrido[3,4-b]indole, harmane, harmine, harmaline or a combination thereof suspended in an organic solvent at a concentration of 10 mg/ml.

In one embodiment, a matrix solution comprises norharmane (NRM) suspended in an organic solvent. In one embodiment, a matrix solution comprises norharmane suspended in an organic solvent at a concentration of 1 to 100 mg/ml. In one embodiment, a matrix solution comprises norharmane suspended in an organic solvent at a concentration of 7 to 13 mg/ml. In a preferable embodiment, a matrix solution comprises norharmane suspended in an organic solvent at a concentration of 10 mg/ml.

In one embodiment, an organic solvent comprises chloroform and methanol at a ratio of about 6:1 to about 12:1, or about 8:1 to about 10:1. Suitably an organic solvent comprises chloroform and methanol at a ratio of about 9:1 v/v.

In one embodiment, the organic solvent comprises one or more of chloroform, methanol, dichloromethane, ether, diethyl-ether, petroleoum ether, isopropanol, butanol, hexane or a combination thereof.

In one embodiment, the organic solvent comprises one or more of acetic acid, acetone, acetonitrile, benzene, 1-butanol, 2-butanol, 2-butanone, t-butyl alcohol, carbon tetrachloride, chlorobenzene, chloroform, cyclohexane, 1,2-dichloroethane, diethylene glycol, diethyl ether, diglyme (diethylene glycol dimethyl ether), 1,2-dimethoxy-ethane (glyme, DME), dimethyl-formamide (DMF), dimethyl sulfoxide (DMSO), 1,4-dioxane, ethanol, ethyl acetate, ethylene glycol, glycerine, heptane, Hexamethylphosphoramide (HMPA), Hexamethylphosphorous triamide (HMPT), hexane, methanol, methyl t-butyl ether (MTBE), methylene chloride, N-methyl-2-pyrrolidinone (NMP), pentane, Petroleum ether (ligroine), 1-propanol, 2-propanol, pyridine, tetrahydrofuran (THF), toluene, triethyl amine, water, water (heavy), o-xylene, m-xylene, p-xylene.

In one embodiment, the ratio of the test sample to the matrix solution is between about 0.1:1 to about 2:1 v/v, or about 0.5:1 to about 0.7:1 v/v. Suitably, the ratio of the test sample to the matrix solution is about 0.66:1 v/v.

In one embodiment, a test sample comprises less than about $10^{10}$ bacterial cells. Suitably, a test sample may comprise less than about $10^9$, $10^8$, $10^7$, $10^6$, $10^5$, $10^4$, $10^3$, $10^2$ or $10^1$ bacterial cells.

In one embodiment a test sample comprises between about $10^1$ to about $10^{10}$ bacterial cells. Suitably, a test sample comprises between about $10^2$ to about $10^8$, about $10^3$ to about $10^6$, or about $10^4$ to about $10^5$ bacterial cells.

In one embodiment, the cyclic cationic polypeptide antibiotic is a polymyxin antibiotic. Suitably, a polymyxin antibiotic may be one or more of Colistin (Polymyxin E), Polymyxin B, Mattacin (Polymyxin M), or a salt thereof.

Preferably a polymyxin antibiotic may be Colistin (Polymyxin E) or a salt thereof. A salt of Colistin (Polymyxin E) may be Colistin sulfate or Colistimethate sodium.

In one embodiment a bacterium as used herein may be one or more selected from the following genera: *Escherichia, Klebsiella, Enterobacter, Pseudomonas, Acinetobacter, Shigella, Salmonella, Citrobacter, Raoultella* or combinations thereof.

Suitably a bacterium may be one or more selected from the following species: *Escherichia coli, Klebsiella pneumoniae, Klebsiella oxytoca, Enterobacter aerogenes, Enterobacter cloacae, Enterobacter asburiae, Pseudomonas aeruginosa, Acinetobacter baumannii, Shigella sonnei, Shigella flexneri, Salmonella enterica, Citrobacter freundii, Citrobacter koseri, Citrobacter amalonaticus, Citrobacter youngae* or combinations thereof.

Any strain of such genera or species may be suitable for use in a method of the invention.

In one embodiment, a bacterium is heat inactivated. A bacterium may be heat inactivated using any technique known in the art, for example by using a dry bath or a water bath. Where a dry bath or water bath is used a bacterium may be heat inactivated by heating for between about 10 to about 50 minutes at 70 to 90° C. (suitably for 30 min at 80° C.). In some embodiments a bacterium may be heat inactivated by heating for at least about 45 minutes (preferably at least 1 hour) to at least about 80° C. (preferably at least 90° C.).

In some embodiments, the bacterium is not heat inactivated.

In one embodiment, a method of the invention comprises the step of recording the data obtained in step (a) on a suitable data carrier. Thus the present invention also provides a data carrier comprising data obtained in step (a) of a method herein.

In one aspect of the invention, there is provided a screening method for identifying an inhibitor of cyclic cationic polypeptide antibiotic resistance in a bacterium, comprising:

a. incubating a sample comprising a bacterium resistant to a cyclic cationic polypeptide antibiotic with a candidate inhibitor;
b. subjecting said sample to mass spectrometry analysis according to a method of the present invention and generating a mass spectrum output; and
c. identifying the presence or absence of said first defined peak in the mass spectrum output;

wherein the presence of said first defined peak indicates said candidate inhibitor is not a substance capable of inhibiting cyclic cationic polypeptide antibiotic resistance in a bacterium, and wherein the absence of said first defined peak indicates said candidate inhibitor is a substance capable of inhibiting cyclic cationic polypeptide antibiotic resistance in a bacterium.

In one aspect of the invention, there is provided a screening method for identifying an inhibitor of cyclic cationic polypeptide antibiotic resistance in a bacterium, comprising:

a. incubating a sample comprising a bacterium resistant to a cyclic cationic polypeptide antibiotic with a candidate inhibitor;
b. subjecting said sample to mass spectrometry analysis according to a method of the present invention and generating a mass spectrum output; and
c. identifying the presence or absence of said first defined peak and/or said third defined peak in the mass spectrum output;

wherein the presence of said first defined peak and/or said third defined peak indicates said candidate inhibitor is not a substance capable of inhibiting cyclic cationic polypeptide antibiotic resistance in a bacterium, and wherein the absence of said first defined peak and/or said third defined peak indicates said candidate inhibitor is a substance capable of inhibiting cyclic cationic polypeptide antibiotic resistance in a bacterium.

In one aspect of the invention, there is provided a screening method for identifying an inhibitor of cyclic cationic polypeptide antibiotic resistance in a bacterium, comprising:

a. incubating a sample comprising a bacterium resistant to a cyclic cationic polypeptide antibiotic with a candidate inhibitor;
b. subjecting said sample to mass spectrometry analysis according to a method of the present invention and generating a mass spectrum output; and
c. identifying the presence or absence of said first defined peak, said third defined peak, said fourth defined peak and/or said fifth defined peak in the mass spectrum output;

wherein the presence of said first defined peak, said third defined peak, said fourth defined peak and/or said fifth defined peak indicates said candidate inhibitor is not a substance capable of inhibiting cyclic cationic polypeptide antibiotic resistance in a bacterium, and wherein the absence of said first defined peak and/or said third defined peak indicates said candidate inhibitor is a substance capable of inhibiting cyclic cationic polypeptide antibiotic resistance in a bacterium.

Said screening method(s) embraces the corresponding use of mass spectrometry for identifying an inhibitor of cyclic cationic polypeptide antibiotic resistance in a bacterium.

In one embodiment, wherein said screening method fails to identify an inhibitor of cyclic cationic polypeptide antibiotic (e.g. polymyxin) resistance in a bacterium, steps a.-c. are repeated with a different candidate inhibitor. This sequence may be repeated iteratively until the absence of the first defined peak is identified, indicating the candidate inhibitor is a substance capable of inhibiting cyclic cationic polypeptide antibiotic resistance in a bacterium. Once the absence of the first defined peak is identified, said candidate inhibitor may be used as an inhibitor of cyclic cationic polypeptide antibiotic resistance in a bacterium.

In one embodiment, a screening method for identifying an inhibitor of cyclic cationic polypeptide antibiotic resistance in a bacterium comprises incubating a sample comprising a bacterium resistant to a cyclic cationic polypeptide antibiotic with a candidate inhibitor and subsequently testing said bacterium for susceptibility to a cyclic cationic polypeptide antibiotic, wherein mass spectrometry analysis according to a method of the present invention is used to confirm whether a substance is capable or is not capable of inhibiting cyclic cationic polypeptide antibiotic resistance in a bacterium by identifying the presence or absence of said first defined peak and/or said third defined peak in a mass spectrum output.

In one embodiment a bacterium resistant to a cyclic cationic polypeptide antibiotic may be isolated from a clinical sample. In an alternative embodiment, the bacterium resistant to a cyclic cationic polypeptide antibiotic may be cultured under laboratory conditions.

A candidate inhibitor may be capable of directly or indirectly inhibiting modification of Lipid A with 4-amino-L-arabinose and/or phosphoethanolamine.

In one embodiment a candidate inhibitor is selected from a small molecule inhibitor, a peptide, a monoclonal or a polyclonal antibody or an antibody fragment.

In one embodiment a candidate inhibitor is a known chemical or pharmaceutical substance selected from a library of such candidate inhibitors.

In one embodiment a sample comprising a bacterium resistant to a cyclic cationic polypeptide antibiotic with a candidate inhibitor is a sample from a human or a non-human animal. A non-human animal may be, for example, a non-human primate, horse, cow, goat, cat, dog, sheep, rodent (e.g. mouse, rate or Guinea pig), fish or amphibian (e.g. *Xenopus*).

In one aspect, there is provided the use of a test sample in mass spectrometry analysis for detection of the presence or absence of a bacterium resistant to a cyclic cationic polypeptide antibiotic (e.g. in said test sample).

Methods of determining nucleic acid percentage sequence identity are known in the art. By way of example, when assessing nucleic acid sequence identity, a sequence having a defined number of contiguous nucleotides may be aligned with a nucleic acid sequence (having the same number of contiguous nucleotides) from the corresponding portion of a nucleic acid sequence of the present invention. Tools known in the art for determining nucleic acid percentage sequence identity include Nucleotide BLAST.

Any of a variety of sequence alignment methods can be used to determine percent identity, including, without limitation, global methods, local methods and hybrid methods, such as, e.g., segment approach methods. Protocols to determine percent identity are routine procedures within the scope of one skilled in the art. Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., CLUSTAL W: Improving the Sensitivity of Progressive Multiple Sequence Alignment Through Sequence Weighting, Position-Specific Gap Penalties and Weight Matrix Choice, 22(22) Nucleic Acids Research 4673-4680 (1994); and iterative refinement, see, e.g., Osamu Gotoh, Significant Improvement in Accuracy of Multiple Protein. Sequence Alignments by Iterative Refinement as Assessed by Reference to Structural Alignments, 264(4) J. Mol. Biol. 823-838 (1996). Local methods align sequences by identifying one or more conserved motifs shared by all of the input sequences. Non-limiting methods include, e.g., Match-box, see, e.g., Eric Depiereux and Ernest Feytmans, Match-Box: A Fundamentally New Algorithm for the Simultaneous Alignment of Several Protein Sequences, 8(5) CABIOS 501-509 (1992); Gibbs sampling, see, e.g., C. E. Lawrence et al., Detecting Subtle Sequence Signals: A Gibbs Sampling Strategy for Multiple Alignment, 262(5131) Science 208-214 (1993); Align-M, see, e.g., Ivo Van Walle et al., Align-M—A New Algorithm for Multiple Alignment of Highly Divergent Sequences, 20(9) Bioinformatics:1428-1435 (2004).

Thus, percent sequence identity is determined by conventional methods. See, for example, Altschul et al., Bull. Math. Bio. 48: 603-16, 1986 and Henikoff and Henikoff, Proc. Natl. Acad. Sci. USA 89:10915-19, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown below (amino acids are indicated by the standard one-letter codes).

Alignment Scores for Determining Sequence Identity

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |

-continued

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

The percent identity is then calculated as:

$$\frac{\text{Total number of identical matches}}{\left[\begin{array}{c}\text{length of the longer sequence plus the}\\ \text{number of gaps introduced into the longer}\\ \text{sequence in order to align the two sequences}\end{array}\right]}\times 100$$

Substantially homologous polypeptides are characterized as having one or more amino acid substitutions, deletions or additions. These changes are preferably of a minor nature, that is conservative amino acid substitutions (see below) and other substitutions that do not significantly affect the folding or activity of the polypeptide; small deletions, typically of one to about 30 amino acids; and small amino- or carboxyl-terminal extensions, such as an amino-terminal methionine residue, a small linker peptide of up to about 20-25 residues, or an affinity tag.

Conservative Amino Acid Substitutions

Basic: arginine
lysine
histidine
Acidic: glutamic acid
aspartic acid
Polar: glutamine
asparagine
Hydrophobic: leucine
isoleucine
valine
Aromatic: phenylalanine
tryptophan
tyrosine
Small: glycine
alanine
serine
threonine
methionine In addition to the 20 standard amino acids, non-standard amino acids (such as 4-hydroxyproline, 6-N-methyl lysine, 2-aminoisobutyric acid, isovaline and α-methyl serine) may be substituted for amino acid residues of the polypeptides of the present invention. A limited number of non-conservative amino acids, amino acids that are not encoded by the genetic code, and unnatural amino acids may be substituted for polypeptide amino acid residues. The polypeptides of the present invention can also comprise non-naturally occurring amino acid residues.

Non-naturally occurring amino acids include, without limitation, trans-3-methylproline, 2,4-methano-proline, cis-4-hydroxyproline, trans-4-hydroxy-proline, N-methylglycine, allo-threonine, methyl-threonine, hydroxy-ethylcysteine, hydroxyethyl homo-cysteine, nitro-glutamine, homoglutamine, pipecolic acid, tert-leucine, norvaline, 2-azaphenylalanine, 3-azaphenyl-alanine, 4-azaphenyl-alanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell free system comprising an *E. coli* S30 extract and commercially available enzymes and other reagents. Proteins are purified by chromatography. See, for example, Robertson et al., J. Am. Chem. Soc. 113:2722, 1991; Ellman et al., Methods Enzymol. 202:301, 1991; Chung et al., Science 259:806-9, 1993; and Chung et al., Proc. Natl. Acad. Sci. USA 90:10145-9, 1993). In a second method, translation is carried out in *Xenopus* oocytes by microinjection of mutated mRNA and chemically aminoacylated suppressor tRNAs (Turcatti et al., J. Biol. Chem. 271:19991-8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the polypeptide in place of its natural counterpart. See, Koide et al., Biochem. 33:7470-6, 1994. Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395-403, 1993).

A limited number of non-conservative amino acids, amino acids that are not encoded by the genetic code, non-naturally occurring amino acids, and unnatural amino acids may be substituted for amino acid residues of polypeptides of the present invention.

Essential amino acids in the polypeptides of the present invention can be identified according to procedures known in the art, such as site-directed mutagenesis or alanine-scanning mutagenesis (Cunningham and Wells, Science 244: 1081-5, 1989). Sites of biological interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., Science 255:306-12, 1992; Smith et al., J. Mol. Biol. 224:899-904, 1992; Wlodaver et al., FEBS Lett. 309:59-64, 1992. The identities of essential amino acids can also be inferred from analysis of homologies with related components (e.g. the translocation or protease components) of the polypeptides of the present invention.

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Multiple amino acid substitutions can be made and tested using known methods of mutagenesis and screening, such as those disclosed by Reidhaar-Olson and Sauer (Science 241: 53-7, 1988) or Bowie and Sauer (Proc. Natl. Acad. Sci. USA 86:2152-6, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30:10832-7, 1991; Ladner et al., U.S. Pat. No. 5,223,409; Huse, WIPO Publication WO 92/06204) and region-directed mutagenesis (Derbyshire et al., Gene 46:145, 1986; Ner et al., DNA 7:127, 1988).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide the skilled person with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range.

The headings provided herein are not limitations of the various aspects or embodiments of this disclosure.

Other definitions of terms may appear throughout the specification. Before the exemplary embodiments are described in more detail, it is to be understood that this disclosure is not limited to particular embodiments described, and as such may vary. It is also to be understood that the terminology used herein is for the purpose of describing particular embodiments only, and is not intended to be limiting, since the scope of the present disclosure will be defined only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "a bacterium" includes a plurality of such a bacterium and reference to "the bacterium" includes reference to one or more bacterial cells and equivalents thereof known to those skilled in the art, and so forth.

The publications discussed herein are provided solely for their disclosure prior to the filing date of the present application. Nothing herein is to be construed as an admission that such publications constitute prior art to the claims appended hereto. All publications mentioned in the above specification are herein incorporated by reference.

The invention will now be described, by way of example only, with reference to the following Examples.

FIGURES

Embodiments of the invention will now be described, by way of example only, with reference to accompanying figures, in which:

FIG. 1 shows a scheme representing the analysis of lipids on intact bacteria through mass spectrometry. The test sample is placed (11) onto the MALDI target (10) and overlaid with a suitable matrix solution (12). Mass spectrometry in negative or positive ion mode is undertaken using any suitable mass spectrometry machine (12) (e.g. 4800 MALDI TOF/TOF Analyser from Applied Biosystems). MS may involve use of atypical solvents matrix (organic solvents, $CHCL_3$, MeOH, PE, DE). MS=mass spectrometry; $CHCl_3$=Chlorine; MeOH=Methanol; PE=Petroleum Ether; DE=diethyl-ether.

FIG. 2(A) shows typical structures of: native Lipid A (21) having a size of 1976 m/z; Lipid A modified with phosphoethanolamine (pETN) at the 1' phosphate with concomitant loss of the 4' phosphate (22) having a size of 1821 m/z; (B) shows Lipid A modified with pETN having a size of 1919 m/z (23); and Lipid A modified with 4-amino-L-arabinose (L-Ara4N) and pETN. Numbers indicate the number of carbon atoms in each fatty acid chain.

FIG. 3 shows a schematic of Lipid A modifications related to cyclic polypeptide antibiotic (e.g. polymyxin) resistance in a bacterium of the family Enterobacteriaceae. The modification of Lipid A (31) with phosphoethanolamine (pETN) occurs in bacteria comprising a plasmid having a Mobilised colistin resistance (MCR) or mcr-like gene (32). The modification of Lipid A with 4-amino-L-arabinose (L-Ara4N) and/or phosphoethanolamine (33) occurs in bacteria comprising certain alterations in genes (e.g. pmrA, pmrB, pmrC, pmrD, pmrE, pmrR, phoP, phoQ, mgrB, arnA, arnB, arnC, arnD, arnE, arnF, arnF, arnT, cptA, eptB).

FIG. 4 shows examples of MALDI mass spectra generated by a method of the present invention, demonstrating the discrimination between polymyxin susceptible *Escherichia coli* (A), chromosome-encoded polymyxin resistant *E. coli* (B), and plasmid-encoded polymyxin resistant (e.g. mcr-1 positive) *E. coli* (C). For each mass spectrum, the peak at m/z 1796.2 was assigned to native Lipid A, the peak at m/z 1919.2 was assigned to Lipid A modified by phosphoethanolamine, and the peak at 1821.2 was assigned to Lipid A modified by phosphoethanolamine at the 1' position with concomitant loss of the 4' phosphate.

FIG. 5 shows examples of MALDI mass spectra generated by a method of the present invention, demonstrating the discrimination between polymyxin susceptible *Escherichia coli* (e.g. *E. coli* J53) (top panel) and plasmid-encoded polymyxin resistant (e.g. mcr-1 positive) *E. coli* (e.g. *E. coli*

R4) (bottom panel). For each mass spectrum, the peak at m/z 1796.2 (50) was assigned to native Lipid A (e.g. a second defined peak), the peak at m/z 1919.2 (51) was assigned to Lipid A modified by phosphoethanolamine (e.g. a first defined peak).

FIG. 6 shows distribution of the Polymyxin Resistance Ratios (PPR) for the 79 *E. coli* strains tested (see FIG. 18). Three independent experiments were performed for each strain. Cut-off values for discrimination between polymyxin-resistance and polymyxin-susceptibility (0.1) and for discrimination between chromosome- and MCR-encoded resistance to polymyxin (0.5) are indicated by grey and black dotted lines, respectively. $PRR_{E.\ coli}=(I_{1919}+I_{1821})/I_{1796}$. I=Intensity (e.g. peak intensity on a mass spectrum).

FIG. 7 shows examples of MALDI mass spectra generated by a method of the present invention, demonstrating the discrimination between polymyxin susceptible *Klebsiella pneumoniae* (top panel) and plasmid encoded polymyxin-resistant (e.g. mcr-1 positive) *K. pneumoniae* (bottom panel). For each mass spectrum, the peak at m/z 1796.2 and m/z 1840 (71) is assigned to native Lipid A, the peak at m/z 1919.2 (72) is assigned to Lipid A modified by phosphoethanolamine.

FIG. 8 shows examples of MALDI mass spectra generated by a method of the present invention, demonstrating the discrimination between polymyxin susceptible *Klebsiella* spp. (first panel), chromosome encoded polymyxin-resistant *Klebsiella* spp. (second panel), plasmid encoded polymyxin-resistant (e.g. mcr-1 positive) *Klebsiella* spp. (third panel) and *Klebsiella* spp. which are both chromosome encoded plasmid encoded polymyxin-resistant (bottom panel). For each mass spectrum, the peaks at m/z 1824, m/z 1840, m/z 2062, and m/z 2078 were assigned to native Lipid A, the peaks at m/z 1971 and m/z 2209 were assigned to Lipid A modified by L-Ara4N and the peaks at m/z 1963 and m/z 2201 were assigned to Lipid A modified by pETN.

FIG. 9 shows examples of MALDI mass spectra generated with the *A. baumannii* strains S1 and R1. For each mass spectrum, the peak at m/z 1910.3 (90) is assigned to native Lipid A, the peak at m/z 2033.3 (91) is assigned to Lipid A modified by phosphoethanolamine. Top panel represents mass spectra obtained from polymyxin susceptible *A. baumannii* S1. Bottom panel represents mass spectra obtained from polymyxin resistant *A. baumannii* R1.

FIG. 10 shows examples of MALDI mass spectra generated with the *E. coli* strains S1 J53, R4 J53, R4 and R1. For each mass spectrum, the peak at m/z 1796.2 is assigned to native Lipid A (e.g. a second defined peak), the peak at m/z 1919.2 is assigned to Lipid A modified by phosphoethanolamine (e.g. a first defined peak). The peak at m/z 1821 (+25 m/z from the native lipid A) (e.g. a third defined peak) is typical of a mass spectrum generated through a method of the invention with plasmid encoded polymyxin-resistant Enterobacteriaceae (e.g. *Escherichia coli, Klebsiella pneumoniae, Klebsiella oxytoca, Enterobacter aerogenes, Enterobacter cloacae, Enterobacter asburiae, Shigella sonnei, Shigella flexneri, Salmonella enterica, Citrobacter freundii, Citrobacter koseri, Citrobacter amalonaticus* or *Citrobacter youngae*) bacteria. Top panel represents mass spectra obtained from polymyxin susceptible *E. coli* J53. Middle panel represents mass spectra obtained from plasmid-encoded polymyxin resistant *E. coli* R4. Bottom panel represents mass spectra obtained from polymyxin resistant *E. coli* R1.

FIG. 11 shows examples of MALDI mass spectra generated with the *K. pneumoniae* strains S32, R46, R42. For each mass spectrum, the peak at m/z 1796.2 is assigned to native Lipid A (e.g. a second defined peak), the peak at m/z 1919.2 is assigned to Lipid A modified by phosphoethanolamine (e.g. a first defined peak). The peak at m/z 1821 (+25 m/z from the native lipid A) (e.g. a third defined peak) is typical of a mass spectrum generated through a method if the invention with plasmid encoded polymyxin-resistant Enterobacteriaceae (e.g. *Escherichia coli, Klebsiella pneumoniae, Klebsiella oxytoca, Enterobacter aerogenes, Enterobacter cloacae, Enterobacter asburiae, Shigella sonnei, Shigella flexneri, Salmonella enterica, Citrobacter freundii, Citrobacter koseri, Citrobacter amalonaticus* or *Citrobacter youngae*) bacteria. Top panel represents mass spectra obtained from polymyxin susceptible *K. pneumoniae* S32. Middle panel represents mass spectra obtained from plasmid-encoded polymyxin resistant *K. pneumoniae* R46. Bottom panel represents mass spectra obtained from chromosome-encoded polymyxin resistant *K. pneumoniae* KpR42.

FIG. 12 shows examples of MALDI mass spectra generated by a method of the present invention, demonstrating the discrimination between polymyxin susceptible *Salmonella* spp. (top panel), chromosome-encoded polymyxin resistant *Salmonella* spp. (middle panel), and plasmid-encoded polymyxin resistant *Salmonella* spp (bottom panel). For each mass spectrum, the peak at m/z 1796 was assigned to native Lipid A, the peaks at m/z 1919 and m/z 2034 were assigned to Lipid A modified by phosphoethanolamine, the peak at m/z was assign to Lipid A modified with L-Ara4N, and the peaks at 1919 and 2157 were assigned to Lipid A modified by phosphoethanolamine.

FIG. 13 shows a plot of example ratios of phosphoethanolamine modified Lipid A to native Lipid A, obtained for polymyxin susceptible (n=44) and polymyxin-resistant (n=8) *E. coli*, calculated as follows: Intensity of Lipid A modified by phosphoethanolamine peak/Intensity of native Lipid A peak, e.g. Intensity of m/z 1919 peak/Intensity of m/z 1796 peak. The box plot represents the data by its quartiles.

FIG. 14 shows examples of MALDI mass spectra generated by a method of the present invention from *E. coli* grown on various clinically relevant media. (A) shows mass spectra for bacteria grown on Mueller-Hinton media; representative mass spectra are shown for polymyxin susceptible bacteria (top panel) having $PRR_{E.\ coli}=0$, plasmid-encoded polymyxin resistant bacteria (middle panel) having $PRR_{E.\ coli}=3.83$, and chromosome-encoded polymyxin resistant bacteria (bottom panel) having $PRR_{E.\ coli}=0.24$. (B) shows mass spectra for bacteria grown on Lysogeny Broth media; representative mass spectra are shown for polymyxin susceptible bacteria (top panel) having $PRR_{E.\ coli}=0$, plasmid-encoded polymyxin resistant bacteria (middle panel) having $PRR_{E.\ coli}=2.89$, and chromosome-encoded polymyxin resistant bacteria (bottom panel) having $PRR_{E.\ coli}=0.35$. (C) shows mass spectra for bacteria grown on Mueller-Hinton+Polymyxin B (1 mg/ml) media; representative mass spectra are shown for plasmid-encoded polymyxin resistant bacteria (top panel) having $PRR_{E.\ coli}=4.58$, and chromosome-encoded polymyxin resistant bacteria (bottom panel) having $PRR_{E.\ coli}=0.37$. (D) shows mass spectra for bacteria grown on Mueller-Hinton+Polymyxin B (2 mg/ml) media; representative mass spectra are shown for plasmid-encoded polymyxin resistant bacteria (top panel) having $PRR_{E.\ coli}=5.69$, and chromosome-encoded polymyxin resistant bacteria (bottom panel) having $PRR_{E.\ coli}=0.21$. *E. coli* strains used were: J53 (susceptible), J53+mcr-1 (plasmid-encoded resistant) and CNR20160235 (chromosome-encoded resistant).

FIG. 15 Resume of the peaks of interest (e.g. particular interest) profiles observed in *Escherichia coli, Klebsiella pneumoniae, Salmonella* spp (e.g. *Salmonella enterica*) and *Acinetobacter baumannii.*

FIG. 16 shows alignment of the nucleic acid sequences of MCR variants.

Figure 1:
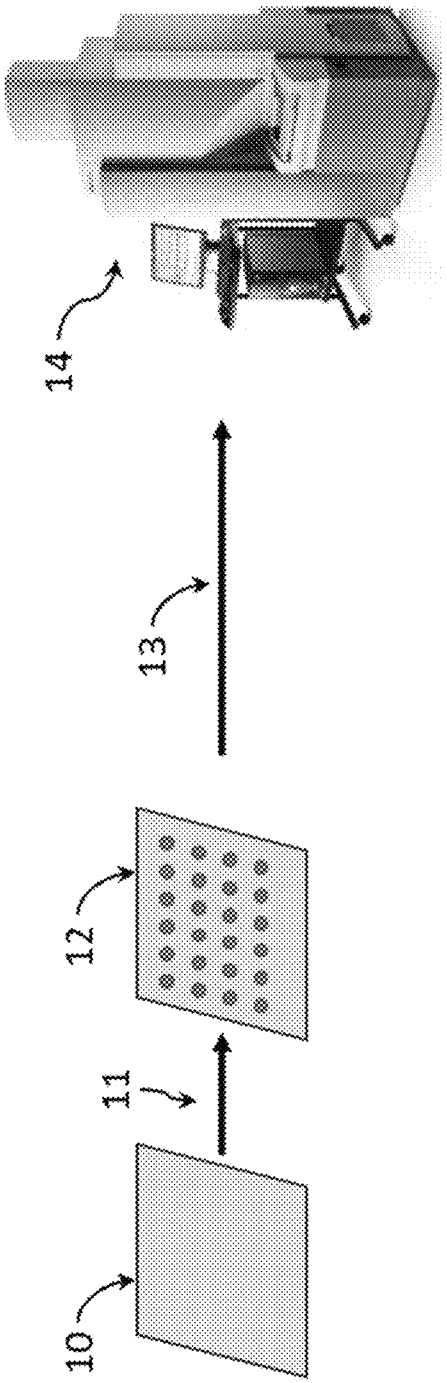
Figure 3:
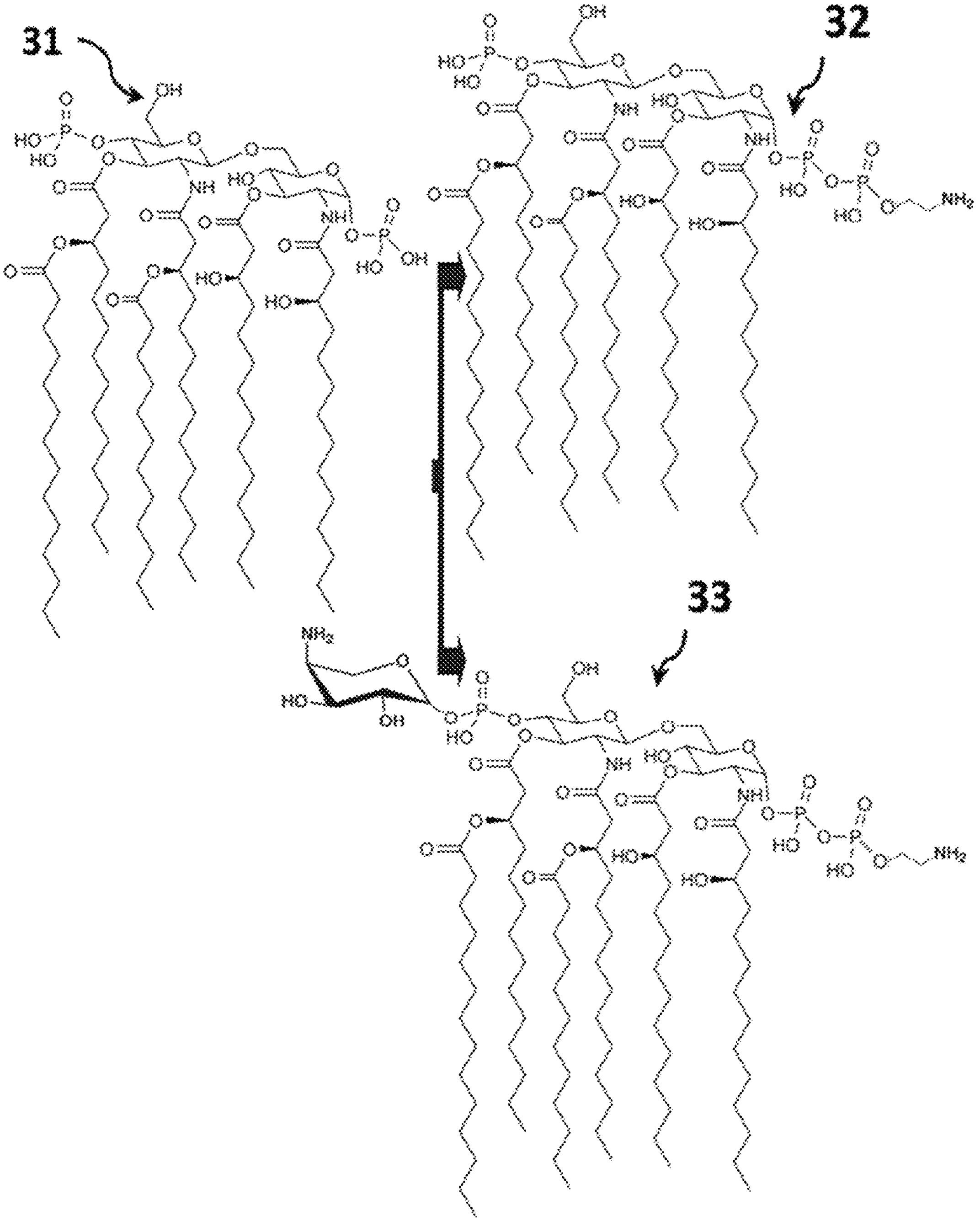

FIG. 18 shows characteristics and MALDIxin test results for *E. coli* strains.[a] Laboratory strains are underlined, all other strains are clinical isolates. [b] For unknown mechanisms absence of mutation in mgrB, pmrA, pmrB, phoP and phoQ have been checked by PCR and sequencing, and the strain was negative for mcr-like genes. [c] Carbapenemases are shown in bold and extended spectrum β-lactamases are underlined. [d] PRR stands for Polymyxin Resistance Ratio. [e] The MCR-2 producing *E. coli* R12 F5 has been previously described by Xavier B B et al. (Euro surveillance 2016; 21(27)). * natural plasmids, the natural mcr-5 carrying plasmid has been previously described by Borowiak M et al. (Journal of Antimicrobial Chemotherapy (2017), 72(12), 3317-3324). ** functional mcr-like gene cloned into pDM1, an IPTG-inducible (final concentration 0.5 mM), $Tet^R$ derivative of pACYC184. The genes mcr-1, mcr-2 and mcr-5 were cloned into the SacI/XmaI sites of the vector, while for mcr-3, the NdeI/XmaI sites were used.

FIG. 19 shows results of a method of the invention (e.g. the MALDIxin test) on bacterial colonies after 24 hours, 48 hours, one week and two weeks. [a] Laboratory strains are underlined, all other strains are clinical isolates. [b] For unknown mechanisms absence of mutation in mgrB, pmrA, pmrB, phoP and phoQ have be checked by PCR and sequencing, and the strain was negative for mcr-like genes. PRR stands for Polymyxin Resistance Ratio. * natural plasmid.

EXAMPLES

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

Materials & Methods

Bacterial Strains

The following bacterial strains, representative of clinical isolates, were used in a method of the invention: *E. coli* 51 J53, *E. coli* R4 J53, *E. coli* R1, *K. pneumoniae* R46, *K. pneumoniae* R42, *A. baumannii* 51 and *A. baumannii* R1.

Additionally, a collection of 79 *E. coli* strains were used, including 33 polymyxin-resistant isolates, of which 29 were MCR producers (18 MCR-1, two MCR-1.5, three MCR-2, two MCR-3 and four MCR-5). The 46 polymyxin-susceptible *E. coli* strains were of various phenotypes, from wild-type to carbapenemase producers (FIG. 18). The MALDIxin test was prospectively evaluated using a collection of 78 isolates of carbapenemase-producing *E. coli* received during October and November 2016, from the French National Reference Centre (NRC) for Antimicrobial Resistance (Table 2).

Plasmid encoded polymyxin-resistant bacterial strains comprise a plasmid having an mcr-like gene, such as mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4 or mcr-5gene, or a sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16. Addition of phosphoethanolamine to Lipid A in such strains is plasmid mediated through the mcr-like gene, which confers plasmid-encoded resistance to polymyxin antibiotics (e.g. colistin) in isolates from humans and animals.

Chromosome encoded polymyxin-resistant bacterial strains comprise a mutation and/or truncation in any one of the genes pmrA, pmrB, pmrC, pmrD, pmrE, pmrR, phoP, phoQ, mgrB, arnA, arnB, arnC, arnD, arnE, arnF, arnF, arnT, cptA, eptB. For example, missense mutations in pmrA or pmrB can cause the constitutive activation of the PmrA/PmrB system, leading to upregulation of pmrC and the arnBCADTEF operon, and thus synthesis and addition of phosphoethanolamine and 4-amino-L-arabinose to Lipid A. Disruption (e.g. mutation or truncation) of mgrB prevents negative feedback on the PhoP/PhoQ regulatory system, leading to the addition of phosphoethanolamine and 4-amino-L-arabinose to Lipid A. Disruption of mgrB can be due to insertional inactivation (e.g. with ISKpn25).

Susceptibility Testing

Minimal inhibitory concentrations (MICs) were determined by BMD according to the guidelines of the CLSI and EUCAST joint subcommittee. Results were interpreted using EUCAST breakpoint as updated in 2017.

Methods

A one microliter loop (equivalent to one or less than one colony equivalent to $10^4$ to $10^7$ bacterial cells) of bacteria, recovered from colonies grown on any bacteria culture medium or from any enrichment liquid medium (including blood cultures or other clinical samples with enough amount of bacteria) was collected. This colony was transferred into an Eppendorf tube (0.5 to 2 mL) containing 100 microliter of water (distilled or double-distilled). The culture medium was Luria Broth agar; or other non-selective media such as blood agar or chocolate blood agar, Gram-negative selective media such as Drigalski or MacConkey media, and several chromogenic media may be used. Strains may be cultivated under aerobic conditions in Luria Broth agar medium at 37° C. overnight.

Bacteria were then heat inactivated (facultative step) using a dry bath or a water bath for 30 min at 80° C., or alternatively for 1 h at 90° C.

Bacteria were pelleted and washed at least once by 200 µl double-distilled water to remove salts excess resulting from the culture medium. Failure to wash the bacterial pellet to remove the remaining salts can lead to an undesirable background on the final MALDI-TOF spectrum, obscuring or removing the interpretability of the results. Bacteria may alternatively be washed through a commercially available solution (e.g. salt absorbing columns). Bacteria may be washed three times with 0.5 ml of double distilled water and centrifuged at 9000×g for 5 min.

The washed bacteria were resuspended in 50 μl of double-distilled water to provide a bacterial suspension at a final concentration of about $10^4$ to $10^7$ bacteria per μl and 0.4 μl was loaded on the MALDI-TOF target. Such classical MALDI-TOF targets as used in the average clinical microbiology lab are suitable for use with the present invention.

0.6 μl (or 0.8 μl) of a designed atypical matrix was admixed with the 0.4 μl of bacterial suspension. Suitably, the atypical matrix comprises 2,5-dihydroxybenzoic acid at a final concentration of 10 mg/ml suspended in organic solvents, usually Chloroform/Methanol 9:1 v/v. Additional organic solvents suitable for use with the invention include chloroform, dichloromethane, methanol, ether, diethylether, petroleum ether, isopropanol, butanol, hexane. Table 1 provides examples of solvents suitable for use with the present invention. The sample and matrix solution were deposited on the target (e.g. MALDI target), mixed with a micropipette and dried gently under a stream of air. After optimization, this solvent system and solvent system to sample ratio allows selective ionization of Lipid A (e.g. on intact bacteria).

Alternatively, two colonies of bacterial cells grown on any bacteria culture medium or from any enrichment liquid medium (including blood cultures or other clinical samples with enough amount of bacteria) are collected and transferred into an Eppendorf tube (0.5 to 2 ml). This may be followed by suspended the colonies in water (distilled or double distilled) followed by pelleting and washing the bacteria at least once (e.g. 2-5 times) with distilled or double distilled water, e.g. to remove excess salts. The bacteria may be resuspended in 2% acetic acid in water (e.g. 200 μl 2% acetic acid in water). The bacterial suspension may then be heated by any suitable means, for example using a heat-block, preferably for 2 hours at 100° C. This may be followed by pelleting the bacteria (e.g. by centrifuging for 5 seconds at 15,000 g) and resuspending the bacteria in distilled or double distilled water (e.g. 50 μl $ddH_20$). Norharmane (e.g. N6252 Sigma) matrix or any of its derivatives (e.g. 3-Hydroxymethyl-β-carboline; 3-Methyl-a-carboline; Ethyl 2,3,4,9-tetrahydro-1H-β-carboline-3-carboxylate; Ethyl β-carboline-3-carboxylate; 1-Methylindole-2-carboxylic acid; norharman methiodide; β-Carboline-3-carboxylic acid N-methylamide; Harmaline hydrochloride dehydrate; 1,2,3,4-tetrahydro-beta-carboline-1-carboxylic acid; 1,2,3,4-Tetrahydro-9H-pyrido[3,4-b]indole; Harmane; Harmine; Harmaline) may be admixed with the bacterial suspension. Suitably, 0.6 μl of said matrix may be admixed with 0.4 μl of bacterial suspension. Suitably, the Norharmane matrix or any of its derivatives (as outlined above) is present at a final concentration of 10 mg/ml suspended in organic solvents, usually Chloroform/Methanol 9:1 v/v. This protocol is particularly suitable for use in a method of the invention where the Lipid A composition of *Klebsiella* and/or *Salmonella* bacteria are being investigated.

A mass spectrum was generated. Typical MALDI-TOF mass spectrometry machines suitable for use in a method of the present invention include the Bioyper from Bruker Daltonics and VITEK-MS from bioMerieux. Alternatively, MALDI-TOF MS analysis is performed on a 4800 Proteomics Analyzer (with TOF-TOF Optics, Applied Biosystems) (e.g. using the reflectron mode). Samples are typically analyzed operating at 20 kV in the negative ion mode using an extraction delay time set at 20 ns. Typically, spectra from 500 to 2000 laser shots are summed to obtain the final spectrum. All experiments are typically carried out on three independent samples and in three technical replicates. The negative control consisted of 0.5 μl of double distilled water and 0.5 μl of the matrix solution. Mass spectrometry data are typically analyzed using Data Explorer version 4.9 from Applied Biosystems. The mass spectrum may scanned between m/z 1000 and 2200, preferably between m/z 1,500 and 2,500.

The resulting mass spectrum was analysed, and peaks corresponding to intact Lipid A (e.g. 1796 m/z for *Escherichia coli*) and modified Lipid A (addition of phosphoethanolamine (pETN) [+123 m/z]) were identified and used to calculate intensity ratios. The modified Lipid A to native Lipid A ratio is used to discriminate between polymyxin-susceptible and polymyxin-resistant bacteria. For polymyxin-resistant Enterobacteriaceae discrimination between plasmid encoded resistance and chromosome encoded resistance has been assessed using the third peak [+25 m/z] (e.g. 1821 m/z for *Escherichia coli* and *Klebsiella pneumoniae*).

Patients infected with plasmid encoded polymyxin-resistant bacteria, as determined by a method of the present invention, were quarantined to prevent transmission to other patients and/or subjects.

This method (e.g. according to the claims) allowed the detection of polymyxin resistance directly on bacteria (e.g. using samples comprising a bacterial membrane) in less than 15 minutes.

Statistical Analysis

Data were compared two-by-two using unpaired Welch's t-test. P values<0.05 were considered statistically different.

TABLE 1

List of suitable organic solvents suitable for use in a matrix solution of the invention.

| Solvent | Formula | MW | Boiling point (° C.) | Melting point (° C.) | Density (g/mL) | Solubility in water (g/100 g) | Dielectric Constant 3, 4 | Flash point (° C.) |
|---|---|---|---|---|---|---|---|---|
| acetic acid | $C_2H_4O_2$ | 60.052 | 118 | 16.6 | 1.0446 | Miscible | 6.2 | 39 |
| acetone | $C_3H_6O$ | 58.079 | 56.05 | −94.7 | 0.7845 | Miscible | 21.01 | −20 |
| acetonitrile | $C_2H_3N$ | 41.052 | 81.65 | −43.8 | 0.7857 | Miscible | 36.64 | 6 |
| benzene | $C_6H_6$ | 78.11 | 80.1 | 5.5 | 0.8765 | 0.18 | 2.28 | −11 |
| 1-butanol | $C_4H_{10}O$ | 74.12 | 117.7 | −88.6 | 0.8095 | 6.3 | 17.8 | 37 |
| 2-butanol | $C_4H_{10}O$ | 74.12 | 99.5 | −88.5 | 0.8063 | 15 | 17.26 | 24 |
| 2-butanone | $C_4H_8O$ | 72.11 | 79.6 | −86.6 | 0.7999 | 25.6 | 18.6 | −9 |
| t-butyl alcohol | $C_4H_{10}O$ | 74.12 | 82.4 | 25.7 | 0.7887 | Miscible | 12.5 | 11 |
| carbon tetrachloride | $CCl_4$ | 153.82 | 76.8 | −22.6 | 1.594 | 0.08 | 2.24 | — |
| chlorobenzene | $C_6H_5Cl$ | 112.56 | 131.7 | −45.3 | 1.1058 | 0.05 | 5.69 | 28 |
| chloroform | $CHCl_3$ | 119.38 | 61.2 | −63.4 | 1.4788 | 0.795 | 4.81 | — |
| cyclohexane | $C_6H_{12}$ | 84.16 | 80.7 | 6.6 | 0.7739 | <0.1 | 2.02 | −20 |

TABLE 1-continued

List of suitable organic solvents suitable for use in a matrix solution of the invention.

| Solvent | Formula | MW | Boiling point (° C.) | Melting point (° C.) | Density (g/mL) | Solubility in water (g/100 g) | Dielectric Constant 3, 4 | Flash point (° C.) |
|---|---|---|---|---|---|---|---|---|
| 1,2-dichloroethane | $C_2H_4Cl_2$ | 98.96 | 83.5 | −35.7 | 1.245 | 0.861 | 10.42 | 13 |
| diethylene glycol | $C_4H_{10}O_3$ | 106.12 | 246 | −10 | 1.1197 | 10 | 31.8 | 124 |
| diethyl ether | $C_4H_{10}O$ | 74.12 | 34.5 | −116.2 | 0.713 | 7.5 | 4.267 | −45 |
| diglyme (diethylene glycol dimethyl ether) | $C_6H_{14}O_3$ | 134.17 | 162 | −68 | 0.943 | Miscible | 7.23 | 67 |
| 1,2-dimethoxy-ethane (glyme, DME) | $C_4H_{10}O_2$ | 90.12 | 84.5 | −69.2 | 0.8637 | Miscible | 7.3 | −2 |
| dimethyl-formamide (DMF) | $C_3H_7NO$ | 73.09 | 153 | −60.48 | 0.9445 | Miscible | 38.25 | 58 |
| dimethyl sulfoxide (DMSO) | $C_2H_6OS$ | 78.13 | 189 | 18.4 | 1.092 | 25.3 | 47 | 95 |
| 1,4-dioxane | $C_4H_8O_2$ | 88.11 | 101.1 | 11.8 | 1.033 | Miscible | 2.21(25) | 12 |
| ethanol | $C_2H_6O$ | 46.07 | 78.5 | −114.1 | 0.789 | Miscible | 24.6 | 13 |
| ethyl acetate | $C_4H_8O_2$ | 88.11 | 77 | −83.6 | 0.895 | 8.7 | 6(25) | −4 |
| ethylene glycol | $C_2H_6O_2$ | 62.07 | 195 | −13 | 1.115 | Miscible | 37.7 | 111 |
| glycerin | $C_3H_8O_3$ | 92.09 | 290 | 17.8 | 1.261 | Miscible | 42.5 | 160 |
| heptane | $C_7H_{16}$ | 100.2 | 98 | −90.6 | 0.684 | 0.01 | 1.92 | −4 |
| Hexamethylph osphoramide (HMPA) | $C_6H_{18}N_3OP$ | 179.2 | 232.5 | 7.2 | 1.03 | Miscible | 31.3 | 105 |
| Hexamethyl-phosphorous triamide (HMPT) | $C_6H_{18}N_3P$ | 163.2 | 150 | −44 | 0.898 | Miscible | — | 26 |
| hexane | $C_6H_{14}$ | 86.18 | 69 | −95 | 0.659 | 0.014 | 1.89 | −22 |
| methanol | $CH_4O$ | 32.04 | 64.6 | −98 | 0.791 | Miscible | 32.6(25) | 12 |
| methyl t-butyl ether (MTBE) | $C_5H_{12}O$ | 88.15 | 55.2 | −109 | 0.741 | 5.1 | — | −28 |
| methylene chloride | $CH_2Cl_2$ | 84.93 | 39.8 | −96.7 | 1.326 | 1.32 | 9.08 | 1.6 |
| N-methyl-2-pyrrolidinone (NMP) | $CH_5H_9NO$ | 99.13 | 202 | −24 | 1.033 | 10 | 32 | 91 |
| pentane | $C_5H_{12}$ | 72.15 | 36.1 | −129.7 | 0.626 | 0.04 | 1.84 | −49 |
| Petroleum ether (ligroine) | — | — | 30-60 | −40 | 0.656 | — | — | −30 |
| 1-propanol | $C_3H_8O$ | 88.15 | 97 | −126 | 0.803 | Miscible | 20.1(25) | 15 |
| 2-propanol | $C_3H_8O$ | 88.15 | 82.4 | −88.5 | 0.785 | Miscible | 18.3(25) | 12 |
| pyridine | $C_5H_5N$ | 79.1 | 115.2 | −41.6 | 0.982 | Miscible | 12.3(25) | 17 |
| tetrahydrofuran (THF) | $C_4H_8O$ | 72.106 | 65 | −108.4 | 0.8833 | 30 | 7.52 | −14 |
| toluene | $C_7H_8$ | 92.14 | 110.6 | −93 | 0.867 | 0.05 | 2.38(25) | 4 |
| triethyl amine | $C_6H_{15}N$ | 101.19 | 88.9 | −114.7 | 0.728 | 0.02 | 2.4 | −11 |
| water | $H_2O$ | 18.02 | 100 | 0 | 0.998 | — | 78.54 | — |
| water, heavy | $D_2O$ | 20.03 | 101.3 | 4 | 1.107 | Miscible | — | — |
| o-xylene | $C_8H_{10}$ | 106.17 | 144 | −25.2 | 0.897 | Insoluble | 2.57 | 32 |
| m-xylene | $C_8H_{10}$ | 106.17 | 139.1 | −47.8 | 0.868 | Insoluble | 2.37 | 27 |
| p-xylene | $C_8H_{10}$ | 106.17 | 138.4 | 13.3 | 0.861 | Insoluble | 2.27 | 27 |

Example 1

Detection of the Presence or Absence of a Polymyxin-Resistant *Escherichia Coli* in a Test Sample Test samples comprising intact bacterial cells of *E. coli* (e.g. bacterial suspensions, washed to remove salt), as follows, were subjected mass spectrometry according to a method of the present invention: (i) Polymyxin-susceptible *E. coli*; (ii) chromosome encoded polymyxin-resistant *E. coli*; and (iii) plasmid encoded polymyxin-resistant *E. coli* (comprising a plasmid having the mcr-1 gene).

For polymyxin susceptible *E. coli*, the mass spectrum was dominated by a peak at m/z 1796.2 (FIG. 5, top panel; and FIG. 10, top panel) assigned to native Lipid A. The absence of a peak indicating the presence of Lipid A modified with phosphoethanolamine at m/z 1919.2 (i.e. 123 mass units greater than native Lipid A) successfully indicated the absence of a bacterium resistant to a polymyxin antibiotic.

Figure 5:
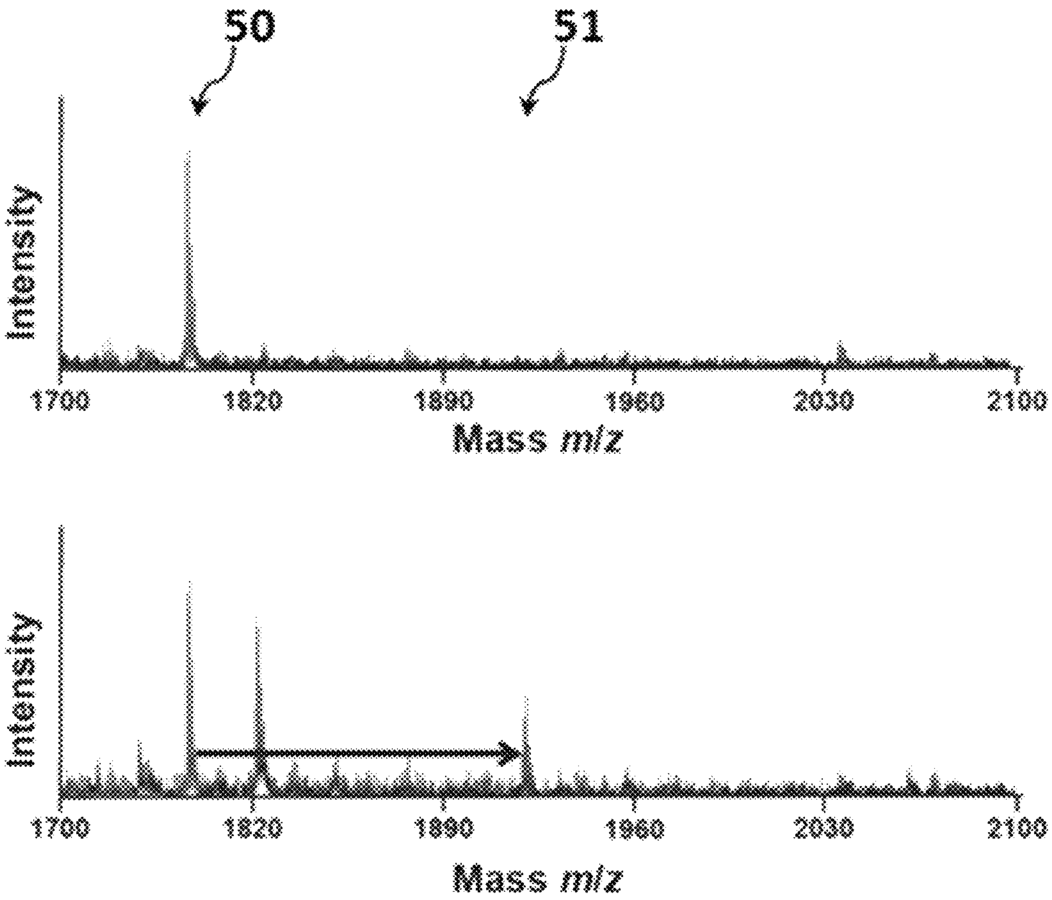
Figure 10:
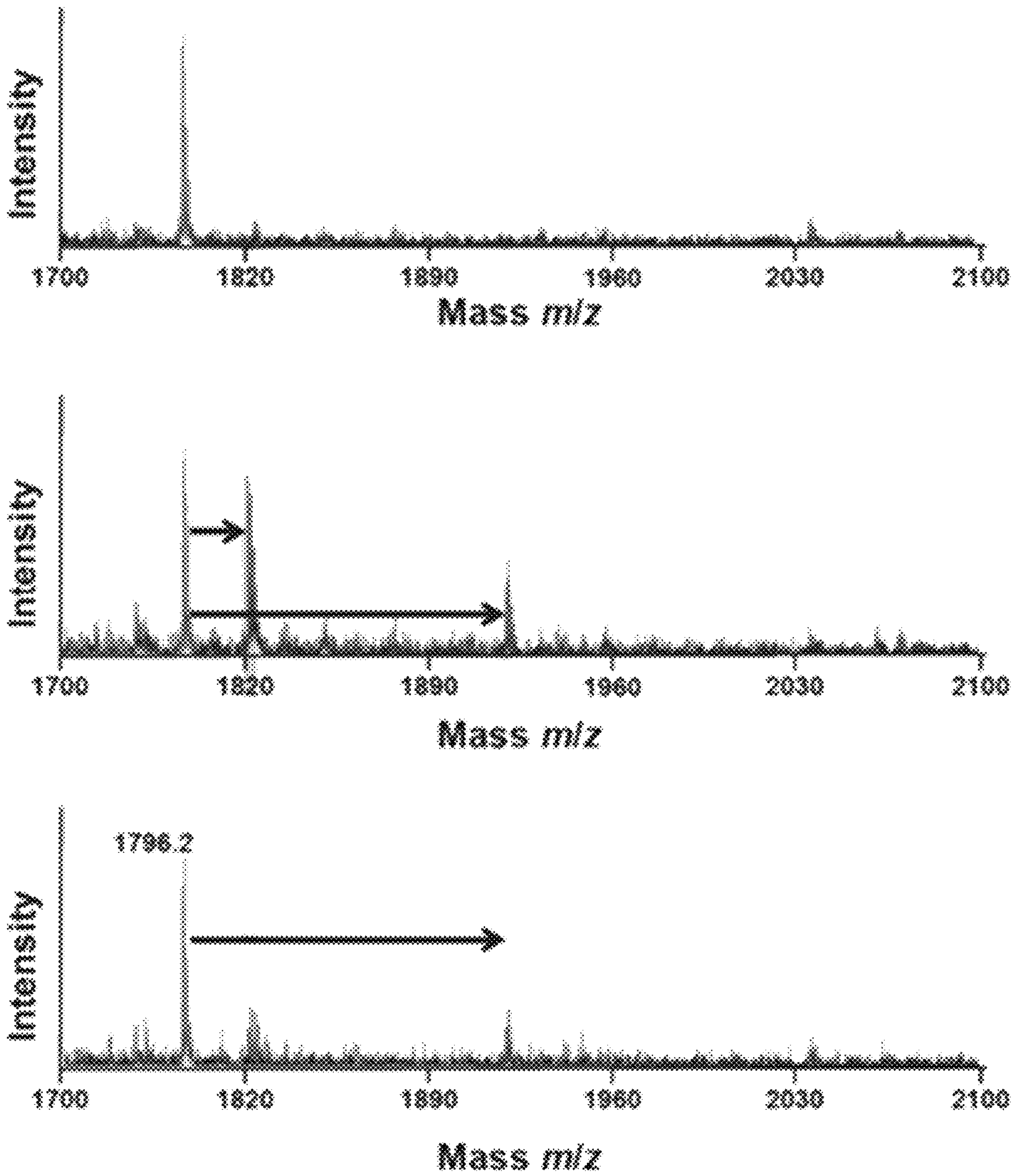

In plasmid encoded polymyxin-resistant *E. coli*, the mass spectrum further comprised peaks at m/z 1919.2 (i.e. 123 m/z units greater than native Lipid A), assigned to Lipid A modified by phosphoethanolamine and an unassigned peak at m/z 1821.2 (i.e. 25 mass units greater than native Lipid A, m/z 1796.2) (FIG. 5, bottom panel; and FIG. 10, middle panel). In one embodiment, said unassigned peak at m/z 1821.2 is assigned to Lipid A modified with pETN at 1' phosphate group with concomitant loss of the 4' phosphate group.

For chromosome encoded polymyxin-resistant *E. coli*, the mass spectrum further comprised peaks at m/z 1919.2 (i.e. 123 mass units greater than native Lipid A), assigned to Lipid A modified with phosphoethanolamine, and did not comprise the unassigned peak (which the present inventors have assigned to Lipid A modified with pETN at 1' phosphate group with concomitant loss of the 4' phosphate group) at m/z 1821.2.

The method of the present invention was further validated with strains of *E. coli* S1 J53, *E. coli* R4 J53 and *E. coli* R1 (FIG. 10).

Example 2

Detection of the Presence or Absence of a Polymyxin-Resistant *Klebsiella Pneumoniae* in a Test Sample Test samples comprising intact bacterial cells of *K. pneumoniae* (e.g. bacterial suspensions, washed to remove salt), as follows, were subjected to mass spectrometry according to a method of the present invention: (i) chromosome encoded polymyxin-resistant *K. pneumoniae* R46; and (ii) plasmid encoded polymyxin-resistant *K. pneumoniae* R42 (comprising a plasmid comprising the mcr-1 gene).

For polymyxin susceptible *K. pneumoniae*, the mass spectrum was dominated by a peak at m/z 1840.2 and m/z 1796.2 (FIG. 7, top panel; and FIG. 11, top panel) assigned to native Lipid A. The absence of a peak indicating the presence of Lipid A modified with phosphoethanolamine at m/z 1919.2 (i.e. 123 mass units greater than native Lipid A) successfully indicated the absence of a bacterium resistant to a polymyxin antibiotic.

Figure 7:
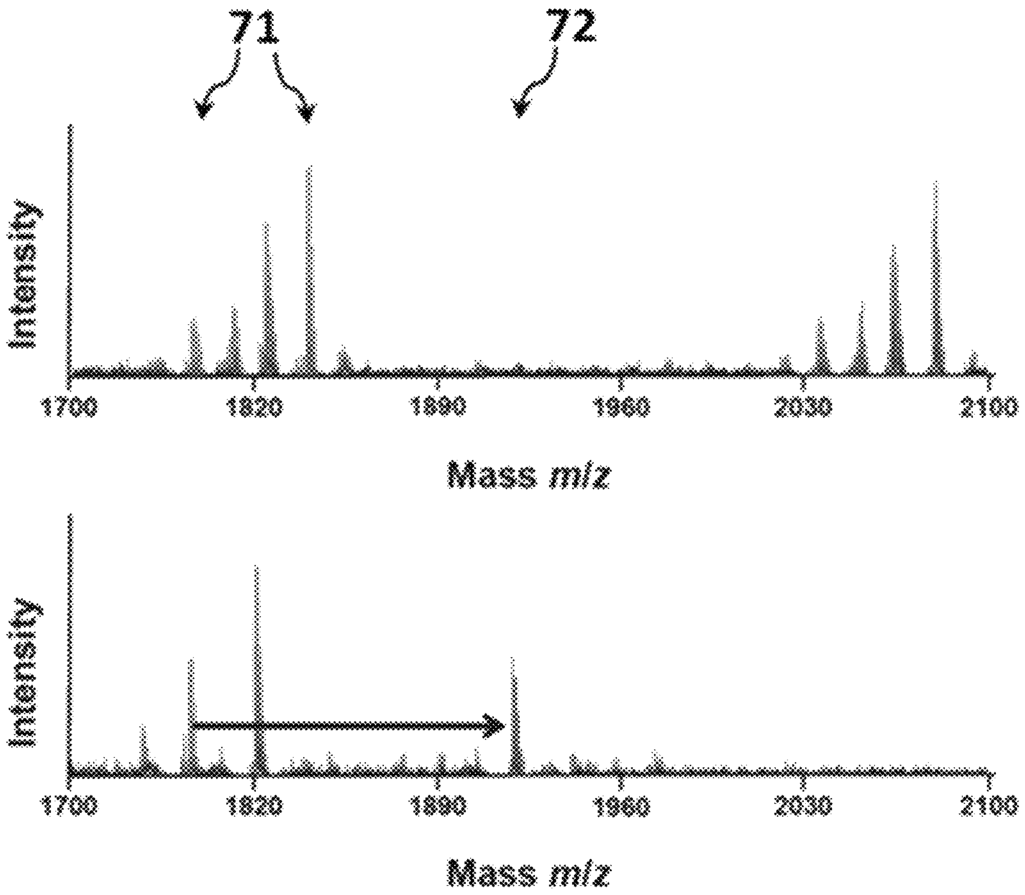
Figure 8:
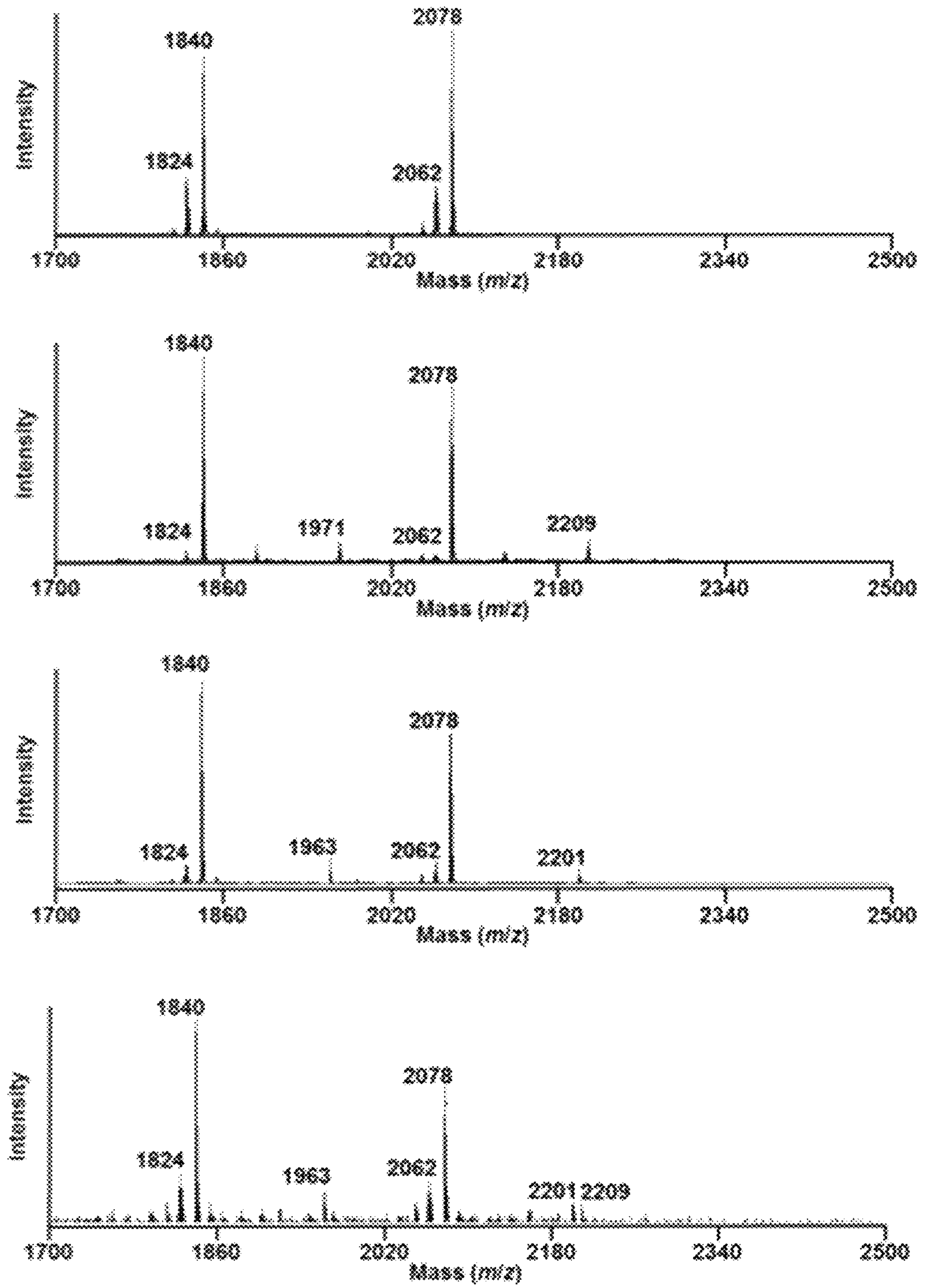
Figure 11:
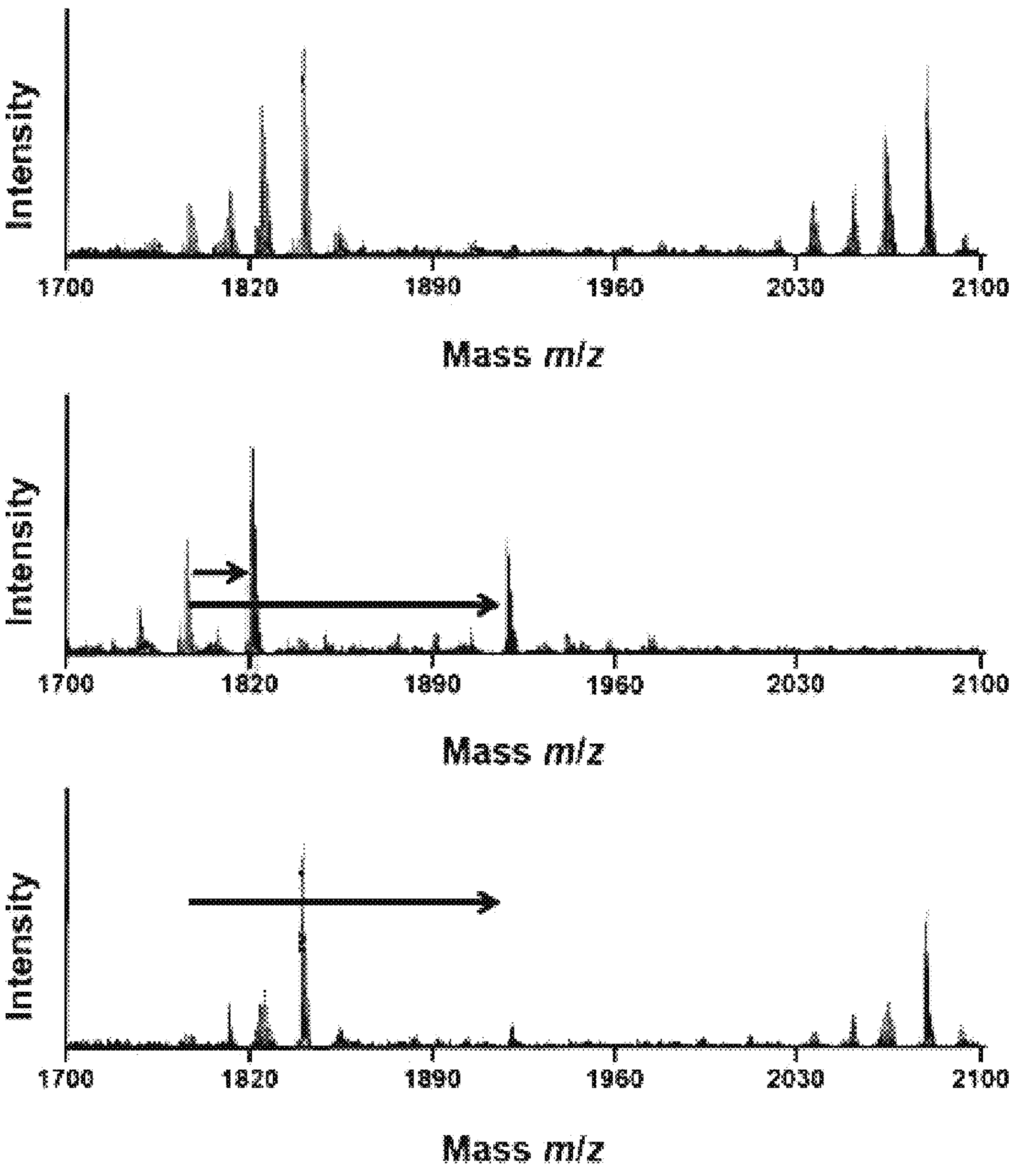
Figure 12:
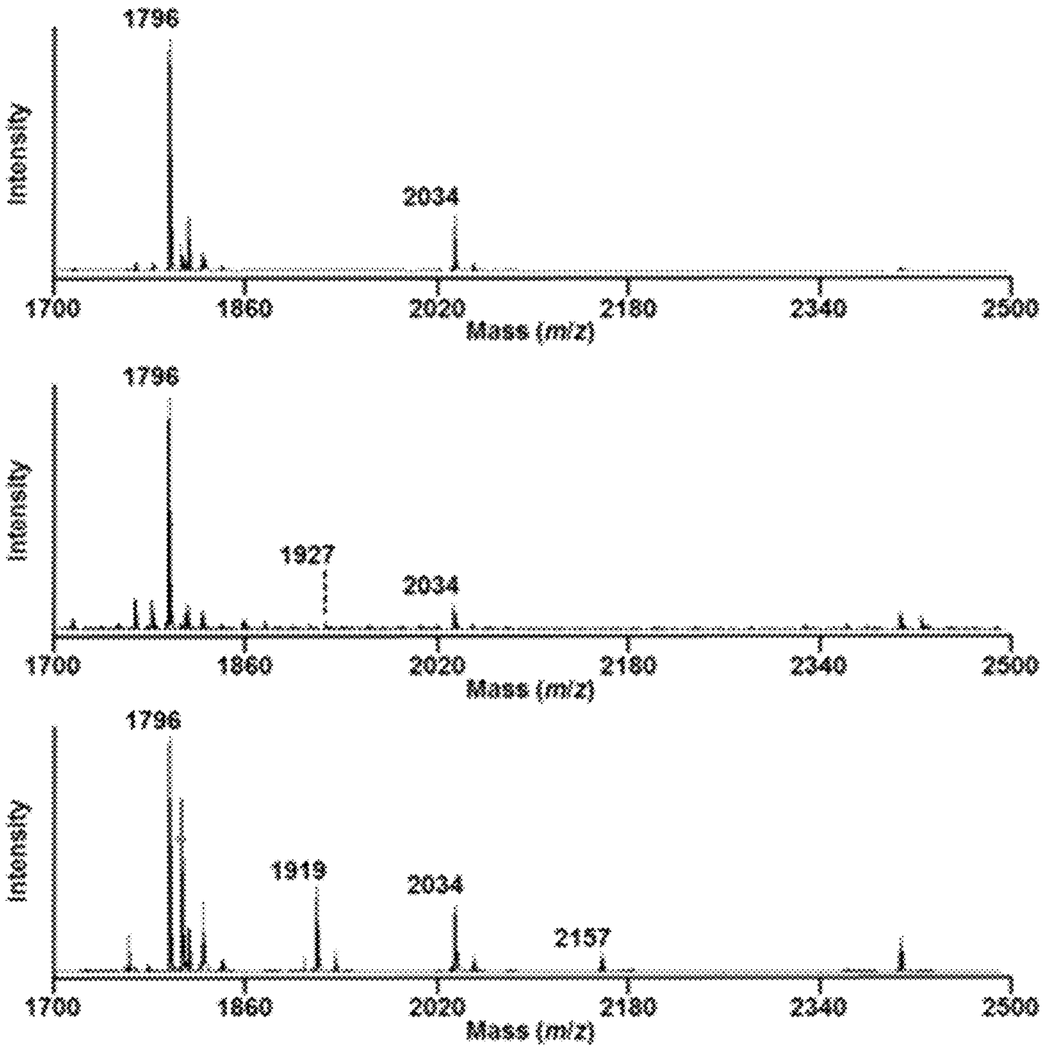

In polymyxin-resistant *K. pneumoniae*, the mass spectrum comprised a peak at m/z 1919.2 (i.e. 123 mass units greater than native Lipid A, m/z 1796.2), assigned to Lipid A modified by phosphoethanolamine (FIG. 7, bottom panel; and FIG. 11, middle panel). The presence of a peak indicating the presence of Lipid A modified by phosphoethanolamine successfully indicated the presence of a bacterium resistant to a polymyxin antibiotic.

Similarly to *E. coli*, an unassigned peak (which the present inventors have assigned to Lipid A modified with pETN at 1' phosphate group with concomitant loss of the 4' phosphate group) at m/z 1821.2 (i.e. 25 mass units greater than native Lipid A, m/z 1796) was also indicative of the presence of a *K. pneumoniae* bacterium (e.g. Enterobacteriaceae) resistant to a polymyxin antibiotic through plasmid encoded polymyxin-resistance (FIG. 11, middle panel). Said m/z 1821.2 was not present for a *K. pneumoniae* bacterium (e.g. Enterobacteriaceae) resistant to a polymyxin antibiotic through chromosome encoded polymyxin-resistance (FIG. 11, bottom panel; and FIG. 15), highlighting the applicability of this peak in discriminating between the two resistance mechanisms (plasmid—and chromosome encoded resistance).

Example 3

Detection of the Presence or Absence of a Polymyxin-Resistant *Acinetobacter Baumannii* in a Test Sample Test samples comprising intact bacterial cells of *A. baumannii* (e.g. bacterial suspensions, washed to remove salt), as follows, were subjected to mass spectrometry according to a method of the present invention: (i) Polymyxin susceptible *A. baumannii*; (ii) polymyxin-resistant *A. baumannii.*

In polymyxin susceptible *A. baumannii*, the mass spectrum was dominated by a peak at m/z 1910.3 (FIG. 9, top panel) assigned to native Lipid A. The absence of a peak indicating the presence of phosphoethanolamine successfully indicated the absence of a bacterium resistant to a polymyxin antibiotic.

Figure 9:
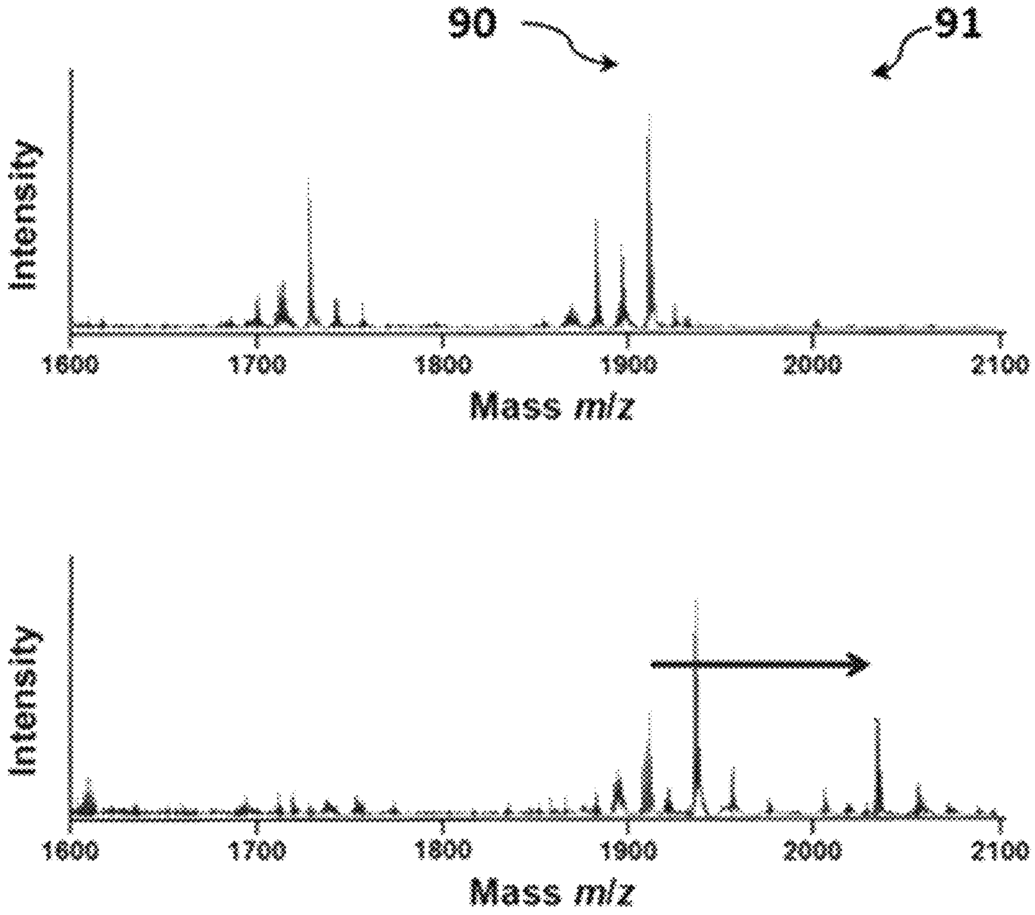

In polymyxin-resistant *A. baumannii*, the mass spectrum further comprised a peak at m/z 2033.3 (i.e. 123 mass units greater than native Lipid A), assigned to Lipid A modified by phosphoethanolamine (FIG. 9, bottom panel).

Example 4

Peak Intensity Ratios Allow the Detection of the Presence or Absence of a Polymyxin-Resistant Bacterium in a Test Sample Calculation of the ratio of the intensity of Lipid A modified by phosphoethanolamine to the intensity of the peak corresponding to native Lipid A, allows the detection of the presence or absence of a polymyxin-resistant bacterium in a test sample.

Figure 13:
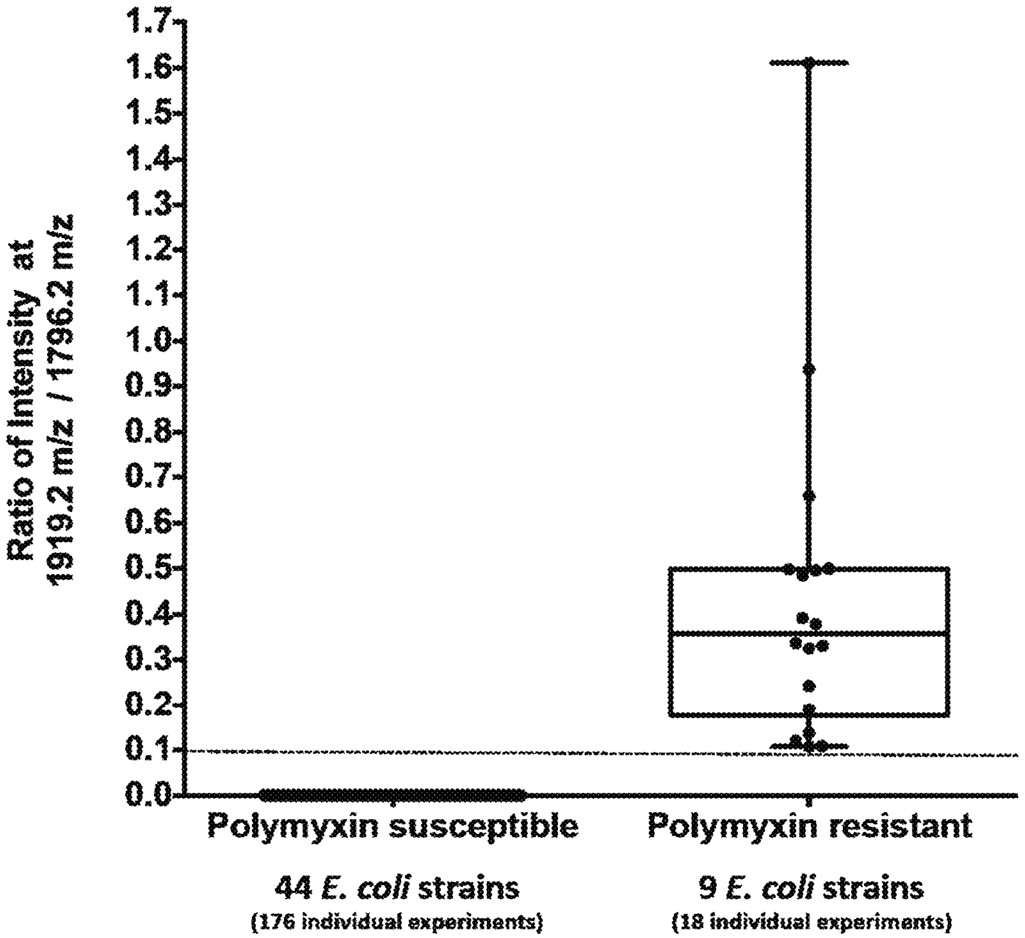
Figure 14A:
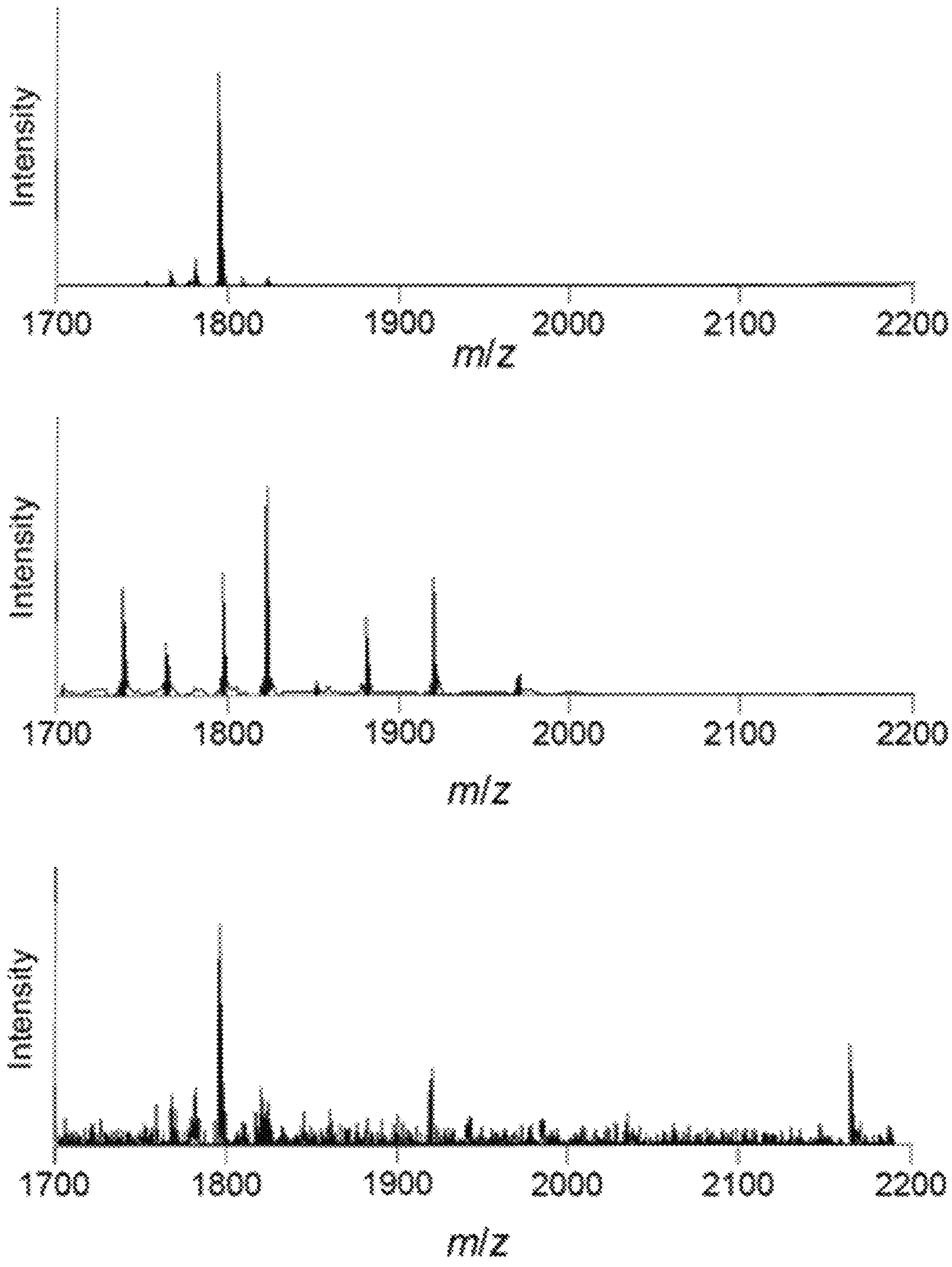
Figure 14B:
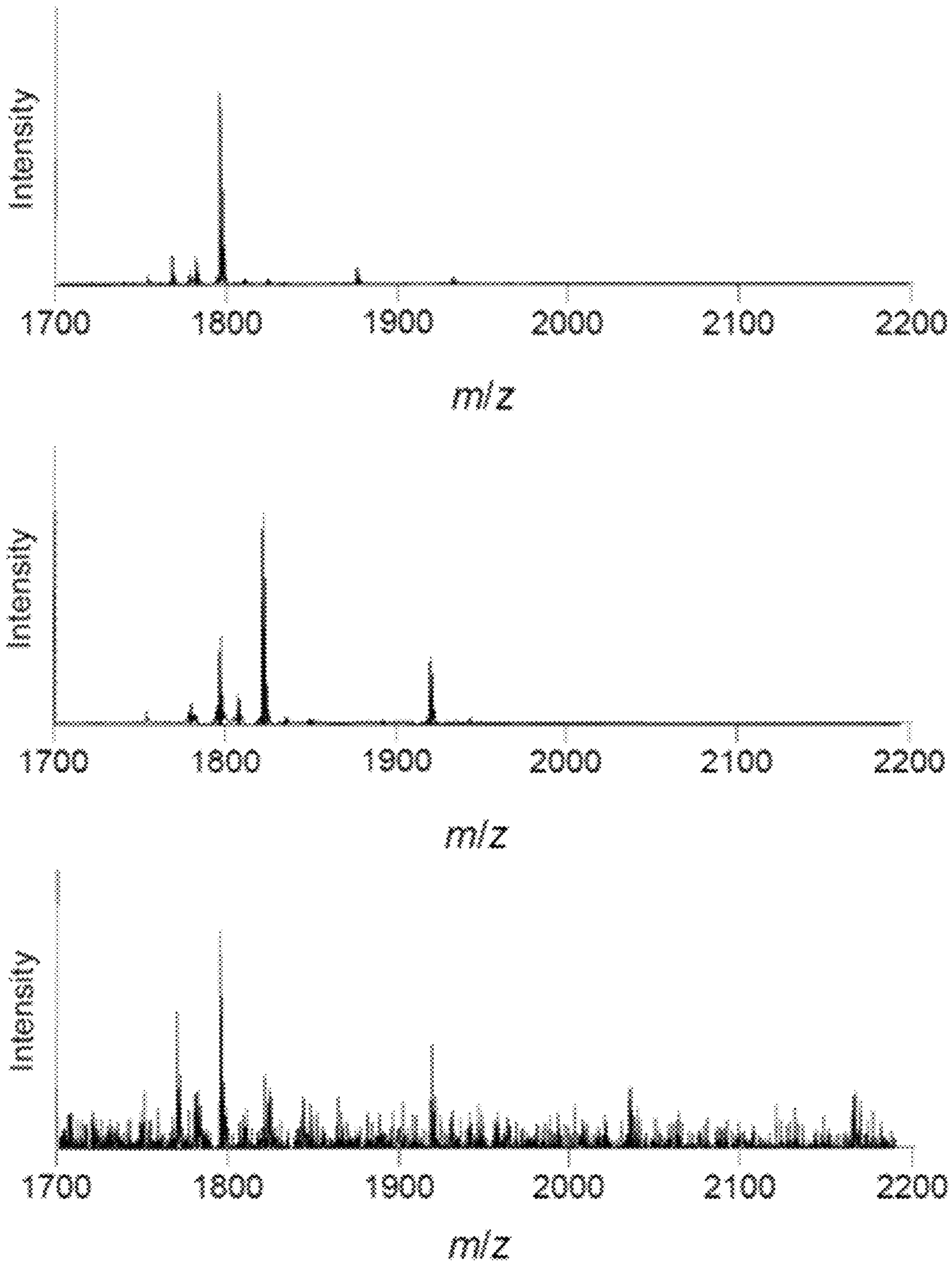
Figure 14C:
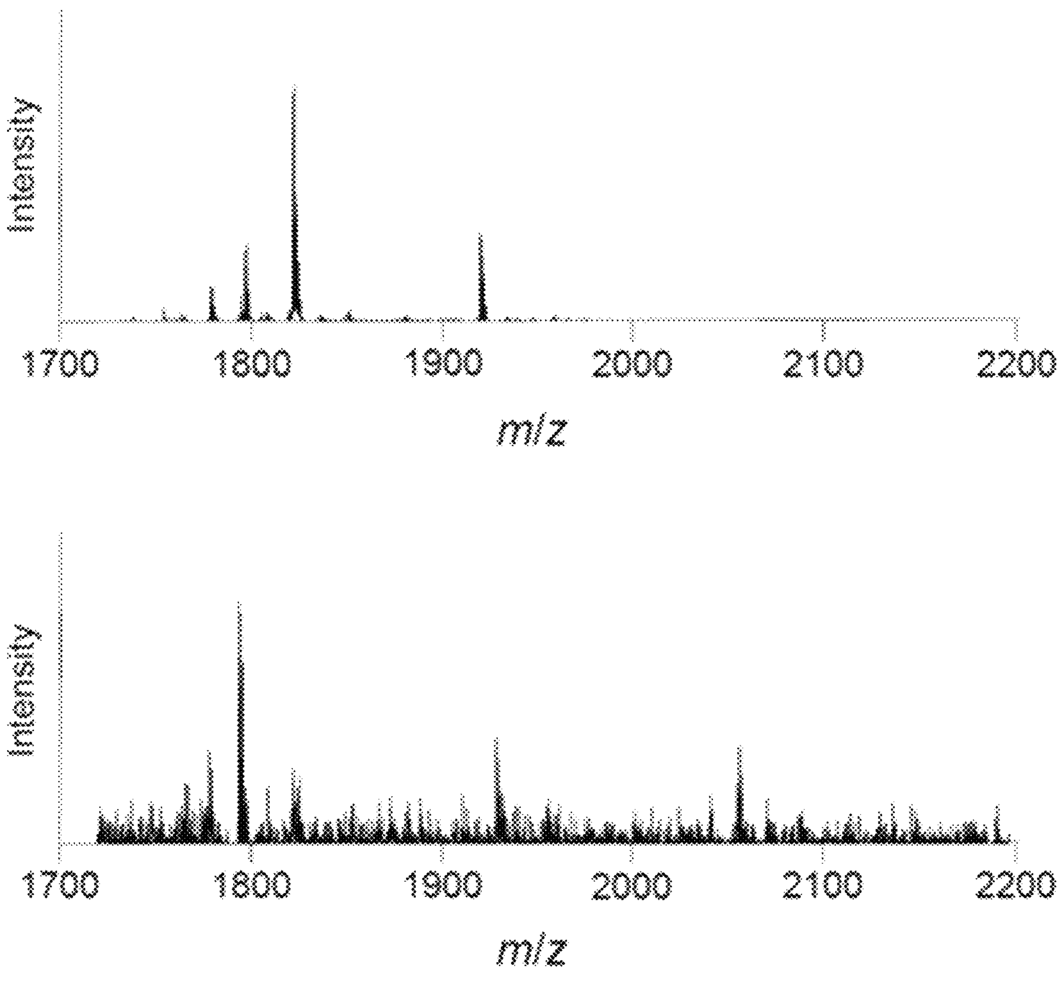
Figure 14D:
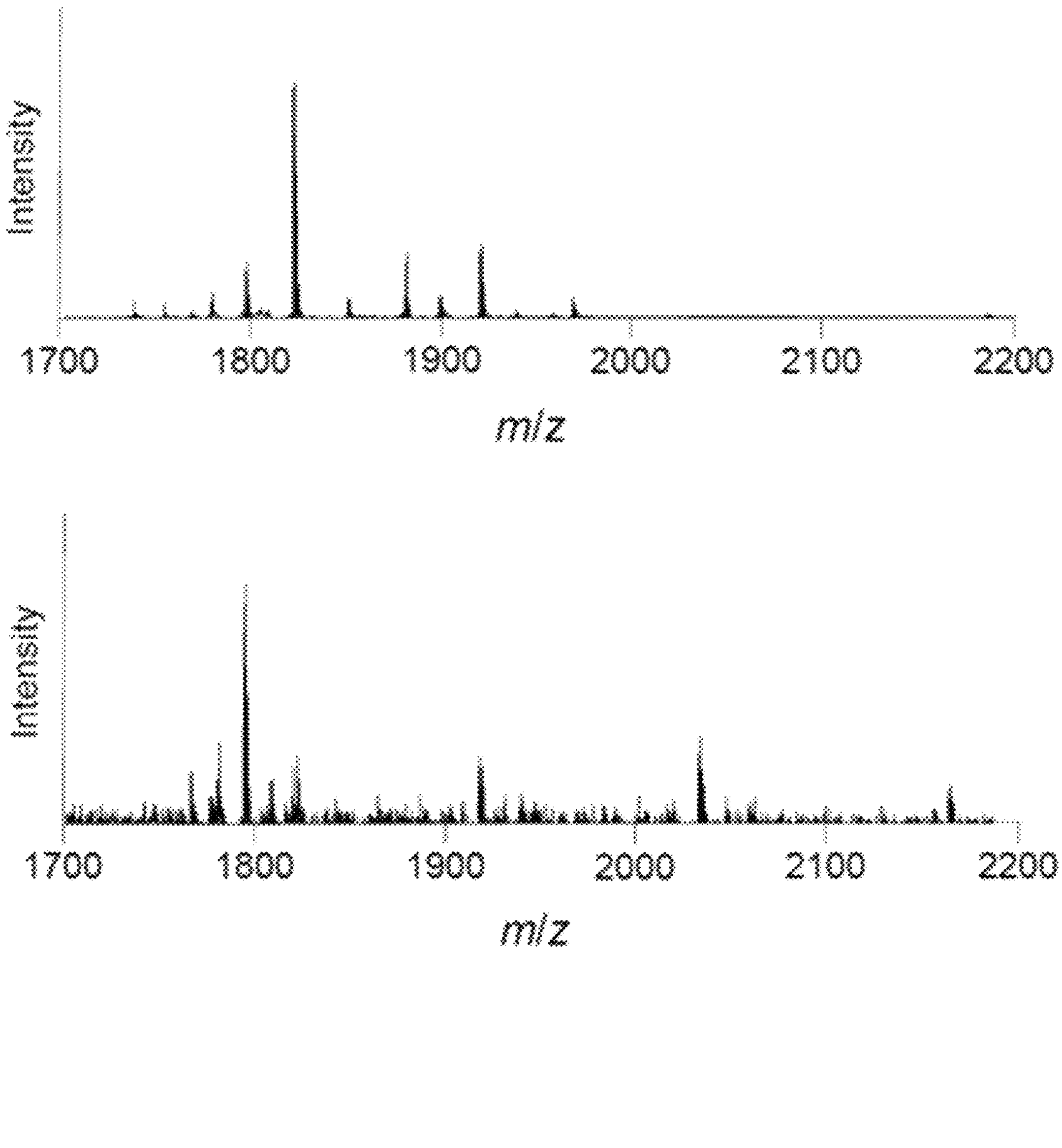

This ratio was shown to typically be between 0.10 to 1.7 in a polymyxin resistant bacterium, and close to 0 (typically less than 0.05) in a polymyxin-susceptible bacterium (FIG. 13).

Example 5

Figure 4:
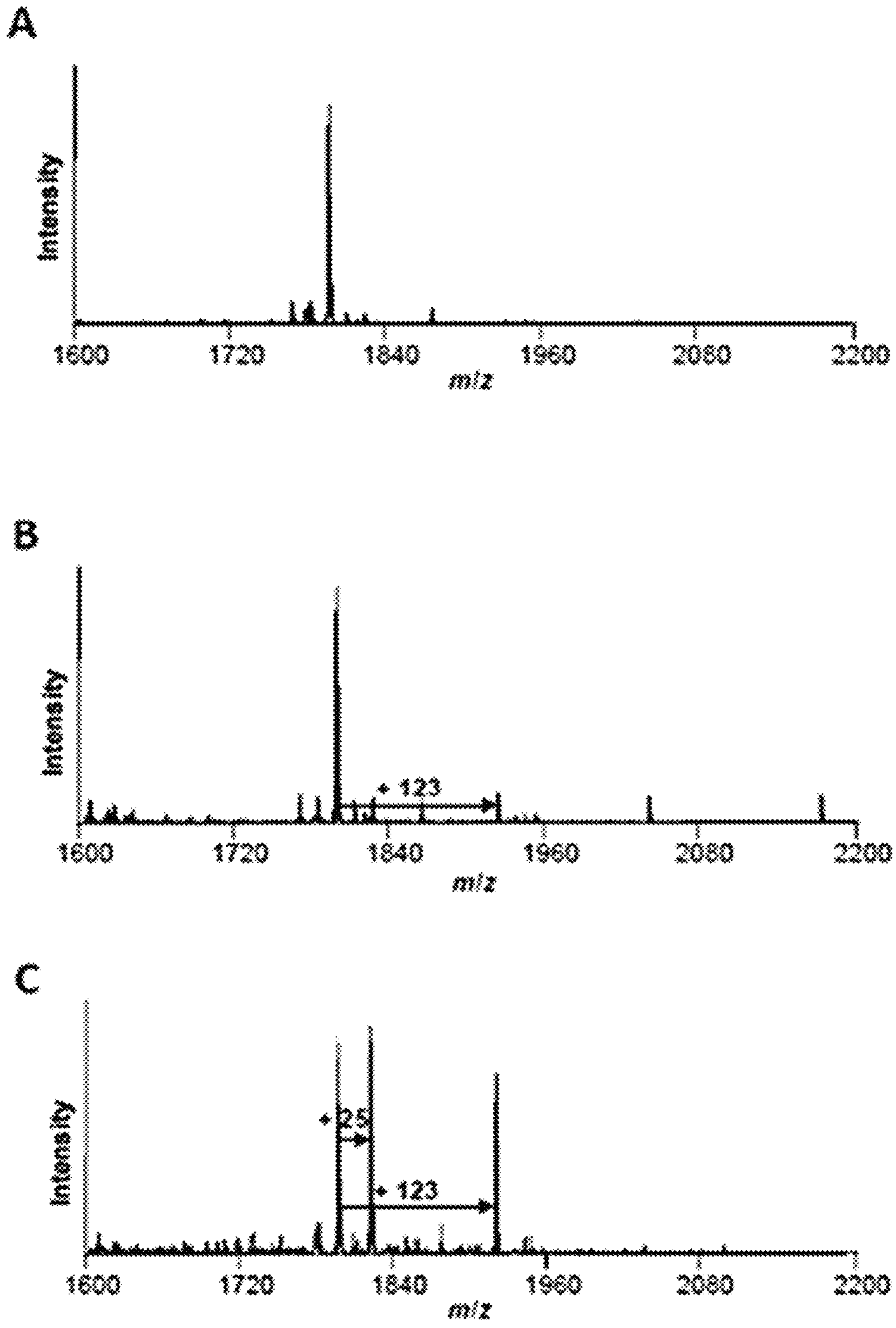

Further Detection of the Presence or Absence of a Polymyxin-Resistant *Escherichia Coli* in a Test Sample In polymyxin-susceptible *E. coli* strains the negative mass spectrum scanned between m/z 1600 and 2200 was dominated by a set of peaks assigned to bis-phosphorylated hexa-acyl lipid A (FIG. 4). The major peak at m/z 1796.2 is known to correspond to the hexa-acyl diphosphoryl lipid A containing four C14:0 3-OH, one C14:0 and one C12:0, and referred to as native lipid A (FIG. 2A (21)).

In all polymyxin-resistant *E. coli* strains, an additional peak at m/z 1919.2 was observed (FIGS. 4B and 4C) independent of the resistance mechanism involved (chromosome- or plasmid-encoded). This peak corresponds to the addition of one pETN moiety onto the phosphate group at position 4 of native lipid A (FIG. 2B (23)), leading to an increase of 123 mass units compared to the mass assigned to native lipid A (FIGS. 4B and C).

In the case of plasmid-encoded resistance (mcr-like genes in Enterobacteriaceae), a third peak at m/z 1821.2 was systematically observed in addition to the peaks corresponding to the native lipid A (m/z 1796.2) and the pETN-modified lipid A (m/z 1919.2) (FIG. 4C). This m/z 1821.2 peak was assigned to the addition of a pETN moiety onto the phosphate group at position 1' of native lipid A with concomitant loss of the phosphate group on position 4 (FIG. 2A (22)), and is a specific marker of MCR-like enzymes.

Figure 6:
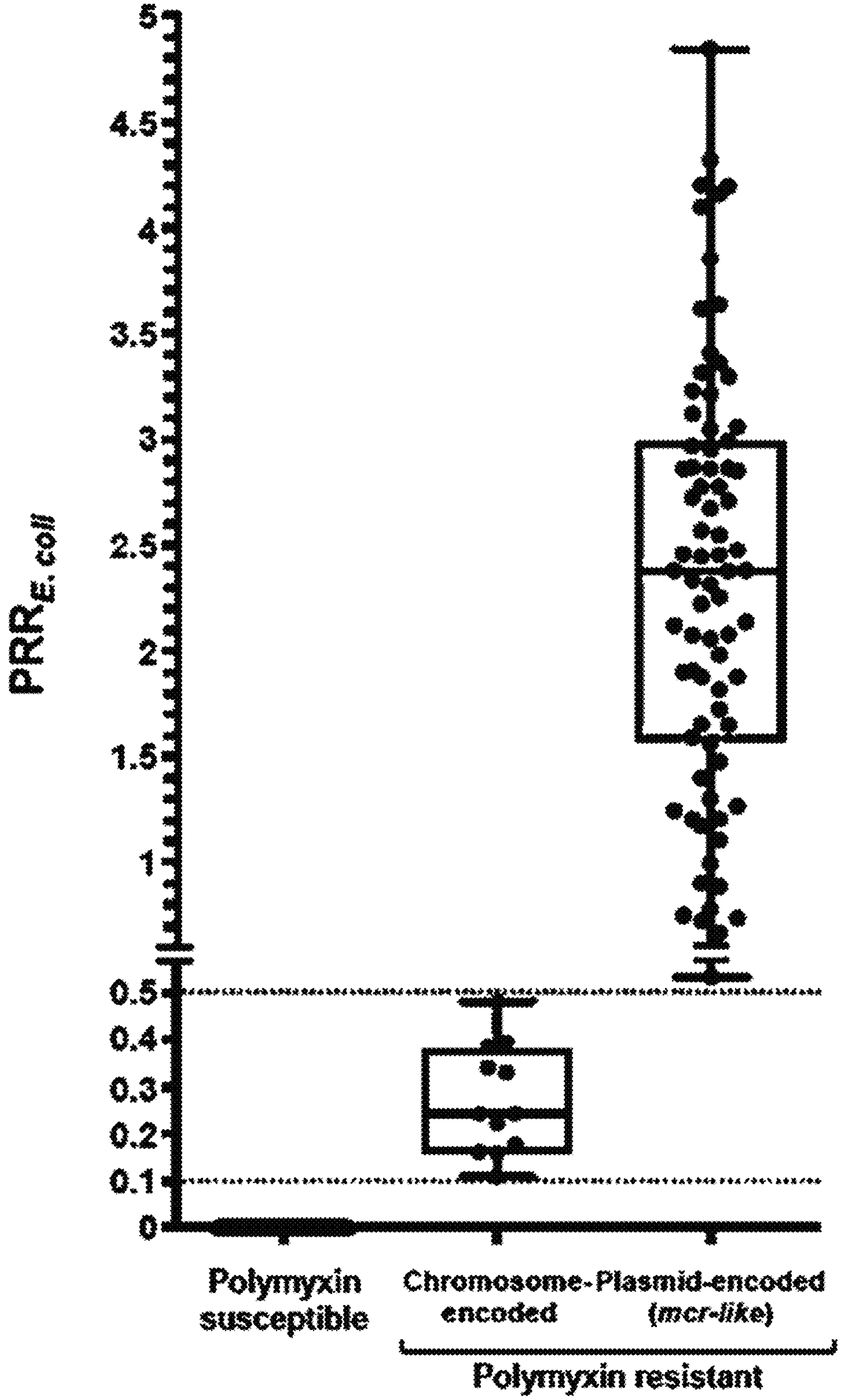

To further support this observation, 73 *E. coli* isolates were analysed including 46 polymyxin susceptible strains with various antimicrobial resistance phenotypes. Of these strains four strains possess chromosome-encoded resistance to polymyxin and 23 are MCR-producers (FIG. 18). The intensity of the peaks corresponding to the native lipid A (m/z 1796.2), the pETN-modified lipid A (m/z 1919.2) and the specific marker of MCR resistance (m/z 1821.2) were recorded from three independent experiments. The ratio (termed Polymyxin Resistance Ratio (PRR) from here after) of the sum of the intensities of the peaks associated with modified lipid A (for *E. coli* peaks at m/z 1919.2 and m/z 1821.2) over the intensity of the peak of native lipid A (for *E. coli* m/z 1796.2) allows accurate distinction between polymyxin-susceptible and polymyxin-resistant isolates, but also discrimination between chromosome-encoded and MCR-related (i.e. plasmid-encoded) resistance to polymyxin (FIG. 6). The PRR value for all susceptible *E. coli* strains was found to be 0 (FIG. 18 and FIG. 6). The ratio ranged from 0.109 to 0.481 (average of 0.245) for *E. coli* strains with chromosome-encoded resistance to polymyxin, and from 0.533 to 4.844 (average of 2.340) for all MCR-producers (FIG. 18 and FIG. 6). The distribution of the $PRR_{E.\ coli}$ values of polymyxin-susceptible isolates compared to *E. coli* strains with chromosome-encoded resistance to polymyxin and MCR-producers were all significantly different ($p<0.001$, Welch's t-test). Analysis of ROC curves allowed definition of two cut-off values for $PRR_{E.\ coli}$ (0.1 and 0.5) which discriminate polymyxin-susceptible ($PRR_{E.\ coli}<0.1$) and polymyxin resistant isolates ($PRR_{E.\ coli}>0.1$) and also allows further discrimination between chromosome-encoded ($0.1<PRR_{E.\ coli}<0.5$) and plasmid-encoded resistance ($PRR_{E.\ coli}>0.5$).

Example 6

Detection of the Presence or Absence of a Polymyxin-Resistant *Escherichia Coli* Grown on Clinically-Relevant Media The performance of methods of the invention (e.g. the "MALDIxin test") was tested using colonies grown on media routinely used to test for antimicrobial susceptibility, i.e. Mueller-Hinton (MH) agar. In addition, because of the rapid rise of MCR-1-producing Enterobacteriaceae since 2016, it has also been suggested to screen infected patients using polymyxin-supplemented media. Accordingly, methods of the invention were conducted on three *E. coli* strains (a wild-type strain, a strain with chromosome-encoded resistance and an MCR-1 producing strain), grown on LB agar, MH agar and polymyxin B-supplemented MH agar at final concentrations of either 1 mg/L or 2 mg/L. As shown in FIG. 14, similar spectra were obtained independently of the growth medium, with the $PRR_{E.\ coli}$ being between 2.89 and 5.69 for MCR-1-producing strains and between 0.21 and 0.37 for strains harbouring chromosome-encoded resistance. To identify any impact of the age of the colonies grown on LB and MH agar, a method of the invention (e.g. the MALDIxin test) was performed on fresh colonies (overnight incubation), colonies aged by 48 hours, one week and two weeks (agar plates were kept at 4° C.). Similar spectra were obtained for all tested colonies leading to no significant differences in their $PRR_{E.\ coli}$ (FIG. 19).

Example 7

Validation of the Method on a Prospective Collection of Carbapenemase Producing *E. Coli* from the French NRC In order to validate the methods of the invention (e.g. the MALDIxin test), all carbapenemase-producing *E. coli* received from the French NRC during October and November 2016 were blindly analysed in triplicate (three colonies selected from the same MH agar plate). The collection of 78 carbapenemase producing *E. coli* strains that were obtained included two KPC-producers, eleven NDM producers, two VIM-producers, 63 OXA-48-like producers, and one isolate producing two carbapenemases (Table 2). Among these isolates, two NDM-1 and one OXA-48 producer were also found to be resistant to colistin with MICs of 4 mg/L. PCR analysis revealed that these three isolates were positive for the mcr-1 gene (Table 2). When analysed using the methods of the invention (e.g. the MALDIxin test), all polymyxin-susceptible isolates (n=75) showed a $PRR_{E.\ coli}$ of 0, corresponding to polymyxin susceptibility, while for the three MCR-1-producing isolates a $PRR_{E.\ coli}$ above 0.5 was obtained (more specifically 1.73±0.23 and 2.34±0.12 for the two NDM-1-producers and 1.29±0.63 for the OXA-48-producer), accurately classifying them as resistant to polymyxin by a plasmid-encoded mechanism (Table 2). Therefore, in this study, the methods of the invention (e.g. the MALDIxin test) reliably and rapidly identified all MCR-producing strains where conventional methods would have needed 24 to 48 hours (broth dilution method (around 16 to 24 hours) and subsequent DNA extraction and PCR for mcr-1 and mcr-2 on resistant isolates (around 4 hours)).

TABLE 2

Detection and characterization of polymyxin resistance using conventional techniques (MICs and PCR) and a method of the present invention (e.g. the MALDIxin test) on 78 carbapenemase-producing *E. coli* strains received by the French NRC during October and November 2016.

| | | Polymyxin resistance | | | |
|---|---|---|---|---|---|
| Carbapen-emase | N | Colistin MIC (mg/L) | mcr-1/-2 PCR | MALDI-TOF results $PRR_{E.\ coli}$ | Interpretation |
| KPC-2 | 1 | 0.25 | – | 0 | Susceptible |
| KPC-3* | 1 | 0.25 | – | 0 | Susceptible |
| NDM-1 | 3 | 0.25 | – | 0 | Susceptible |
| NDM-1 | 1 | 0.5 | – | 0 | Susceptible |
| NDM-1 | 1 | 4 | + (mcr-1) | 1.73 ± 0.23 | Plasmid-encoded resistance |
| NDM-1 | 1 | 4 | + (mcr-1) | 2.34 ± 0.12 | Plasmid-encoded resistance |
| NDM-5 | 2 | 0.25 | – | 0 | Susceptible |
| NDM-5 | 3 | 0.5 | – | 0 | Susceptible |
| VIM-1 | 1 | 0.5 | – | 0 | Susceptible |
| VIM-4 | 1 | 0.25 | – | 0 | Susceptible |
| OXA-48 | 27 | 0.25 | – | 0 | Susceptible |
| OXA-48 | 26 | 0.5 | – | 0 | Susceptible |
| OXA-48 | 1 | 1 | – | 0 | Susceptible |
| OXA-48* | 1 | 4 | + (mcr-1) | 1.29 ± 0.63 | Plasmid-encoded resistance |
| OXA-181 | 4 | 0.25 | – | 0 | Susceptible |
| OXA-204 | 1 | 0.25 | – | 0 | Susceptible |
| OXA-244 | 1 | 0.25 | – | 0 | Susceptible |
| OXA-244 | 1 | 0.5 | – | 0 | Susceptible |
| OXA-181 + NDM-5 | 1 | 0.25 | – | 0 | Susceptible |

N, number of isolates; MIC, minimal inhibition concentration; PPR, Polymyxin Resistance Ratio.

+, positive PCR; – negative PCR for the gene indicated in parenthesis.

*These two strains were isolated from the same patient.

Example 8

Analysis of mcr Family Genes

Chromosome-encoded genes associated with polymyxin resistance are numerous, and the gene modifications (disruptions, deletions mutations) involved are not systematically described nor characterized. As for plasmid-encoded resistance, five families of mcr genes are known in Enterobacteriaceae.

Figure 17:
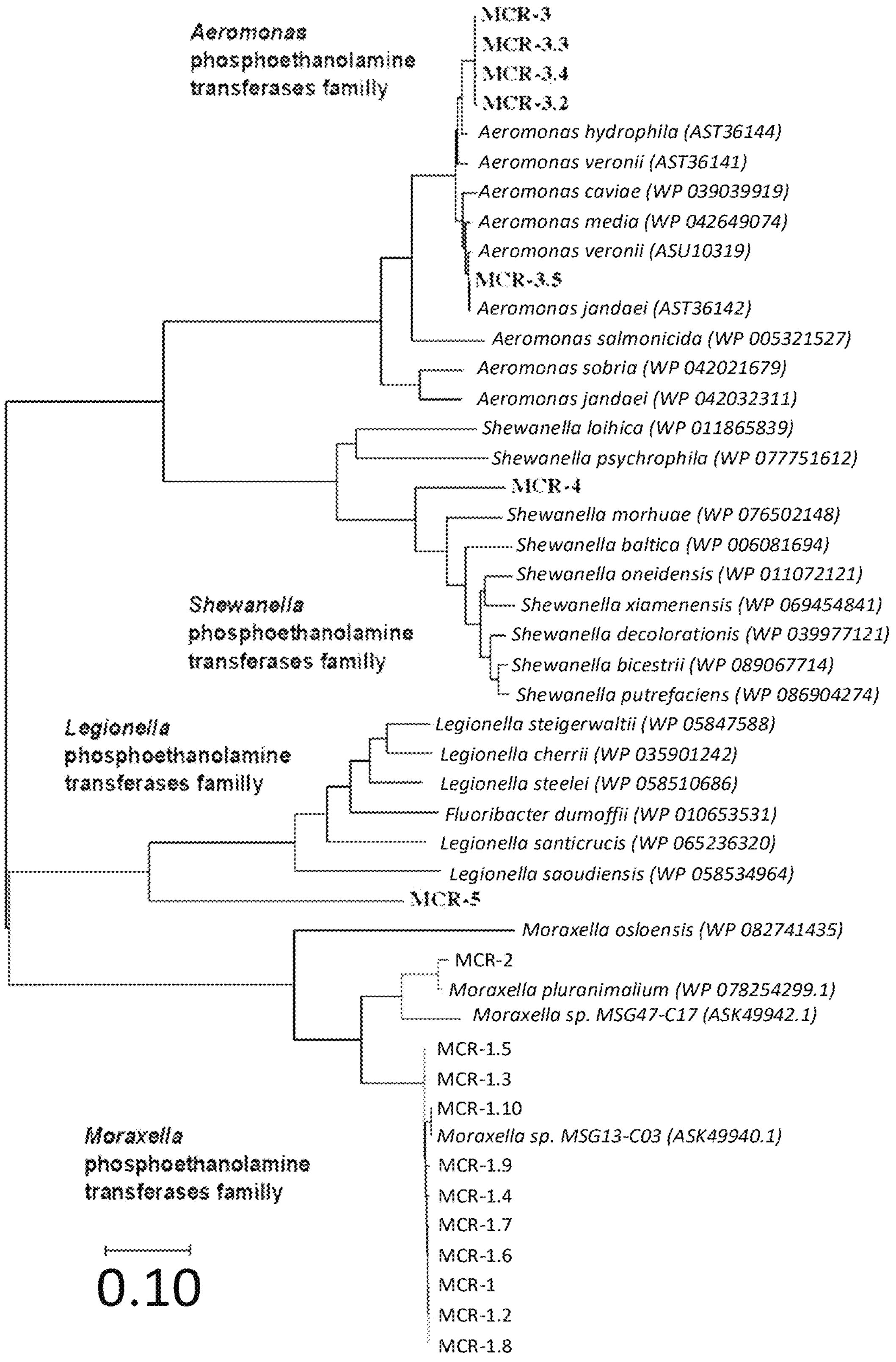
FIG. 17 shows divergence of MCR variant from different families.

Sequence homology of MCR-2, MCR-3, MCR-4 and MCR-5 with MCR-1 was analysed. MCR-2, MCR-3, MCR-4 and MCR-5 share only 81%, 34%, 33% and 31% amino acid identity with MCR-1, respectively (FIG. 17). This diversity would inevitably lead to failure in systematic detection of polymyxin resistance, if it relies on using available molecular biology tools dedicated to mcr-1 and/or mcr-2 detection (FIG. 16).

These issues are overcome by methods of the present invention (e.g. the MALDIxin test), which provides a cost-effective tool (method) based on MALDI-TOF technology that aims to detect polymyxin resistance using a single Gram-negative bacterial colony, in less than 15 minutes.

SEQUENCES

SEQ ID NO: 1 (mcr-1)
ATGATGCAGCATACTTCTGTGTGGTACCGACGCTCGGTCAGTCCGTTTGTTCTTGTGGC
GAGTGTTGCCGTTTTCTTGACCGCGACCGCCAATCTTACCTTTTTTGATAAAATCAGCCA
AACCTATCCCATCGCGGACAATCTCGGCTTTGTGCTGACGATCGCTGTCGTGCTCTTTG
GCGCGATGCTACTGATCACCACGCTGTTATCATCGTATCGCTATGTGCTAAAGCCTGTG
TTGATTTTGCTATTAATCATGGGCGCGGTGACCAGTTATTTTACTGACACTTATGGCACG
GTCTATGATACGACCATGCTCCAAAATGCCCTACAGACCGACCAAGCCGAGACCAAGG
ATCTATTAAACGCAGCGTTTATCATGCGTATCATTGGTTTGGGTGTGCTACCAAGTTTGC
TTGTGGCTTTTGTTAAGGTGGATTATCCGACTTGGGGCAAGGGTTTGATGCGCCGATTG
GGCTTGATCGTGGCAAGTCTTGCGCTGATTTTACTGCCTGTGGTGGCGTTCAGCAGTCA
TTATGCCAGTTTCTTTCGCGTGCATAAGCCGCTGCGTAGCTATGTCAATCCGATCATGC
CAATCTACTCGGTGGGTAAGCTTGCCAGTATTGAGTATAAAAAAGCCAGTGCGCCAAAA
GATACCATTTATCACGCCAAAGACGCGGTACAAGCAACCAAGCCTGATATGCGTAAGCC
ACGCCTAGTGGTGTTCGTCGTCGGTGAGACGGCACGCGCCGATCATGTCAGCTTCAAT
GGCTATGAGCGCGATACTTTCCCACAGCTTGCCAAGATCGATGGCGTGACCAATTTTAG
CAATGTCACATCGTGCGGCACATCGACGGCGTATTCTGTGCCGTGTATGTTCAGCTATC
TGGGCGCGGATGAGTATGATGTCGATACCGCCAAATACCAAGAAAATGTGCTGGATAC
GCTGGATCGCTTGGGCGTAAGTATCTTGTGGCGTGATAATAATTCGGACTCAAAAGGCG
TGATGGATAAGCTGCCAAAAGCGCAATTTGCCGATTATAAATCCGCGACCAACAACGCC
ATCTGCAACACCAATCCTTATAACGAATGCCGCGATGTCGGTATGCTCGTTGGCTTAGA
TGACTTTGTCGCTGCCAATAACGGCAAAGATATGCTGATCATGCTGCACCAAATGGGCA
ATCACGGGCCTGCGTATTTTAAGCGATATGATGAAAAGTTTGCCAAATTCACGCCAGTG
TGTGAAGGTAATGAGCTTGCCAAGTGCGAACATCAGTCCTTGATCAATGCTTATGACAAT
GCCTTGCTTGCCACCGATGATTTCATCGCTCAAAGTATCCAGTGGCTGCAGACGCACAG
CAATGCCTATGATGTCTCAATGCTGTATGTCAGCGATCATGGCGAAAGTCTGGGTGAGA
ACGGTGTCTATCTACATGGTATGCCAAATGCCTTTGCACCAAAAGAACAGCGCAGTGTG
CCTGCATTTTTCTGGACGGATAAGCAAACTGGCATCACGCCAATGGCAACCGATACCGT
CCTGACCCATGACGCGATCACGCCGACATTATTAAAGCTGTTTGATGTCACCGCGGACA
AAGTCAAAGACCGCACCGCATTCATCCGCTGA SEQ ID NO: 2 (mcr-1.2)
ATGATGCTGCATACTTCTGTGTGGTACCGACGCTCGGTCAGTCCGTTTGTTCTTGTGGC
GAGTGTTGCCGTTTTCTTGACCGCGACCGCCAATCTTACCTTTTTTGATAAAATCAGCCA
AACCTATCCCATCGCGGACAATCTCGGCTTTGTGCTGACGATCGCTGTCGTGCTCTTTG
GCGCGATGCTACTGATCACCACGCTGTTATCATCGTATCGCTATGTGCTAAAGCCTGTG
TTGATTTTGCTATTAATCATGGGCGCGGTGACCAGTTATTTTACTGACACTTATGGCACG
GTCTATGATACGACCATGCTCCAAAATGCCCTACAGACCGACCAAGCCGAGACCAAGG
ATCTATTAAACGCAGCGTTTATCATGCGTATCATTGGTTTGGGTGTGCTACCAAGTTTGC
TTGTGGCTTTTGTTAAGGTGGATTATCCGACTTGGGGCAAGGGTTTGATGCGCCGATTG
GGCTTGATCGTGGCAAGTCTTGCGCTGATTTTACTGCCTGTGGTGGCGTTCAGCAGTCA
TTATGCCAGTTTCTTTCGCGTGCATAAGCCGCTGCGTAGCTATGTCAATCCGATCATGC
CAATCTACTCGGTGGGTAAGCTTGCCAGTATTGAGTATAAAAAAGCCAGTGCGCCAAAA
GATACCATTTATCACGCCAAAGACGCGGTACAAGCAACCAAGCCTGATATGCGTAAGCC
ACGCCTAGTGGTGTTCGTCGTCGGTGAGACGGCACGCGCCGATCATGTCAGCTTCAAT
GGCTATGAGCGCGATACTTTCCCACAGCTTGCCAAGATCGATGGCGTGACCAATTTTAG
CAATGTCACATCGTGCGGCACATCGACGGCGTATTCTGTGCCGTGTATGTTCAGCTATC
TGGGCGCGGATGAGTATGATGTCGATACCGCCAAATACCAAGAAAATGTGCTGGATAC
GCTGGATCGCTTGGGCGTAAGTATCTTGTGGCGTGATAATAATTCGGACTCAAAAGGCG
TGATGGATAAGCTGCCAAAAGCGCAATTTGCCGATTATAAATCCGCGACCAACAACGCC
ATCTGCAACACCAATCCTTATAACGAATGCCGCGATGTCGGTATGCTCGTTGGCTTAGA
TGACTTTGTCGCTGCCAATAACGGCAAAGATATGCTGATCATGCTGCACCAAATGGGCA
ATCACGGGCCTGCGTATTTTAAGCGATATGATGAAAAGTTTGCCAAATTCACGCCAGTG
TGTGAAGGTAATGAGCTTGCCAAGTGCGAACATCAGTCCTTGATCAATGCTTATGACAAT
GCCTTGCTTGCCACCGATGATTTCATCGCTCAAAGTATCCAGTGGCTGCAGACGCACAG
CAATGCCTATGATGTCTCAATGCTGTATGTCAGCGATCATGGCGAAAGTCTGGGTGAGA
ACGGTGTCTATCTACATGGTATGCCAAATGCCTTTGCACCAAAAGAACAGCGCAGTGTG
CCTGCATTTTTCTGGACGGATAAGCAAACTGGCATCACGCCAATGGCAACCGATACCGT
CCTGACCCATGACGCGATCACGCCGACATTATTAAAGCTGTTTGATGTCACCGCGGACA
AAGTCAAAGACCGCACCGCATTCATCCGCTGA SEQ ID NO: 3 (mcr-1.3)
ATGATGCAGCATACTTCTGTGTGGTACCGACGCTCGGTCAGTCCGTTTGTTCTTGTGGC
GAGTGTTGCCGTTTTCTTGACCGCGACCGCCAATCTTACCTTTTTTGATAAGGTCAGCCA
AACCTATCCCATCGCGGACAATCTCGGCTTTGTGCTGACGATCGCTGTCGTGCTCTTTG
GCGCGATGCTACTGATCACCACGCTGTTATCATCGTATCGCTATGTGCTAAAGCCTGTG
TTGATTTTGCTATTAATCATGGGCGCGGTGACCAGTTATTTTACTGACACTTATGGCACG
GTCTATGATACGACCATGCTCCAAAATGCCCTACAGACCGACCAAGCCGAGACCAAGG
ATCTATTAAACGCAGCGTTTATCATGCGTATCATTGGTTTGGGTGTGCTACCAAGTTTGC
TTGTGGCTTTTGTTAAGGTGGATTATCCGACTTGGGGCAAGGGTTTGATGCGCCGATTG
GGCTTGATCGTGGCAAGTCTTGCGCTGATTTTACTGCCTGTGGTGGCGTTCAGCAGTCA
TTATGCCAGTTTCTTTCGCGTGCATAAGCCGCTGCGTAGCTATGTCAATCCGATCATGC
CAATCTACTCGGTGGGTAAGCTTGCCAGTATTGAGTATAAAAAAGCCAGTGCGCCAAAA
GATACCATTTATCACGCCAAAGACGCGGTACAAGCAACCAAGCCTGATATGCGTAAGCC
ACGCCTAGTGGTGTTCGTCGTCGGTGAGACGGCACGCGCCGATCATGTCAGCTTCAAT
GGCTATGAGCGCGATACTTTCCCACAGCTTGCCAAGATCGATGGCGTGACCAATTTTAG
CAATGTCACATCGTGCGGCACATCGACGGCGTATTCTGTGCCGTGTATGTTCAGCTATC
TGGGCGCGGATGAGTATGATGTCGATACCGCCAAATACCAAGAAAATGTGCTGGATAC
GCTGGATCGCTTGGGCGTAAGTATCTTGTGGCGTGATAATAATTCGGACTCAAAAGGCG
TGATGGATAAGCTGCCAAAAGCGCAATTTGCCGATTATAAATCCGCGACCAACAACGCC -continued

| SEQUENCES |
|---|
| ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAGTGCGAACATCAGTCCTTGATCAATGCTTATGACAAT<br>GCCTTGCTTGCCACCGATGATTTCATCGCTCAAAGTATCCAGTGGCTGCAGACGCACAG<br>CAATGCCTATGATGTCTCAATGCTGTATGTCAGCGATCATGGCGAAAGTCTGGGTGAGA<br>ACGGTGTCTATCTACATGGTATGCCAAATGCCTTTGCACCAAAAGAACAGCGCAGTGTG<br>CCTGCATTTTTCTGGACGGATAAGCAAACTGGCATCACGCCAATGGCAACCGATACCGT<br>CCTGACCCATGACGCGATCACGCCGACATTATTAAAGCTGTTTGATGTCACCGCGGACA<br>AAGTCAAAGACCGCACCGCATTCATCCGCTGA |
| SEQ ID NO: 4 (mcr-1.4)<br>ATGATGCAGCATACTTCTGTGTGGTACCGACGCTCGGTCAGTCCGTTTGTTCTTGTGGC<br>GAGTGTTGCCGTTTTCTTGACCGCGACCGCCAATCTTACCTTTTTTGATAAAATCAGCCA<br>AACCTATCCCATCGCGGACAATCTCGGCTTTGTGCTGACGATCGCTGTCGTGCTCTTTG<br>GCGCGATGCTACTGATCACCACGCTGTTATCATCGTATCGCTATGTGCTAAAGCCTGTG<br>TTGATTTTGCTATTAATCATGGGCGCGGTGACCAGTTATTTTACTGACACTTATGGCACG<br>GTCTATGATACGACCATGCTCCAAAATGCCCTACAGACCGACCAAGCCGAGACCAAGG<br>ATCTATTAAACGCAGCGTTTATCATGCGTATCATTGGTTTGGGTGTGCTACCAAGTTTGC<br>TTGTGGCTTTTGTTAAGGTGGATTATCCGACTTGGGGCAAGGGTTTGATGCGCCGATTG<br>GGCTTGATCGTGGCAAGTCTTGCGCTGATTTTACTGCCTGTGGTGGCGTTCAGCAGTCA<br>TTATGCCAGTTTCTTTCGCGTGCATAAGCCGCTGCGTAGCTATGTCAATCCGATCATGC<br>CAATCTACTCGGTGGGTAAGCTTGCCAGTATTGAGTATAAAAAAGCCAGTGCGCCAAAA<br>GATACCATTTATCACGCCAAAGACGCGGTACAAGCAACCAAGCCTGATATGCGTAAGCC<br>ACGCCTAGTGGTGTTCGTCGTCGGTGAGACGGCACGCGCCGATCATGTCAGCTTCAAT<br>GGCTATGAGCGCGATACTTTCCCACAGCTTGCCAAGATCGATGGCGTGACCAATTTTAG<br>CAATGTCACATCGTGCGGCACATCGACGGCGTATTCTGTGCCGTGTATGTTCAGCTATC<br>TGGGCGCGGATGAGTATGATGTCGATACCGCCAAATACCAAGAAAATGTGCTGGATAC<br>GCTGGATCGCTTGGGCGTAAGTATCTTGTGGCGTGATAATAATTCGGACTCAAAAGGCG<br>TGATGGATAAGCTGCCAAAAGCGCAATTTGCCGATTATAAATCCGCGACCAACAACGCC<br>ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAGTGCGAACATCAGTCCTTGATCAATGCTTATGACAAT<br>GCCTTGCTTGCCACCGATAATTTCATCGCTCAAAGTATCCAGTGGCTGCAGACGCACAG<br>CAATGCCTATGATGTCTCAATGCTGTATGTCAGCGATCATGGCGAAAGTCTGGGTGAGA<br>ACGGTGTCTATCTACATGGTATGCCAAATGCCTTTGCACCAAAAGAACAGCGCAGTGTG<br>CCTGCATTTTTCTGGACGGATAAGCAAACTGGCATCACGCCAATGGCAACCGATACCGT<br>CCTGACCCATGACGCGATCACGCCGACATTATTAAAGCTGTTTGATGTCACCGCGGACA<br>AAGTCAAAGACCGCACCGCATTCATCCGCTGA |
| SEQ ID NO: 5 (mcr-1.5)<br>ATGATGCAGCATACTTCTGTGTGGTACCGACGCTCGGTCAGTCCGTTTGTTCTTGTGGC<br>GAGTGTTGCCGTTTTCTTGACCGCGACCGCCAATCTTACCTTTTTTGATAAAATCAGCCA<br>AACCTATCCCATCGCGGACAATCTCGGCTTTGTGCTGACGATCGCTGTCGTGCTCTTTG<br>GCGCGATGCTACTGATCACCACGCTGTTATCATCGTATCGCTATGTGCTAAAGCCTGTG<br>TTGATTTTGCTATTAATCATGGGCGCGGTGACCAGTTATTTTACTGACACTTATGGCACG<br>GTCTATGATACGACCATGCTCCAAAATGCCCTACAGACCGACCAAGCCGAGACCAAGG<br>ATCTATTAAACGCAGCGTTTATCATGCGTATCATTGGTTTGGGTGTGCTACCAAGTTTGC<br>TTGTGGCTTTTGTTAAGGTGGATTATCCGACTTGGGGCAAGGGTTTGATGCGCCGATTG<br>GGCTTGATCGTGGCAAGTCTTGCGCTGATTTTACTGCCTGTGGTGGCGTTCAGCAGTCA<br>TTATGCCAGTTTCTTTCGCGTGCATAAGCCGCTGCGTAGCTATGTCAATCCGATCATGC<br>CAATCTACTCGGTGGGTAAGCTTGCCAGTATTGAGTATAAAAAAGCCAGTGCGCCAAAA<br>GATACCATTTATCACGCCAAAGACGCGGTACAAGCAACCAAGCCTGATATGCGTAAGCC<br>ACGCCTAGTGGTGTTCGTCGTCGGTGAGACGGCACGCGCCGATCATGTCAGCTTCAAT<br>GGCTATGAGCGCGATACTTTCCCACAGCTTGCCAAGATCGATGGCGTGACCAATTTTAG<br>CAATGTCACATCGTGCGGCACATCGACGGCGTATTCTGTGCCGTGTATGTTCAGCTATC<br>TGGGCGCGGATGAGTATGATGTCGATACCGCCAAATACCAAGAAAATGTGCTGGATAC<br>GCTGGATCGCTTGGGCGTAAGTATCTTGTGGCGTGATAATAATTCGGACTCAAAAGGCG<br>TGATGGATAAGCTGCCAAAAGCGCAATTTGCCGATTATAAATCCGCGACCAACAACGCC<br>ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAGTGCGAACATCAGTCCTTGATCAATGCTTATGACAAT<br>GCCTTGCTTGCCACCGATGATTTCATCGCTCAAAGTATCCAGTGGCTGCAGACGTACAG<br>CAATGCCTATGATGTCTCAATGCTGTATGTCAGCGATCATGGCGAAAGTCTGGGTGAGA<br>ACGGTGTCTATCTACATGGTATGCCAAATGCCTTTGCACCAAAAGAACAGCGCAGTGTG<br>CCTGCATTTTTCTGGACGGATAAGCAAACTGGCATCACGCCAATGGCAACCGATACCGT<br>CCTGACCCATGACGCGATCACGCCGACATTATTAAAGCTGTTTGATGTCACCGCGGACA<br>AAGTCAAAGACCGCACCGCATTCATCCGCTGA |
| SEQ ID NO: 6 (mcr-1.6)<br>ATGATGCAGCATACTTCTGTGTGGTACCGACGCTCGGTCAGTCCGTTTGTTCTTGTGGC<br>GAGTGTTGCCGTTTTCTTGACCGCGACCGCCAATCTTACCTTTTTTGATAAAATCAGCCA<br>AACCTATCCCATCGCGGACAATCTCGGCTTTGTGCTGACGATCGCTGTCGTGCTCTTTG<br>GCGCGATGCTACTGATCACCACGCTGTTATCATCGTATCGCTATGTGCTAAAGCCTGTG<br>TTGATTTTGCTATTAATCATGGGCGCGGTGACCAGTTATTTTACTGACACTTATGGCACG |

-continued

| SEQUENCES |
|---|
| GTCTATGATACGACCATGCTCCAAAATGCCCTACAGACCGACCAAGCCGAGACCAAGG<br>ATCTATTAAACGCAGCGTTTATCATGCGTATCATTGGTTTGGGTGTGCTACCAAGTTTGC<br>TTGTGGCTTTTGTTAAGGTGGATTATCCGACTTGGGGCAAGGGTTTGATGCGCCGATTG<br>GGCTTGATCGTGGCAAGTCTTGCGCTGATTTTACTGCCTGTGGTGGCGTTCAGCAGTCA<br>TTATGCCAGTTTCTTTCGCGTGCATAAGCCGCTGCGTAGCTATGTCAATCCGATCATGC<br>CAATCTACTCGGTGGGTAAGCTTGCCAGTATTGAGTATAAAAAAGCCAGTGCGCCAAAA<br>GATACCATTTATCACGCCAAAGACGCGGTACAAGCAACCAAGCCTGATATGCGTAAGCC<br>ACGCCTAGTGGTGTTCGTCGTCGGTGAGACGGCACGCGCCGATCATGTCAGCTTCAAT<br>GGCTATGAGCGCGATACTTTCCCACAGCTTGCCAAGATCGATGGCGTGACCAATTTTAG<br>CAATGTCACATCGTGCGGCACATCGACGGCGTATTCTGTGCCGTGTATGTTCAGCTATC<br>TGGGCGCGGATGAGTATGATGTCGATACCGCCAAATACCAAGAAAATGTGCTGGATAC<br>GCTGGATCGCTTGGGCGTAAGTATCTTGTGGCGTGATAATAATTCGGACTCAAAAGGCG<br>TGATGGATAAGCTGCCAAAAGCGCAATTTGCCGATTATAAATCCGCGACCAACAACGCC<br>ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAATGCGAACATCAGTCCTTGATCAATGCTTATGACAAT<br>GCCTTGCTTGCCACCGATGATTTCATCGCTCAAAGTATCCAGTGGCTGCAGACGCACAG<br>CAATGCCTATGATGTCTCAATGCTGTATGTCAGCGATCATGGCGAAAGTCTGGGTGAGA<br>ACGGTGTCTATCTACATGGTATGCCAAATGCCTTTGCACCAAAAGAACAGCGCAGTGTG<br>CCTGCATTTTTCTGGACGGATAAGCAAACTGGCATCACGCCAATGGCAACCGATACCGT<br>CCTGACCCATGACGCGATCACGCCGACATTATTAAAGCTGTTTGATGTCACCGCGGACA<br>AAGTCAAAGACCACACCGCATTCATCCGCTGA<br><br>SEQ ID NO: 7 (mcr-1.7)<br>ATGATGCAGCATACTTCTGTGTGGTACCGACGCTCGGTCAGTCCGTTTGTTCTTGTGGC<br>GAGTGTTGCCGTTTTCTTGACCGCGACCGCCAATCTTACCTTTTTTGATAAAATCAGCCA<br>AACCTATCCCATCGCGGACAATCTCGGCTTTGTGCTGACGATCGCTGTCGTGCTCTTTG<br>GCGCGATGCTACTGATCACCACGCTGTTATCATCGTATCGCTATGTGCTAAAGCCTGTG<br>TTGATTTTGCTATTAATCATGGGCGCGGTGACCAGTTATTTTACTGACACTTATGGCACG<br>GTCTATGATACGACCATGCTCCAAAATGCCCTACAGACCGACCAAGCCGAGACCAAGG<br>ATCTATTAAACGCAGCGTTTATCATGCGTATCATTGGTTTGGGTGTGCTACCAAGTTTGC<br>TTGTGGCTTTTGTTAAGGTGGATTATCCGACTTGGGGCAAGGGTTTGATGCGCCGATTG<br>GGCTTGATCGTGGCAAGTCTTGCGCTGATTTTACTGCCTGTGGTGGCGTTCAGCAGTCA<br>TTATGCCAGTTTCTTTCGCGTGCATAAGCCGCTGCGTAGCTATGTCAATCCGATCATGC<br>CAATCTACTCGGTGGGTAAGCTTGCCAGTATTGAGTATAAAAAAGCCAGTACGCCAAAA<br>GATACCATTTATCACGCCAAAGACGCGGTACAAGCAACCAAGCCTGATATGCGTAAGCC<br>ACGCCTAGTGGTGTTCGTCGTCGGTGAGACGGCACGCGCCGATCATGTCAGCTTCAAT<br>GGCTATGAGCGCGATACTTTCCCACAGCTTGCCAAGATCGATGGCGTGACCAATTTTAG<br>CAATGTCACATCGTGCGGCACATCGACGGCGTATTCTGTGCCGTGTATGTTCAGCTATC<br>TGGGCGCGGATGAGTATGATGTCGATACCGCCAAATACCAAGAAAATGTGCTGGATAC<br>GCTGGATCGCTTGGGCGTAAGTATCTTGTGGCGTGATAATAATTCGGACTCAAAAGGCG<br>TGATGGATAAGCTGCCAAAAGCGCAATTTGCCGATTATAAATCCGCGACCAACAACGCC<br>ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAGTGCGAACATCAGTCCTTGATCAATGCTTATGACAAT<br>GCCTTGCTTGCCACCGATGATTTCATCGCTCAAAGTATCCAGTGGCTGCAGACGCACAG<br>CAATGCCTATGATGTCTCAATGCTGTATGTCAGCGATCATGGCGAAAGTCTGGGTGAGA<br>ACGGTGTCTATCTACATGGTATGCCAAATGCCTTTGCACCAAAAGAACAGCGCAGTGTG<br>CCTGCATTTTTCTGGACGGATAAGCAAACTGGCATCACGCCAATGGCAACCGATACCGT<br>CCTGACCCATGACGCGATCACGCCGACATTATTAAAGCTGTTTGATGTCACCGCGGACA<br>AAGTCAAAGACCGCACCGCATTCATCCGCTGA<br><br>SEQ ID NO: 8 (mcr-1.8)<br>ATGATGCGGCATACTTCTGTGTGGTACCGACGCTCGGTCAGTCCGTTTGTTCTTGTGGC<br>GAGTGTTGCCGTTTTCTTGACCGCGACCGCCAATCTTACCTTTTTTGATAAAATCAGCCA<br>AACCTATCCCATCGCGGACAATCTCGGCTTTGTGCTGACGATCGCTGTCGTGCTCTTTG<br>GCGCGATGCTACTGATCACCACGCTGTTATCATCGTATCGCTATGTGCTAAAGCCTGTG<br>TTGATTTTGCTATTAATCATGGGCGCGGTGACCAGTTATTTTACTGACACTTATGGCACG<br>GTCTATGATACGACCATGCTCCAAAATGCCCTACAGACCGACCAAGCCGAGACCAAGG<br>ATCTATTAAACGCAGCGTTTATCATGCGTATCATTGGTTTGGGTGTGCTACCAAGTTTGC<br>TTGTGGCTTTTGTTAAGGTGGATTATCCGACTTGGGGCAAGGGTTTGATGCGCCGATTG<br>GGCTTGATCGTGGCAAGTCTTGCGCTGATTTTACTGCCTGTGGTGGCGTTCAGCAGTCA<br>TTATGCCAGTTTCTTTCGCGTGCATAAGCCGCTGCGTAGCTATGTCAATCCGATCATGC<br>CAATCTACTCGGTGGGTAAGCTTGCCAGTATTGAGTATAAAAAAGCCAGTGCGCCAAAA<br>GATACCATTTATCACGCCAAAGACGCGGTACAAGCAACCAAGCCTGATATGCGTAAGCC<br>ACGCCTAGTGGTGTTCGTCGTCGGTGAGACGGCACGCGCCGATCATGTCAGCTTCAAT<br>GGCTATGAGCGCGATACTTTCCCACAGCTTGCCAAGATCGATGGCGTGACCAATTTTAG<br>CAATGTCACATCGTGCGGCACATCGACGGCGTATTCTGTGCCGTGTATGTTCAGCTATC<br>TGGGCGCGGATGAGTATGATGTCGATACCGCCAAATACCAAGAAAATGTGCTGGATAC<br>GCTGGATCGCTTGGGCGTAAGTATCTTGTGGCGTGATAATAATTCGGACTCAAAAGGCG<br>TGATGGATAAGCTGCCAAAAGCGCAATTTGCCGATTATAAATCCGCGACCAACAACGCC<br>ATCTGCAACACCAATCCTTATAACGAATGCCGCGATGTCGGTATGCTCGTTGGCTTAGA<br>TGACTTTGTCGCTGCCAATAACGGCAAAGATATGCTGATCATGCTGCACCAAATGGGCA<br>ATCACGGGCCTGCGTATTTTAAGCGATATGATGAAAAGTTTGCCAAATTCACGCCAGTG<br>TGTGAAGGTAATGAGCTTGCCAAGTGCGAACATCAGTCCTTGATCAATGCTTATGACAAT |

-continued

| SEQUENCES |
| --- |

GCCTTGCTTGCCACCGATGATTTCATCGCTCAAAGTATCCAGTGGCTGCAGACGCACAG
CAATGCCTATGATGTCTCAATGCTGTATGTCAGCGATCATGGCGAAAGTCTGGGTGAGA
ACGGTGTCTATCTACATGGTATGCCAAATGCCTTTGCACCAAAAGAACAGCGCAGTGTG
CCTGCATTTTTCTGGACGGATAAGCAAACTGGCATCACGCCAATGGCAACCGATACCGT
CCTGACCCATGACGCGATCACGCCGACATTATTAAAGCTGTTTGATGTCACCGCGGACA
AAGTCAAAGACCGCACCGCATTCATCCGCTGA

SEQ ID NO: 9 (mcr-1.9)
GTGTGGTACCGACGCTCGGTCAGTCCGTTTGTTCTTGTGGCGAGTGTTGCCGTTTTCTT
GACCGCGACCGCCAATCTTACCTTTTTTGATAAAATCAGCCAAACCTATCCCATCGCGG
ACAATCTCGGCTTTGTGCTGACGATCGCTGTCGTGCTCTTTGGCGCGATGCTACTGATC
ACCACGCTGTTATCATCGTATCGCTATGTGCTAAAGCCTGTGTTGATTTTGCTATTAATC
ATGGGCGCGGTGACCAGTTATTTTACTGACACTTATGGCACGGTCTATGATACGACCAT
GCTCCAAAATGCCCTACAGACCGACCAAGCCGAGACCAAGGATCTATTAAACGCAGCG
TTTATCATGCGTATCATTGGTTTGGGTGTGCTACCAAGTTTGCTTGTGGCTTTTGTTAAG
GTGGATTATCCGACTTGGGGCAAGGGTTTGATGCGCCGATTGGGCTTGATCGTGGCAA
GTCTTGCGCTGATTTTACTGCCTGTGGTGGCGTTCAGCAGTCATTATGCCAGTTTCTTTC
GCGTGCATAAGCCGCTGCGTAGCTATGTCAATCCGATCATGCCAATCTACTCGGTGGGT
AAGCTTGCCAGTATTGAGTATAAAAAAGCCAGTGCGCCAAAAGATACCATTTATCACGC
CAAAGACGCGGTACAAGCAACCAAGCCTGATATGCGTAAGCCACGCCTAGTGGTGTTC
GTCGTCGGTGAGACGGCACGCGCCGATCATGTCAGCTTCAATGGCTATGAGCGCGATA
CTTTCCCACAGCTTGCCAAGATCGATGGCGTGACCAATTTTAGCAATGTCACATCGTGC
GGCACATCGACGGCGTATTCTGTGCCGTGTATGTTCAGCTATCTGGGCGCGGATGAGT
ATGATGTCGATACCGCCAAATACCAAGAAAATGTGCTGGATACGCTGGATCGCTTGGGC
GTAAGTATCTTGTGGCGTGATAATAATTCGGACTCAAAAGGCGTGATGGATAAGCTGCC
AAAAGCGCAATTTGCCGATTATAAATCCGCGACCAACAACGCCATCTGCAACACCAATC
CTTATAACGAATGCCGCGATGTCGGTATGCTCGTTGGCTTAGATGACTTTGTCGCTGCC
AATAACGGCAAAGATATGCTGATCATGCTGCACCAAATGGGCAATCACGGGCCTGCGTA
TTTTAAGCGATATGATGAAAAGTTTGCCAAATTCACGCCAGCGTGTGAAGGTAATGAGCT
TGCCAAGTGCGAACATCAGTCCTTGATCAATGCTTATGACAATGCCTTGCTTGCCACCG
ATGATTTCATCGCTCAAAGTATCCAGTGGCTGCAGACGCACAGCAATGCCTATGATGTC
TCAATGCTGTATGTCAGCGATCATGGCGAAAGTCTGGGTGAGAACGGTGTCTATCTACA
TGGTATGCCAAATGCCTTTGCACCAAAAGAACAGCGCAGTGTGCCTGCATTTTTCTGGA
CGGATAAGCAAACTGGCATCACGCCAATGGCAACCGATACCGTCCTGACCCATGACGC
GATCACGCCGACATTATTAAAGCTGTTTGATGTCACCGCGGACAAAGTCAAAGACCGCA
CCGCATTCATCCGCTGA SEQ ID NO: 10 (mcr-1.10)
GTGTGGTACCGACGCTCGGTCAGTCCGTTTGTTCTTGTGGCGAGTGTTGCCGTTTTCTT
GACCGCGACCGCCAATCTTACCTTTTTTGATAAAATCAGCCAAACCTATCCCATCGCGG
ACAATCTCGGCTTTGTGCTGACGATCGCTGTCGTGCTCTTTGGCGCGATGCTACTGATC
ACCACGCTGTTATCATCGTATCGCTATGTGCTAAAGCCTGTGTTGATTTTGCTATTAATC
ATGGGCGCGGTGACCAGTTATTTTACTGACACTTATGGCACGGTCTATGATACGACCAT
GCTCCAAAATGCCCTACAGACCGACCAAGCCGAGACCAAGGATCTATTAAACGCAGCG
TTTATCATGCGTATCATTGGTTTGGGTGTGCTACCAAGTTTGCTTGTGGCTTTTGTTAAG
GTGGATTATCCGACTTGGGGCAAGGGTTTGATGCGCCGATTGGGCTTGATCGTGGCAA
GTCTTGCGCTGATTTTACTGCCTGTGGTGGCGTTCAGCAGTCATTATGCCAGTTTCTTTC
GCGTGCATAAGCCGCTGCGTAGCTATGTCAATCCGATCATGCCAATCTACTCGGTGGGT
AAGCTTGCCAGTATTGAGTATAAAAAAGCCAGTGCGCCAAAAGATACCATTTATCACGC
CAAAGACGCGGTACAAGCAACCAAGCCTGATATGCGTAAGCCACGCCTAGTGGTGTTC
GTCGTCGGTGAGACGGCACGCGCCGATCATGTCAGCTTCAATGGCTATGAGCGCGATA
CTTTCCCACAGCTTGCCAAGATCGATGGCGTGACCAATTTTAGCAATGTCACATCGTGC
GGCACATCGACGGCGTATTCTGTGCCGTGTATGTTCAGCTATCTGGGCGCGGATGAGT
ATGATGTCGATACCGCCAAATACCAAGAAAATGTGCTGGATACGCTGGATCGCTTGGGC
GTAAGTATCTTGTGGCGTGATAATAATTCGGACTCAAAAGGCGTGATGGATAAGCTGCC
AAAAGCGCAATTTGCCGATTATAAATCCGCGACCAACAACGCCATCTGCAACACCAATC
CTTATAACGAATGCCGCGATGTCGGTATGCTCGTTGGCTTAGATGACTTTGTCGCTGCC
AATAACGGCAAAGATATGCTGATCATGCTGCACCAAATGGGCAATCACGGGCCTGCGTA
TTTTAAGCGATATGATGAAAAGTTTGCCAAATTCACGCCAGCGTGTGAAGGTAATGAGCT
TGCCAAGTGCGAACATCAGTCCTTGATCAATGCTTATGACAATGCCTTGCTTGCCACCG
ATGATTTCATCGCTCAAAGTATCCAGTGGCTGCAGACGCACAGCAATGCCTATGATGTC
TCAATGCTGTATGTCAGCGATCATGGCGAAAGTCTGGGTGAGAACGGTGTCTATCTACA
TGGTATGCCAAATGCCTTTGCACCAAAAGAACAGCGCAGTGTGCCTGCATTTTTCTGGA
CGGATAAGCAAACTGGCATCACGCCAATGGCAACCGATACCGTCCTGACCCATGACGC
GATCACGCCGACATTATTAAAGCTGTTTGATGTCACCGCGGACAAAGTCAAAGACCGCA
CCGCATTCATCCGCTGA SEQ ID NO: 11 (mcr-2)
ATGACATCACATCACTCTTGGTATCGCTATTCTATCAATCCTTTTGTGCTGATGGGTTTG
GTGGCGTTATTTTTGGCAGCGACAGCGAACCTGACATTTTTTGAAAAAGCGATGGCGGT
CTATCCTGTATCGGATAACTTAGGCTTTATCATCTCAATGGCGGTGGCGGTGATGGGTG
CTATGCTACTGATTGTCGTGCTGTTATCCTATCGCTATGTGCTAAAGCCTGTCCTGATTT
TGCTACTGATTATGGGTGCGGTGACGAGCTATTTTACCGATACTTATGGCACGGTCTAT
GACACCACCATGCTCCAAAATGCCATGCAAACCGACCAAGCCGAGTCTAAGGACTTGAT
GAATTTGGCGTTTTTTGTGCGAATTATCGGGCTTGGCGTGTTGCCAAGTGTGTTGGTCG
CAGTTGCCAAAGTCAATTATCCAACATGGGGCAAAGGTCTGATTCAGCGTGCGATGACA
TGGGGTGTCAGCCTTGTGCTGTTGCTTGTGCCGATTGGACTATTTAGCAGTCAGTATGC -continued

| SEQUENCES |
|---|

GAGTTTCTTTCGGGTGCATAAGCCAGTGCGTTTTTATATCAACCCGATTACGCCGATTTA
TTCGGTGGGTAAGCTTGCCAGTATCGAGTACAAAAAAGCCACTGCGCCAACAGACACCA
TCTATCATGCCAAAGACGCCGTGCAGACCACCAAGCCGAGCGAGCGTAAGCCACGCCT
AGTGGTGTTCGTCGTCGGTGAGACGGCGCGTGCTGACCATGTGCAGTTCAATGGCTAT
GGCCGTGAGACTTTCCCGCAGCTTGCCAAAGTTGATGGCTTGGCGAATTTTAGCCAAGT
GACATCGTGTGGCACATCGACGGCGTATTCTGTGCCGTGTATGTTCAGCTATTTGGGTC
AAGATGACTATGATGTCGATACCGCCAAATACCAAGAAAATGTGCTAGATACGCTTGAC
CGCTTGGGTGTGGGTATCTTGTGGCGTGATAATAATTCAGACTCAAAAGGCGTGATGGA
TAAGCTACCTGCCACGCAGTATTTTGATTATAAATCAGCAACCAACAATACCATCTGTAA
CACCAATCCCTATAACGAATGCCGTGATGTCGGTATGCTTGTCGGGCTAGATGACTATG
TCAGCGCCAATAATGGCAAAGATATGCTCATCATGCTACACCAAATGGGCAATCATGGG
CCGGCGTACTTTAAGCGTTATGATGAGCAATTTGCCAAATTCACCCCCGTGTGCGAAGG
CAACGAGCTTGCCAAATGCGAACACCAATCACTCATCAATGCCTATGACAATGCGCTAC
TTGCGACTGATGATTTTATCGCCAAAAGCATCGATTGGCTAAAAACGCATGAAGCGAAC
TACGATGTCGCCATGCTCTATGTCAGTGACCACGGCGAGAGCTTGGGCGAAAATGGTG
TCTATCTGCATGGTATGCCAAATGCCTTTGCACCAAAAGAACAGCGAGCTGTGCCTGCG
TTTTTTTGGTCAAATAATACGACATTCAAGCCAACTGCCAGCGATACTGTGCTGACGCAT
GATGCGATTACGCCAACACTGCTTAAGCTGTTTGATGTCACAGCGGGCAAGGTCAAAGA
CCGCGCGGCATTTATCCAGTAA

SEQ ID NO: 12 (mcr-2.2)
GTGTGGTACCGACGCTCGGTCAGTCCGTTTGTTCTTGTGGCGAGTGTTGCCGTTTTCTT
GACCGCGACCGCCAATCTTACCTTTTTTGATAAAATCAGCCAAACCTATCCCATCGCGG
ACAATCTCGGCTTTGTGCTGACGATCGCTGTCGTGCTCTTTGGCGCGATGCTACTGATC
ACCACGCTGTTATCATCGTATCGCTATGTGCTAAAGCCTGTGTTGATTTTGCTATTAATC
ATGGGCGCGGTGACCAGTTATTTTACTGACACTTATGGCACGGTCTATGATACGACCAT
GCTCCAAAATGCCCTACAGACCGACCAAGCCGAGACCAAGGATCTATTAAACGCAGCG
TTTATCATGCGTATCATTGGTTTGGGTGTGCTACCAAGTTTGCTTGTGGCTTTTGTTAAG
GTGGATTATCCGACTTGGGGCAAGGGTTTGATGCGCCGATTGGGCTTGATCGTGGCAA
GTCTTGCGCTGATTTTACTGCCTGTGGTGGCGTTCAGCAGTCATTATGCCAGTTTCTTTC
GCGTGCATAAGCCGCTGCGTAGCTATGTCAATCCGATCATGCCAATCTACTCGGTGGGT
AAGCTTGCCAGTATTGAGTATAAAAAAGCCAGTGCGCCAAAAGATACCATTTATCACGC
CAAAGACGCGGTACAAGCAACCAAGCCTGATATGCGTAAGCCACGCCTAGTGGTGTTC
GTCGTCGGTGAGACGGCACGCGCCGATCATGTCAGCTTCAATGGCTATGAGCGCGATA
CTTTCCCACAGCTTGCCAAGATCGATGGCGTGACCAATTTTAGCAATGTCACATCGTGC
GGCACATCGACGGCGTATTCTGTGCCGTGTATGTTCAGCTATCTGGGCGCGGATGAGT
ATGATGTCGATACCGCCAAATACCAAGAAAATGTGCTGGATACGCTGGATCGCTTGGGC
GTAAGTATCTTGTGGCGTGATAATAATTCGGACTCAAAAGGCGTGATGGATAAGCTGCC
AAAAGCGCAATTTGCCGATTATAAATCCGCGACCAACAACGCCATCTGCAACACCAATC
CTTATAACGAATGCCGCGATGTCGGTATGCTCGTTGGCTTAGATGACTTTGTCGCTGCC
AATAACGGCAAAGATATGCTGATCATGCTGCACCAAATGGGCAATCACGGGCCTGCGTA
TTTTAAGCGATATGATGAAAAGTTTGCCAAATTCACGCCAGCGTGTGAAGGTAATGAGCT
TGCCAAGTGCGAACATCAGTCCTTGATCAATGCTTATGACAATGCCTTGCTTGCCACCG
ATGATTTCATCGCTCAAAGTATCCAGTGGCTGCAGACGCACAGCAATGCCTATGATGTC
TCAATGCTGTATGTCAGCGATCATGGCGAAAGTCTGGGTGAGAACGGTGTCTATCTACA
TGGTATGCCAAATGCCTTTGCACCAAAAGAACAGCGCAGTGTGCCTGCATTTTTCTGGA
CGGATAAGCAAACTGGCATCACGCCAATGGCAACCGATACCGTCCTGACCCATGACGC
GATCACGCCGACATTATTAAAGCTGTTTGATGTCACCGCGGACAAAGTCAAAGACCGCA
CCGCATTCATCCGCTGA SEQ ID NO: 13 (mcr-3)
ATGCCTTCCCTTATAAAAATAAAAATTGTTCCGCTTATGTTCTTTTTGGCACTGTATTTTG
CATTTATGCTGAACTGGCGTGGAGTTCTCCATTTTTACGAAATCCTTTACAAATTAGAAG
ATTTTAAGTTTGGTTTCGCCATTTCATTACCAATATTGCTTGTTGCAGCGCTTAACTTTGT
ATTTGTTCCATTTTCGATACGGTATTTAATAAAGCCTTTTTTTGCACTTCTTATCGCACTTA
GTGCAATCGTTAGTTACACAATGATGAAGTATAGAGTCTTGTTTGATCAAAACATGATTC
AGAATATTTTTGAAACCAATCAAAATGAGGCGTTAGCATATTTAAGCTTACCAATTATAGT
ATGGGTTACTATTGCTGGTTTTATCCCTGCCATTTTACTTTTCTTTGTTGAAATTGAATAT
GAGGAAAAATGGTTCAAAGGGATTCTAACTCGTGCCCTATCGATGTTTGCATCACTTATA
GTGATTGCGGTTATTGCAGCACTATACTATCAAGATTATGTGTCAGTGGGGCGCAACAA
TTCAAACCTCCAGCGTGAGATTGTTCCAGCCAATTTCGTTAATAGTACCGTTAAATACGT
TTACAATCGTTATCTTGCTGAACCAATCCCATTTACAACTTTAGGTGATGATGCAAAACG
GGATACTAATCAAAGTAAGCCCACGTTGATGTTTCTGGTCGTTGGTGAAACCGCTCGTG
GTAAAAATTTCTCGATGAATGGCTATGAGAAAGACACCAATCCATTTACCAGTAAATCTG
GTGGCGTGATCTCCTTTAATGATGTTCGTTCGTGTGGGACTGCAACCGCTGTATCCGTC
CCCTGCATGTTCTCCAATATGGGGAGAAAGGAGTTTGATGATAATCGCGCTCGCAATAG
CGAGGGCCTGCTAGATGTGTTGCAAAAAACGGGGATCTCCATTTTTTGGAAGGAGAACG
ATGGAGGCTGCAAAGGCGTCTGCGACCGAGTACCTAACATCGAAATCGAACCAAAGGA
TCACCCTAAGTTCTGCGATAAAAACACATGCTATGACGAGGTTGTCCTTCAAGACCTCG
ATAGTGAAATTGCTCAAATGAAAGGGGATAAGCTGGTTGGCTTCCACCTGATAGGTAGC
CATGGCCCAACCTACTACAAGCGCTACCCTGATGCTCATCGTCAGTTCACCCCTGACTG
TCCACGCAGTGATATTGAAAACTGCACAGATGAAGAGCTCACCAACACCTATGACAACA
CCATCCGCTACACCGATTTCGTGATTGGAGAGATGATTGCCAAGTTGAAAACCTACGAA
GATAAGTACAACACCGCGTTGCTCTACGTCTCCGATCATGGTGAATCACTGGGAGCATT
AGGGCTTTACCTACACGGTACACCGTACCAGTTTGCACCGGATGATCAGACCCGTGTTC
CTATGCAGGTGTGGATGTCACCTGGATTTACCAAAGAGAAAGGCGTTGATATGGCGTGT
TTGCAGCAGAAAGCCGCTGATACTCGTTACTCACACGATAATATTTTCTCATCTGTATTG -continued

| SEQUENCES |
| --- |

GGTATCTGGGACGTCAAAACATCAGTTTACGAAAAGGGTCTAGATATTTTCAGTCAATGT
CGTAATGTTCAATAA

SEQ ID NO: 14 (mcr-3.2)
ATGCCTTCCCTTATAAAAATAAAAATTGTTCCGCTTATGTTCTTTTTGGCACTGTATTTTG
CATTTATGCTGAACTGGCGTGGAGTTCTCCATTTTTACGAAATCCTTTACAAATTAGAAG
ATTTTAAGTTTGGTTTCGCCATTTCATTACCAATATTGCTTGTTGCAGCGCTTAACTTTGT
ATTTGTTCCATTTTCGATACGGTATTTAATAAAGCCTTTTTTTGCACTTCTTATCGCACTTA
GTGCAATCGTTAGTTACACAATGATGAAGTATAGAGTCTTGTTTGATCAAAACATGATTC
AGAATATTTTTGAAACCAATCAAAATGAGGCGTTAGCATATTTAAGCTTACCAATTATAGT
ATGGGTTACTATTGCTGGTTTTATCCCTGCCATTTTACTTTTCTTTGTTGAAATTGAATAT
GAGGAAAAATGGTTCAAAGGGATTCTAACTCGTGCCCTATCGATGTTTGCATCACTTATA
GTGATTGCGGTTATTGCAGCACTATACTATCAAGATTATGTGTCAGTGGGGCGCAACAA
TTCAAACCTCCAGCGTGAGATTGTTCCAGCCAATTTCGTTAATAGTACCGTTAAATACGT
TTACAATCGTTATCTTGCTGAACCAATCCCATTTACAACTTTAGGTGATGATGCAAAACG
GGATACTAATCAAAGTAAGCCCACGTTGATGTTTCTGGTCGTTGGTGAAACCGCTCGTG
GTAAAAATTTCTCGATGAATGGCTATGAGAAAGACACCAATCCATTTACCAGTAAATCTG
GTGGCGTGATCTCCTTTAATGATGTTCGTTCGTGTGGGACTGCAACCGCTGTATCCGTC
CCCTGCATGTTCTCCAATATGGGGAGAAAGGAGTTTGATGAAAATCGCGCTCGCAATAG
CGAGGGCCTGCTAGATGTGTTGCAAAAAACGGGGATCTCCATTTTTTGGAAGGAGAACG
ATGGAGGCTGCAAAGGCGTCTGCGACCGAGTACCTAACATCGAAATCGAACCAAAGGA
TCACCCTAAGTTCTGCGATAAAAACACATGCTATGACGAGGTTGTCCTTCAAGACCTCG
ATAGTGAAATTGCTCAAATGAAAGGGGATAAGCTGGTTGGCTTCCACCTGATAGGTAGC
CATGGCCCAACCTACTACAAGCGCTACCCTGATGCTCATCGTCAGTTCACCCCTGACTG
TCCACGCAGTGATATTGAAAACTGCACAGATGAAGAGCTCACCAACACCTATGACAACA
CCATCCGCTACACCGATTTCGTGATTGGAGAGATGATTGCCAAGTTGAAAACCTACGAA
GATAAGTACAACACCGCGTTGCTCTACGTCTCCGATCATGGTGAATCACTGGGAGCATT
AGGGCTTTACCTACACGGTACACCGTACCAGTTTGCACCGGATGATCAGACCCGTGTTC
CTATGCAGGTGTGGATGTCACCTGGATTTACCAAAGAGAAAGGCGTTGATATGGCGTGT
TTGCAGCAGAAAGCCGCTGATACTCGTTACTCACACGATAATATTTTCTCATCTGTATTG
GGTATCTGGGACGTCAAAACATCAGTTTACGAAAAGGGTCTAGATATTTTCAGTCAATGT
CGTAATGTTCAATAA SEQ ID NO: 15 (mcr-4)
GTGATTTCTAGATTTAAGACGTTATCGGTTAACCAATTCACTTTCATCACTGCGTTGTTTT
ATGTTGCCATTTTCAATCTACCGCTCTTTGGTATAGTGCGAAAAGGAATTGAAAAACAAC
CAGAAGTTGATCCCCTTTTCATCGCATCTATGCCGCTATTTTTAACATTTGCGCTGAGTT
TTTTGTTTTCAATTTTTACCGTCAAATACCTGCTGAAGCCCTTTTTTATCGTATTGACGTT
ACTTTCCTCAAGTGTATTTTTTGCAGCCTATCAATACAATGTCGTGTTTGACTACGGCAT
GATAGAAAACACGTTTCAAACACATCCTGCTGAAGCATTGATGTATGTAAATCTTGCATC
AATTACCAATCTACTGCTGACTGGGCTATTACCGTCATATCTTATTTATAAGGCCGATATT
CATTATCAGCCCTTTTTTAAGGAGTTATTGCATAAATTAGCCTTTATGCTGCTAATGTTCG
TTGGCATTGGGATAGTCGCCTTTTTTTACTATCAAGATTATGCTGCATTTGTTCGAAACAA
CAGTGAGTTAAGGCGTTACATTGTCCCTACCTATTTTGTCAGTAGTGCATCTAAATATCT
CAATGAGCACTATTTGCAGACGCCCATGGAATACCAACAACTTGGCCTAGATGCGAAGA
ATGCCAGTCGTAACCCGAACACTAAACCTAACTTATTAGTGGTTGTTGTGGGTGAAACT
GCGCGCTCAATGAGCTATCAATATTATGGATATAACAAGCCAACCAATGCTCATACCCAA
AATCAGGGGCTGATTGCGTTTAACGATACTAGCTCATGCGGCACGGCCACGGCGGTGT
CTCTACCCTGTATGTTTTCACGAATGGGGCGGGCAGACTATGATCCTCGCCGTGCTAAT
GCTCAAGACACAGTGATTGATGTGTTAAGTCATAGTGGTATAAAAGTACAGTGGTTTGAT
AATGATTCTGGCTGTAAAGGTGTGTGTGATCAGGTTGAAAATCTCACGATAGATTTGAAG
AGTGATCCGAAGCTGTGTTCTGGCCAATATTGTTTTGACCAAGTATTGCTCAACAAATTA
GATAAAATTCTGGCAGTAGCACCAAGTCAAGATACAGTAATTTTTTTGCATATCATTGGT
AGTCATGGACCAACTTATTATCTTAGATACCCGCCAGAGCATCGTAAATTTATACCGGAT
TGTCCGCGCAGTGATATTCAAAATTGCAGTCAAGAAGAACTGATTAACACCTACGACAA
CACTATTCTATATACGGATTTTATTCTCAGTGAAGTGGTGAATAAATTAAAAGGTAAGCA
GGATATGTTCGATACTGCAATGCTGTATCTCTCTGACCATGGTGAGTCTTTGGGTGAAAA
GGGCATGTATTTACATGGTGCGCCCTATAGTATTGCACCGAAAGAACAAACTAGCGTAC
CAATGCTGGCTTGGGTATCTAATGACTTTAGCCAAGATAATCAGTTGAACATGACTTGTG
TTGCACAGCGAGCAGAACAGGGCGGCTTTTCCCACGACAATTTGTTCGACAGTTTGCTA
GGACTTATGAATGTAAAAACCACCGTCTATCAGAGCCAACTCGATATTTTTGCACCTTGC
AGGTATTAG SEQ ID NO: 16 (mcr-5)
ATGCGGTTGTCTGCATTTATCACTTTCTTGAAAATGCGCCCGCAAGTGCGCACTGAATTT
TTGACTCTGTTCATCAGCCTTGTGTTCACCCTGCTGTGCAATGGCGTGTTTTGGAATGC
CCTTCTTGCTGGACGCGACTCCCTAACTTCTGGAACATGGCTAATGCTCCTTTGCACTG
GGTTGCTGATCACCGGGCTGCAATGGTTGTTGCTCCTTCTGGTGGCCACGCGCTGGAG
TGTCAAGCCACTACTGATTCTGCTTGCTGTCATGACGCCCGCCGCCGTTTATTTCATGC
GCAACTACGGGGTTTATCTCGACAAGGCCATGCTGCGGAATCTGATGGAGACGGACGT
CAGGGAAGCCAGTGAGCTGTTGCAATGGAGAATGCTGCCCTACTTGTTGGTTGCAGCC
GTATCCGTGTGGTGGATTGCGAGAGTCAGGGTTTTACGAACGGGCTGGAAACAAGCGG
TAATGATGCGCAGCGCTTGTCTGGCTGGCGCTCTCGCCATGATTTCCATGGGTCTGTG
GCCAGTCATGGATGTGCTGATACCCACGCTTCGTGAAAACAAGCCGCTTCGCTATTTGA
TCACTCCTGCAAACTACGTCATCTCGGGCATTCGGGTTTTGACTGAACAGGCGTCATCG
TCAGCAGACGAAGCAAGGGAAGTCGTTGCAGCCGATGCGCATCGAGGGCCTCAAGAAC
AAGGCCGCCGTCCTCGTGCTCTCGTACTGGTTGTCGGGGAAACCGTCAGGGCGGCTAA -continued

| SEQUENCES |
|---|
| TTGGGGGTTGAGCGGCTATGAACGACAAACCACCCCTGAGTTGGCCGCACGCGACGTG<br>ATCAATTTTTCCGATGTCACCAGTTGCGGGACGGATACGGCTACATCCCTTCCCTGCAT<br>GTTTTCCCTCAATGGTCGGCGCGACTACGACGAACGCCAGATTCGTCGGCGCGAGTCC<br>GTGCTGCACGTTTTAAACCGTAGTGACGTCAACATTCTCTGGCGCGATAACCAGTCGGG<br>CTGTAAAGGCGTCTGTGATGGACTGCCCTTTGAAAACCTGTCTTCGGCAGGCCATCCCA<br>CACTGTGCCATGGCGAGCGCTGCCTGGATGAAATTCTGCTCGAAGGGTTGGCCGAGAA<br>GATAACAACAAGCCGCAGCGATATGCTGATCGTTCTGCATATGCTGGGCAATCACGGCC<br>CAGCGTATTTCCAGCGCTATCCCGCAAGCTACCGACGCTGGTCGCCAACCTGCGACAC<br>CACCGATCTGGCCAGCTGTTCGCATGAAGCCTTGGTGAACACCTACGACAACGCCGTG<br>CTTTACACCGATCATGTGCTTGCCCGTACCATTGACCTGCTGTCCGGCATCCGCTCACA<br>CGACACGGCGCTGCTGTACGTTTCCGATCATGGGGAATCGCTCGGCGAGAAAGGCCTG<br>TATCTCCATGGCATACCTTACGTCATCGCGCCGGATGAGCAGATCAAGGTGCCGATGAT<br>CTGGTGGCAGTCGAGTCAGGTTTATGCCGACCAAGCCTGTATGCAAACTCATGCCTCTC<br>GGGCACCGGTAAGTCACGATCACCTGTTTCACACCTTGCTCGGGATGTTCGACGTGAAA<br>ACCGCTGCCTACACGCCAGAGTTGGACCTTCTGGCAACATGCAGAAAAGGACAACCAC<br>AATGA |

The invention claimed is:

1. A method for detecting the presence or absence of a bacterium resistant to a cyclic cationic polypeptide antibiotic in a test sample comprising intact bacterial cells, unpurified bacterial membranes or fragments thereof, or a combination thereof, the method comprising:

performing a hydrolysis step in which an acidic hydrolysis on the test sample is performed without performing a subsequent purification step for extracting/isolating lipids, to provide a hydrolyzed test sample;

admixing the hydrolyzed test sample with a MALDI matrix solution to provide a sample/matrix mixture that is subjected to mass spectrometry analysis and generating a mass spectrum output; and identifying in said mass spectrum output a first defined peak indicative of the presence of Lipid A modified by phosphoethanolamine, wherein said first defined peak is a peak present in a mass spectrum output for Lipid A modified by phosphoethanolamine and wherein said first defined peak is absent from a corresponding mass spectrum output for native Lipid A;

wherein the presence of said first defined peak indicates the presence of a bacterium resistant to a cyclic cationic polypeptide antibiotic, and wherein the absence of said first defined peak indicates the absence of a bacterium resistant to a cyclic cationic polypeptide antibiotic.

2. A method according to claim 1, wherein said Lipid A modified by phosphoethanolamine is an integral part of a bacterial membrane or a fragment thereof.

3. A method according to claim 1, wherein said test sample is processed to remove salt.

4. A method according to claim 1, wherein said mass spectrometry analysis comprises MALDI-TOF mass spectrometry analysis.

5. A method according to claim 1, wherein said first defined peak comprises a mass-to-charge ratio (m/z) of about 120 to about 125 m/z units greater than a second defined peak indicative of the presence of native Lipid A.

6. A method according to claim 5, wherein said second defined peak is selected from the group consisting of:

(a) a peak comprising a mass-to-charge ratio (m/z) of about 1793 to about 1799 m/z, for *Escherichia coli, Shigella, Klebsiella pneumoniae, Salmonella enterica, Enterobacter* spp. and *Klebsiella oxytoca;*

(b) a peak comprising a mass-to-charge ratio (m/z) of about 1820 to about 1826 m/z, for *Klebsiella pneumoniae;*

(c) a peak comprising a mass-to-charge ratio (m/z) of about 1837 to about 1843 m/z, for *Klebsiella pneumoniae;*

(d) a peak comprising a mass-to-charge ratio (m/z) of about 1847 to about 1853 m/z, for *Klebsiella pneumoniae;*

(e) a peak comprising a mass-to-charge ratio (m/z) of about 2059 to about 2065 m/z, for *Klebsiella pneumoniae;*

(f) a peak comprising a mass-to-charge ratio (m/z) of about 2075 to about 2081 m/z, for *Klebsiella pneumoniae;*

(g) a peak comprising a mass-to-charge ratio (m/z) of about 1614 to about 1620 m/z, for *Pseudomonas aeruginosa;*

(h) a peak comprising a mass-to-charge ratio (m/z) of about 1907 to about 1913 m/z, for *Acinetobacter baumannii;*

(i) a peak comprising a mass-to-charge ratio (m/z) of about 1793 to about 1799 m/z, for *Salmonella* spp;

(j) a peak comprising a mass-to-charge ratio (m/z) of about 1820 to about 1826 m/z, for *Salmonella* spp; or (k) a peak comprising a mass-to-charge ratio (m/z) of about 2031 to about 2037 m/z, for *Salmonella* spp.

7. A method according to claim 1, wherein a ratio of intensity of:

the first defined peak; to the second defined peak is least 0.10:1.

8. A method according to claim 1, further comprising identifying in said mass spectrum output a third defined peak comprising a mass-to-charge ratio (m/z) of about 22 to about 28 m/z units greater than a second defined peak indicative of the presence of native Lipid A.

9. A method according to claim 8, wherein said second defined peak is selected from the group consisting of:

(a) a peak comprising a mass-to-charge ratio (m/z) of about 1793 to about 1799 m/z, for *Escherichia coli, Shigella, Klebsiella pneumoniae, Salmonella enterica, Enterobacter* spp. and *Klebsiella oxytoca;*

(b) a peak comprising a mass-to-charge ratio (m/z) of about 1820 to about 1826 m/z, for *Klebsiella pneumoniae;*

(c) a peak comprising a mass-to-charge ratio (m/z) of about 1837 to about 1843 m/z, for *Klebsiella pneumoniae;*

(d) a peak comprising a mass-to-charge ratio (m/z) of about 1847 to about 1853 m/z, for *Klebsiella pneumoniae;*

(e) a peak comprising a mass-to-charge ratio (m/z) of about 2059 to about 2065 m/z, for *Klebsiella pneumoniae;*

(f) a peak comprising a mass-to-charge ratio (m/z) of about 2075 to about 2081 m/z, for *Klebsiella pneumoniae;*

(g) a peak comprising a mass-to-charge ratio (m/z) of about 1793 to about 1799 m/z, for *Salmonella* spp;

(h) a peak comprising a mass-to-charge ratio (m/z) of about 1820 to about 1826 m/z, for *Salmonella* spp; or (i) a peak comprising a mass-to-charge ratio (m/z) of about 2031 to about 2037 m/z, for *Salmonella* spp.

10. A method according to claim 8, wherein a ratio of intensity of:

the third defined peak; to the second defined peak is at least about 0.15:1.

11. A method according to claim 8, wherein a ratio of:

the sum of the intensity of said first defined peak and the intensity of said third defined peak; to the intensity of said second defined peak is least about 0.15:1.

12. A method according to claim 1, wherein said bacterium resistant to a cyclic cationic polypeptide antibiotic through plasmid-encoded resistance comprises a plasmid having a mobilised colistin resistance gene.

13. A method according to claim 12, wherein said mobilised colistin gene comprises one or more of an mcr-like gene, mcr-1, mcr-1.1, mcr-1.2, mcr-1.3, mcr-1.4, mcr-1.5, mcr-1.6, mcr-1.7, mcr-1.8, mcr-1.9, mcr-1.10, mcr-2, mcr-2.2, mcr-3, mcr-3.2, mcr-4, mcr-5, SEQ ID: 1, SEQ ID: 2, SEQ ID: 3, SEQ ID: 4, SEQ ID: 5, SEQ ID: 6, SEQ ID: 7, SEQ ID: 8, SEQ ID: 9, SEQ ID: 10, SEQ ID: 11, SEQ ID: 12, SEQ ID: 13, SEQ ID: 14, SEQ ID: 15, SEQ ID: 16, or a sequence having at least 50% homology thereto.

14. A method according to claim 1, wherein said MALDI matrix solution allows for the selective extraction, co-crystallization and ionisation of native Lipid A and/or modified Lipid A as an integral part of a bacterial membrane.

15. A method according to claim 1, wherein the MALDI matrix solution comprises 2,5-dihydroxybenzoic acid suspended in an organic solvent.

16. A method according to claim 15, wherein said organic solvent comprises chloroform and methanol at a ratio of about 6:1 to about 12:1 v/v.

17. A method according to claim 15, wherein said organic solvent comprises chloroform, methanol, dichloromethane, ether, diethyl-ether, petroleum ether, isopropanol, butanol, hexane or a combination thereof.

18. A method according to claim 1, wherein the ratio of the hydrolyzed test sample to the MALDI matrix solution is between about 0.1:1 to about 2:1 v/v.

19. A method according to claim 1, wherein said test sample comprises between about $10^1$ to about $10^{10}$ bacterial cells.

20. A method according to claim 1, wherein said cyclic cationic polypeptide antibiotic is a polymyxin antibiotic.

21. A method according to claim 20, wherein said polymyxin antibiotic is one or more of Colistin (Polymyxin E), Polymyxin B, Mattacin (Polymyxin M), or a salt thereof.

22. A method according to claim 1, wherein said bacterium is selected from the following genera: *Escherichia, Klebsiella, Enterobacter, Pseudomonas, Acinetobacter, Shigella, Salmonella, Citrobacter, Raoultella* and combinations thereof.

23. A method according to claim 1, wherein said bacterium is selected from the following species: *Escherichia coli, Klebsiella pneumoniae, Klebsiella oxytoca, Enterobacter aerogenes, Enterobacter cloacae, Enterobacter asburiae, Pseudomonas aeruginosa, Acinetobacter baumannii, Shigella sonnei, Shigella flexneri, Salmonella enterica, Citrobacter freundii, Citrobacter koseri, Citrobacter amalonaticus, Citrobacter youngae* and combinations thereof.

24. A method according to claim 1, wherein said bacterium is heat inactivated or wherein said bacterium is not heat inactivated.

25. A method according to claim 1, further comprising the step of recording the data obtained in step (a) on a suitable data carrier.

26. A method according to claim 1, wherein the acidic hydrolysis is performed with acetic acid.

27. A method according to claim 1, wherein an acid is added to the sample for the hydrolysis step and the test sample with the added acid is heated.

28. A method according to claim 1, wherein the hydrolysis step comprises a washing of the sample.

* * * * *